(12) United States Patent
Stuyver et al.

(10) Patent No.: US 8,859,203 B2
(45) Date of Patent: Oct. 14, 2014

(54) METHOD FOR TYPING AND DETECTING HBV

(75) Inventors: Lieven Stuyver, Herzele (BE); Rudi Rossau, Ekeren (BE); Geert Maertens, Bruges (BE)

(73) Assignee: Fujirebio Europe N.V., Ghent (BE)

( * ) Notice: Subject to any disclaimer, the term of this patent is extended or adjusted under 35 U.S.C. 154(b) by 880 days.

(21) Appl. No.: 10/606,879

(22) Filed: Jun. 27, 2003

(65) Prior Publication Data

US 2005/0175990 A1 Aug. 11, 2005

Related U.S. Application Data

(62) Division of application No. 09/155,885, filed as application No. PCT/EP97/02002 on Apr. 21, 1997, now Pat. No. 6,709,812.

(30) Foreign Application Priority Data

Apr. 19, 1996 (EP) ...................................... 96870053

(51) Int. Cl.
*C12Q 1/68* (2006.01)
*C12Q 1/70* (2006.01)
*C07H 21/04* (2006.01)

(52) U.S. Cl.
CPC ...................................... *C12Q 1/706* (2013.01)
USPC ............................ 435/6.11; 435/5; 536/24.32

(58) Field of Classification Search
None
See application file for complete search history.

(56) References Cited

U.S. PATENT DOCUMENTS

| | | | |
|---|---|---|---|
| 6,228,575 B1 | 5/2001 | Gingeras | |
| 6,555,311 B1 | 4/2003 | Locarnini | |
| 6,709,812 B1 | 3/2004 | Stuyver et al. | |
| 7,313,357 B2 | 12/2007 | Stuyver et al. | |
| 2004/0029110 A1 | 2/2004 | Stuyver et al. | |
| 2005/0175990 A1 | 8/2005 | Stuyver | |

FOREIGN PATENT DOCUMENTS

| | | |
|---|---|---|
| EP | 0 229 701 A | 7/1987 |
| EP | 0569237 A2 * | 6/1993 |
| EP | 0 569 237 A | 11/1993 |
| WO | WO 91 10746 A | 7/1991 |
| WO | WO 93 13120 A | 7/1993 |
| WO | WO 94/12670 * | 6/1994 |
| WO | 94/26904 | 11/1994 |
| WO | WO 95 02690 A | 1/1995 |
| WO | 95/11995 | 5/1995 |
| WO | WO 96/03152 | 2/1996 |
| WO | 97/40193 | 10/1997 |

OTHER PUBLICATIONS

Ashton-Reckardt PG "Mutants of the hepatitis B virus surface antigen that define some antigenically essential residues in the immunodominant a region". J. Med. Virol Nov. 1989;29(3):196-203.*

Stuyver LJ et al. "Nomenclature for antiviral-resistant human hepatitis B virus mutations in the polymerase region". Hepatology. Mar. 2001;33(3):751-7.*
G.A. Tipples et al.: "Mutation in HBV RNA-dependent DNA polymerase confers resistance to lamivudine in vitro" Hepatology, vol. 24, No. 3, Sep. 1996, Philadelphia US, pp. 714-717, XP002044246.
R. Ling et al.: "Selection of mutations in the hepatitis B virus polymerase during therapy of transplant recipients with lamivudine" Hepatology, vol. 24, No. 3, Sep. 1996, Philadelphia US, pp. 711-713, XP002044247.
A. Bartholomeusz et al.: "Mutations in the hepatitis B virus polymerase gene that are associated with resistance to famciclovir and lamivudine" International Antiviral News, vol. 5, No. 8, 1997, London GB, pp. 123-124, XP002044248 see the whole document.
Grandjacques et al.: "Rapid detection of genotypes and mutations in the pre-core promoter and the pre-core region of hepatitis B virus genome: correlation with viral; persistence and disease severity", Journal of Hepatology 2000; 33:430-439.
Lau et al.:"Features of response and resistance to lamivudine in patients with chronic hepatitis B with and without HbeAg", AASLD Abstract, Hepatology Oct. 1998, p. 318A.
Stuyver et al.: A new genotype of hepatitis B virus: complete genome and phylogenetic relatedness:, Journal of General Virlogy (2000) 81, 67-74.
File History (FH) of U.S. Appl. No. 09/155,885.
File History (FH) of U.S. Appl. No. 10/453,792.
Claims of U.S. Appl. No. 11/802,328, filed May 22, 2007.
Nature(1979), vol. 282, Pasek M et al, pp. 575-579, "Hepatitis B virus genes and their expression in *E. Coli*" Figure 2. copy contained in attached FH of U.S. Appl. No. 10/453,792.

(Continued)

*Primary Examiner* — Nicole Kinsey White
(74) *Attorney, Agent, or Firm* — Nixon & Vanderhye P.C.

(57) ABSTRACT

The present invention relates to a method for detection and/or genetic analysis of HBV in a biological sample, comprising hybridizing the polynucleic acids of the sample with a combination of at least two nucleotide probes, with said combination hybridizing specifically to a mutant target sequence chosen from the HBV RT pol gene region and/or to a mutant target sequence chosen from the HBV preCore region and/or to a mutant target sequence chosen from the HBsAg region of HBV and/or to a HBV genotype-specific target sequence, with said target sequences being chosen from FIG. 1, and with said probes being applied to known locations on a solid support and with said probes being capable of hybridizing to the polynucleic acids of the sample under the same hybridization and wash conditions, or with said probes hybridizing specifically with a sequence complementary to any of said target sequences, or a sequence where T of said target sequence is replaced by U; and detecting the hybrids formed; and inferring the HBV genotype and/or mutants present in said sample from the differential hybridization signal(s) obtained. The invention further relates to sets of nucleotide probes and possibly primers useful in said methods as well as to their use in a method for typing and/or detecting HBV and to assay kits using the same.

8 Claims, 28 Drawing Sheets

(56) References Cited

OTHER PUBLICATIONS

Figure 1D:
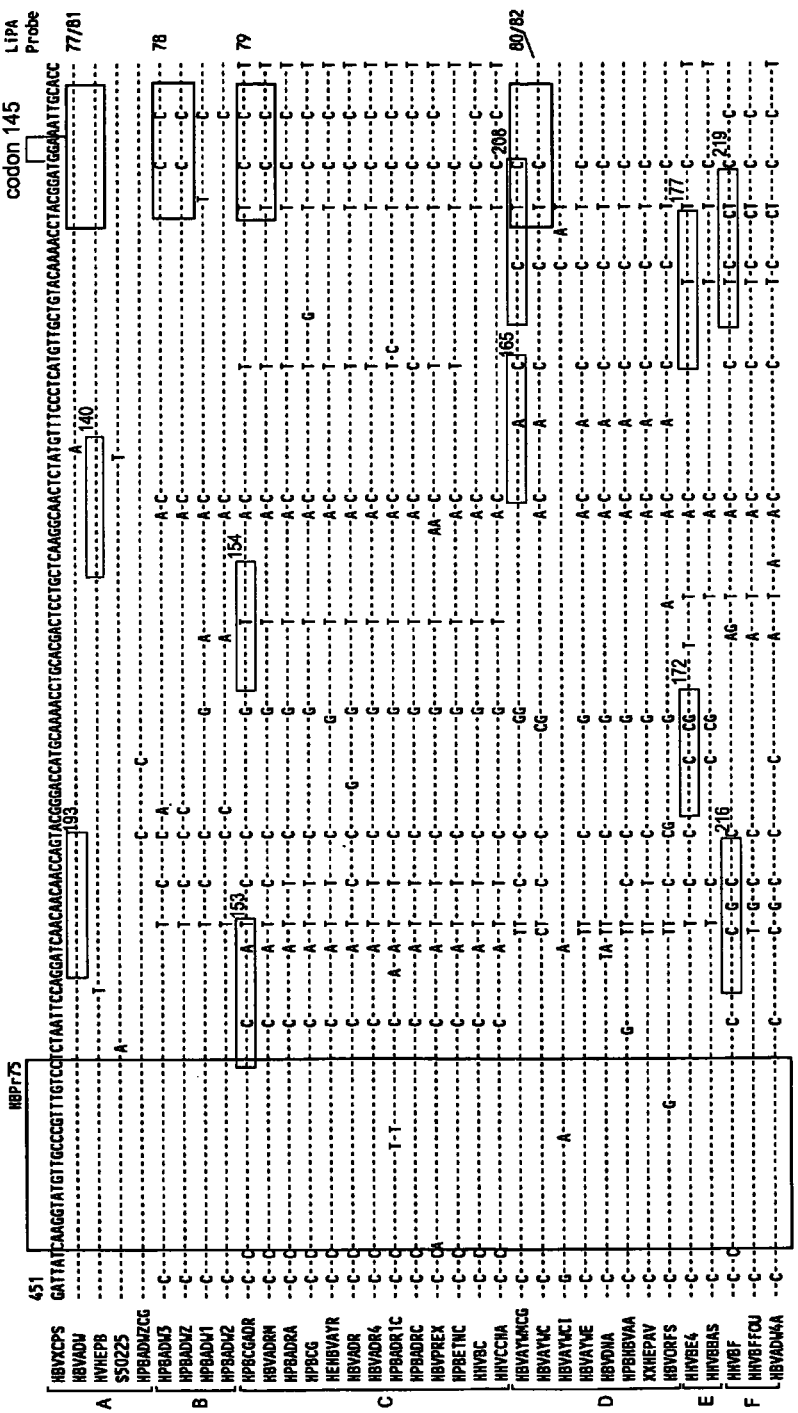
Figure 1E:
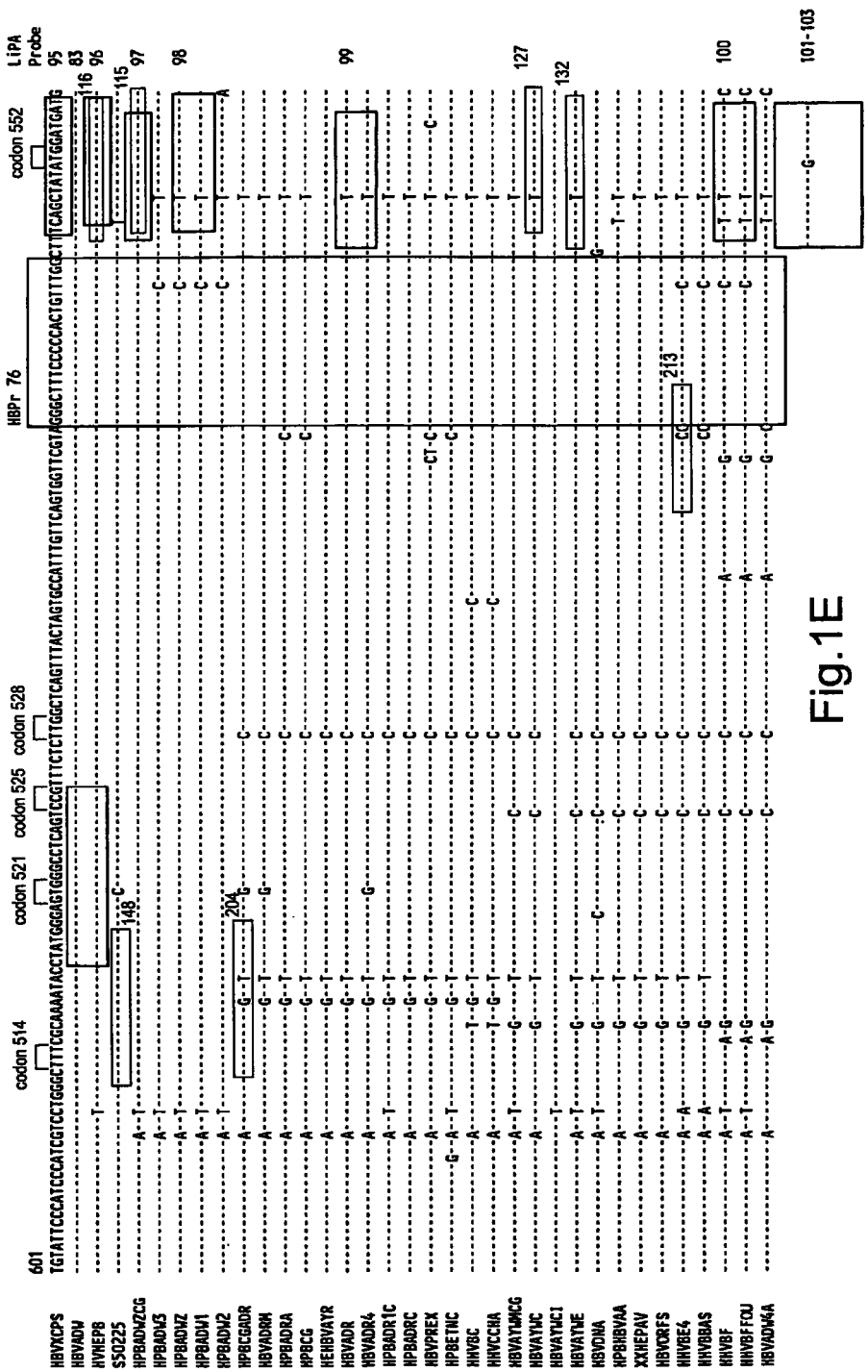
Figure 1F:
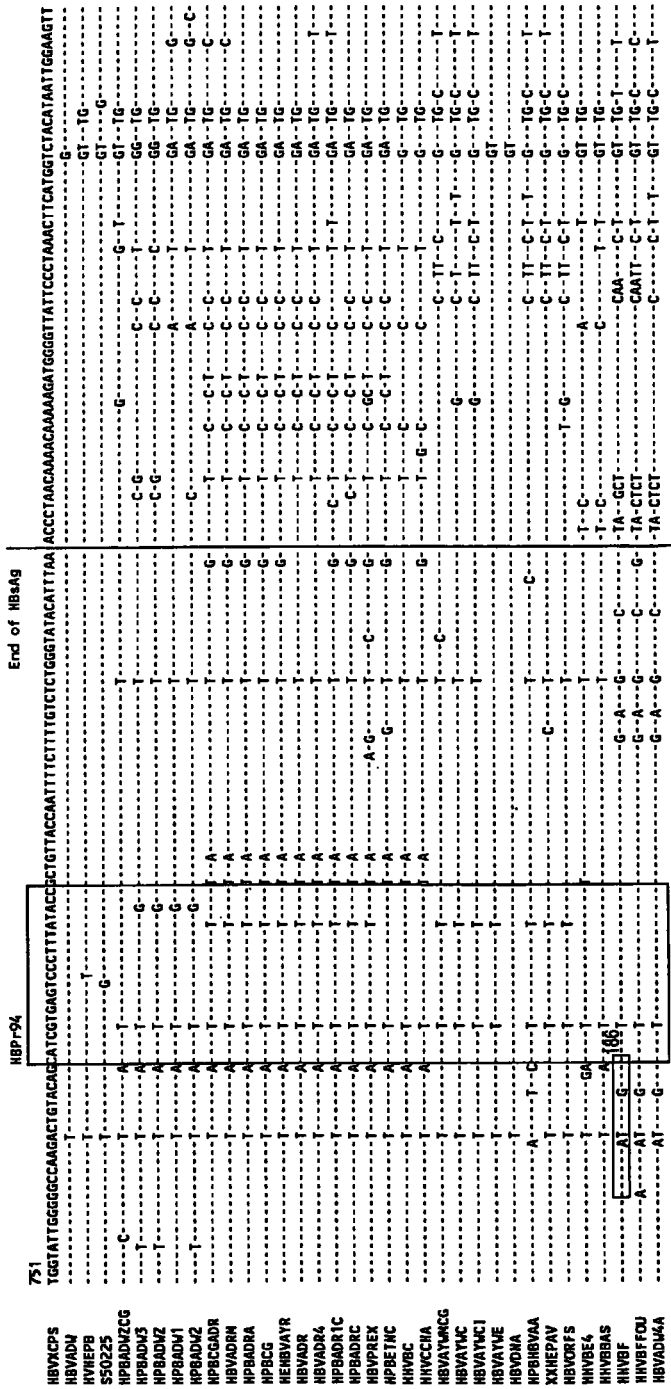
Figure 1L:
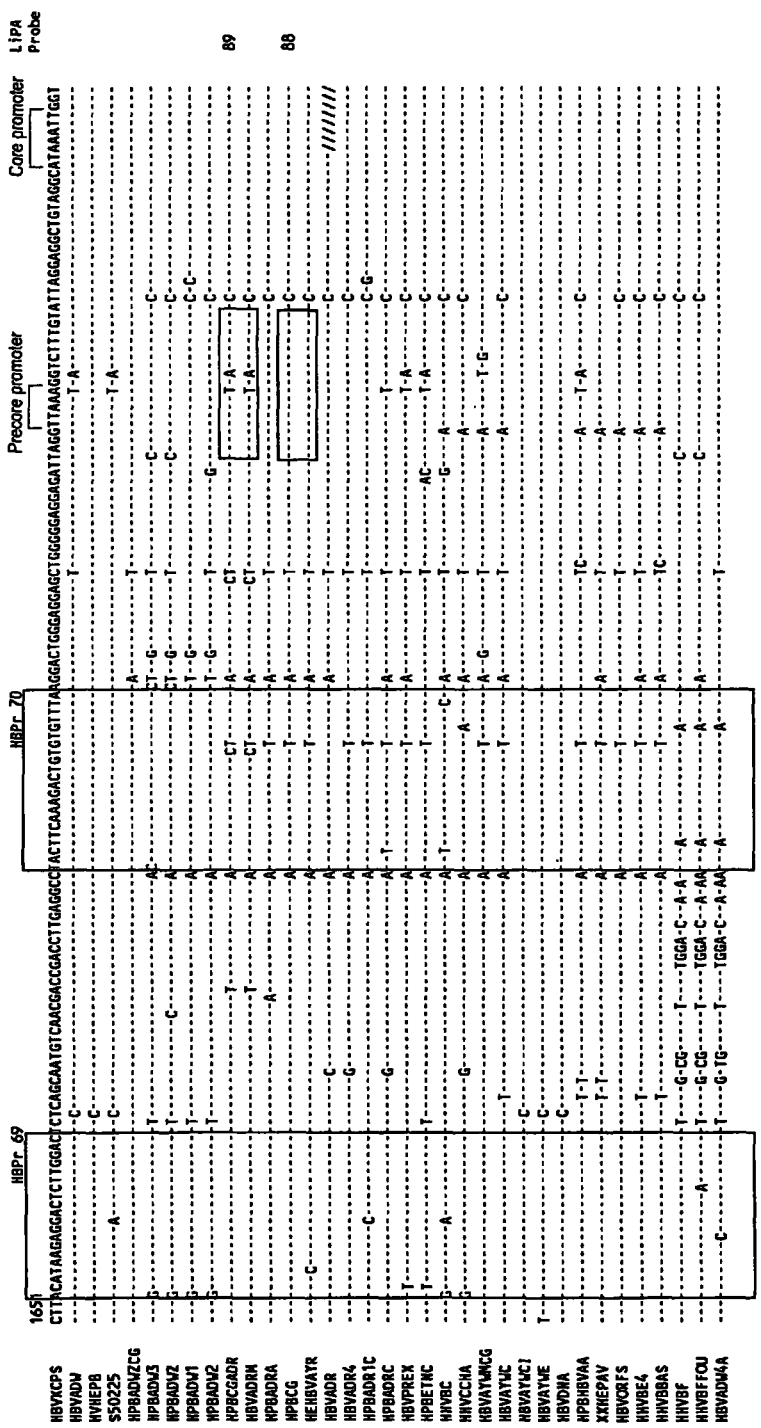
Figure 1M:
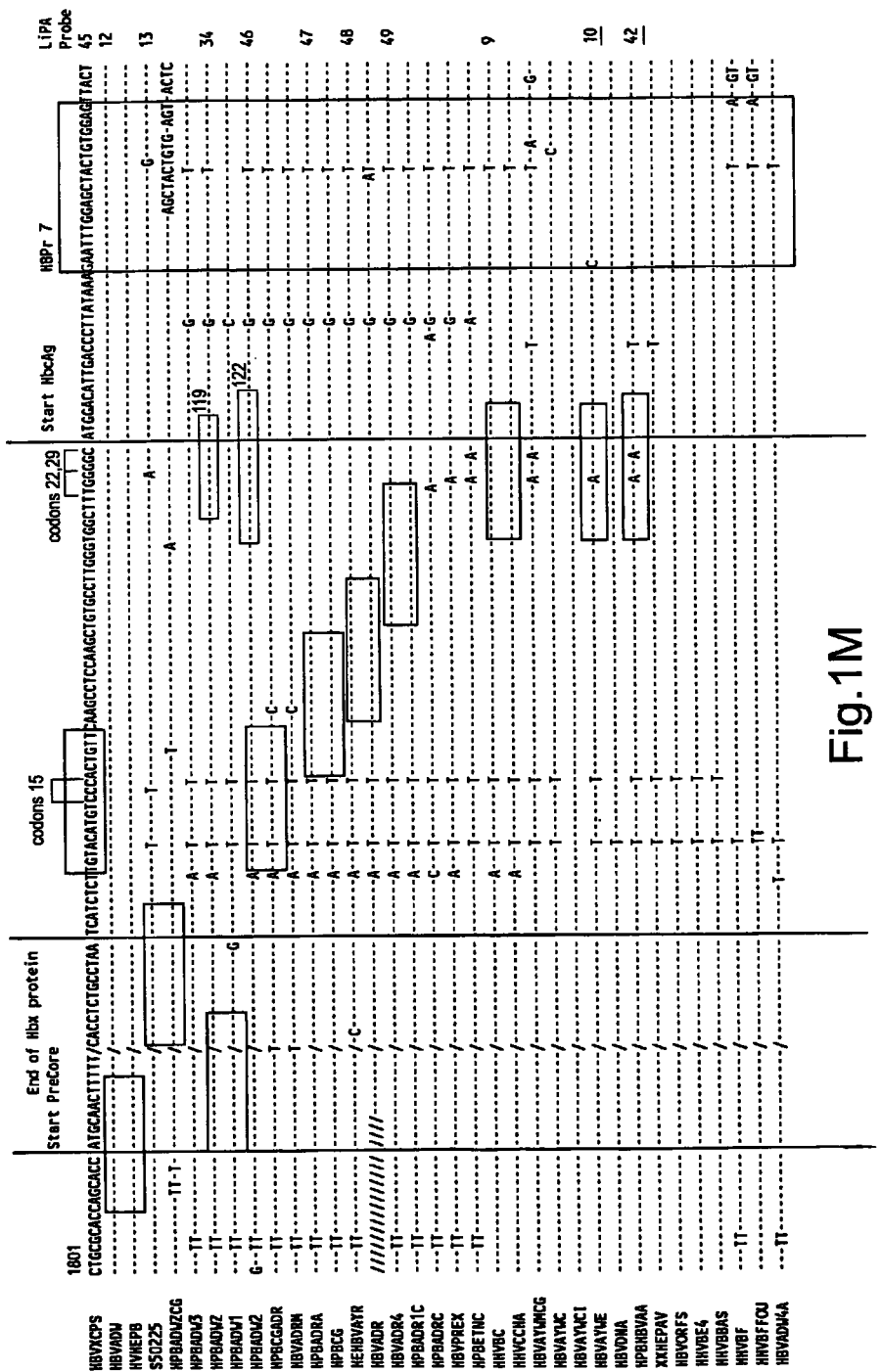
Figure 1P:
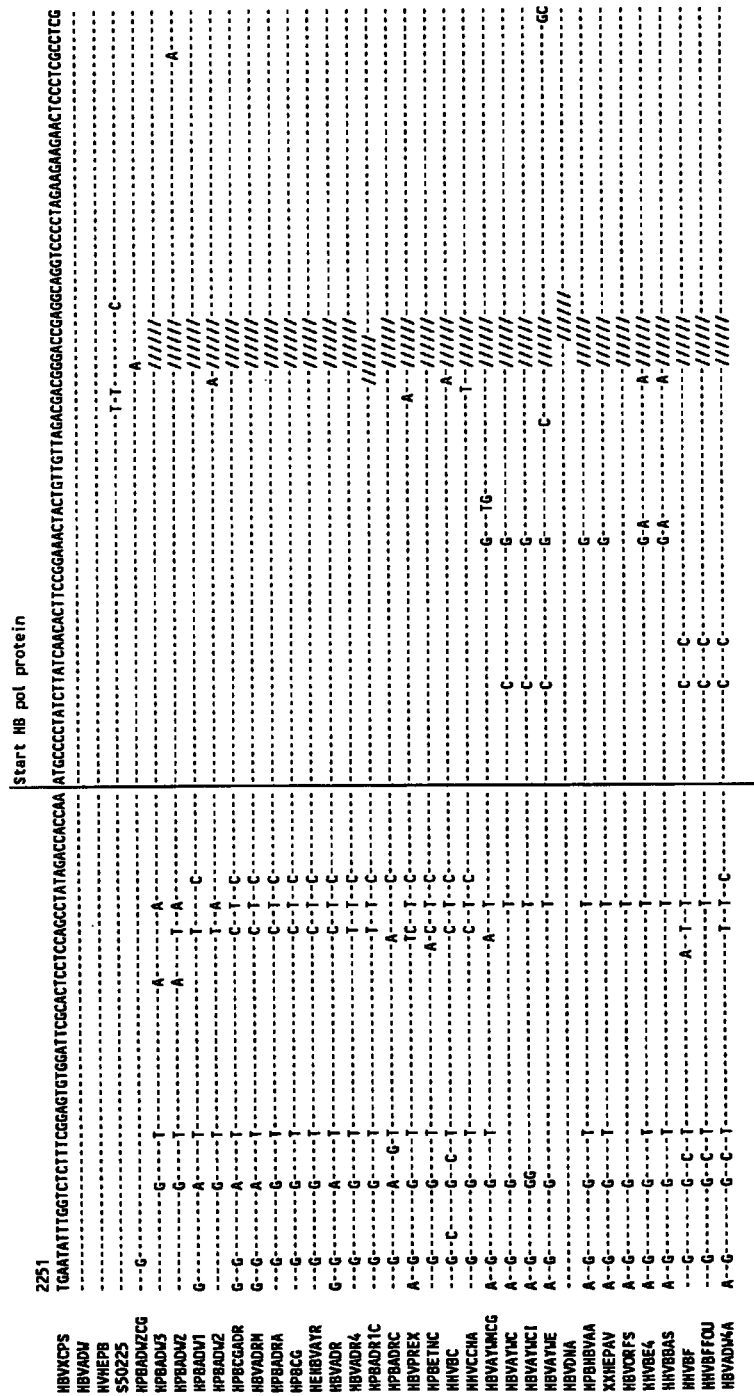
Figure 1T:
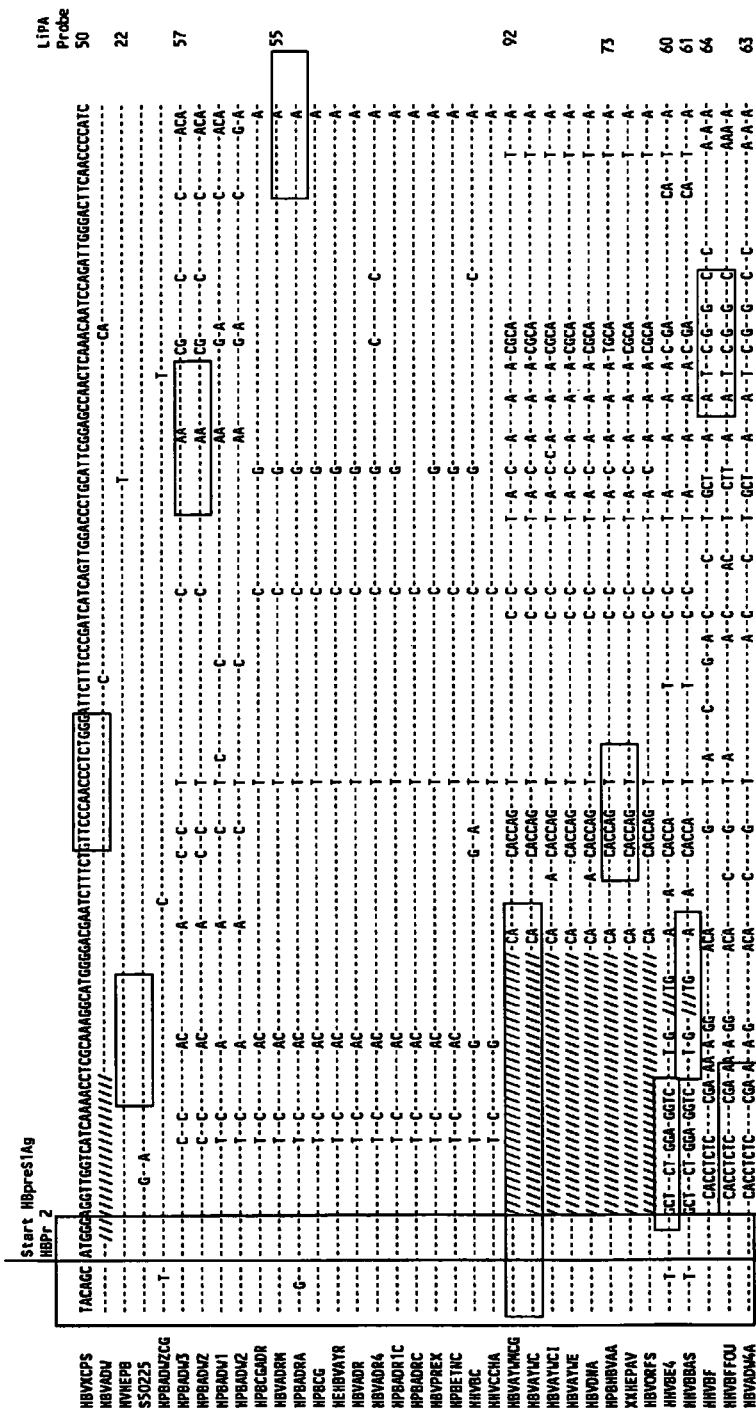
Figure 3:
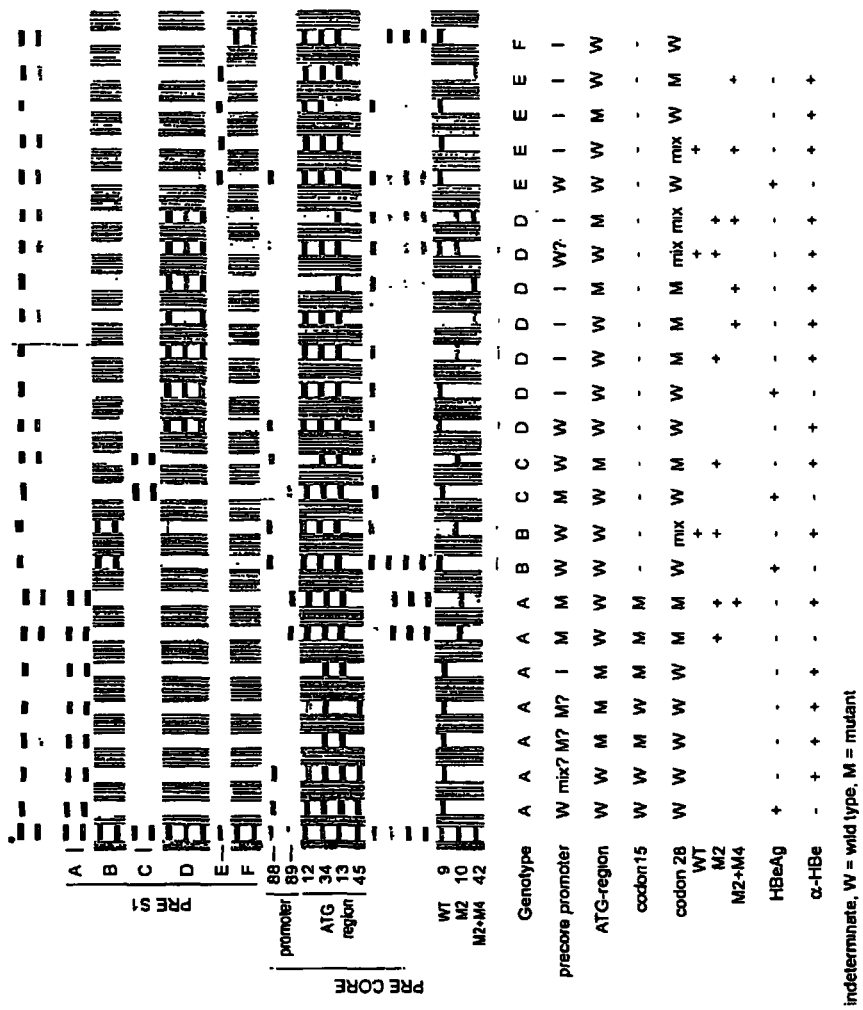

Nucleic Acids Research(1983), vol. 11(6), Ono Y et al, pp. 1747-1757, "The complete nucleotide of the cloned hepatitis B virus DNA; subtype adr and adw" Figure 2 and 3. copy contained in attached FH of U.S. Appl. No. 10/453,792.
J. General Virology (1988), vol. 69, Vaudin M et al, pp. 1383-1389, "The complete nucleotide sequence of the genome of a hepatitis B virus isolated from a naturally infected chimpanzee" Figure 1. copy contained in attached FH of U.S. Appl. No. 10/453,792.
J. General Virology (1988), vol. 69, Okamoto F et al, pp. 2575-2583, "Typing hepatitis B virsu by homology in nucleotide sequence: comparison of surface antigen subtypes" Figure 1. copy contained in attached FH of U.S. Appl. No. 10/453,792.
Gene (1988), vol. 64, Rivkina M et al, pp. 285-296, "Nucleotide sequence of integrated hepatitis B virus DNA and human flanking regions in the genome of the PLC/PRF/5 cell line" Figure 5. copy contained in attached FH of U.S. Appl. No. 10/453,792.
J General Virology (1993), vol. 74, Norder H et al, pp. 1341-1348, "Genetic relatedness of hepatitis B viral strains of diverse geographical origin and natural variations in the primary structure of the surface antigen" Figure 2. copy contained in attached FH of U.S. Appl. No. 10/453,792.
J Medical Virology (1994), vol. 44(1), Horikita M et al, pp. 96-103, "Differences in the entire nucleotide sequence between hepatitis B virus genomes from carriers positive for antibody to hepatitis B e antigen with and without active disease" Table IV. copy contained in attached FH of U.S. Appl. No. 10/453,792.
GenBank Accession No. D50489, "Hepatitis B virus DNA, complete genome" (no date available). copy contained in attached FH of U.S. Appl. No. 10/453,792.
J General Virology (1995), vol. 45, Uchida T et al, pp. 247-252, Complete nucleotide sequences and the characteristics of two hepatitis B virus mutants causing serologically negtive acute or chronic hepatitis B: p. 249. copy contained in attached FH of U.S. Appl. No. 10/453,792.
J General Virology (1996), vol. 3, Alexopoulou A et al, pp. 173-181, "Whole genome analysis of hepatitis B virus from four cases of fulminant hepatitis: genetic variability and its potential role in disease pathogenicity" Table 3. copy contained in attached FH of U.S. Appl. No. 10/453,792.
J General Virology (1997), vol. 78, Bowyer S et al, pp. 1719-1729, "A unique segment of the hepatitis B virus group A genotype identified in isolates from South Africa" Figure 5 copy contained in attached FH of U.S. Appl. No. 10/453,792.
Carman et al, "Vaccine-induced escape mutant . . . ", The Lancet, vol. 336, 1990 (8711) pp. 325-329. copy contained in attached FH of U.S. Appl. No. 10/453,792.
Fujii et al, "Gly[145] to Arg Substitution in HBs Antigen of . . . ", Biochemical and Biophysical Research Communications, vol. 184, No. 3, May 15, 1992, pp. 1152-1157. copy contained in attached FH of U.S. Appl. No. 10/453,792.
Yamamoto et al, "Naturally Ocurring Escape Mutants of Hepatitis B Virus with . . . ", Journal of Virology, vol. 68, No. 4, Apr. 1994, pp. 2671-2676. copy contained in attached FH of U.S. Appl. No. 10/453,792.
Carman, "The clinical significance of surface antigen variants . . . ", Journal of Viral Hepatitis, 1997. 4 (Suppl. 1) 11-20. copy contained in attached FH of U.S. Appl. No. 10/453,792.
Wang GT et al, Chung Hua I Hseuh Tsa Chih, "Sequencing of hepatitis B Virus DNA fragment coding major HBsAg of escape mutant", Jun. 1994 74(6) pp. 355-357, 391 (PubMed English Abstract PMID 7994645) copy contained in attached FH of U.S. Appl. No. 10/453,792.
Ren H et al, Chung Hua I Hseuh Tsa Chih, "Expression of 12 antibody escape mutants of hepatitis B virus surface antigen gene in mammalian cell by using an Epstein-Barr based vector", 1995 75(7) pp. 396-398 (PubMed English Abstract PMID 7553156). copy contained in attached FH of U.S. Appl. No. 10/453,792.

Chenault, "Patterns of nucleotide sequence variation among cauliflower mosaic virus isolates", (Biochimie 76:3-8, 1994) copy contained in attached FH of U.S. Appl. No. 10/453,792.
Fischer, "Generation of Duck Hepatitis B Virus Polymerase Mutants through Site-Directed Mutagenesis . . . ", (Antimicrobial Agents and Chemotherapy 40(8): 1957-1960, Aug. 7, 1996 copy contained in attached FH of U.S. Appl. No. 10/453,792.
Norder, "Complete Genomes, Phylogenetic Relatedness, and Structural Proteins of Six Strains of the Hepatitis B Virus, Four of Which Represent Two New Genotypes", (Virology 198: 489-503, 1994). copy contained in attached FH of U.S. Appl. No. 10/453,792.
Bartholomew, "Hepatitis-B-Virus resistance to lamivudine given for recurrent infection after orthotopic liver transplantation", (Lancet 349: 20-22, Jan. 1997). copy contained in attached FH of U.S. Appl. No. 10/453,792.
Aye et al, "Hepatitis B virus polymerase mutations Famciclovir therapy in patients following liver transplantation", Hepatology vol. 24, No. 4, Pt.2, Sep. 1996. copy contained in attached FH of U.S. Appl. No. 10/453,792.
Delaney et al, "Resistance of hepatitis B virus to antiviral drugs: current aspects and directions for future investigation", Antiviral Chemistry & Chemotherapy 12:1-35 (2001). copy contained in attached FH of U.S. Appl. No. 10/453,792.
Aye et al, "Hepatitis B virus polymerase mutations during antiviral therapy in a patient following liver transplantation", Journal of Hepatology, 1997; 26: 1148-1153. copy contained in attached FH of U.S. Appl. No. 10/453,792.
de Man et al, "The sequential occurrence of viral mutations in a liver transplant recipient re-infected with hepatitis B: hepatitis B immune globulin escape, famciclovir non-response, followed by lamivudine resistance resulting in graft loss", Journal of Hepatology, 1998; 29: 669-675. copy contained in attached FH of U.S. Appl. No. 10/453,792.
Ho et al, "A Family Cluster of an Immune Escape Variant of Hepatitis B Virus Infecting a Mother and Her Two Fully Immunized Children", Clinical and Diagnostic Laboratory Immunology, 1995, vol. 2, No. 6, pp. 760-762. copy contained in attached FH of U.S. Appl. No. 10/453,792.
Weiss et al, "The HBV-Producing Cell Line HepG2-4A5: A New in vitro System for Studying the Regulation of HBV Replication and for Screening Anti-Hepatitis B Virus Drugs", Virology 216:214,218, 1996. copy contained in attached FH of U.S. Appl. No. 10/453,792.
Poch et al, "Identification of four conserved motifs among the RNA-dependent polymerase encoding elements", EMBO Journal 8:3867-3874, 1989. copy contained in attached FH of U.S. Appl. No. 10/453,792.
Blum, H.E., "Variants of Hepatitis B, C and D Viruses: Molecular Biology and Clinical Significance" Digestion 56:85-95 (1995).
Harrison, T.J., "Genetic Variation in Hepatitis B Virus" European Journal of Gastroenterology & Hepatology 8(4): 306-311 (1996).
Carman et al., "Molecular Variants of Hepatitis B Virus" Hepatitis and Chronic Liver Disease. 16(2): 407-428 (Jun. 1996).
Ling et al., "Selection of Mutations in the Hepatitis B Virus Polymerase During Therapy of Transplant Recipients With Lamivudine" Hepatology 24(3): 711-713 (Sep. 1996).
Ni et al., "A New Immune Escape Mutant of Hepatitis B Virus with an Asp to Ala Substitution in aa144 of the Envelope Major Protein" (Res. Virol. 146:397-407, 1995).
Zhang et al., "Analysis of Hepatitis B Virus Genotypes and Pre-Core Region Variability During Interferon Treatment of HBe Antigen Negative Chronic Hepatitis B" (Journal of Medical Virology 48:8-16, 1996).
Rodriquez-Frias et al., "Hepatitis B Virus Infection: Precore Mutants and Its Relation to Viral Genotypes and Core Mutations" (Hepatology 22(6): 1641-1647, 1995).
Norder, "Comparison of the Amino Acid Sequences of Nine Different Serotypes of Hepatitis B Surface Antigen and Genomic Classification of the Corresponding Hepatitis B Virus Strains" (Journal of General Virology 73:1201-1208, 1992).
Blum,"Naturally occurring missense mutation in the polymerase gene terminating hepatitis B virus replication" (Journal of Virology, Apr. 1991, pp. 1836-1842, vol. 65, No. 4.

(56) References Cited

OTHER PUBLICATIONS

Korba et al, "Antisense oligonucleotides are effective inhibitors of hepatitis B virus replication in vitro", Antiviral Research 28 (1995) 225-242.

Magnius et al, "Subtypes, Genotypes and Molecular Epidemiology of the Hepatitis B Virus as Reflected by Sequence Variability of the S-Gene", Intervirology 1995;38:24-34.

Miller et al, "Compact Organization of the Hepatitis B Virus Genome", Hepatology, vol. 9, No. 2, pp. 322-327, 1989.

Tong et al, "Replication Capacities of Natural and Artificial Precore Stop Codon Mutants of Hepatitis B Virus: Relevance of Pregenome Encapsidation Signal", Virology 191, 237-245 (1992).

Extended European Search Report dated Feb. 23, 2012, issued in connection with European Patent Application No. 10181900.1.

Li et al, "Rapid detection and further characterization of infection with hepatitis B virus variants containing a stop codon in the distal pre-C region", Journal of General Virology (1990), 71, 1993-1998.

Zhang et al, "Analysis of Hepatitis B Virus Genotypes and Pre-Core Region Variability During Interferon Treatment of HBe Antigen Negative Chronic Hepatitis B", Journal of Medical Virology 48:8-16 (1996).

Kinoshita et al, "A detection method for point mutation in the precore region of human hepatitis B virus (HBV)-DNA using mutation-site-specific assay", Clinica Chimica Acta 228 (1994) 83-90.

Birkenmeyer et al, "Detection of hepatitis A, B and D virus by the polymerase chain reaction", Journal of Virological Methods 49 (1994) 101-112.

Yamashita et al, MEDLINE Database Accession No. NLM7474444, Aug. 1995.

Extended European Search Report dated Feb. 23, 2012, issued in connection with European Patent Application No. 10182184.1.

Gerken et al, "Hepatitis B Defective Virus with Rearrangements in the PreS Gene during Chronic HBV Infection", Virology 183, 555-565 (1991).

Asahina et al, "Complete Nucleotide Sequences of Hepatitis B Virus Genomes Associated with Epidemic Fulminant Hepatitis", Journal of Medical Virology 48:171-178 (1996).

\* cited by examiner

| | LiPA HBV design | | | |
|---|---|---|---|---|
| LiPA line | Region | Purpose | HBPr Probe number/SEQ ID NO | sequence |
| 0 | | Pencil line | | |
| 1 | | biotinylated DNA | | |
| 2 | PreS1 | ampl. contr. | 33 | CTGAGGGCTCCACCCCA |
| 3 | PreS1 | Genotype A | 22 | AACCTCGCAAAGGCAT |
| 4 | PreS1 | Genotype A | 50 | CCCAGAGGGTTGGGAAC |
| | PreS1 | Genotype A | 15 | GCCAGCAGCCAACCAG |
| 5 | PreS1 | Genotype B | 57 | CTGCATTCAAAGCCAACT |
| | PreS1 | Genotype B | 58 | CCCCATGGGGACTGTTG |
| 6 | PreS1 | Genotype B | 59 | CATACTCACAACTGTGCCA |
| 7 | PreS1 | Genotype C | 55 | TTCAACCCCAACAAGGATC |
| 8 | PreS1 | Genotype C | 54 | TCAGGAAGACAGCCTAC |
| 9 | PreS1 | Genotype D | 92 | TTCTGCCCCATGCTGTA |
| 10 | PreS1 | Genotype D | 56 | AATGCTCCAGCTCCTAC |
| 11 | PreS1 | Genotype D | 73 | TTCCACCAGCAATCCTC |
| 12 | PreS1 | Genotype E | 60 | GGGCTTTCTTGGACGGTCC |
| | PreS1 | Genotype E | 61 | CTCTCGAATGGGGGAAGA |
| | PreS1 | Genotype E | 62 | CCTACCCCAATCACTCCA |
| 13 | PreS1 | Genotype F | 63 | AGCACCTCTCTCAACGACA |
| 14 | PreS1 | Genotype F | 64 | GCAAATTCCAGCAGTCCCG |
| | PreS1 | Genotype F | 65 | GCCAATGGCAAACAAGGTA |
| 15 | preCore | promotor | 88 | TAGGTTAAAGGTCTTTGT |
| 16 | preCore | promotor | 89 | TAGGTTAATGATCTTTGT |
| 17 | preCore | scan codon -2 to +3 | 12 | AAGTTGCATGGTGCTG |
| 18 | preCore | scan codon 1 to 5 | 34 | ATGCAACTTTTTCACC |
| 19 | preCore | scan codon 5 to 9 | 13 | CACCTCTGCCTAATCAT |
| 20 | preCore | scan codon 12 to 17 | 45 | TGTACATGTCCCACTGTT |
| 21 | preCore | scan codon 12 to 17 | 46 | TGTTCATGTCCTACTGTT |
| 22 | preCore | scan codon 16 to 20 | 47 | ACTGTTCAAGCCTCCAAG |
| 23 | preCore | scan codon 19 to 23 | 48 | GGCACAGCTTGGAGGCTT |
| 24 | preCore | scan codon 23 to 27 | 49 | AAAGCCACCCAAGGCACA |
| 25 | preCore | codon 28 wt | 9 | TGGCTTTGGGGCATGG |
| 26 | preCore | codon 28 mt | 10 | TGGCTTTAGGGCATGG |
| 27 | preCore | codon 28+29 mt | 42 | TGGCTTTAGGACATGGA |

Fig. 2

Genotyping in HBsAg

| Genotype | Oligo | Sequence |
|---|---|---|
| A | HBPr 193 | GGA TCA ACA ACA ACC AGT |
|  | HBPr 140 | CT CAA GGC AAC TCT ATG GG |
|  | HBPr 77 | CTA CGG ATG GAA ATT GC |
| B | HBPr 78 | TAC GGA CGG AAA CTG C |
| C | HBPr 153 | CT CTA CTT CCA GGA ACA G |
|  | HBPr 154 | C TGC ACG ATT CCT GCT |
|  | HBPr 204 | CT TTC GCA AGA TTC CTA TGG G |
| D | HBPr 165 | AC TCT ATG TAT CCC TCC T |
|  | HBPr 208 | GC TGT ACC AAA CCT TCG GAT |
| E | HBPr 172 | G GGA CCC TGC CGA AC |
|  | HBPr 213 | AG TGG TTC GCC GGG CTG G |
| F | HBPr 216 | CA GGA TCC ACG ACC ACC AGG |
|  | HBPr 219 | GC TGT TCC AAA CCC TCG GAG |
|  | HBPr 186 | G CCA AAT CTG TGC AGC |
| A/B | HBPr 148 | CT TTC GCA AAA TAC CTA TG |
| C/D/E | HBPr 80 | CTT CGG ACG GAA ATT GC |
| E/F | HBPr 177 | ATG TTG CTG TTC AAA ACC TG |

Drug resistance in RT pol gene

| Genotype | Oligo | Sequence | |
|---|---|---|---|
| A | HBPr 115 | TCA GCT ATA TGG ATG ATG | wild type |
|  | HBPr 116 | TTC AGC TAT GTG GAT GAT | mutant |
| D | HBPr 127 | TC AGT TAT ATG GAT GAT G | wild type |
|  | HBPr 132 | T TTC AGT TAT GTG GAT GAT | mutant |

PreCore region

| Genotype | Oligo | Sequence | |
|---|---|---|---|
|  | HBPr 88 | TAG GTT AAA GGT CTT TGT | promoter wild type |
|  | HBPr 89 | TAG GTT AAT GAT CTT TGT | promoter mutant |
|  | HBPr 119 | TGG CTT TGG GGC ATG | wild type codon 28 |
|  | HBPr 10 | TGG CTT TAG GGC ATG G | mutant M2 codon 28 |
|  | HBPr 122 | TGG CTT TGG GAC ATG G | mutant M4 codon 29 |
|  | HBPr 42 | TGG CTT TAG GAC ATG GA | mutant M2/M4 codo |

Fig. 4

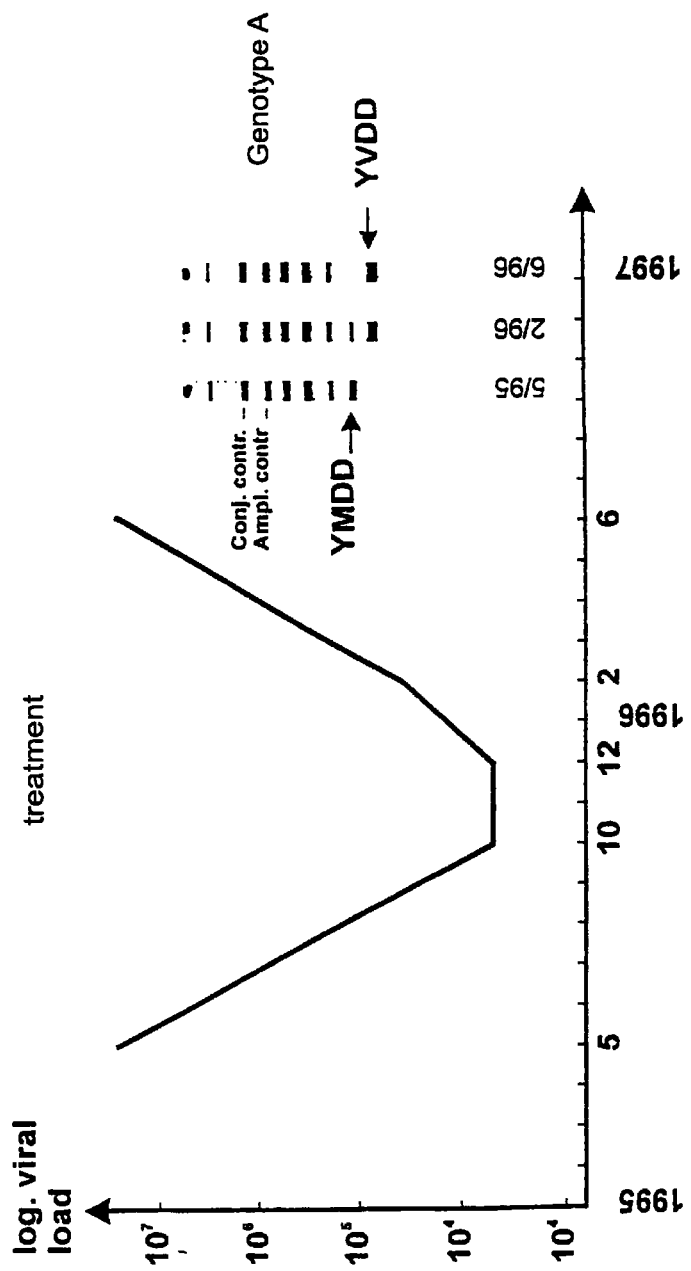

METHOD FOR TYPING AND DETECTING HBV

The present application is a divisional of application Ser. No. 09/155,885, filed Oct. 8, 1998 (which issued as U.S. Pat. No. 6,709,812 on Mar. 23, 2004), which is a 371 U.S. National Phase of International Application No. PCT/EP97/02002, filed Apr. 21, 1997.

The present invention relates to the field of Hepatitis B virus (HBV) diagnosis. More particularly, the present invention relates to the field of HBV genotyping and/or determination of the presence of HBV mutants in test samples.

The present invention relates particularly to a method for the rapid and reliable detection of HBV mutants and/or genotypes occurring in a test sample using specific sets of probes optimized to function together in a reverse-hybridisation assay.

Hepatitis B virus is a small enveloped DNA virus of approximately 3200 bp long. Historically it has been characterized on the basis of immunological reaction of the HBsAg with sets of monoclonal antibodies. Isolates were described as a, indicating the common determinant for all different subtypes, followed by subtype-specific combinations: dw, dr, yw, or yr. The latter are mutually exclusive pairs of determinants, covering the HBsAg amino acids 122 (d=lys, y=arg) and 160 (w=lys, r=arg) Several subdeterminants for w exist and can be ascribed to the appearance of certain amino acid variants at codon 127. More recently, a genetic classification has been proposed, based on molecular analysis of the virus. This kind of analysis showed that in total six different genotypes exist, indicated from A to F, with a maximum genetic divergence of 8% when comparing complete genomes (reviewed by Magnius and Norder, 1995).

The genetic variability of HBV might be clinically important indeed, the genome variability might include some mechanisms by which HBV avoids immune clearance, and hence induces chronic infection. An important protein marker in inducing immune tolerance, virus elimination, and chronic infection, is HBeAg. The expression of this protein is strictly controlled both at the transcriptional and translational level (Li et al., 1993; Okamoto et al., 1990; Yuan et al., 1995; Sato et al., 1995). Therefore, in the natural course of HBV infection, a well characterized stage of the disease is indicated as HBe-negative chronic hepatitis B (reviewed by Hadziyannis S. J., 1995). This phase is mostly due to the appearence of preCore translational stop cordon mutations. The overal genetic variability determines the frequency and physical location on the viral genome where these translational stop-codon mutations appear. The transcriptional regulation was proposed to be the mechanism for genotype A (and possibly also F), whereas the translational control was more likely to be found in the other genotypes (Li et al.; 1993; Sato et al., 1995). Contradictory to the translational regulation, it was shown that the transcriptional regulation was unable to block the HBeAg expression completely and was therefore proposed to categorize the phenotype of this mutant as HBe-suppressed, rather than as HBe-negative (Takahashi et al., 1995). In any case, these precore mutants would lead to a destruction of the preexisting balance between HBeAg in circulation and the HBc-derived peptides presented by class I HLA molecules on the surface of infected hepatocytes, thereby diminishing the supressive effect of HBeAg on T cells, finally resulting in partial liberation of core-specific CTLs and leading to apoptosis of the infected hepatocytes. In general, after the emergence of the HBe-minus variants, the course of the viral infection is characterized by the progression of chronic hepatitis, which may lead to the development of cirrhosis and hepatocellular carcinoma (Hadziyannis, 19995).

Another issue for which the genetic variability or genotyping of the virus might be of relevance is in the development of vaccines where the response may be mediated by the virus type. Protection against HBV infection of all subtypes is conferred by antibodies to the common 'a' determinant of the HB surface antigen (HBsAg). It has been shown that this 'a' determinant presents a number of epitopes, and that its tertiary structure is most important for its antigenicity. The most important region lies between amino acid 124 and 147, but can be extended from amino acid 114 to 150. An adequate anti-HBs response, built up after vaccination, is in principle fully protective. Infection with a HBV strain harboring mutations in the 'a' determinant region might result in vaccine failure, because the vaccine induced humoral immune response does not recognize the mutant HBsAc. The most common vaccine-associated escape mutants are the substitutions of a glycine at position 145 to an arginine (G145R), K141E, and T126N. But a 2-aa insertion between aa position 122 and 123, and 8-aa insertion between aa 123 and 124 have also been found (Carman et al., 1990, 1995; Crawford, 1990; Waters et al., 1992).

Lamivudine is a (−) enantiomer of 3' thiacytidine, a 2'3'-dideoxynucleoside analogue, and is known to be a potent inhibitor of HBV replication through inhibition of the reverse transcriptase (RT) activity of the HBV polymerase. Lamivudine treatment can result in histological improvements in chronic hepatitis patients, and when given pre- and post-liver transplantation, it can prevent graft reinfection (Honkoop et al., 1995; Naoumov et al., 1995). However, after treatment, a hepatitis flare-up can be observed in most patients, with ALT elevations and HBV DNA that becomes detectable again. This HBV DNA rebound is associated with a new quasi species equilibrium. In a few cases, virus breakthrough during therapy was observed, due to the selection of lamivudine resistant HBV strains. The exact nature of this breakthrough has been ascribed to the accumulation of mutations in the RT part of the Polymerase. A similar mechanism in the HIV RT polymerase has been found, where upon lamivudine treatment, mutations accumulate in the YMDD motif (Gao et al., 1993). This YMDD motif is also present in the RT part of the HBV polymerase, and lamivudine-selected mutations in HBV have been found in this region (Tipples et al., 1996), as well as in other regions of the RT part of the polymerase (Ling et al., 1996). Penciclovir is another drug that has been shown to inhibit the reverse transcriptase activity of the HBV polymerase (Shaw et al., 1996), and mutations in the HBV polymerase may also be detected upon treatment with this drug.

From all this it can be concluded that the information on the following issues is essential for proper in vitro diagnosis, monitoring and follow-up of HBV infections:
  genotype;
  preCore mutations;
  vaccine escape mutations;
  RT gene mutations selected by treatment with drugs such as lamivudune and penciclovir.

To obtain all this information using existing technologies is complicated, time-consuming, and requires highly-skilled and experienced personel.

It is thus an aim of the present invention to develop a rapid and reliable detection method for determination of the presence or absence of one or more HBV genotypes possibly present in a biological sample.

More particularly, it is an aim of the present invention to develop a rapid and reliable detection method for determination of the presence or absence of one or more variations in the HBV preS1 region and/or in the HBsAg region representing one or more HBV genotypes possibly present in a biological sample in one single experiment.

More particularly, it is an aim of the present invention to develop a rapid and reliable detection method for determination of the presence or absence of one or more HBV mutants possibly present in a biological sample in one single experiment.

More particularly, it is an aim of the present invention to develop a rapid and reliable detection method for determination of one or more mutations in the preCore region of HBV possibly present in a biological sample in one single experiment.

More particularly, it is an aim of the present invention to develop a rapid and reliable detection method for determination of one or more mutations in the HBsAg region of HBV possibly present in a biological sample in one single experiment.

More particularly, it is an aim of the present invention to develop a rapid and reliable detection method for determination of one or more mutations in the polymerase (pol) gene region of HBV possibly present in a biological sample in one single experiment.

More particularly, it is an aim of the present invention to develop a rapid and reliable detection method for the simultaneous determination of one or several HBV genotypes in combination with one or several HBV mutants possibly present in a biological sample in one single experiment.

It is also an aim of the present invention to provide a genotyping assay or method which allows to infer the nucleotide sequence at codons of interest and/or the HBV mutants of interest, and/or infer the HBV genotype possibly present in a biological sample.

Even more particularly it is also an aim of the present invention to provide a genotyping assay allowing the detection of the different HBV mutants and genotypes in one single experimental setup.

It is another aim of the present invention to select particular probes able to discriminate one or more HBV mutations in one of the above mentioned regions of the HBV genome and/or able to discriminate one or more HBV genotypes.

It is more particularly an aim of the present invention to select particular probes able to discriminate wild-type HBV from mutant HBV sequences.

It is also an aim of the present invention to select particular probes able to discriminate wild-type and polymorphic variants of HBV from mutant HBV sequences.

It is also an aim of the present invention to select particular probes able to discriminate HBV genotype sequences.

It is moreover an aim of the present invention to combine a set of selected probes able to genotype HBV and/or discriminate different HBV mutants possibly present in a biological sample, whereby all probes can be used under the same hybridisation and wash conditions.

It is also an aim of the present invention to select primers enabling the amplification of the gene fragment(s) determining the HBV genomic mutations or variations of interest as discussed above.

The present invention also aims at diagnostic kits comprising said probes useful for developing such a genotyping assay and/or assays for detecting, monitoring or following-up HBV infection and/or assays for detecting HBV mutations.

All the aims of the present invention have been met by the following specific embodiments.

As a solution to the above-mentioned problem that it is essential for proper diagnosis, monitoring and follow-up of HBV infection to have information on the genotype of HBV present, the present invention provides an elegant way to tackle problems of such complexity which involves residing to a reverse hybridization approach (particularly on Line Probe Assays strips, as described by Stuyver et al., 1993). Using this technology it is possible to conveniently obtain all essential data in one test run. To achieve this goal, a set of probes needs to be designed and assembled which can detect all relevant polymorphisms in the HBV gene regions of interest.

The present invention thus particularly relates to a method for determining the presence or absence of one or more HBV genotypes in a biological sample, comprising:
(i) if need be releasing, isolating or concentrating the polynucleic acids present in the sample;
(ii) if need be amplifying the relevant part of a suitable HBV gene present in said sample with at least one suitable primer pair;
(iii) hybridizing the polynucleic acids of step (i) or (ii) with at least two nucleotide probes hybridizing specifically to a HBV genotype specific target sequence chosen from FIG. 1; with said probes being applied to known locations on a solid support and with said probes being capable of hybridizing to polynucleic acids of step (i) or (ii) under the same hybridization and wash conditions or with said probes hybridizing specifically with a sequence complementary to any of said target sequences, or a sequence wherein T of said target sequence is replaced by U;
(iv) detecting the hybrids formed in step (iii);
(v) inferring the HBV genotype present in said sample from the differential hybridization signal(s) obtained in step (iv).

The genotype specific target sequences can be any nucleotide variation appearing upon alignment of the different HBV genomes that permits classification of a certain HBV isolate as a certain genotype (see FIG. 1).

The expression "relevant part of a suitable HBV gene" refers to the part of the HBV gene encompassing the HBV genotype specific target sequence chosen from FIG. 1 to be detected.

According to a preferred embodiment of the present invention, step (iii) is performed using a set of at least 2, preferably at least 3, more preferably at least 4 and most preferably at least 5 probes all meticulously designed such that they show the desired hybridization results, when used in a reverse hybridisation assay format, more particularly under the same hybridization and wash conditions implying that each of said probes is able to form a complex upon hybridisation with its target sequence present in the polynucleic acids of the sample as obtained after step (i) or (ii).

The numbering of the HBV gene encoded amino acids and nucleotides is as generally accepted in literature.

More particularly, the present invention relates to a set of at least 2 probes allowing the detection of a genotype specific variation, possibly also including one or more probes allowing the detection of a wild-type sequence, a polymorphic or a mutated sequence at any one of the nucleotide positions showing a sequence diversity upon alignment of all known or yet to be discovered HBV sequences as represented in FIG. 1 for all complete HBV genomes found in the EMBL/NCBI/DDBJ/Genbank.

The sets of probes according to the present invention have as a common characteristic that all the probes in said set are designed so that they can be used together in a reverse-hybridization assay, more particularly under similar or identical hybridization and wash conditions as indicated above and below.

Selected sets of probes according to the present invention include probes which allow to differentiate any of the HBV genotype specific nucleotide changes as represented in FIG. 1, preferably in the preS1 or HBsAg region of HBV. Said probes being characterized in that they can function in a method as set out above.

In order to solve the above-mentioned problem of obtaining information on the possible presence of HBV mutants in a given sample, the present invention provides an elegant way to tackle this problem which involves residing to a reverse hybridisation approach (particularly on Line Probe Assays strips, as described by Stuyver et al., 1993). Using this technology it is possible to conveniently obtain all essential data in one test run. To achieve this goal, a set of probes needs to be designed and assembled which can detect all relevant mutations and possibly also wild-type sequences or polymorphisms in the HBV gene regions of interest.

Another particularly preferred embodiment of the present invention thus is a method for determining the presence or absence of one or more HBV mutants in a biological sample, comprising:
(i) if need be releasing, isolating or concentrating the polynucleic acids present in the sample;
(ii) if need be amplifying the relevant part of a suitable HBV gene present in said sample with at least one suitable primer pair;
(iii) hybridizing the polynucleic acids of step (i) or (ii) with at least two nucleotide probes hybridizing specifically to a HBV mutant target sequence chosen from FIG. 1, with said probes being applied to known locations on a solid support and with said probes being capable of hybridizing to the polynucleic acids of step (i) or (ii) under the same hybridization and wash conditions, or with said probes hybridizing specifically with a sequence complementary to any of said target sequences, or a sequence wherein T of said target sequence is replaced by U and with said set or probes possibly also comprising one or more wild-type HBV probes corresponding with the respective mutated HBV target sequence;
(iv) detecting the hybrids formed in step (iii);
(v) inferring the HBV mutant(s) present in said sample from the differential hybridization signal(s) obtained in step (iv).

It is to be understood that the term "mutant target sequence" not only covers the sequence containing a mutation, but also the corresponding wild-type sequence. The HBV mutant target sequence according to the present invention can be any sequence including a HBV mutated codon known in the art or yet to be discovered. Particularly preferred HBV mutant target regions are set out below.

In order to solve the problem as referred to above of obtaining information on the essential issues for proper diagnosis of HBV (namely genotype and different mutations particularly mutations in the preCore region, vaccine escape mutations and RT gene mutations selected by treatment with drugs such as lamivudine and penciclovir), the present invention provides a particularly elegant way to obtain such complex information.

Moreover, careful analysis of the data obtained by the present inventors clearly revealed that combining the information concerning the preCore and escape mutants with data on the genotype is essential to allow adequate interpretation of the results. Hence it is highly advantageous to be able to produce all relevant data simultaneously.

In this method for diagnosing HBV mutants, preferably in combination with HBV genotyping, a set of probes selected as defined above may be used, wherein said set of probes is characterized as being chosen such that for a given HBV mutation, the following probes are included in said set
at least one probe for detecting the presence of the mutated nucleotide(s) at said position;
at least one probe for detecting the presence of the wild-type nucleotide(s) at said position;
possibly also (an) additional probe(s) for detecting wild-type polymorphism's at positions surrounding the mutation position.
Inclusion of the latter two types of probes greatly contributes to increasing the sensitivity of said assays as demonstrated in the examples section.

Selected sets of probes according to the present invention include at least one probe, preferably at least two probes, characterizing the presence of a HBV mutation at nucleotide positions chosen from the preCore region of HBV, more particularly from the following list of codons susceptible to mutations in the HBV preCore regions such as codon 15 in genotype A, and for all genotypes: codon 28, codon 29, and codon 28 and 29, or in the preCore promoter region (see FIG. 1).

Said probes being characterized in that they can function in a method as set out above.

An additional embodiment of the present invention includes at least one probe, preferably at least two probes, characterizing the presence of a vaccine escape mutation in codon positions chosen from the HBsAg region of HBV, more particularly from the list of codons susceptible to mutations in the HBV HBsAg region, such as at codons 122, 126, 141, 143, 144 or 145 (see FIG. 1).

An additional embodiment of the present invention includes at least one probe, preferably at least two probes, characterizing the presence of a mutation in the RT pol gene region of HBV, that gives rise to resistance to drugs such as lamivudine and penciclovir, for instance mutation of M to V or to I at position 552 (in the YMDD motif), mutation of V to I at position 555, mutation of F to L at position 514, mutation of V to L at position 521, mutation of P to L at position 525 and mutation of L to M at position 528 (see FIG. 1).

In a selected embodiment, a combination of at least two oligonucleotide probes is used and said combination of probes hybridizes specifically to at least two of the following groups of target sequences:
a mutant target sequence chosen from the HBV RT pol gene region,
a mutant target sequence chosen from the HBV preCore region,
a mutant target sequence chosen from the HBsAg region of HBV,
a HBV genotype-specific target sequence.

For instance, an embodiment involves hybridizing with at least one nucleotide probe hybridizing specifically to a genotype specific target sequence chosen from FIG. 1 and at least one nucleotide probe hybridizing specifically to a HABV mutant target sequence chosen from FIG. 1.

Another selected embodiment involves, for instance, hybridizing with at least one nucleotide probe hybridizing specifically to a genotype specific target sequence chosen from FIG. 1 and at least one nucleotide probe hybridizing specifically to a HBV mutant target sequence chosen from the RT pol gene region as represented in FIG. 1.

Another selected embodiment involves, for instance, hybridizing with at least one nucleotide probe hybridizing specifically to a genotype specific target sequence chosen from FIG. 1 and at least one nucleotide probe hybridizing specifically to a HBV mutant target sequence chosen from the preCore region as represented in FIG. 1.

Another selected embodiment involves, for instance, hybridizing with at least one nucleotide probe hybridizing specifically to a genotype specific target sequence chosen from FIG. 1 and at least one nucleotide probe hybridizing specifically to a HBV vaccine escape mutant target sequence within the HBsAg region as represented in FIG. 1.

In a selected embodiment, a combination of at least three oligonucleotide probes is used and said combination of probes hybridizes specifically to at least three of the following groups of target sequences:
a mutant target sequence chosen from the HBV RT pol gene region,
a mutant target sequence chosen from the HBV preCore region,
a mutant target sequence chosen from the HBsAg region of HBV,
a HBV genotype-specific target sequence.

For instance, an embodiment involves hybridizing with at least one nucleotide probe hybridizing specifically to a genotype specific target sequence chosen from FIG. 1, and at least one nucleotide probe hybridizing specifically to a HBV mutant target sequence chosen from the preCore region as represented in FIG. 1, and at least one nucleotide probe hybridizing specifically to a HBV vaccine escape mutant target sequence chosen from the HBsAg region as represented in FIG. 1.

For instance, another embodiment involves hybridizing with at least one probe hybridizing specifically to a mutant target sequence from the HBV RMT pol gene region of HBV, and at least one probe hybridizing specifically to a mutant target sequence from the HBsAg region of HBV, and at least one probe hybridizing specifically to a genotype specific target sequence from the HBsAg region of HBV. According to this embodiment, the relevant part of the HBV genome can be amplified by use of one primer pair, for instance HBPr 7: and HBPr 94.

In a selected embodiment, a combination of at least four oligonucleotide probes is used and said combination of probes hybridizes specifically to all of the following groups of target sequences:
a mutant target sequence chosen from the HBV RT pol gene region,
a mutant target sequence chosen from the HBV preCore region,
a mutant target sequence chosen from the HEsAg region of HBV,
a HBV genotype-specific target sequence.

Particularly preferred embodiments of the invention thus include a set of probes as set out above comprising at least one, preferably at least two, at least three, at least four or more probe(s) for targeting one, preferably two, three or more nucleotide changes appearing in the alignment of HBV genomes as represented in FIG. 1.

Even more preferred selected sets of probes according to the present invention include probes derived from two of the same or different regions of HBV bearing HBV mutated nucleotides, or in addition also a third (set of) probe(s) characterizing the presence of a third HBV mutation at any of the positions shown in FIG. 1, or particular combinations thereof.

Particularly preferred is also a set of probes which allows simultaneous detection of HBV mutations at codons 15, 28 and 29 in the preCore region, possibly in combination with mutations in the preCore promoter regions, in combination with mutations at codons 122, 126, 141, 143, 144, 145 in the HBsAg region, possibly also in combination with mutations in the HBV pol gene at codons 514, 521, 525, 528, 552 or 555.

In the instances where the alignment of HBV genomes of FIG. 1 is referred to in this invention, it should be construed as referring to an alignment of all existing and future HBV genomes. The existing HBV genome sequences can be deduced from any database, such as the EMBL/NCBI/DDBJ/GENBANK database.

A preferred set of preCore, preS1, HBsAg and RT pol gene probes of this invention are the probes with SEQ ID NO 1 to 278 of Table 1 (see also FIG. 1).

Particularly preferred sets of probes in this respect are shown in FIG. 2 and in FIG. 4. The probes in FIG. 2 and in FIG. 4 were withheld after a first selection for preCore, preS1, HBsAg and RT pol probes.

The probes of the invention are designed for obtaining optimal performance under the same hybridization conditions so that they can be used in sets of at least 2 probes for simultaneous hybridization. This highly increases the usefulness of these probes and results in a significant gain in time and labour. Evidently, when other hybridization conditions would be preferred, all probes should be adapted accordingly by adding or deleting a number of nucleotides at their extremities. It should be understood that these concomitant adaptations should give rise to essentially the same result, namely that the respective probes still hybridize specifically with the defined target. Such adaptations might also be necessary if the amplified material should be RNA in nature and not DNA as in the case for the NASBA system.

The selection of the preferred probes of the present invention is based on a reverse hybridization assay format using immobilized oligonucleotide probes present at distinct locations on a solid support. More particularly the selection of preferred probes of the present invention is based on the use of the Line Probe Assay (LiPA) principle which is a reverse hybridization assay using oligonucleotide probes immobilized as parallel lines on a solid support strip (Stuyver et al. 1993; international application WO 94112670). This approach is particularly advantageous since it is fast and simple to perform. The reverse hybridization format and more particularly the LiPA approach has many practical advantages as compared to other DNA techniques or hybridization formats, especially when the use of a combination of probes is preferable or unavoidable to obtain the relevant information sought.

It is to be understood, however, that any other type of hybridization assay or format using any of the selected probes as described further in the invention, is also covered by the present invention.

The reverse hybridization approach implies that the probes are immobilized to certain locations on a solid support and that the target DNA is labelled in order to enable the detection of the hybrids formed.

The following definitions serve to illustrate the terms and expressions used in the present invention.

The term "genetic analysis" refers to the study of the nucleotide sequence of the genome of HBV by any appropriate technique.

The term "HBV mutant" refers to any HBV strain harbouring genomic variations with serological, genetical or clinical consequences.

The term "vaccine escape mutant" is reviewed in the introduction section and in Example 7. The most important region lies between amino acid 124 and 147 of the HBsAg region, but can be extended from amino acid 114 to 150.

The term "mutant resistant to drugs such as lamivudine and penciclovir" is reviewed in the introduction section and in Example 8.

The term "HBV genotype" refers to HBV strains with an intergenotype variation of 8% or more based on a comparison of complete genomes.

The target material in the samples to be analyzed may either be DNA or RNA, e.g. genomic DNA, messenger RNA, viral RNA or amplified versions thereof. These molecules are also termed polynucleic acids.

It is possible to use genomic DNA or RNA molecules from samples susceptible of containing HBV in the methods according to the present invention.

Well-known extraction and purification procedures are available for the isolation of RNA or DNA from a sample (f.i. in Maniatis et al., Molecular Cloning: A Laboratory Manual, 2nd Edition, Cold Spring Harbour Laboratory Press (1989)).

The term "probe" refers to single stranded sequence-specific oligonucleotides which have a sequence which is complementary to the target sequence to be detected.

The term "target sequence" as referred to in the present invention describes the nucleotide sequence of a part of wild-type, polymorphic or mutant HBV gene sequence to be specifically detected by a probe according to the present invention. The polymorphic sequence may encompass one or more polymorphic nucleotides; the mutant sequence may encompass one or more nucleotides that are different from the wild-type sequence. It is to be understood that the term "mutant target sequence" not only covers the sequence containing a mutation, but also the corresponding wild-type sequence. Target sequences may generally refer to single nucleotide positions, codon positions, nucleotides encoding amino acids or to sequences spanning any of the foregoing positions. In the present invention said target sequence often includes one, two or more variable nucleotide positions. In the present invention polynucleic acids detected by the probes of the invention will comprise the target sequence against which the probe is detected.

It is to be understood that the complement of said target sequence is also a suitable target sequence in some cases. The target sequences as defined in the present invention provide sequences which should at least be complementary to the central part of the probe which is designed to hybridize specifically to said target region. In most cases the target sequence is completely complementary to the sequence of the probe.

The term "complementary" as used herein means that the sequence of the single stranded probe is exactly the (inverse) complement of the sequence of the single-stranded target, with the target being further defined as the sequence where the mutation to be detected is located.

Since the current application requires the detection of single basepair mismatches, stringent conditions for hybridization are required, allowing in principle only hybridization of exactly complementary sequences. However, variations are possible in the length of the probes (see below). It should also be noted that, since the central part of the probe is essential for its hybridization characteristics, possible deviations of the probe sequence versus the target sequence may be allowable towards head and tail of the probe when longer probe sequences are used. These variations, which may be conceived from the common knowledge in the art, should however always be evaluated experimentally, in order to check if they result in equivalent hybridization characteristics as the exactly complementary probes.

Preferably, the probes of the invention are about D to 50 nucleotides long, more preferably from about 10 to 25 nucleotides. Particularly preferred lengths of probes include 10, 11, 12, 13, 14, 15, 16, 17, 13, 19, 20, 21, 22, 23, 24 or 25 nucleotides. The nucleotides as used in the present invention may be ribonucleotides, deoxyribonucleotides and modified nucleotides such as inosine or nucleotides containing modified groups which do not essentially alter their hybridisation characteristics.

Probe sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phospho-triester method.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (19388) or Bej et al. (1990) or labelled primers, or by any other method known to the person skilled in the art. The nature of the label may be isotopic ($^{32}P$, $^{35}S$, etc.) or non-isotopic (biotin, digoxigenin, etc.).

The term "primer" refers Lo a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products preferably the primer is about 5-50 nucleotides long. Specific length and sequence will depend on the complexity of the required DNA or RNA targets, as well as on the conditions of primer use such as temperature and ionic strength.

The expression "suitable primer pair" in this invention refers to a pair of primers allowing the amplification of part or all of the HBV gene for which probes are immobilized.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules known in the art.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention these variations will necessitate adaptions with respect to the conditions under which the oligonucleotide should be used to obtain the required specificity and sensitivity. However the eventual results of hybridisation will be essentially the same as those obtained with the unmodified oligonucleotides.

The introduction of these modifications may be advantageous in order to positively influence characteristics such aa hybridization kinetics, reversibility of the hybrid-formation, biological stability of the oligonucleotide molecules, etc.

The "sample" may be any biological material taken either directly from the infected human being (or animal), or after culturing (enrichment). Biological material may be e.g. expectorations of any kind, broncheolavages, blood, skin tissue, biopsies, sperm, lymphocyte blood culture material, colonies, liquid cultures, faecal samples, urine etc.

The sets of probes of the present invention will include at least 2, 3, 4, 3, 6, 7, 8, 9, 10, 11, 12, 13, 14, 15, 16, 17, 18, 19, 20, 21, 22, 23, 24, 25, 26, 27, 28, 29, 30 or more probes. Said probes may be applied in two or more (possibly as many as there are probes) distinct and known positions on a solid substrate. Often it is preferable to apply two or more probes together in one and the same position of said solid support.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the [probe:target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and %GC result in a Tm about 2-10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account when designing a probe. It is known that hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid. In the present case, single base pair changes need to be detected, which requires conditions of very high stringency.

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, preferred oligonucleotide probes of this invention are between about 5 to 50 (more particularly 10-25) bases in length and have a sufficient stretch in the sequence which is perfectly complementary to the target nucleic acid sequence.

Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

Standard hybridization and wash conditions are disclosed in the Materials & Methods section of the Examples. Other conditions are for instance 3×SSC (Sodium Saline Citrate), 20% deionized FA (Formamide) at 50° C.

Other solutions (SSPE (Sodium saline phosphate EDTA), TMACl (Tetramethyl ammonium Chloride), etc.) and temperatures can also be used provided that the specificity and sensitivity of the probes is maintained. If need be, slight modifications of the probes in length or in sequence have to be carried out to maintain the specificity and sensitivity required under the given circumstances.

In a more preferential embodiment, the above-mentioned polynucleic acids from step (i) or (ii) are hybridized with at least two, three, four, five, six, seven, eight, nine, ten, eleven, twelve, thirteen, fourteen, fifteen, sixteen, seventeen, eighteen, nineteen, twenty, or more of the above-mentioned target region specific probes, preferably with 5 or 6 probes, which, taken together, cover the "mutation region" of the relevant HBV gene.

The Term "mutation region" means the region in the relevant HBV gene sequence where at least one mutation encoding a HBV mutant is located in a preferred part of this mutation region is represented in FIG. 1.

Apart from mutation regions as defined above the HBV wild-type or mutant genomes may also show polymorphic nucleotide variations at positions other than those referred to as genotype specific or mutant specific variated positions as shown in FIG. 1.

Since some mutations may be more frequently occurring than others, e.g. in certain geographic areas or in specific circumstances (e.g. rather closed communities) it may be appropriate to screen only for specific mutations, using a selected set of probes as indicated above. This would result in a more simple test, which would cover the needs under certain circumstances.

In order to detect HBV genotypes and/or HBV mutants with the selected set of oligonucleotide probes, any hybridization method known in the art can be used (conventional dot-blot, Southern blot, sandwich, etc.).

However, in order to obtain fast and easy results if a multitude of probes are involved, a reverse hybridization format may be most convenient.

In a preferred embodiment the selected set of probes are immobilized to a solid support in known distinct locations (dots, lines or other figures). In another preferred embodiment the selected set of probes are immobilized to a membrane strip in a line fashion. Said probes may be immobilized individually or as mixtures to delineated locations on the solid support.

A specific and very user-friendly embodiment of the above-mentioned preferential method is the LiPA method, where the above-mentioned set of probes is immobilized in parallel lines on a membrane, as further described in the examples.

The invention also provides for a set of primers allowing amplification of the region of the respective HBV gene to be detected by means of probes. Examples of such primers of the invention are given in Table 1 and FIG. 1.

Primers may be labelled with a label of choice (e.g. biotine). Different primer-based target amplification systems may be used, and preferably PCR-amplificatior, as set out in the examples. Single-round or nested PCR may be used.

The invention also provides a kit for detection and/or genetic analysis of HBV genotypes and/or HBV mutants present in a biological sample comprising the following components:
(i) when appropriate, a means for releasing, isolating or concentrating the polynucleic acids present in said sample;
(ii) when appropriate, at least one suitable primer pair;
(iii) at least two of the probes as defined above, possibly fixed to a solid support;
(iv) a hybridization buffer, or components necessary for producing said buffer;
(v) a wash solution, or components necessary for producing said solution;
(vi) when appropriate, a means for detecting the hybrids resulting from the preceding hybridization.
(vii) when appropriate, a means for attaching said probe to a known location on solid support.

The term "hybridization buffer" means a buffer enabling a hybridization reaction to occur between the probes and the polynucleic acids present in the sample, or the amplified products, under the appropriate stringency conditions.

The term "wash solution" means a solution enabling washing of the hybrids formed under the appropriate stringency conditions.

As illustrated in the Examples section, a line probe assay (LiPA) was designed for screening for HBV genotypes and/or HBV mutants. The principle of the assay is based on reverse hybridization of an amplified polynucleic acid fragment such as a biotinylated PCR fragment of the HBV gene onto short oligonucleotides. The latter hybrid can then, via a biotine-streptavidine coupling, be detected with a non-radioactive colour developing system.

The following examples only serve to illustrate the present invention. These examples are in no way intended to limit the scope of the present invention.

FIGURE AND TABLE LEGENDS

FIG. 1: Alignment of 35 complete HBV genomes. Isolates belonging to genotype A are: HBVXCPS, HBVADW, HVHEPB, S50225, HPBADWZCG; genotype B: HPBADW3, HPBADWZ, HPBADW1, HPBADW2; genotype C: HPBCGADR, HBVADRM, HPBADRA, HPBCG, HEHBVAYR, HBVADR, HBVADR4, HPBADR1C, HPBADRC, HBVPREX, HPBETNC, HHVBC, HHVC-CHA; genotype D: HBVAYWMCG, HBVAYWC, HBVAY-WCI, HBVAYWE, HBVDNA, HPBHBVAA, XXHEPAV, HBVORFS; genotype E: HHVBE4, HHVBBAS; and genotype F: HHBF, HHVBFFOU, HBVADW4A. To preserve alignment, several gaps were created in the alignment and are indicated with /. Positions of start and end of the different HBV encoded genes is indicated: HBBsAg: hepatitis B surface antigen (small surface antigen); HBx: hepatitis B X protein; HB Pol: hepatitis B polymerase protein, encoding a terminal protein, a spacer, a RT/DNA polymerase region, and an RNAse H activity; HBcAg: hepatitis B Core antigen; HBpreS1Ag: hepatitis B preS1 antigen (large surface antigen); HBpreS2Ag: hepatitis B preS2 antigen (middle surface antigen). The position of the PCR primers is indicated with a large box over all 35 sequences. The polarity of the PCR primer can be deduced from the position of the name above these boxes: left=antisense primer; right=sense primer. LiPA proboes are indicated with small boxes, the numbers of the probes are indicated next to the probes or to the right of the alignment, and correspond to the probe numbers in Table 1.

The following lists the correspondence between the sequences of FIG. 1 and the sequences of the Sequence Listing: HBVXCPS, SEQ ID NO:279; HBVADW, SEQ ID NO:280; HVHEPB, SEQ ID NO:281; S50225, SEQ ID NO:282; HPBADWZCG, SEQ ID NO:283; HPBADW3, SEQ ID NO:284; HPBADWZ, SEQ ID NO:285; HPBADW1, SEQ ID NO:286; HPBADW2, SEQ ID NO:287; HPBCGADR, SEQ ID NO:288; HBVADRM, SEQ ID NO:289; HPBADRA, SEQ ID NO:290; HPBCG, SEQ ID NO:291; HEHBVAYR, SEQ ID NO:292; HBVADR, SEQ ID NO:293; HBVADR4, SEQ ID NO:294; HPBADR1C, SEQ ID NO:295; HPBADRC, SEQ ID NO:296; HBVPREX, SEQ ID NO:297; HPBETNC, SEQ ID NO:298; HHVBC, SEQ ID NO:299; HHVCCHA, SEQ ID NO:300; HBVAYWMCG, SEQ ID NO:301; HBVAYWC, SEQ ID NO:302; HBVAY-WCI, SEQ ID NO:303; HBVAYWE, SEQ ID NO:304; HBVDNA, SEQ ID NO:305; HPBHBVAA, SEQ ID NO:306; XXHEPAV, SEQ ID NO:307; HBVORFS, SEQ ID NO:308; HHVBE4, SEQ ID NO:309; HHVBBAS, SEQ ID NO:310; HHBF, SEQ ID NO:311; HHVBFFOU, SEQ ID NO:312; and HBVADW4A. SEQ ID NO:313;

FIG. 2: LiPA HBV design. The content of a HBV LiPA strip is detailed. For each line number, the region on the viral genome is indicated, together with the genotype that is detected, the probe number that corresponds with the boxes from the alignment in FIG. 1, and the sequence of the probe.

FIG. 3: Combined result of genotype determination in the preS1 region and preCore scanning on 24 samples. The interpretation of each sample is given under each strip. Probe reactivities on lines 3 to 14 are obtained from the preS1 PCR fragment, probe reactivities on lines 15 to 27 are due to the preCore PCR fragment. Genotypes are indicated from A to F. The interpretation for the preCore region is as follows: W=wild type; M=mutant; I=indeterminate, meaning that no reactivity is observed, which is due to mutations that could not yet be detected with the selected probes; mix=mixture of wild type and mutant; interpretation of codon 15 is only relevant for genotype A, the absence of reactivity on HBPr 45 for genotypes B to F is of no use as is indicated with—(not applicable). Since the presence or absence of preCore mutations has effect on the serological HBeAg status, this is also indicated.

FIG. 4: Probes used in HBV LiPA. Probes were designed for genotyping in the HBsAg region and for detection of drug resistance mutations in the YMDD motif (see also FIG. 5), as well as for detection of mutations in the pre Core region (see also FIG. 6).

Figure 5:
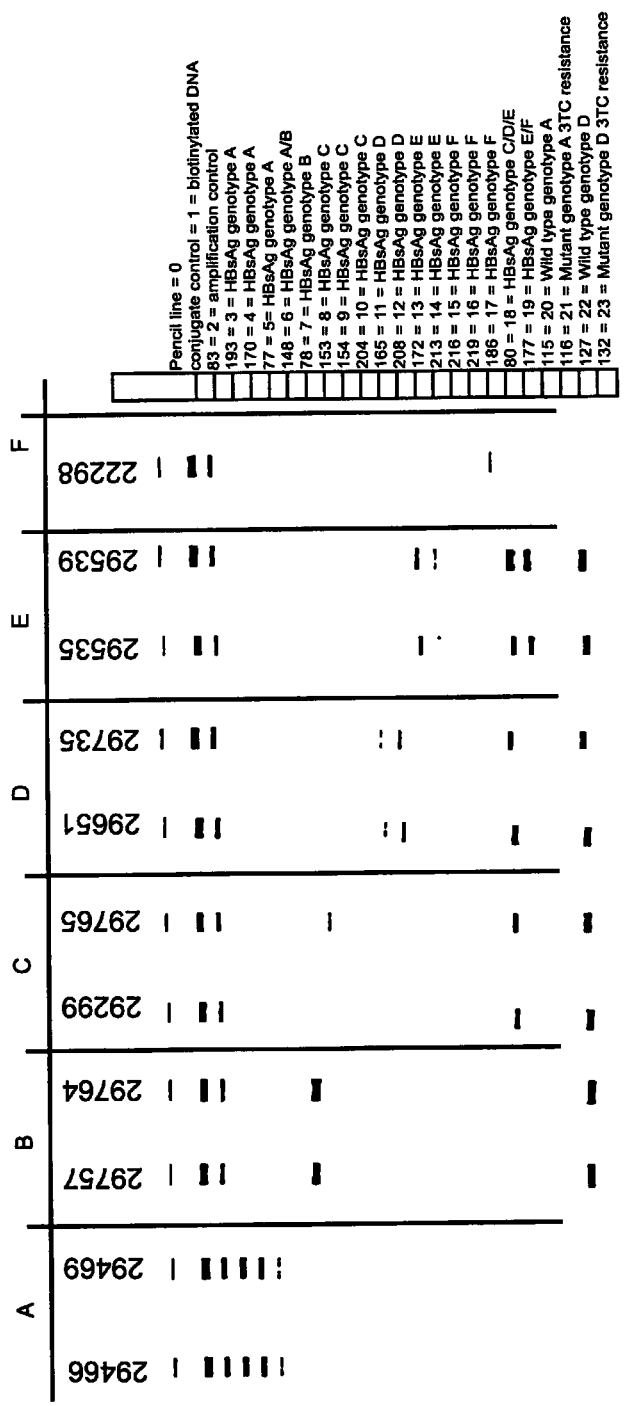

FIG. 5: Example of a LiPA assay combining HBV genotyping in the HBsAg region and detection of drug resistance mutations in the YMDD motif. Genotypes are indicated from A to F. The design of the strip is shown to the right, with the numbers of the probes corresponding to the numbers in Table 1 and in FIG. 4. The genotypes and mutant motifs to which each probe hybridizes are written to the outer right. The combination of reactive probes allows the determination of a unique genotype.

Figure 6:
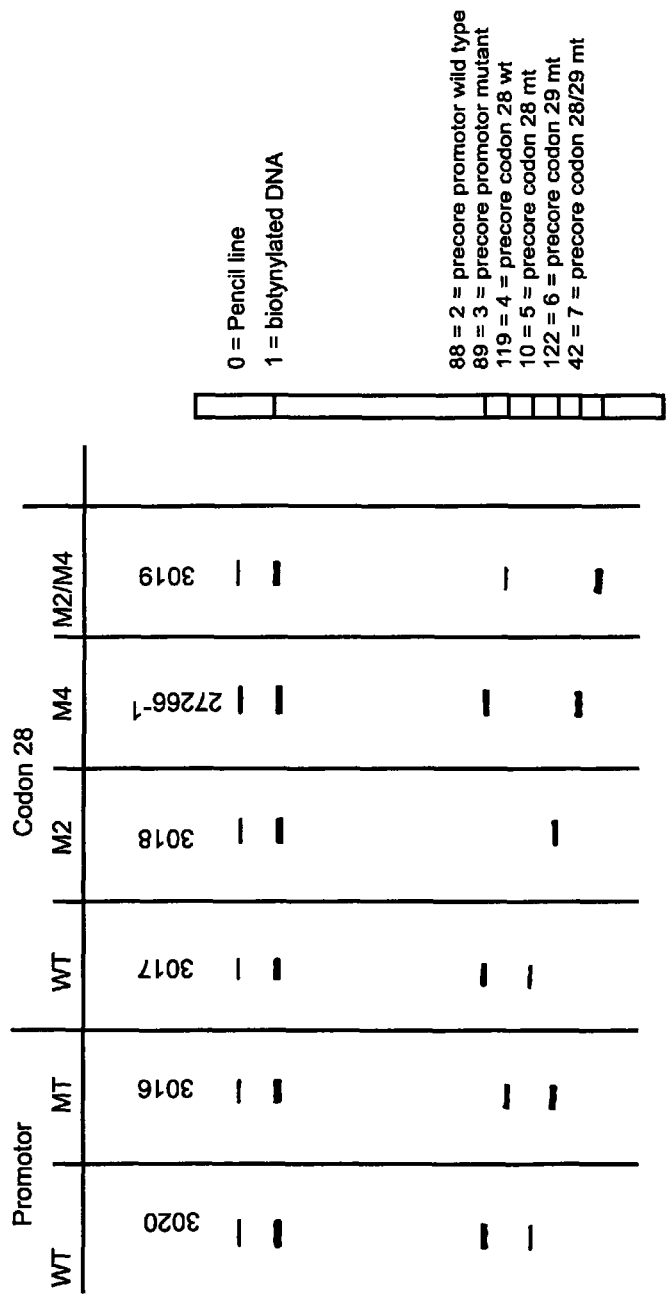

FIG. 6: Example of the determination of preCore mutations by the LiPA technique. The design of the strip is shown to the right, with the numbers of the probes corresponding to the numbers in Table 1. The mutant target sequences to which the probes hybridize are indicated to the outer right. Motif M2 corresponds to a mutation in codon 28, M4 corresponds to a mutation in codon 29. M2/M4 has mutations in both 28 and 29.

FIG. 7: Detection of a mutation in the YMDD motif of HBV pol upon treatment with lamivudine. The graph shows a time course of the viral load during lamivudine treatment. To the right LIPA strips are shown, corresponding to assays at the beginning of the treatment (5/95), 10 months of treatment (2/96) and 14 months of treatment (6/96). The assay shows that during treatment the YMDD motif mutates to YVDD.

Table 1: Overview of all primers and probes referred to in the Figures with an indication of their respective SEQ ID NO and the region of the HBV genome they are designed for. Primers from the PreS1 region include 1, 106, 2 (sense primers) and 4, 107 and 3 (antisense primers). Primers from the HBsAg region include 75 and 104 (sense primers) and 76, 94 and 105 (antisense primers). Primers from the PreCore region include 5, 6, 69, 70, 84, 86, 87 and 108 (sense primers) and 7, 8, 85 and 109 (antisense primers). The remaining oligonucleotides are probes from the PreCore, PreS1, HBsAg and RT pol gene regions of HBV as indicated. The YMDDV motif and its mutants consist of amino acids 551 to 555 of the RT pol protein; the sequence MGVGL and its mutant consist of amino acids 519 to 523 of the RT pol protein; the sequence SPFLL and its mutants and genotypic variants consist of amino acids 524 to 528 of the RT pol protein.

TABLE 1

HBV probe and primer design

| Name | Sequence | SEQ ID NO | Region |
|---|---|---|---|
| HBPr1 | GGGTCACCATATTCTTGGG | 1 | preS1 primer sense |
| HBPr2 | GAACAGAGCTACAGCATGGG | 2 | preS1 primer sense |
| HBPr3 | CCACTGCATGGCCTGAGGATG | 3 | preS1 primer anti-sense |
| HBPr4 | GTTCCT/GGAACTGGAGCCACCAG | 4 | preS1 primer anti-sense |
| HBPr5 | TCTTTGTATTAGGAGGCTGTAG | 5 | preCore primer sense |
| HBPr6 | GCTGTAGGCATAAATTGGTCTG | 6 | preCore primer sense |
| HBPr7 | CTCCACAGT/AAGCTCCAAATTC | 7 | preCore primer anti-sense |
| HBPr8 | GAAGGAAAGAAGTCAGAAGGC | 8 | preCore primer anti-sense |
| HBPr9 | TGGCTTTGGGGCATGG | 9 | preCore |
| HBPr10 | TGGCTTTAGGGCATGG | 10 | preCore |
| HBPr11 | TGGCTTTAGGACATGG | 11 | preCore |
| HBPr12 | AAGTTGCATGGTGCTG | 12 | preCore |
| HBPr13 | CACCTCTGCCTAATCAT | 13 | preCore |
| HBPr14 | TGGGGTGGAGCCCTCAG | 14 | preS1 |
| HBPr15 | GCCAGCAGCCAACCAG | 15 | preS1 |
| HBPr16 | CCCATGGGGACTGT | 16 | preS1 |
| HBPr17 | AACCCCAACAAGGATG | 17 | preS1 |

TABLE 1-continued

HBV probe and primer design

| Name | Sequence | SEQ ID NO | Region |
|---|---|---|---|
| HBPr18 | TCCACCAGCAATCCT | 18 | preS1 |
| HBPr19 | TGGGGGAAGAATATTT | 19 | preS1 |
| HBPr20 | AAATTCCAGCAGTCCC | 20 | preS1 |
| HBPr21 | GTTCCCAACCCTCTGG | 21 | preS1 |
| HBPr22 | AACCTCGCAAAGGCAT | 22 | preS1 |
| HBPr23 | TGCATTCAAAGCCAAC | 23 | preS1 |
| HBPr24 | TACTCACAACTGTGCC | 24 | preS1 |
| HBPr25 | ACCCTGCGTTCGGAGC | 25 | preS1 |
| HBPr26 | CAGGAAGACAGCCTAC | 26 | preS1 |
| HBPr27 | GATCCAGCCTTCAGAG | 27 | preS1 |
| HBPr28 | ATGCTCCAGCTCCTAC | 28 | preS1 |
| HBPr29 | GCTTTCTTGGACGGTC | 29 | preS1 |
| HBPr30 | CTACCCCAATCACTCC | 30 | preS1 |
| HBPr31 | AGCACCTCTCTCAACG | 31 | preS1 |
| HBPr32 | CCAATGGCAAACAAGG | 32 | preS1 |
| HBPr33 | CTGAGGGCTCCACCCCA | 33 | preS1 |
| HBPr34 | ATGCAACTTTTTCACC | 34 | preCore |
| HBPr35 | ATCTCTTGTACATGTC | 35 | preCore |
| HBPr36 | ATCTCATGTTCATGTC | 36 | preCore |
| HBPr37 | CAGTGGGACATGTACA | 37 | preCore |
| HBPr38 | CAGTAGGACATGAACA | 38 | preCore |
| HBPr39 | CTGTTCAAGCCTGGAA | 39 | preCore |
| HBPr40 | AGCCTCCAAGCTGTGC | 40 | preCore |
| HBPr41 | AAAGCCACCCAAGGCA | 41 | preCore |
| HBPr42 | TGGCTTTAGGACATGGA | 42 | preCore |
| HBPr43 | GACATGTACAAGAGATGA | 43 | preCore |
| HBPr44 | GACATGAACATGAGATGA | 44 | preCore |
| HBPr45 | TGTACATGTCCCACTGTT | 45 | preCore |
| HBPr46 | TGTTCATGTCCTACGTT | 46 | preCore |
| HBPr47 | ACTGTTCAAGCCTCCAAG | 47 | preCore |
| HBPr48 | GGCACAGGCTTGGAGGCTT | 48 | preCore |
| HBPr49 | AAAGCCACCCAAGGCACA | 49 | preCore |
| HBPr50 | CCCAGAGGGTTGGGAAC | 50 | preS1 |
| HBPr51 | CAGCATGGGGCAGAATCT | 51 | preS1 |
| HBPr52 | TCCACCAGCAATCCTCTG | 52 | preS1 |
| HBPr53 | GGATCCAGCCTTCAGAGC | 53 | preS1 |
| HBPr54 | TCAGGAAGACAGCCTAC | 54 | preS1 |

TABLE 1-continued

HBV probe and primer design

| Name | Sequence | SEQ ID NO | Region |
|---|---|---|---|
| HBPr55 | TTCAACCCCAACAAGGATC | 55 | preS1 |
| HBPr56 | AATGCTCCAGCTCCTAC | 56 | preS1 |
| HBPr57 | CTGCATTCAAAGCCAACT | 57 | preS1 |
| HBPr58 | CCCCATGGGGACTGTTG | 56 | preS1 |
| HBPr59 | CATACTCACAACTGTGCCA | 59 | preS1 |
| HBPr60 | GGGCTTTCTTGGACGGTCC | 60 | preS1 |
| HBPr61 | CTCTCGAATGGGGAAGA | 61 | preS1 |
| HBPr62 | CCTACCCCAATCACTCCA | 62 | preS1 |
| HBPr63 | AGCACCTCTCTCAACGACA | 63 | preS1 |
| HBPr64 | GCAAATTCCAGCAGTCCCG | 64 | preS1 |
| HBPr65 | GCCAATGGCAAACAAGGTA | 65 | preS1 |
| HBPr66 | GACATGAACATGAGATG | 66 | preCore |
| HBPr67 | GGACATGAACAAGAGAT | 67 | preCore |
| HBPr68 | GACATGTACAAGAGATG | 68 | preCore |
| HBPr69 | ACATAAGAGGACTCTTGGAC | 69 | preCore primer sense |
| HBPr70 | TACTTCAAAGACTGTGTGTTTA | 70 | preCore primer sense |
| HBPr71 | ACAAAGACCTTTAAC/TCT | 71 | preCore promoter |
| HBPr72 | ACAAAGATCATTAAC/TCT | 72 | preCore promoter |
| HBPr73 | TTCCACCAGCAATCCTC | 73 | preS1 |
| HBPr74 | GATCCAGCCTTCAGAGC | 74 | preS1 |
| HBPr75 | CAAGGTATGTTGCCCGTTTGTCC | 75 | HBsAg primer sense |
| HBPr76 | CCAAACAGTGGGGGAAAGCCC | 76 | HBsAg primer anti-sense |
| HBPr77 | CTACGGATGGAAATTGC | 77 | HBsAg codon 145 wild type |
| HBPr78 | TACGGACGGAAACTGC | 78 | HBsAg codon 145 wild type |
| HBPr79 | TTCGGACGGAAACTGC | 79 | HBsAg codon 145 wild type |
| HBPr80 | CTTCGGACGGAAATTGC | 80 | HBsAg codon 145 wild type |
| HBPr81 | CTACGGATAGAAATTGC | 81 | HBsAg codon 145 mutant |
| HBPr82 | CTTCGGACAGAAATTGC | 82 | HBsAg codon 145 mutant |
| HBPr83 | CTATGGGAGTGGGCCTCAGT/CC | 83 | HB Pol |
| HBPr84 | GCTGTAGGCATAAATTGGTCTG | 84 | preCore primer sense |
| HBPr85 | CTCCACAGT/AAGCTCCAAATTC | 85 | preCore primer anti-sense |
| HBPr86 | ACATAAGAGGACTCTTGGAC | 86 | preCore primer sense |
| HBPr87 | TACCTTCAAAGACTGTGTGTTTA | 87 | preCore primer sense |
| HBPr88 | TAGGTTAAAGGTCTTGT | 88 | preCore promoter |
| HBPr89 | TAGGTTAATGATCTTTGT | 89 | preCore promoter |
| HBPr90 | CATGTCCCACTGTTCAA | 90 | preCore |
| HBPr91 | CATGTCCTACTGTTCAA | 91 | preCore |

TABLE 1-continued

HBV probe and primer design

| Name | Sequence | SEQ ID NO | Region |
|---|---|---|---|
| HBPr92 | TTCTGCCCCATGCTGTA | 92 | preS1 |
| HBPr93 | TTCTGCCCCATGCTGTAG | 93 | preS1 |
| HBPr94 | GGTAA/TAAAGGGACTCAC/AGATG | 94 | HBsAg primer anti-sense |
| HBPr95 | TCAGCTATATGGATGAT | 95 | HB Pol |
| HBPr96 | CAGCTATATGGATGAT | 96 | HB Pol |
| HBPr97 | TTCAGCTATATGGATG | 97 | HB Pol |
| HBPr98 | TCAGTTATATGGATGAT | 98 | HB Pol |
| HBPr99 | TTTCAGTTATATGGATG | 99 | HB Pol |
| HBPr100 | TTTAGTTATATGGATGA | 100 | HB Pol |
| HBPr101 | TCAGCTATGTGGATGAT | 101 | HB Pol |
| HBPr102 | TCAGTTATGTGGATGAT | 102 | HB Pol |
| HBPr103 | TTTCAGCTATGTGGATG | 103 | HB Pol |
| HBPr104 | CAAGGTATGTTGCCCGTTTGTCC | 104 | HBsAg primer sense |
| HBPr105 | GGT/CAA/TAAAGGGACTCAC/AGATG | 105 | HBsAg primer anti-sense |
| HBPr106 | GGGTCACCATATTCTTGGG | 106 | preS1 primer sense |
| HBPr107 | GTTCCT/GGAACTGGAGCCACCAG | 107 | preS1 primer anti-sense |
| HBPr108 | CCGGAAAGCTTGAGCTCTTCTTTTTCACCTCTGCCTAATC | 108 | preCore primer sense |
| HBPr109 | CCGGAAAGCTTGAGCTCTTCAAAAAGTTGCATGGTGCTGG | 109 | preCore primer anti-sense |
| HBPr110 | CCTCTGCCGATCCATACTGCGGAAC | 110 | preX primer sense |
| HBPr111 | CTGCGAGGCGAGGGAGTTCTTCTTC | 111 | HB Core primer anti-sense |
| HBPr112 | TGCCATTTGTTCAGTGGTTCGTAGGGC | 112 | HBsAg primer sense |
| HBPr113 | CCGGCAGATGAGAAGGCACAGACGG | 113 | HBX primer antisense |
| HBPr114 | TTCAGCTATATGGATGAT | 114 | YMDD motif |
| HBPr115 | TCAGCTATATGGATGATG | 115 | YMDD motif |
| HBPr116 | TTCAGCTATGTGGATGAT | 116 | YMDD motif |
| HBPr117 | TCAGCTATGTGGATGATG | 117 | YMDD motif |
| HBPr118 | GGCTTTGGGGCATGG | 118 | preCore codon 28 wild type |
| HBPr119 | TGGCTTTGGGGCATG | 119 | preCore codon 28 wild type |
| HBPr120 | GTGGCTTTGGGGCATG | 120 | preCore codon 28 wild type |
| HBPr121 | GGCTTTGGGGCATGGA | 121 | preCore codon 28 wild type |
| HBPr122 | TGGCTTTGGGACATGG | 122 | preCore codon 28 wild type, codon 29 mutant |
| HBPr123 | GGCTTTGGGACATGG | 123 | preCore codon 28 wild type, codon 29 mutant |
| HBPr124 | TGGCTTTGGGACATG | 124 | preCore codon 28 wild type, codon 29 mutant |
| HBPr125 | GTGGCTTTGGGACATG | 125 | preCore codon 28 wild type, codon 29 mutant |
| HBPr126 | GGCTTTGGGACATGGA | 126 | preCore codon 28 wild type, codon 29 mutant |

TABLE 1-continued

HBV probe and primer design

| Name | Sequence | SEQ ID NO | Region |
|---|---|---|---|
| HBPr127 | TCAGTTATATGGATGATG | 127 | YMDD genotype D, wild type |
| HBPr128 | TTCAGTTATATGGATGAT | 128 | YMDD genotype D, wild type |
| HBPr129 | TTTCAGTTATATGGTGAT | 129 | YMDD genotype D, wild type |
| HBPr130 | TCAGTTATGTGGATGATG | 130 | YMDD genotype D, mutant |
| HBPr131 | TTCAGTTATGTGGATGAT | 131 | YMDD genotype D, mutant |
| HBPr132 | TTTCAGTTATGTGGATGAT | 132 | YMDD genotype D, mutant |
| HBPr133 | TTTCAGTTATGTGGATGA | 133 | YMDD genotype D, mutant |
| HBPr134 | TGCTGCTATGCCTCATCTTC | 134 | outer HBsAg primer sense |
| HBPr135 | CA(G/A)AGACAAAAGAAAATTGG | 135 | outer HBsAg primer anti-sense |
| HBPr136 | CTATGGATGGAAATTGC | 136 | HBsAg mutant codon 143 |
| HBPr137 | CCTATGGATGGAAATTG | 137 | HBsAg mutant codon 143 |
| HBPr138 | ACCTATGGATGGAAATT | 138 | HBsAg mutant codon 143 |
| HBPr139 | CT CAA GGC AAC TCT ATG TGG | 139 | HBsAg, genotype A |
| HBPr140 | CT CAA GGC AAC TCT ATG GG | 140 | HBsAg, genotype A |
| HBPr141 | T CAA GGC AAC TCT ATG TTG | 141 | HBsAg, genotype A |
| HBPr142 | ATC CCA TCA TCT TGG G | 142 | HBsAg, genotype B |
| HBPr143 | ATC CCA TCA TCT TGG GCG G | 143 | HBsAg, genotype B |
| HBPr144 | TC CCA TCA TCT TGG GCG G | 144 | HBsAg, genotype B |
| HBPr145 | C CCA TCA TCT TGG GCT GG | 145 | HBsAg, genotype B |
| HBPr146 | TTC GCA AAA TAC CTA TGG | 146 | HBsAg, genotype B |
| HBPr147 | T TTC GCA AAA TAC CTA TG | 147 | HBsAg, genotype B |
| HBPr148 | CT TTC GCA AAA TAC CTA TG | 148 | HBsAg, genotype B |
| HBPr149 | TC GCA AAA TAC CTA TGG G | 149 | HBsAg, genotype B |
| HBPr150 | T CTA CTT CCA GGA ACA T | 150 | HBsAg, genotype C |
| HBPr151 | T CTA CTT CCA GGA ACA TC | 151 | HBsAg, genotype C |
| HBPr152 | CT CTA CTT CCA GGA ACA T | 152 | HBsAg, genotype C |
| HBPr153 | CT CTA CTT CCA GGA ACA G | 153 | HBsAg, genotype C |
| HBPr154 | C TGC ACG ATT CCT GCT | 154 | HBsAg, genotype C |
| HBPr155 | TGC ACG ATT CCT GCT CA | 155 | HBsAg, genotype C |
| HBPr156 | C TGC ACG ATT CCT GCT C | 156 | HBsAg, genotype C |
| HBPr157 | TGC ACG ATT CCT GCT CAA | 157 | HBsAg, genotype C |
| HBPr158 | TTC GCA AGA TTC CTA TG | 158 | HBsAg, genotype C |
| HBPr159 | CT TTC GCA AGA TTC CTA T | 159 | HBsAg, genotype C |
| HBPr160 | CT TTC GCA AGA TTC CTA | 160 | HBsAg, genotype C |
| HBPr161 | CT TTC GCA AGA TTC CTA TG | 161 | HBsAg, genotype C |
| HBPr162 | C TCT ATG TAT CCC TCC T | 162 | HBsAg, genotype D |
| HBPr163 | TCT ATG TAT CCC TCC TG | 163 | HBsAg, genotype D |

TABLE 1-continued

HBV probe and primer design

| Name | Sequence | SEQ ID NO | Region |
|---|---|---|---|
| HBPr164 | C TCT ATG TAT CCC TCC TGG | 164 | HBsAg, genotype D |
| HBPr165 | CC TCT ATG TAT CCC TCC T | 165 | HBsAg, genotype D |
| HBPr166 | C TGT ACC AAA CCT TCG G | 166 | HBsAg, genotype D |
| HBPr167 | C TGT ACC AAA CCT TCG | 167 | HBsAg, genotype D |
| HBPr168 | GC TGT ACC AAA CCT TCG G | 168 | HBsAg, genotype D |
| HBPr169 | TGT ACC AAA CCT TCG GAG | 169 | HBsAg, genotype D |
| HBPr170 | GGA CCC TGC CGA ACC T | 170 | HBsAg, genotype E |
| HBPr171 | GGA CCC TGC CGA ACC G | 171 | HBsAg, genotype E |
| HBPr172 | G GGA CCC TGC CGA AC | 172 | HBsAg, genotype E |
| HBPr173 | GGA CCC TGC CGA AC | 173 | HBsAg, genotype E |
| HBPr174 | GT TGC TGT TCA AAA CCT T | 174 | HBsAg, genotype E |
| HBPr175 | GT TGC TGT TCA AAA CCT G | 175 | HBsAg, genotype E |
| HBPr176 | TGT TGC TGT TCA AAA CCT G | 176 | HBsAg, genotype E |
| HBPr177 | A TGT TGC TGT TCA AAA CCT G | 177 | HBsAg, genotype E |
| HBPr178 | GA TCC ACG ACC ACC A | 178 | HBsAg, genotype F |
| HBPr179 | GGA TCC ACG ACC ACC A | 179 | HBsAg, genotype F |
| HBPr180 | GGA TCC ACG ACC ACC | 180 | HBsAg, genotype F |
| HBPr181 | GA TCC ACG ACC ACC AGG | 181 | HBsAg, genotype F |
| HBPr182 | TGT TCC AAA CCC TCG G | 182 | HBsAg, genotype F |
| HBPr183 | C TGT TCC AAA CCC TCG | 183 | HBsAg, genotype F |
| HBPr184 | C TGT TCC AAA CCC TCG G | 184 | HBsAg, genotype F |
| HBPr185 | GT TCC AAA CCC TCG GAT | 185 | HBsAg, genotype F |
| HBPr186 | G CCA AAT CTG TGC AGC | 186 | HBsAg, genotype F |
| HBPr187 | CCA AAT CTG TGC AGC AT | 187 | HBsAg, genotype F |
| HBPr188 | G CCA AAT CTG TGC AGC AG | 188 | HBsAg, genotype F |
| HBPr189 | GG CCA AAT CTG TGC AGC | 189 | HBsAg, genotype F |
| HBPr190 | A TCA ACA ACA ACC AGT A | 190 | HBsAg, genotype A |
| HBPr191 | GA TCA ACA ACA ACC AGT | 191 | HBsAg, genotype A |
| HBPr192 | GA TCA ACA ACA ACC AGT A | 192 | HBsAg, genotype A |
| HBPr193 | GGA TCA ACA ACA ACC AGT | 193 | HBsAg, genotype A |
| HBPr194 | T CAA GGC AAC TCT ATG TGG | 194 | HBsAg, genotype A |
| HBPr195 | AGG TTA AAG GTC TTT GT | 195 | promoter genotype A wild type |
| HBPr196 | T AGG TTA AAG GTC TTT GG | 196 | promoter genotype A wild type |
| HBPr197 | TT AGG TTA AAG GTC TTT | 197 | promoter genotype A wild type |
| HBPr198 | GG TTA AAG GTC TTT GTA GG | 198 | promoter genotype A wild type |
| HBPr199 | AGG TTA ATG ATC TTT GT | 199 | promoter genotype A mutant |
| HBPr200 | T AGG TTA ATG ATC TTT GG | 200 | promoter genotype A mutant |

TABLE 1-continued

HBV probe and primer design

| Name | Sequence | SEQ ID NO | Region |
|---|---|---|---|
| HBPr201 | CT TTC GCA AGA TTC CTA TGG | 201 | HBsAg genotype C codon 160 |
| HBPr202 | GCT TTC GCA AGA TTC CTA TG | 202 | HBsAg genotype C codon 160 |
| HBPr203 | GCT TTC GCA AGA TTC CTA TGG | 203 | HBsAg genotype C codon 160 |
| HBPr204 | CT TTC GCA AGA TTC CTA TGG G | 204 | HBsAg genotype C codon 160 |
| HBPr205 | GC TGT ACC AAA CCT TCG GAG | 205 | HBsAg genotype D codon 140 |
| HBPr206 | TGC TGT ACC AAA CCT TCG G | 206 | HBsAg genotype D codon 140 |
| HBPr207 | TGC TGT ACC AAA CCT TCG GAG | 207 | HBsAg genotype D codon 140 |
| HBPr208 | GC TGT ACC AAA CCT TCG GAT | 209 | HBsAg genotype D codon 140 |
| HBPr209 | TGG TTC GCC GGG CTT T | 209 | HBsAg genotype E codon 184 |
| HBPr210 | G TGG TTC GCC GGG CTT G | 210 | HBsAg genotype E codon 184 |
| HBPr211 | GG TTC GCC GGG CTT TC | 211 | HBsAg genotype E codon 184 |
| HBPr212 | TGG TTC GCC GGG CTT TC | 212 | HBsAg genotype E codon 184 |
| HBPr213 | AG TGG TTC GCC GGG CTG G | 213 | HBsAg genotype E codon 184 |
| HBPr214 | A GGA TCC ACG ACC ACC AGG | 214 | HBsAg genotype F |
| HBPr215 | A GGA TCC ACG ACC ACC AGT | 215 | HBsAg genotype F |
| HBPr216 | CA GGA TCC ACG ACC ACC AGG | 216 | HBsAg genotype F |
| HBPr217 | C TGT TCC AAA CCC TCG GAG | 217 | HBsAg genotype F |
| HBPr218 | C TGT TCC AAA CCC TCG GAT | 218 | HBsAg genotype F |
| HBPr219 | GC TGT TCC AA CCC TCG GAG | 219 | HBsAg genotype F |
| HBPr220 | CTGAACCTTTACCCCGTTGC | 220 | enhancer primer |
| HBPr221 | CTCGCCAACTTACAAGGCCTTC | 221 | enhancer primer |
| HBPr222 | AGAATGGCTTGCCTGAGTGC | 222 | Core primer anti-sense |
| HBPr223 | GCT TTC GCA AGA TTC CTA TGG G | 223 | HBsAg genotype C codon 160 |
| HBPr224 | G GCT TTC GCA AGA TTC CTA TGG | 224 | HBsAg genotype C codon 160 |
| HBPr225 | G GCT TTC GCA AGA TTC CTA TGG G | 225 | HBsAg genotype C codon 160 |
| HBPr226 | G GCT TTC GCA AGA TTC CTA TGG GA | 226 | HBsAg genotype C codon 160 |
| HBPr227 | C AGC TAT ATG GAT GAT GTG | 227 | YMDDV motif |
| HBPr228 | AGC TAT ATG GAT GAT GTG GG | 228 | YMDDV motif |
| HBPr229 | GC TAT ATG GAT GAT GTG GT | 229 | YMDVV motif |
| HBPr230 | AGC TAT ATG GAT GAT GTG GT | 230 | YMDDV motif |
| HBPr231 | C AGC TAT ATG GAT GAT ATA | 231 | YMDDI MOTIF |
| HBPr232 | AGC TAT ATG GAT GAT ATA GG | 232 | YMDDI MOTIF |
| HBPr233 | GC TAT ATG GAT GAT ATA GT | 233 | YMDDI MOTIF |
| HBPr234 | AGC TAT ATG GAT GAT ATA GT | 234 | YMDDI MOTIF |
| HBPr235 | CCA TCA TCT TGG GCT TG | 235 | HBSAg GENOTYPE B CODON 155 |
| HBPr236 | CA TCA TCT TGG GCT TT | 236 | HBSAg GENOTYPE B CODON 155 |
| HBPr237 | CCA TCA TCT TGG GCT TT | 237 | HBSAg GENOTYPE B CODON 155 |

TABLE 1-continued

HBV probe and primer design

| Name | Sequence | SEQ ID NO | Region |
|---|---|---|---|
| HBPr238 | CCA TCA TCT TGG GCT TTC | 238 | HBSAg GENOTYPE B CODON 155 |
| HBPr239 | CCC ACT GTC TGG CTT TC | 239 | HBSAg GENOTYPE B CODON 190 |
| HBPr240 | CC ACT GTC TGG CTT TC | 240 | HBSAg GENOTYPE B CODON 190 |
| HBPr241 | CC ACT GTC TGG CTT T | 241 | HBSAg GENOTYPE B CODON 190 |
| HBPr242 | CCC ACT GTC TGG CTT G | 242 | HBSAg GENOTYPE B CODON 190 |
| HBPr243 | TAT ATG GAT GAT GTG GTA | 243 | YMDDV MOTIF |
| HBPr244 | TAT GTG GAT GAT GTG GTA | 244 | YVDDV MOTIF |
| HBPr245 | TAT ATA GAT GAT GTG GTA | 245 | YIDDV MOTIF |
| HBPr246 | TAT ATT GAT GAT GTG GTA | 246 | YIDDV MOTIF |
| HBPr247 | TAT GTA GAT GAT GTG GTA | 247 | YVDDV MOTIF |
| HBPr248 | TAT GTT GAT GAT GTG GTA | 248 | YVDDV MOTIF |
| HBPr249 | TAT ATG GAT GAT ATA GTA | 249 | YMDDI MOTIF |
| HBPr250 | TAT ATG GAT GAT ATC GTA | 250 | YMDDI MOTIF |
| HBPr251 | TAT GTG GAT GAT ATA GTA | 251 | YVDDI MOTIF |
| HBPr252 | TAT GTG GAT GAT ATC GTA | 252 | YVDDI MOTIF |
| HBPr253 | TAT ATA GAT GAT ATA GTA | 253 | YIDDI MOTIF |
| HBPr254 | TAT ATA GAT GAT ATC GTA | 254 | YIDDI MOTIF |
| HBPr255 | TAT ATT GAT GAT ATA GTA | 255 | YIDDI MOTIF |
| HBPr256 | TAT ATT GAT GAT ATC GTA | 256 | YIDDI MOTIF |
| HBPr257 | TAT GTA GAT GAT ATA GTA | 257 | YVDDI MOTIF |
| HBPr258 | TAT GTA GAT GAT ATC GTA | 258 | YVDDI MOTIF |
| HBPr259 | TAT GTT GAT GAT ATA GTA | 259 | YVDDI MOTIF |
| HBPr260 | TAT GTT GAT GAT ATC GTA | 260 | YVDDI MOTIF |
| HBPr261 | TAT ATG GAT GAT CTG GTA | 261 | YMDDL MOTIF |
| HBPr262 | TAT GTG GAT GAT CTG GTA | 262 | YVDDL MOTIF |
| HBPr263 | TAT ATA GAT GAT CTG GTA | 263 | YIDDL MOTIF |
| HBPr264 | TAT ATT GAT GAT CTG GTA | 264 | YIDDL MOTIF |
| HBPr265 | TAT GTA GAT GAT CTG GTA | 265 | YVDDL MOTIF |
| HBPr266 | TAT GTT GAT GAT CTG GTA | 266 | YVDDL MOTIF |
| HBPr267 | T ATG GGA GTG GGC CTC AG | 267 | MGVGL |
| HBPr260 | T ATG GGA TTG GGC CTC AG | 268 | MGLGL |
| HBPr269 | C AGT CCG TTT CTC TTG GC | 269 | SPFLL |

EXAMPLES

Example 1

HBV DNA Preparation and PCR Amplification

Serum samples were collected from HBsAg-positive individuals and stored at minus 20° C. until use in 0.5 ml aliquots. To prepare the viral genome, 18 µl serum was mixed with 2 µl 1N NaOH and incubated at 37° C. for 60 minutes. The denaturation was stopped and neutralized by adding 20 µl of 0.1N HCl. After a 15 minutes centrifugation step, the supernatant was collected and the pellet discarded. PCR was carried out on this lysate as follows: 32 µl H₂O was mixed with 5 µl of 10×PCR buffer, 1 µl 10 mM dXTPs, 1 µl of each biotinylated primer (10 pmol/µl), 10 µl of serum lysate, and 2 U Taq enzyme. The amplification scheme contained 40 cycles of 95° C. 1 min, annealing at 45° C. for 1 min, and extension at 72° C. for 1 min. Amplification products were visualized on 3% agarose gel.

The outer primer set for preS1 has the following sequence:

```
outer sense: HBPr 1:
                                    (SEQ ID NO: 1)
5'-bio-GGGTCACCATATTCTTGGG-3' outer antisense HBPr 4:
                                    (SEQ ID NO: 4)
5'-bio-GTTCC(T/G)GAACTGGAGCCACCAG-3'
```

The outer primer set for preCore has the following sequence:

```
outer sense: HBPr 69:
                                    (SEQ ID NO: 69)
5'-bio-ACATAAGAGGACTCTTGGAC-3' outer antisense: HBPr 8:
                                    (SEQ ID NO: 8)
5'-bio-GAAGGAAAGAAGTCAGAAGGC-3'
```

The outer primer set for HBsAg has the following sequence:

```
outer sense: HBPr 134:
                                    (SEQ ID NO: 134)
5'-bio-TGCTGCTATGCCTCATCTTC-3' outer antisense: HBPr 135:
                                    (SEQ ID NO: 135)
5'-bio-CA(G/A)AGACAAAAGAAAATTGG-3'.
```

Samples that were negative in the first round PCR were retested in a nested reaction composed of the following: µl H₂O, 5 µl 10× Taq buffer, 1 µl 10 mM dXTPs, 1 µl of each nested primer (10 pmol/µl), 1 µl of the first round PCR product, and 2 U Taq polymerase. The amplification scheme was identical as for the first round PCR. The sequence of the nested primers were as follows, for the preS1 region:

```
nested sense HBPr 2:
                                    (SEQ ID NO: 2)
5'-bio-GAACAAGAGCTACAGCATGGG-3' nested antisense HBPr 3:
                                    (SEQ ID NO: 3)
5'-bio-CCACTGCATGGCCTGAGGATG-3';
``` and for the preCore region:

```
nested sense HBPr 70:
                                    (SEQ ID NO: 70)
5'-bio-TACTTCAAAGACTGTGTGTTTA-3' nested antisense HBPr 7:
                                    (SEQ ID NO: 7)
5'-bio-CTCCACAG(T/A)AGCTCCAAATTC-3'
```

In a second reaction the HBsAg region can be amplified in a similar protocol by using the following primers: HBPr 75: 5'-bio-CAAGGTATGTTGCCCGTTTGTCC-3' (SEQ ID NO:75) in combination with either HBPr 76: 5='-bio-CCAAACAGTGGGGGAAAGCCC-3'; or (SEQ ID NO:76) with HBPr 94: 5'-bio-GGTA(A/AAAGGGACTCA(C/A) GATG-3'. (SEQ ID NO:94)

Example 2

Preparation of the Line Probe Assays

Probes were designed to cover the universal, genotypic and mutant motifs. In principle only probes that discriminate between one single nucleotide variation were retained. However, for certain polymorphisms at the extreme ends of the probe, cross-reactivity was tolerated. Specificity was reached experimentally for each probe individually after considering the % (G+C), the probe length, the final concentration, and hybridization temperature. Optimized probes were provided enzymatically with a poly-T-tail using the Td T (Pharmacia) in a standard reaction condition. Briefly, 400 pmol probe was incubated at 37° C. in a 30 µl reaction mix containing 5.3 mM dTTP, 25 mM TrisHCL DH 7.5, 0.1 M sodium cacodylate, 1 mM CoCl₂, 0.1 M DTT and 170 U terminal deoxynucleotidyl transferase (Pharmacia). After one hour incubation, the reaction was stopped and the tailed probes were precipitated and washed with ice-cold ethanol. Probes were dissolved in 6×SSC at their respectively specific concentrations and applied as horizontal lines on membrane strips in concentrations between 0.2 and 2.5 pM/ml. Biotinylated DNA was applied alongside as positive control (LiPA line 1). The oligonucleotides were fixed to the membrane by baking at 80° C. for 12 hours. The membrane was than sliced into 4 mm strips. The design of this strip is indicated in FIG. 2.

Example 3

LiPA Test Performance

Equal volumes (10 µl each) of the biotinylated PCR fragment and of the denaturation solution (DS; 400 mM NaOH/ 10 mM EDTA) were mixed in test troughs and incubated at room temperature for 5 minutes. Then, 2 ml of the 37° C. prewarmed hybridization solution (HS, 3×SSC/0.1% SDS) was added, followed by the addition of one strip per test trough. Hybridisation occurred for 1 hour at 50±0.50° C. in a closed shaking water bath. The strips were washed twice with 2 ml of stringent wash solution (3×SSC/0.1% SDS) at room temperature for 20 seconds, and once at 50° C. for 30 minutes. Following this stringent wash, strips were rinsed two times with 2 ml of the Innogenetics standard Rinse Solution (RS). Strips were incubated on a rotating platform with the alkaline phosphatase-labelled streptavidin conjugate, diluted in standard Conjugate Solution for 30 minutes at room temperature (20 to 25° C.). Strips were than washed twice with 2 ml of RS and once with standard Substrate Buffer (SB), and the colour reaction was started by adding BCIP and NBT to the SB. After maximum 30 minutes at room temperature, the colour reaction was stopped by replacing the colour compounds by distilled water. Immediately after drying, the strips were interpreted. Reactivities were considered positive whenever the reactivity was stronger than the reaction on the negative control. Strips can be stored on a dry dark place. The complete procedure described above can also be replaced by the standardized inno-LiPA automation device (auto-LiPA).

Example 4

Selection of Reference Material

PCR fragments were prepared, derived from members of the different genotypes, the different preCore wild type and mutant sequences, drug resistant motifs and vaccine escape mutants. The PCS fragments were amplified with primers lacking the boitine group at their 5'-end and cloned into the pretreated EcoRv site of the pGEMT vector (Promega). Recombinant clones were selected after α-complementation and restriction fragment length analysis, and sequenced with plasmid primers. Other biotinylated fragments were directly sequenced with a dye-terminator protocol (Applied Biosystems) using the amplification primers. Alternatively, nested PCR was carried out with analogs of the primers, in which the biotine group was replaced with the T7- and SP6-primer sequence, respectively. These amplicons were than sequenced with an SP6- and T7-dye-primer procedure. By doing so, a reference panel of recombinant clones was prepared, which is necessary for optimizing LiPA probes.

Example 5

Genotyping HBV-Infected Serum Samples

Only after creating, a sequence alignment as shown in FIG. 1, it became clear which regions could be useful for HBV genotyping. The pres1 region seems to be suitable because of the high degree of variability. Probes were therefore designed to cover most of these variable regions as shown in Table 1. Only a limited selection of probes was retained because of their specific reaction with the reference panel. The most important ones are indicated as boxed regions in FIG. 1. These selected probes were then applied in a LiPA format indicated in FIG. 2, as line number 2 to 14. Some of the probes could be applied together in one line, because of their universal character, while others need to be applied separately. With the selection of probes thus obtained, serum samples collected in different parts of the world (Europe, South-America, Africa, Middle-East) were tested. The upper part of FIG. 3 shows the reactivity of a selection of samples on these probes. Genotyping of these samples is straightforward, with samples 2 to 8 belonging to genotype A, samples 9 and 10 belonging to genotype B, samples 11 and 12 belonging To genotype C, samples 13 to 19 belonging to genotype D, samples 20 to 23 belonging to genotype E, and sample 24 belonging to genotype F.

Genotyping can also be performed in the HBsAg region. Again, probes were designed to cover most of the variable regions shown in FIG. 1. Only a limited selection of probes were retained. These probes are boxed in FIG. 1 and are listed in FIG. 4. A LiPA strip was prepared carrying these probes and samples belonging to the different genotypes were characterized, as shown in FIG. 5.

Example 6

Scanning the preCore Region for Mutations

HBeAg expression can be regulated at the transcriptional and translational level. It is postulated that a transcriptional regulation exists due to the presence of a dinucleotide variation in the promoter region of the preCore mRNA. Probes covering the wild type (e.g. probe HBPr 88) and the mutant (e.g. HBPr 89) motif were selected and their positions are indicated in the alignment shown in FIG. 1, and applied on the LiPA strip as line 15 and 16 (FIG. 2).

At the translational level, much more mutations might arise, all possibly resulting in abrogation of the HBeAg expression: any mutations at codon 1 (ATG) destroying translation initiation, codon 2 (CAA to TAA), codon 7 (TGC to TGA), codon 12 (TGT to TGA), codon 13 in genotype B, C, D, E, F (TCA to TGA or TAA), codon 14 (TGT to TGA), codon 18 (CAA to TAA), codon 21 (AAG to TAG), codon 23 (TGC to TGA), codon 26 (TGG to TAG or TGA), codon 28 (TGG to TAG or TGA). However, due to secondary constrain of the encapsidation signal, most of the mutations occur at codon 28 (TGG to TAG). Along with the mutation at codon 28, a second mutation at codon 29 (GGC to GAC) is often observed. In the case of genotype A and again as a consequence of the secondary constrain, stop codon mutations at codon 28 are only likely to occur after selection of a codon 15 mutation (CCC to CCT). Hence, correct interpretation of preCore mutations is genotype dependent. In addition to the above mentioned stop codons, a huge amount of different deletion- or insertion-mutations in the preCore open reading frame might give essentially the same result.

In order to develop a sensitive assay to detect the relevant mutations and the hypothetical mutations, a probe scanning procedure was developed. Partially overlapping probes were designed and applied in a LiPA format (FIG. 2, line 17 to 27). In this assay format, wild type sequences over the complete preCore region, together with the codon 15 variation for genotype A versus non-A genotypes, and the most common mutations at codon 23 (TAG), at codon 29 (GAC) and the combination of codon 28 and 29 (TAGGAC) are positively recognized. Absence of reactivity at one of the other probes is always indicative for the presence of a variation. The exact nature of this variation can then be revealed by sequence analysis or with further designed LiPA probes.

FIG. 3 shows the reactivity of the selected genotyped samples on the probes for the preCore region. Samples were previously tested for the presence of HBeAg or for anti-HBe. The interpretation of the reactivity on the LiPA probes for each sample is indicated below each strip. This approach allowed for the simultaneous screening of a sample for preCore mutations and the characterization of the viral genotype.

FIG. 6 also shows a panel of samples with mutations in the preCore region, as well as wild type samples. The probes used in this assay are listed in FIG. 4. This assay includes a codon 29 mutant (M4 motif), which was not present in the experiment in FIG. 3.

Example 7

Detection of Mutants in the HBsAg Region

Vaccine escape mutants have been described. The most commonly found mutant is the variation at codon 145 of HBsAg (G145R or GGA to AGA). LIPA probes are designed to detect wild type and mutant probes. Genotypic variations are present in the vicinity of codon 145. Therefore, genotype A is covered by probe 77, genotype B by probe 78, genotype C by probe 79, and genotype D/E by probe 80. Hence, in principle, it is possible to genotype and detect the wild type strains of the virus in one single experiment. Mutant target sequences are covered by probe 81 and 82 for genotype A and D, respectively. Probe 83 can be used as a positive control in these experiments. Further detection of mutants in the a determinant region is possible by means of a probe scanning approach. Herefore, probes are designed to cover the wild type sequence of the different genotypes over the HsAg epitope region and applied in a LiPA format. Again here, absence of staining at one of these probes is indicative for the presence of a mutant strain. The exact nature of this variant is then determined by sequencing analysis.

Example 8

Detection of HBV Strains Resistant to Lamivudine

Through analogy with HIV and the resistance against the anti-viral compound 3TC (lamivudine or (-)-β-1-2',3'-dideoxy-3'-thiazytidine), it was predicted that upon treatment of HBV-infected patients with 3TC, viral strains would be selected showing resistance at the YMDD motif in the HB pol gene. The YMDD motif is physically located in the HBsAg region, but is encoded in another reading frame. Hence, this part of the HBV pol region is amplified with the primer combination HBPr 74-HBr 94, but not with the combination HBPr 74-HBr 76. Probes covering the wild type YMDD motif and YVDD mutant motif are indicated in FIG. 1, respectively probes 95 to 100 and 101 to 103, as well as probes 115, 116, 127 and 132, the latter probes yielding the best results in the LiPA assay. Such an assay was used to determine the presence of mutations in the YMDD motif in serum of a HBV-infected patient during treatment with lamivudine. FIG. 7 shows that in the first phase of the treatment (May 1995) no mutations were detected. During the treatment, the viral load decreased, reaching a level of approximately $10^4$ during November and December 1995, whereafter a breakthrough was observed, resulting in a level as high as during the first months of the treatment by June 1996. Interestingly, a LIPA assay performed in February 1996 indicated that the majority of virus present, possessed a mutation in the YMDD motif, which had changed to YVDD. In June 1996, no more wild type motif, but only mutant YVDD could be detected. With this assay, resistant HBV strains can thus easily be detected. Furthermore, the combined detection of the YMDD motif and preCore mutants might be clinically important in prediction and prognosis of further treatment.

REFERENCES

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad Sci. USA B1(11):3297-301.

Barany F. Genetic disease detection and DNA amplification using cloned thermostable ligase. Proc Natl Acad Sci USA 1991; 88: 189-193.

Bej A, Mahbubani M, Miller R, Di Cesare J, Haff L, Atlas R. Mutiplex PCR amplification and immobilized capture probes for detection of bacterial pathogens and indicators in water. Mol Cell Probes 1990; 4:353-365.

Boom R., Spol C. J. A., Salimans M. M. M., et al. Rapid and simple method for purification of nucleic acids. J Clin Microbiol 1990; 28: 495-503.

Carman W, Zanetti A, Karayiannis D, Waters J, Manzillo G, Tanzi E, Zuckerman A, and Thomas H. Vaccine induced escape mutants. Lancet 1990; 336:325-329.

Carman W, Koruia J. Wallace L, MacPhee R, Mimms L, and Decker R. Fulminant reactivation of hepatitis B due to envelope protein mutant that escaped detection by monoclonal HBsAG ELISA. Lancet 1995; 345: 1406-1407.

Compton J. Nucleic acid sequence-based amplification. Nature 1991; 350: 91-92.

Crawford D. Hepatitis B virus 'escape' mutants: A rare event which causes vaccinationfailare. British Med. J. 1990; 301: 1058-1059.

Duck P. Probe amplifier system based on chimeric cycling oligonucleotides. Biotechniques 1990; 9: 142-147.

GaQ Q, Gu Z, Parniak M, Cameron I, Cammack N, Boucher C, and Wainberg M. The same mutation that encodes low-level human immunodeficiency virus type-1 resistance to 2',3'-dideoxyinosine and 2',3'-dideoxycytidine confers high level resistance to the (-) enantiomer of 2',3'-dideoxy-3'-thiacytidine. Antimicrob. Agents Chemother. 1993; 37: 1390-1392.

Guatelli J, Whitfield K, Kwoh D, Barringer K, Richman D, Gengeras T. Isothermal, in vitro amplification of nucleic acids by a multienzyme reaction modeled after retroviral replication. Proc Natl Acad Sci USA 1990; 87: 1874-1878.

Hadziyannis S. Hepaptis B e antigen negative chronic hepatitis B: from clinical recognitionto pathogenesis and treatment. Viral Hepatitis 1995; 1: 7-36.

Honkoop P, de Man R, Zondervan P, Niesters H, and Schalm S. Histological improvement in patients with chronic hepatitis B virus infection treated with lavimudine is associated with a decrease in HBV-DNA by PCR. Hepatol. 1995; 22: abstract 887.

Kwoh D, Davis G, Whitfield K, Chappelle H, Dimichele L, Gingeras T. Transcription-based amplification system and detection of amplified human immunodeficiency virus type 1 with 2 bead-based sandwich hybridization format. Proc Natl Acad Sci USA 1989; 86: 1173-1177.

Kwok S, Kellogg D, McKinney N, Spasic D, Goda L, Levenson C, Sinisky J. Effects of primer-template mismatches on the polymerase chain reaction: Human immunodeficiency views type 1 model studies. Nucl. Acids Res. 1990; 18: 999.

Landgren U, Kaiser R, Sanders J, Hood L. A ligase-mediated gene detection technique. Science 1988; 241:1077-1080.

Li J-S, Tong S-P, Wen Y-M, Vivitski L, Zhang Q, and Trepo C. Hepatitis B virus genotype A rarely circulates as an Hbe-minus mutant: possible contribution of a single nucleotide in the preCore region. J. Virol. 1993; 67: 5402-5410.

Ling, R., Mutimer, D., Ahmed, M., Boxall, E. H., Elias, E., Dusheiko, G. M. and Harrison, T. J. Selection of mutations in the Hepatitis B Virus polymerase during therapy of transplant recipients with lamivudune. Hepatology 1996; 24: 711-713.

Lok A, Akarca U, and Greene S. Mutations in the precore region of hepatitis B virus serve to enhance of the secondary structure of the pre-genome encapsidation signal. Proc. Natl. Acad. Sci. USA 1994; 91: 4077-4081.

Lomeii H, Tyagi S. Printchard C, Lisardi P, Kramer F. Quantitative assays based on the use of replicatable hybridization probes. Clin Chem 1989; 35: 1826-1831.

Magnius L, and Norder H. Subtypes, genotypes and molecular epidemiology of the hepatitis B virus as reflected by sequence variability of the S-gene. Intervirology 1995; 38: 24-34.

Matsukura M, Shinozuka K, Zon G. Misuya H, Reitz M, Cohen J, Broder S (1987) Phosphorothioate analogs of oligodeoxynucleotides: inhibitors of replication and cyopathic effects of human immunodeficiency virus. Proc. Natl. Acad. Sci. USA 84(21):7706-10.

Miller P, Yano J, Carroli C, Jayaram K, Ts'o P (1979) Nonionic nucleic acid analogues. Synthesis and characterization of dideoxyribonucleoside methylphosphonates. Biochemistry 18(23):5134-43.

Naoumov N, Perilio R, Chokshi S, Dienstag J, Vicary C, Brown N, and Williams R. Reduction in hepatitis B virus quasispecies during lamivudine treatment is associated with enhanced virus replication and hepatocytolisis. Hepatol. 1995; 22: abstract 885.

Nielsen P, Egholm M. Berg R, Buchardt O (1991) Sequence-selective recognition of DNA by strand displacement with a thymine-substituted polyamide. Science 254(5037):1497-500.

Nielsen P, Egholm M, Berg R, Buchardt O (1993) Sequence specific inhibition of DNA restriction enzyme cleavage by PNA. Nucleic-Acids-Res. 21(2):197-200.

Okamoto H, Yotsumoto S, Akahane Y, Yamanaka T, Miyazaki Y, Sugai Y, Tsuda F, Tanaka T, Miyakawa Y, and Mayumi M. Hepatitis B virus with precore region defects prevail in persistently infected hosts along with seroconversion to the antibody against e antigen. J. Virol. 1990; 64: 1298-1303.

Saiki R, Walsh P, Levenson C, Erlich H. Genetic analysis of amplified DNA with immobilized sequence-specific oligonucleotide probes Proc Natl Acad Sci USA 1989; 86:6230-6234.

Sato S, Suzuki K, Akahane Y, Akamatsu K, Akiyama K, Yunomura K, Tsuda F, Tanaka T, Okamoto H, Miyakawa Y, Mayumi M. Hepatitis B virus strains with mutations in the core promoter in patients with fulminant hepatitis. Ann. Intern. Medicine 1995; 122: 241-248.

Shaw, T., Mok, S. S., Locarnini, S. A. Inhibition of hepatitis B virus DNA polymerase by enantiomers of penciclovir triphosphate and metabolic basis for selective inhibition of HVV replication by penciclovir Hepatology 1996; 24: 996-1002.

Stuyver L, Rossau A, Wyseur A, et al. Typing of hepatitis C virus isolates and characterization of new subtypes using a line probe assay. J. Gen. Virol. 1993; 74: 1093-1102.

Takahashi K, Aoyama K, Onhno N, Iwata K, Akahane Y, Baba K, Yoshizawa H, and Mishiro S. The precore/core promoter mutant (T1762A1764) of hepatitis B virus: clinical significance and an easy method for detection. J. Gen. Virol. 1995; 76: 3159-3164.

Tipples, G. A., Ma, M. M., Fischer, K. P., Bain, V. G., Kneteman, N. M. and Tyrell, D. L. J. Mutation in HBV RNA-dependent DNA polymerase confers resistance to lamivudine in vivo. Hepatology 1996; 24: 714-717.

Waters J, Kennedy M, Voet P, Hauser P, Petre J, Carman W, and Thomas H. Loss of the common 'a' determinant of hepatitis B surface antigen by vaccine-induced escape mutants. J. Clin. Invest. 1992; 90: 2543-2547.

Wu D, Wallace B. The ligation amplification reaction (LAR)—amplification of specific DNA sequences using sequential rounds of template-dependent ligation. Genomics 1989; 4:560-569.

Yuan T, Faruqi A, Shih J, and Shih C. The mechanism of natural occurrence of two closely linked HBV precore predominant mutations. Virol. 1995; 211: 144-156.

Zhang X, Zoulim F, Habersetzer F, Xiong S, and Trépo C. Analysis of hepatitis B virus genotypes and precore region variability during interferon treatment of Hbe antigen negative chronic hepatitis B. J. Med. Virol. 1996; xxx-xxx.

---

The invention claimed is:

1. A method for determining the presence or absence of HBV genotype A in a biological sample, comprising:
   (i) providing a biological sample comprising polynucleic acids;
   (ii) optionally releasing, isolating and/or concentrating the polynucleic acids present in the sample;
   (iii) optionally amplifying the HBsAg region, or part thereof, of the HBV gene present in said sample with at least one primer pair;
   (iv) hybridizing the polynucleic acids of step (i) or (ii) or (iii) with at least one nucleotide probe selected from the group consisting of SEQ ID NO: 77, SEQ ID NO: 140, SEQ ID NO: 193, the complement of SEQ ID NO:77, the complement of SEQ ID NO:140, and the complement of SEQ ID NO:193;
   (v) detecting the hybrid(s) formed in step (iv);
   (vi) inferring the presence of absence of HBV genotype A in said sample from the hybridization signal(s) obtained in step (v).

2. The method according to claim 1, for further determining the presence or absence of HBV genotype B in the biological sample, whereby step (iv) further comprises hybridizing the polynucleic acids of step (i) or (ii) or (iii) with at least one nucleotide probe selected from the group consisting of SEQ ID NOs:78, 142-147, 149 and their complement sequences.

3. The method according to claim 1, for further determining the presence or absence of HBV genotype C in the biological sample, whereby step (iv) further comprises hybridizing the polynucleic acid of step (i) or (ii) or (iii) with at least one nucleotide probe selected from the group consisting of SEQ ID NOs: 79, 150-161, 204 and their complement sequences.

4. The method according to claim 1, for further determining the presence or absence of HBV genotype D in the biological sample, whereby step (iv) further comprises hybridizing the polynucleic acids of step (i) or (ii) or (iii) with at least one nucleotide probe selected from the group consisting of SEQ ID NOs: 82, 162-169, 208 and their complement sequences.

5. The method according to claim 1, for further determining the presence or absence of HBV genotype E in the biological sample, whereby step (iv) further comprises hybridizing the polynucleic acids of step (i) or (ii) or (iii) with at least one nucleotide probe selected from the group consisting of SEQ ID NOs: 170-176, 213, and their complement sequences.

6. The method according to claim 1, for further determining the presence or absence of HBV genotype F in the biological sample, whereby step (iv) further comprises hybridizing the polynucleic acids of step (i) or (ii) or (iii) with at least one nucleotide probe selected from the group consisting of SEQ ID NOs:178-189, 214-219, and their complement sequences.

7. The method according to claim 1 wherein the primers of said at least one primer pair of step (iii) are selected from the group consisting of SEQ ID NOs: 75-76, 94, 104, 105, 112 and 134-135.

8. The method according to claim 1 wherein step (iv) of hybridizing the polynucleic acids of step (i) or (ii) or (iii) with at least one nucleotide probe is a reverse hybridization step.

* * * * *

SEQUENCE LISTING (1) GENERAL INFORMATION:

(iii) NUMBER OF SEQUENCES: 313

(2) INFORMATION FOR SEQ ID NO: 1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

GGGTCACCAT ATTCTTGGG                      19

(2) INFORMATION FOR SEQ ID NO: 2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

GAACAAGAGC TACAGCATGG G                                                         21

(2) INFORMATION FOR SEQ ID NO: 3:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

CCACTGCATG GCCTGAGGAT G                                                         21

(2) INFORMATION FOR SEQ ID NO: 4:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

GTTCCKGAAC TGGAGCCACC AG                                                        22

(2) INFORMATION FOR SEQ ID NO: 5:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

TCTTTGTATT AGGAGGCTGT AG                                                        22

(2) INFORMATION FOR SEQ ID NO: 6:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

GCTGTAGGCA TAAATTGGTC TG                                                  22

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

CTCCACAGWA GCTCCAAATT C                                                   21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

GAAGGAAAGA AGTCAGAAGG C                                                   21

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

TGGCTTTGGG GCATGG                                                         16

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 10:

TGGCTTTAGG GCATGG                                                         16

(2) INFORMATION FOR SEQ ID NO: 11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

TGGCTTTAGG ACATGG                                            16

(2) INFORMATION FOR SEQ ID NO: 12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

AAGTTGCATG GTGCTG                                            16

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 13:

CACCTCTGCC TAATCAT                                         17

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 14:

TGGGGTGGAG CCCTCAG                                         17

(2) INFORMATION FOR SEQ ID NO: 15:

-continued (i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 15:

GCCAGCAGCC AACCAG                                                    16

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 16:

CCCATGGGGG ACTGT                                                     15

(2) INFORMATION FOR SEQ ID NO: 17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 17:

AACCCCAACA AGGATG                                                    16

(2) INFORMATION FOR SEQ ID NO: 18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 18:

TCCACCAGCA ATCCT                                                     15

(2) INFORMATION FOR SEQ ID NO: 19:

(i) SEQUENCE CHARACTERISTICS:
        (A) LENGTH: 16 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 19:

TGGGGGAAGA ATATTT                                                  16

(2) INFORMATION FOR SEQ ID NO: 20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

AAATTCCAGC AGTCCC                                                  16

(2) INFORMATION FOR SEQ ID NO: 21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 21:

GTTCCCAACC CTCTGG                                                  16

(2) INFORMATION FOR SEQ ID NO: 22:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 22:

AACCTCGCAA AGGCAT                                                  16

(2) INFORMATION FOR SEQ ID NO: 23:

(i) SEQUENCE CHARACTERISTICS:
        (A) LENGTH: 16 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 23:

TGCATTCAAA GCCAAC                                                       16

(2) INFORMATION FOR SEQ ID NO: 24:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 24:

TACTCACAAC TGTGCC                                                       16

(2) INFORMATION FOR SEQ ID NO: 25:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 25:

ACCCTGCGTT CGGAGC                                                       16

(2) INFORMATION FOR SEQ ID NO: 26:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 26:

CAGGAAGACA GCCTAC                                                       16

(2) INFORMATION FOR SEQ ID NO: 27:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 27:

GATCCAGCCT TCAGAG                                                              16

(2) INFORMATION FOR SEQ ID NO: 28:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 28:

ATGCTCCAGC TCCTAC                                                              16

(2) INFORMATION FOR SEQ ID NO: 29:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 29:

GCTTTCTTGG ACGGTC                                                              16

(2) INFORMATION FOR SEQ ID NO: 30:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 30:

CTACCCCAAT CACTCC                                                              16

(2) INFORMATION FOR SEQ ID NO: 31:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 31:

AGCACCTCTC TCAACG                                                   16

(2) INFORMATION FOR SEQ ID NO: 32:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 32:

CCAATGGCAA ACAAGG                                                   16

(2) INFORMATION FOR SEQ ID NO: 33:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 33:

CTGAGGGCTC CACCCCA                                                  17

(2) INFORMATION FOR SEQ ID NO: 34:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 34:

ATCTCTTGTA CATGTC                                                   16

(2) INFORMATION FOR SEQ ID NO: 35:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 35:

ATCTCTTGTA CATGTC                                                   16

(2) INFORMATION FOR SEQ ID NO: 36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 36:

ATCTCATGTT CATGTC                                        16

(2) INFORMATION FOR SEQ ID NO: 37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 37:

CAGTGGGACA TGTACA                                        16

(2) INFORMATION FOR SEQ ID NO: 38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 38:

CAGTAGGACA TGAACA                                        16

(2) INFORMATION FOR SEQ ID NO: 39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 39:

CTGTTCAAGC CTCCAA                                        16

(2) INFORMATION FOR SEQ ID NO: 40:

```
    (i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 40:
```

AGCCTCCAAG CTGTGC                                                         16

```
(2) INFORMATION FOR SEQ ID NO: 41:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 41:
```

AAAGCCACCC AAGGCA                                                         16

```
(2) INFORMATION FOR SEQ ID NO: 42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 42:
```

TGGCTTTAGG ACATGGA                                                        17

```
(2) INFORMATION FOR SEQ ID NO: 43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 43:
```

GACATGTACA AGAGATGA                                                       18

```
(2) INFORMATION FOR SEQ ID NO: 44:

(i) SEQUENCE CHARACTERISTICS:
        (A) LENGTH: 18 base pairs
```

(B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 44:

GACATGAACA TGAGATGA                                                        18

(2) INFORMATION FOR SEQ ID NO: 45:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 45:

TGTACATGTC CCACTGTT                                                        18

(2) INFORMATION FOR SEQ ID NO: 46:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 46:

TGTTCATGTC CTACTGTT                                                        18

(2) INFORMATION FOR SEQ ID NO: 47:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

ACTGTTCAAG CCTCCAAG                                                        18

(2) INFORMATION FOR SEQ ID NO: 48:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

GGCACAGGCT TGGAGGCTT                                                    19

(2) INFORMATION FOR SEQ ID NO: 49:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 49:

AAAGCCACCC AAGGCACA                                                     18

(2) INFORMATION FOR SEQ ID NO: 50:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 50:

CCCAGAGGGT TGGGAAC                                                      17

(2) INFORMATION FOR SEQ ID NO: 51:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

CAGCATGGGG CAGAATCT                                                     18

(2) INFORMATION FOR SEQ ID NO: 52:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

TCCACCAGCA ATCCTCTG                                                          18

(2) INFORMATION FOR SEQ ID NO: 53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

GGATCCAGCC TTCAGAGC                                                          18

(2) INFORMATION FOR SEQ ID NO: 54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 54:

TCAGGAAGAC AGCCTAC                                                           17

(2) INFORMATION FOR SEQ ID NO: 55:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 55:

TTCAACCCCA ACAAGGATC                                                         19

(2) INFORMATION FOR SEQ ID NO: 56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 56:

AATGCTCCAG CTCCTAC                                                         17

(2) INFORMATION FOR SEQ ID NO: 57:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 57:

CTGCATTCAA AGCCAACT                                                        18

(2) INFORMATION FOR SEQ ID NO: 58:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 58:

CCCCATGGGG GACTGTTG                                                        18

(2) INFORMATION FOR SEQ ID NO: 59:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

CATACTCACA ACTGTGCCA                    19

(2) INFORMATION FOR SEQ ID NO: 60:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

```
        GGGCTTTCTT GGACGGTCC            19
```

(2) INFORMATION FOR SEQ ID NO: 61:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

```
CTCTCGAATG GGGGAAGA                                                  18
```

(2) INFORMATION FOR SEQ ID NO: 62:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:

```
CCTACCCCAA TCACTCCA                                                  18
```

(2) INFORMATION FOR SEQ ID NO: 63:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

```
AGCACCTCTC TCAACGACA                                                 19
```

(2) INFORMATION FOR SEQ ID NO: 64:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 64:

```
GCAAATTCCA GCAGTCCCG                                                 19
```

(2) INFORMATION FOR SEQ ID NO: 65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

GCCAATGGCA AACAAGGTA                                            19

(2) INFORMATION FOR SEQ ID NO: 66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

GACATGAACA TGAGATG                                              17

(2) INFORMATION FOR SEQ ID NO: 67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 67:

GGACATGAAC AAGAGAT                                              17

(2) INFORMATION FOR SEQ ID NO: 68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 68:

GACATGTACA AGAGATG                                              17

(2) INFORMATION FOR SEQ ID NO: 69:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 69:

ACATAAGAGG ACTCTTGGAC                                              20

(2) INFORMATION FOR SEQ ID NO: 70:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 70:

TACTTCAAAG ACTGTGTGTT TA                                           22

(2) INFORMATION FOR SEQ ID NO: 71:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 71:

ACAAAGACCT TTAAYCT                                                 17

(2) INFORMATION FOR SEQ ID NO: 72:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 72:

ACAAAGATCA TTAAYCT                                                 17

(2) INFORMATION FOR SEQ ID NO: 73:

(i) SEQUENCE CHARACTERISTICS:
        (A) LENGTH: 17 base pairs
        (B) TYPE: nucleic acid
        (C) STRANDEDNESS: single
```

(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 73:

TTCCACCAGC AATCCTC                                                              17

(2) INFORMATION FOR SEQ ID NO: 74:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 74:

GATCCAGCCT TCAGAGC                                                              17

(2) INFORMATION FOR SEQ ID NO: 75:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 75:

CAAGGTATGT TGCCCGTTTG TCC                                                       23

(2) INFORMATION FOR SEQ ID NO: 76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 76:

CCAAACAGTG GGGGAAAGCC C                                                         21

(2) INFORMATION FOR SEQ ID NO: 77:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 77:

CTACGGATGG AAATTGC                                                    17

(2) INFORMATION FOR SEQ ID NO: 78:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 78:

TACGGACGGA AACTGC                                                     16

(2) INFORMATION FOR SEQ ID NO: 79:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 79:

TTCGGACGGA AACTGC                                                     16

(2) INFORMATION FOR SEQ ID NO: 80:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 80:

CTTCGGACGG AAATTGC                                                    17

(2) INFORMATION FOR SEQ ID NO: 81:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO

```
        (iv) ANTI-SENSE: NO (xi) SEQUENCE DESCRIPTION: SEQ ID NO: 81:

CTACGGATAG AAATTGC                                                  17

(2) INFORMATION FOR SEQ ID NO: 82:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 82:

CTTCGGACAG AAATTGC                                                  17

(2) INFORMATION FOR SEQ ID NO: 83:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 83:

CTATGGGAGT GGGCCTCAGY C                                             21

(2) INFORMATION FOR SEQ ID NO: 84:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 84:

GCTGTAGGCA TAAATTGGTC TG                                            22

(2) INFORMATION FOR SEQ ID NO: 85:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 85:
```

```
CTCCACAGWA GCTCCAAATT C                                              21

(2) INFORMATION FOR SEQ ID NO: 86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 86:

ACATAAGAGG ACTCTTGGAC                                                20

(2) INFORMATION FOR SEQ ID NO: 87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 87:

TACTTCAAAG ACTGTGTGTT TA                                             22

(2) INFORMATION FOR SEQ ID NO: 88:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 88:

TAGGTTAAAG GTCTTTGT                                                  18

(2) INFORMATION FOR SEQ ID NO: 89:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

TAGGTTAATG ATCTTTGT                                                  18
```

(2) INFORMATION FOR SEQ ID NO: 90:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

CATGTCCCAC TGTTCAA                            17

(2) INFORMATION FOR SEQ ID NO: 91:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 91:

CATGTCCTAC TGTTCAA                            17

(2) INFORMATION FOR SEQ ID NO: 92:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 92:

TTCTGCCCCA TGCTGTA                            17

(2) INFORMATION FOR SEQ ID NO: 93:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 93:

TTCTGCCCCA TGCTGTAG                           18

(2) INFORMATION FOR SEQ ID NO: 94:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 94:

GGTAWAAAGG GACTCAMGAT G                                          21

(2) INFORMATION FOR SEQ ID NO: 95:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 95:

TCAGCTATAT GGATGAT                                               17

(2) INFORMATION FOR SEQ ID NO: 96:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 96:

CAGCTATATG GATGAT                                                16

(2) INFORMATION FOR SEQ ID NO: 97:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 97:

TTCAGCTATA TGGATG                                                16

(2) INFORMATION FOR SEQ ID NO: 98:

(i) SEQUENCE CHARACTERISTICS:
        (A) LENGTH: 17 base pairs
        (B) TYPE: nucleic acid
```

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

TCAGTTATAT GGATGAT                                              17

(2) INFORMATION FOR SEQ ID NO: 99:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 99:

TTTCAGTTAT ATGGATG                                              17

(2) INFORMATION FOR SEQ ID NO: 100:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 100:

TTTAGTTATA TGGATGA                                              17

(2) INFORMATION FOR SEQ ID NO: 101:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 101:

TCAGCTATGT GGATGAT                                              17

(2) INFORMATION FOR SEQ ID NO: 102:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 102:

TCAGTTATGT GGATGAT                                                        17

(2) INFORMATION FOR SEQ ID NO: 103:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 103:

TTTCAGCTAT GTGGATG                                                        17

(2) INFORMATION FOR SEQ ID NO: 104:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 104:

CAAGGTATGT TGCCCGTTTG TCC                                                 23

(2) INFORMATION FOR SEQ ID NO: 105:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 105:

GGYAWAAAGG GACTCAMGAT G                                                   21

(2) INFORMATION FOR SEQ ID NO: 106:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 106:

GGGTCACCAT ATTCTTGGG                                                            19

(2) INFORMATION FOR SEQ ID NO: 107:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 107:

GTTCCKGAAC TGGAGCCACC AG                                                        22

(2) INFORMATION FOR SEQ ID NO: 108:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 108:

CCGGAAAGCT TGAGCTCTTC TTTTTCACCT CTGCCTAATC                                     40

(2) INFORMATION FOR SEQ ID NO: 109:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 109:

CCGGAAAGCT TGAGCTCTTC AAAAAGTTGC ATGGTGCTGG                                     40

(2) INFORMATION FOR SEQ ID NO: 110:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 110:

GTGGTTCGCC GGGCTTG                                                          17

(2) INFORMATION FOR SEQ ID NO: 111:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 111:

CTGCGAGGCG AGGGAGTTCT TCTTC                                                 25

(2) INFORMATION FOR SEQ ID NO: 112:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 112:

TGCCATTTGT TCAGTGGTTC GTAGGGC                                               27

(2) INFORMATION FOR SEQ ID NO: 113:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 113:

CCGGCAGATG AGAAGGCACA GACGG                                                 25

(2) INFORMATION FOR SEQ ID NO: 114:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 114:

TTCAGCTATA TGGATGAT                                                         18

(2) INFORMATION FOR SEQ ID NO: 115:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 115:

TCAGCTATAT GGATGATG                                                18

(2) INFORMATION FOR SEQ ID NO: 116:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 116:

TTCAGCTATG TGGATGAT                                                18

(2) INFORMATION FOR SEQ ID NO: 117:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 117:

TCAGCTATGT GGATGATG                                                18

(2) INFORMATION FOR SEQ ID NO: 118:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 118:

GGCTTTGGGG CATGG                                                    15

(2) INFORMATION FOR SEQ ID NO: 119:

```
    (i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 119:

TGGCTTTGGG GCATG                                                         15

(2) INFORMATION FOR SEQ ID NO: 120:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 120:

GTGGCTTTGG GGCATG                                                        16

(2) INFORMATION FOR SEQ ID NO: 121:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 121:

GGCTTTGGGG CATGGA                                                        16

(2) INFORMATION FOR SEQ ID NO: 122:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 122:

TGGCTTTGGG ACATGG                                                        16

(2) INFORMATION FOR SEQ ID NO: 123:

(i) SEQUENCE CHARACTERISTICS:
        (A) LENGTH: 15 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 123:

GGCTTTGGGA CATGG                                                            15

(2) INFORMATION FOR SEQ ID NO: 124:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 124:

TGGCTTTGGG ACATG                                                            15

(2) INFORMATION FOR SEQ ID NO: 125:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 125:

GTGGCTTTGG GACATG                                                           16

(2) INFORMATION FOR SEQ ID NO: 126:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 126:

GGCTTTGGGA CATGGA                                                           16

(2) INFORMATION FOR SEQ ID NO: 127:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
        (ii) MOLECULE TYPE: DNA (genomic)

(iii) HYPOTHETICAL: NO (iv) ANTI-SENSE: NO (xi) SEQUENCE DESCRIPTION: SEQ ID NO: 127:

TCAGTTATAT GGATGATG                                                      18

(2) INFORMATION FOR SEQ ID NO: 128:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 128:

TTCAGTTATA TGGATGAT                                                      18

(2) INFORMATION FOR SEQ ID NO: 129:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 129:

TTTCAGTTAT ATGGATGAT                                                     19

(2) INFORMATION FOR SEQ ID NO: 130:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 130:

TCAGTTATGT GGATGATG                                                      18

(2) INFORMATION FOR SEQ ID NO: 131:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)
```

-continued (iii) HYPOTHETICAL: NO (iv) ANTI-SENSE: NO (xi) SEQUENCE DESCRIPTION: SEQ ID NO: 131:

TTCAGTTATG TGGATGAT                                                  18

(2) INFORMATION FOR SEQ ID NO: 132:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 132:

TTTCAGTTAT GTGGATGAT                                                 19

(2) INFORMATION FOR SEQ ID NO: 133:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 133:

TTTCAGTTAT GTGGATGA                                                  18

(2) INFORMATION FOR SEQ ID NO: 134:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 134:

TGCTGCTATG CCTCATCTTC                                                20

(2) INFORMATION FOR SEQ ID NO: 135:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 135:

CARAGACAAA AGAAAATTGG                                          20

(2) INFORMATION FOR SEQ ID NO: 136:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 136:

CTATGGATGG AAATTGC                                             17

(2) INFORMATION FOR SEQ ID NO: 137:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 137:

CCTATGGATG GAAATTG                                             17

(2) INFORMATION FOR SEQ ID NO: 138:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 138:

ACCTATGGAT GGAAATT                                             17

(2) INFORMATION FOR SEQ ID NO: 139:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 139:

CTCAAGGCAA CTCTATGTGG                                         20

(2) INFORMATION FOR SEQ ID NO: 140:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 140:

CTCAAGGCAA CTCTATGGG                                          19

(2) INFORMATION FOR SEQ ID NO: 141:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 141:

TCAAGGCAAC TCTATGTTG                                          19

(2) INFORMATION FOR SEQ ID NO: 142:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 142:

ATCCCATCAT CTTGGG                                             16

(2) INFORMATION FOR SEQ ID NO: 143:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 143:

ATCCCATCAT CTTGGGCGG                                          19

(2) INFORMATION FOR SEQ ID NO: 144:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 144:

TCCCATCATC TTGGGCGG                                      18

(2) INFORMATION FOR SEQ ID NO: 145:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 145:

CCCATCATCT TGGGCTGG                                      18

(2) INFORMATION FOR SEQ ID NO: 146:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 146:

TTCGCAAAAT ACCTATGG                                      18

(2) INFORMATION FOR SEQ ID NO: 147:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 147:

TTTCGCAAAA TACCTATG                                      18

(2) INFORMATION FOR SEQ ID NO: 148:

(i) SEQUENCE CHARACTERISTICS:

```
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 148:

CTTTCGCAAA ATACCTATG                                                19

(2) INFORMATION FOR SEQ ID NO: 149:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 149:

TCGCAAAATA CCTATGGG                                                 18

(2) INFORMATION FOR SEQ ID NO: 150:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 150:

TCTACTTCCA GGAACAT                                                  17

(2) INFORMATION FOR SEQ ID NO: 151:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 151:

TCTACTTCCA GGAACATC                                                 18

(2) INFORMATION FOR SEQ ID NO: 152:

(i) SEQUENCE CHARACTERISTICS:
        (A) LENGTH: 18 base pairs
        (B) TYPE: nucleic acid
        (C) STRANDEDNESS: single
```

```
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 152:

CTCTACTTCC AGGAACAT                                                    18

(2) INFORMATION FOR SEQ ID NO: 153:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 153:

CTCTACTTCC AGGAACAG                                                    18

(2) INFORMATION FOR SEQ ID NO: 154:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 154:

CTGCACGATT CCTGCT                                                      16

(2) INFORMATION FOR SEQ ID NO: 155:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 155:

TGCACGATTC CTGCTCA                                                     17

(2) INFORMATION FOR SEQ ID NO: 156:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)
```

(iii) HYPOTHETICAL: NO (iv) ANTI-SENSE: NO (xi) SEQUENCE DESCRIPTION: SEQ ID NO: 156:

CTGCACGATT CCTGCTC                                                          17

(2) INFORMATION FOR SEQ ID NO: 157:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 157:

TGCACGATTC CTGCTCAA                                                         18

(2) INFORMATION FOR SEQ ID NO: 158:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 158:

TTCGCAAGAT TCCTATG                                                          17

(2) INFORMATION FOR SEQ ID NO: 159:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 159:

CTTTCGCAAG ATTCCTAT                                                         18

(2) INFORMATION FOR SEQ ID NO: 160:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 160:

CTTTCGCAAG ATTCCTA                                                          17

(2) INFORMATION FOR SEQ ID NO: 161:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 161:

CTTTCGCAAG ATTCCTATG                                                        19

(2) INFORMATION FOR SEQ ID NO: 162:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 162:

CTCTATGTAT CCCTCCT                                                          17

(2) INFORMATION FOR SEQ ID NO: 163:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 163:

TCTATGTATC CCTCCTG                                                          17

(2) INFORMATION FOR SEQ ID NO: 164:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 164:

CTCTATGTAT CCCTCCTGG                                                19

(2) INFORMATION FOR SEQ ID NO: 165:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 165:

CCTCTATGTA TCCCTCCT                                                 18

(2) INFORMATION FOR SEQ ID NO: 166:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 166:

CTGTACCAAA CCTTCGG                                                  17

(2) INFORMATION FOR SEQ ID NO: 167:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 167:

CTGTACCAAA CCTTCG                                                   16

(2) INFORMATION FOR SEQ ID NO: 168:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 168:

GCTGTACCAA ACCTTCGG                                                 18

(2) INFORMATION FOR SEQ ID NO: 169:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 169:

TGTACCAAAC CTTCGGAG     18

(2) INFORMATION FOR SEQ ID NO: 170:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 170:

GGACCCTGCC GAACCT     16

(2) INFORMATION FOR SEQ ID NO: 171:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 171:

GGACCCTGCC GAACCG     16

(2) INFORMATION FOR SEQ ID NO: 172:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 172:

GGGACCCTGC CGAAC     15

(2) INFORMATION FOR SEQ ID NO: 173:

```
        (i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 173:

GGACCCTGCC GAAC                                                        14

(2) INFORMATION FOR SEQ ID NO: 174:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 174:

GTTGCTGTTC AAAACCTT                                                    18

(2) INFORMATION FOR SEQ ID NO: 175:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 175:

GTTGCTGTTC AAAACCTG                                                    18

(2) INFORMATION FOR SEQ ID NO: 176:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 176:

TGTTGCTGTT CAAAACCTG                                                   19

(2) INFORMATION FOR SEQ ID NO: 177:

(i) SEQUENCE CHARACTERISTICS:
            (A) LENGTH: 20 base pairs
            (B) TYPE: nucleic acid
```

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 177:

ATGTTGCTGT TCAAAACCTG                                                   20

(2) INFORMATION FOR SEQ ID NO: 178:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 178:

GATCCACGAC CACCA                                                        15

(2) INFORMATION FOR SEQ ID NO: 179:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 179:

GGATCCACGA CCACCA                                                       16

(2) INFORMATION FOR SEQ ID NO: 180:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 180:

GGATCCACGA CCACC                                                        15

(2) INFORMATION FOR SEQ ID NO: 181:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 181:

GATCCACGAC CACCAGG                                                    17

(2) INFORMATION FOR SEQ ID NO: 182:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 182:

TGTTCCAAAC CCTCGG                                                     16

(2) INFORMATION FOR SEQ ID NO: 183:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 183:

CTGTTCCAAA CCCTCG                                                     16

(2) INFORMATION FOR SEQ ID NO: 184:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 184:

CTGTTCCAAA CCCTCGG                                                    17

(2) INFORMATION FOR SEQ ID NO: 185:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 185:

GTTCCAAACC CTCGGAT                                                      17

(2) INFORMATION FOR SEQ ID NO: 186:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 186:

GCCAAATCTG TGCAGC                                                       16

(2) INFORMATION FOR SEQ ID NO: 187:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 187:

CCAAATCTGT GCAGCAT                                                      17

(2) INFORMATION FOR SEQ ID NO: 188:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 188:

GCCAAATCTG TGCAGCAG                                                     18

(2) INFORMATION FOR SEQ ID NO: 189:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 189:

GGCCAAATCT GTGCAGC                                                    17

(2) INFORMATION FOR SEQ ID NO: 190:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 190:

ATCAACAACA ACCAGTA                                                    17

(2) INFORMATION FOR SEQ ID NO: 191:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 191:

GATCAACAAC AACCAGT                                                    17

(2) INFORMATION FOR SEQ ID NO: 192:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 192:

GATCAACAAC AACCAGTA                                                   18

(2) INFORMATION FOR SEQ ID NO: 193:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 193:

GGATCAACAA CAACCAGT                                                   18

(2) INFORMATION FOR SEQ ID NO: 194:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 194:

TCAAGGCAAC TCTATGTGG    19

(2) INFORMATION FOR SEQ ID NO: 195:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 195:

AGGTTAAAGG TCTTTGT    17

(2) INFORMATION FOR SEQ ID NO: 196:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 196:

TAGGTTAAAG GTCTTTGG    18

(2) INFORMATION FOR SEQ ID NO: 197:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 197:

TTAGGTTAAA GGTCTTT    17

(2) INFORMATION FOR SEQ ID NO: 198:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 198:

GGTTAAAGGT CTTTGTAGG                                                19

(2) INFORMATION FOR SEQ ID NO: 199:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 199:

AGGTTAATGA TCTTTGT                                                  17

(2) INFORMATION FOR SEQ ID NO: 200:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 200:

TAGGTTAATG ATCTTTGG                                                 18

(2) INFORMATION FOR SEQ ID NO: 201:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 201:

CTTTCGCAAG ATTCCTATGG                                               20

(2) INFORMATION FOR SEQ ID NO: 202:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 202:

GCTTTCGCAA GATTCCTATG                                       20

(2) INFORMATION FOR SEQ ID NO: 203:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 203:

GCTTTCGCAA GATTCCTATG G                                     21

(2) INFORMATION FOR SEQ ID NO: 204:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 204:

CTTTCGCAAG ATTCCTATGG G                                     21

(2) INFORMATION FOR SEQ ID NO: 205:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 205:

GCTGTACCAA ACCTTCGGAG                                       20

(2) INFORMATION FOR SEQ ID NO: 206:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 206:

TGCTGTACCA AACCTTCGG                                                19

(2) INFORMATION FOR SEQ ID NO: 207:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 207:

TGCTGTACCA AACCTTCGGA G            21

(2) INFORMATION FOR SEQ ID NO: 208:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 208:

GCTGTACCAA ACCTTCGGAT                                               20

(2) INFORMATION FOR SEQ ID NO: 209:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 209:

TGGTTCGCCG GGCTTT                                                   16

(2) INFORMATION FOR SEQ ID NO: 210:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

-continued (iii) HYPOTHETICAL: NO (iv) ANTI-SENSE: NO (xi) SEQUENCE DESCRIPTION: SEQ ID NO: 210:

GTGGTTCGCC GGGCTTG                17

(2) INFORMATION FOR SEQ ID NO: 211:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 211:

GGTTCGCCGG GCTTTC                                                        16

(2) INFORMATION FOR SEQ ID NO: 212:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 212:

TGGTTCGCCG GGCTTTC                                                       17

(2) INFORMATION FOR SEQ ID NO: 213:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 213:

AGTGGTTCGC CGGGCTGG                                                      18

(2) INFORMATION FOR SEQ ID NO: 214:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 214:

AGGATCCACG ACCACCAGG                                                            19

(2) INFORMATION FOR SEQ ID NO: 215:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 215:

AGGATCCACG ACCACCAGT                                                            19

(2) INFORMATION FOR SEQ ID NO: 216:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 216:

CAGGATCCAC GACCACCAGG                                                           20

(2) INFORMATION FOR SEQ ID NO: 217:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 217:

CTGTTCCAAA CCCTCGGAG                                                            19

(2) INFORMATION FOR SEQ ID NO: 218:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 218:

```
CTGTTCCAAA CCCTCGGAT                                                    19

(2) INFORMATION FOR SEQ ID NO: 219:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 219:

GCTGTTCCAA ACCCTCGGAG                                                   20

(2) INFORMATION FOR SEQ ID NO: 220:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 220:

CTGAACCTTT ACCCCGTTGC                                                   20

(2) INFORMATION FOR SEQ ID NO: 221:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 221:

CTCGCCAACT TACAAGGCCT TTC                                               23

(2) INFORMATION FOR SEQ ID NO: 222:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 222:

AGAATGGCTT GCCTGAGTGC                                                   20
```

(2) INFORMATION FOR SEQ ID NO: 223:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 223:

GCTTTCGCAA GATTCCTATG GG                                        22

(2) INFORMATION FOR SEQ ID NO: 224:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 224:

GGCTTTCGCA AGATTCCTAT GG                                        22

(2) INFORMATION FOR SEQ ID NO: 225:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 225:

GGCTTTCGCA AGATTCCTAT GGG                                       23

(2) INFORMATION FOR SEQ ID NO: 226:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 226:

GGCTTTCGCA AGATTCCTAT GGGA                                     24

(2) INFORMATION FOR SEQ ID NO: 227:

(i) SEQUENCE CHARACTERISTICS:

(A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 227:

CAGCTATATG GATGATGTG                                                19

(2) INFORMATION FOR SEQ ID NO: 228:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 228:

AGCTATATGG ATGATGTGGG                                               20

(2) INFORMATION FOR SEQ ID NO: 229:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 229:

GCTATATGGA TGATGTGGT                                                19

(2) INFORMATION FOR SEQ ID NO: 230:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 230:

AGCTATATGG ATGATGTGGT                                               20

(2) INFORMATION FOR SEQ ID NO: 231:

(i) SEQUENCE CHARACTERISTICS:
        (A) LENGTH: 19 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 231:

CAGCTATATG GATGATATA                                                19

(2) INFORMATION FOR SEQ ID NO: 232:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 232:

AGCTATATGG ATGATATAGG                                               20

(2) INFORMATION FOR SEQ ID NO: 233:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 233:

GCTATATGGA TGATATAGT                                                19

(2) INFORMATION FOR SEQ ID NO: 234:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 234:

AGCTATATGG ATGATATAGT                                               20

(2) INFORMATION FOR SEQ ID NO: 235:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 235:

CCATCATCTT GGGCTTG                                                          17

(2) INFORMATION FOR SEQ ID NO: 236:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 236:

CATCATCTTG GGCTTT                                                           16

(2) INFORMATION FOR SEQ ID NO: 237:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 237:

CCATCATCTT GGGCTTT                                                          17

(2) INFORMATION FOR SEQ ID NO: 238:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 238:

CCATCATCTT GGGCTTTC                                                         18

(2) INFORMATION FOR SEQ ID NO: 239:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 239:

CCCACTGTCT GGCTTTC                                                            17

(2) INFORMATION FOR SEQ ID NO: 240:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 240:

CCACTGTCTG GCTTTC                                                             16

(2) INFORMATION FOR SEQ ID NO: 241:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 241:

CCACTGTCTG GCTTT                                                              15

(2) INFORMATION FOR SEQ ID NO: 242:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 242:

CCCACTGTCT GGCTTG                                                             16

(2) INFORMATION FOR SEQ ID NO: 243:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 243:

TATATGGATG ATGTGGTA                                              18

(2) INFORMATION FOR SEQ ID NO: 244:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 244:

TATGTGGATG ATGTGGTA                                              18

(2) INFORMATION FOR SEQ ID NO: 245:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 245:

TATATAGATG ATGTGGTA                                              18

(2) INFORMATION FOR SEQ ID NO: 246:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 246:

TATATTGATG ATGTGGTA                                              18

(2) INFORMATION FOR SEQ ID NO: 247:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 247:

TATGTAGATG ATGTGGTA                                              18

(2) INFORMATION FOR SEQ ID NO: 248:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 248:

TATGTTGATG ATGTGGTA                                        18

(2) INFORMATION FOR SEQ ID NO: 249:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 249:

TATATGGATG ATATAGTA                                        18

(2) INFORMATION FOR SEQ ID NO: 250:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 250:

TATATGGATG ATATCGTA                                        18

(2) INFORMATION FOR SEQ ID NO: 251:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 251:

TATGTGGATG ATATAGTA                                        18

(2) INFORMATION FOR SEQ ID NO: 252:

```
        (i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 252:

TATGTGGATG ATATCGTA                                                    18

(2) INFORMATION FOR SEQ ID NO: 253:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 253:

TATATAGATG ATATAGTA                                                    18

(2) INFORMATION FOR SEQ ID NO: 254:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 254:

TATATAGATG ATATCGTA                                                    18

(2) INFORMATION FOR SEQ ID NO: 255:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 255:

TATATTGATG ATATAGTA                                                    18

(2) INFORMATION FOR SEQ ID NO: 256:

(i) SEQUENCE CHARACTERISTICS:
            (A) LENGTH: 18 base pairs
            (B) TYPE: nucleic acid
```

(C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 256:

TATATTGATG ATATCGTA                                                     18

(2) INFORMATION FOR SEQ ID NO: 257:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 257:

TATGTAGATG ATATAGTA                                                     18

(2) INFORMATION FOR SEQ ID NO: 258:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 258:

TATGTAGATG ATATCGTA                                                     18

(2) INFORMATION FOR SEQ ID NO: 259:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 259:

TATGTTGATG ATATAGTA                                                     18

(2) INFORMATION FOR SEQ ID NO: 260:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 260:

TATGTTGATG ATATCGTA                                                         18

(2) INFORMATION FOR SEQ ID NO: 261:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 261:

TATATGGATG ATCTGGTA                                                         18

(2) INFORMATION FOR SEQ ID NO: 262:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 262:

TATGTGGATG ATCTGGTA                                                         18

(2) INFORMATION FOR SEQ ID NO: 263:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 263:

TATATAGATG ATCTGGTA                                                         18

(2) INFORMATION FOR SEQ ID NO: 264:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 264:

TATATTGATG ATCTGGTA                                                                    18

(2) INFORMATION FOR SEQ ID NO: 265:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 265:

TATGTAGATG ATCTGGTA                                                                    18

(2) INFORMATION FOR SEQ ID NO: 266:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 266:

TATGTTGATG ATCTGGTA                                                                    18

(2) INFORMATION FOR SEQ ID NO: 267:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 267:

TATGGGAGTG GGCCTCAG                                                                    18

(2) INFORMATION FOR SEQ ID NO: 268:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO

```
        (xi) SEQUENCE DESCRIPTION: SEQ ID NO: 268:

TATGGGATTG GGCCTCAG                                                  18

(2) INFORMATION FOR SEQ ID NO: 269:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 269:

CAGTCCGTTT CTCTTGGC                                                  18

(2) INFORMATION FOR SEQ ID NO: 270:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 270:

CAGTCTGTTT CTCTTGGC                                                  18

(2) INFORMATION FOR SEQ ID NO: 271:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 271:

CAGTCCGTTT CTCATGGC                                                  18

(2) INFORMATION FOR SEQ ID NO: 272:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 272:

CAGTCTGTTT CTCATGGC                                                  18
```

(2) INFORMATION FOR SEQ ID NO: 273:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 273:

```
CAGTCCGTTT CTCCTGGC                                              18
```

(2) INFORMATION FOR SEQ ID NO: 274:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 274:

```
CAGTCTGTTT CTCCTGGC                                              18
```

(2) INFORMATION FOR SEQ ID NO: 275:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 275:

```
CAGCCCGTTT CTCCTGGC                                              18
```

(2) INFORMATION FOR SEQ ID NO: 276:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 276:

```
CAGCCTGTTT CTCCTGGC                                              18
```

(2) INFORMATION FOR SEQ ID NO: 277:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 277:

CAGCCCGTTT CTCATGGC                                                 18

(2) INFORMATION FOR SEQ ID NO: 278:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 278:

CAGCCTGTTT CTCATGGC                                                 18

(2) INFORMATION FOR SEQ ID NO: 279:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 279:

AATTCCACTG CCTTCCACCA AGCTCTGCAG GATCCCAAAG TCAGGGGTCT GTATCTTCCT   60
GCTGGTGGCT CCAGTTCAGG AACAGTAAAC CCTGCTCCGA ATATTGCCTC TCACATCTCG   120
TCAATCTCCG CGAGGACTGG GGACCCTGTG ACGAACATGG AGAACATCAC ATCAGGATTC   180
CTAGGACCCC TGCTCGTGTT ACAGGCGGGG TTTTTCTTGT TGACAAGAAT CCTCACAATA   240
CCGCAGAGTC TAGACTCGTG GTGGACTTCT CTCAATTTTC TAGGGGGGTC ACCCGTGTGT   300
CTTGGCCAAA ATTCGCAGTC CCCAACCTCC AATCACTCAC CAACCTCCTG TCCTCCAATT   360
TGTCCTGGTT ATCGCTGGAT GTGTCTGCGG CGTTTTATCA TATTCCTCTT CATCCTGCTG   420
CTATGCCTCA TCTTCTTGTT GGTTCTTCTG GATTATCAAG GTATGTTGCC CGTTTGTCCT   480
CTAATTCCAG GATCAACAAC AACCAGTACG GGACCATGCA AAACCTGCAC GACTCCTGCT   540
CAAGGCAACT CTATGTTTCC CTCATGTTGC TGTACAAAAC CTACGGATGG AAATTGCACC   600
TGTATTCCCA TCCCATCGTC CTGGGCTTTC GCAAAATACC TATGGGAGTG GGCCTCAGTC   660
CGTTTCTCTT GGCTCAGTTT ACTAGTGCCA TTTGTTCAGT GGTTCGTAGG CTTTCCCCC   720
ACTGTTTGGC TTTCAGCTAT ATGGATGATG TGGTATTGGG GGCCAAGACT GTACAGCATC   780

```
GTGAGTCCCT TTATACCGCT GTTACCAATT TTCTTTTGTC TCTGGGTATA CATTTAAACC    840

CTAACAAAAC AAAAAGATGG GGTTATTCCC TAAACTTCAT GGTCTACATA ATTGGAAGTT    900

GGGGAACATT GCCACAGGAT CATATTGTAC AAAAGATCAA ACACTGTTTT AGAAAACTTC    960

CTGTTAACAG GCCTATTGAT TGGAAAGTAT GTCAAAGAAT GTGGGTCTT TTGGGCTTTG   1020

CTGCTCCATT TACTCAATGT GGATATCCTG CCTTAATGCC TTTGTATGCA TGTATACAAG   1080

CTAAACAGGC TTTCACTTTC TCGCCAACTT ACAAGGCCTT TCTAAGTAAA CAGTACATGA   1140

ACCTTTACCC CGTTGCTCGG CAACGGCCTG GTCTGTGCCA AGTGTTTGCT GACGCAACCC   1200

CCACTGGCTG GGGCTTGGCC ATAGGCCATC AGCGCATGCG TGGAACCTTT GTGGCTCCTC   1260

TGCCGATCCA TACTGCGGAA CTCCTAGCCG CTTGTTTTGC TCGCAGCCGG TCTGGAGCAA   1320

AGCTCATCGG AACTGACAAT TCTGTCGTCC TCTCGCGGAA ATATACATCG TTTCCATGGC   1380

TGCTAGGCTG TACTGCCAAC TGGATCCTTC GCGGGACGTC CTTTGTTTAC GTCCCGTCGG   1440

CGCTGAATCC CGCGGACGAC CCCTCTCGGG GCCGCTTGGG AGTCTCTCGT CCCCTTCTCC   1500

GTCTGCCGTT CCAGCCGACC ACGGGGCGCA CCTCTCTTTA CGCGGTCTCC CCGTCTGTGC   1560

CTTCTCATCT GCCGGTCCGT GTGCACTTCG CTTCACCTCT GCACGTTGCA TGGAGACCAC   1620

CGTGAACGCC CATCAGATCC TGCCCAAGGT CTTACATAAG AGGACTCTTG GACTCTCAGC   1680

AATGTCAACG ACCGACCTTG AGGCCTACTT CAAAGACTGT GTGTTTAAGG ACTGGGAGGA   1740

GCTGGGGGAG GAGATTAGGT TAAAGGTCTT TGTATTAGGA GGCTGTAGGC ATAAATTGGT   1800

CTGCGCACCA GCACCATGCA ACTTTTTCAC CTCTGCCTAA TCATCTCTTG TACATGTCCC   1860

ACTGTTCAAG CCTCCAAGCT GTGCCTTGGG TGGCTTTGGG GCATGGACAT TGACCCTTAT   1920

AAAGAATTTG GAGCTACTGT GGAGTTACTC TCGTTTTTGC CTTCTGACTT CTTTCCTTCC   1980

GTCAGAGATC TCCTAGACAC CGCCTCAGCT CTGTATCGAG AAGCCTTAGA GTCTCCTGAG   2040

CATTGCTCAC CTCACCATAC TGCACTCAGG CAAGCCATTC TCTGCTGGGT GGAATTGATG   2100

ACTCTAGCTA CCTGGGTGGG TAATAATTTG GAAGATCCAG CATCCAGGGA TCTAGTAGTC   2160

AATTATGTTA ATACTAACAT GGGTTTAAAG ATCAGGCAAC TATTGTGGTT TCATATATCT   2220

TGCCTTACTT TTGGAAGAGA GACTGTGCTT GAATATTTGG TCTCTTTCGG AGTGTGGATT   2280

CGCACTCCTC CAGCCTATAG ACCACCAAAT GCCCCTATCT TATCAACACT TCCGGAAACT   2340

ACTGTTGTTA GACGACGGGA CCGAGGCAGG TCCCCTAGAA GAAGAACTCC CTCGCCTCGC   2400

AGACGCAGAT CTCAATCGCC GCGTCGCAGA AGATCTCAAT CTCGGGAATC TCAATGTTAG   2460

TATTCCTTGG ACTCATAAGG TGGGAAACTT TACTGGGCTT TATTCCTCTA CAGTACCTAT   2520

CTTTAATCCT GAATGGCAAA CTCCTTCCTT TCCTAAGATT CATTTACAAG AGGACATTAT   2580

TAATAGGTGT CAACAATTTG TGGGCCCTCT CACTGTAAAT GAAAAGAGAA GATTGAAATT   2640

AATTATGCCT GCCAGATTCT ATCCTACCCA CACTAAATAT TTGCCCTTAG ACAAAGGAAT   2700

TAAACCTTAT TATCCAGATC AGGTAGTTAA TCATTACTTC CAAACCAGAC ATTATTTACA   2760

TACTCTTTGG AAGGCTGGTA TTCTATATAA GAGGGAAACC ACACGTAGCG CATCATTTTG   2820

CGGGTCACCA TATTCTTGGG AACAAGAGCT ACAGCATGGG AGGTTGGTCA TCAAAACCTC   2880

GCAAAGGCAT GGGGACGAAT CTTTCTGTTC CCAACCCTCT GGGATTCTTT CCCGATCATC   2940

AGTTGGACCC TGCATTCGGA GCCAACTCAA ACAATCCAGA TTGGGACTTC AACCCCATCA   3000

AGGACCACTG GCCAGCAGCC AACCAGGTAG GAGTGGGAGC ATTCGGGCCA AGGCTCACCC   3060

CTCCACACGG CGGTATTTTG GGGTGGAGCC CTCAGGCTCA GGGCATATTG ACCACAGTGT   3120

CAACAATTCC TCCTCCTGCC TCCACCAATC GGCAGTCAGG AAGGCAGCCT ACTCCCATCT   3180
```

```
CTCCACCTCT AAGAGACAGT CATCCTCAGG CCATGCAGTG G                    3221
```

(2) INFORMATION FOR SEQ ID NO: 280:

(i) SEQUENCE CHARACTERISTICS:
        (A) LENGTH: 3200 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 280:

```
AATTCCACTG CCTTGCACCA AGCTCTGCAG GATCCCAGAG TCAGGGGTCT GTATCTTCCT      60
GCTGGTGGCT CCAGTTCAGG AACAGTAAAC CCTGCTCCGA ATATTGCCTC TCACATCTCG     120
TCAATCTCCG CGAGGACTGG GGACCCTGTG ACGATCATGG AGAACATCAC ATCAGGATTC     180
CTAGGACCCC TGCTCGTGTT ACAGGCGGGG TTTTTCTTGT TGACAAGAAT CCTCACAATA     240
CCGCAGAGTC TAGACTCGTG GTGGACTTCT CTCAATTTTC TAGGGGGATC ACCCGTGTGT     300
CTTGGCCAAA ATTCGCAGTC CCCAACCTCC AATCACTCAC CAACCTCCTG TCCTCCAATT     360
TGTCCTGGTT ATCGCTGGAT GTGTCTGCGG CGTTTTATCA TATTCCTCTT CATCCTGCTG     420
CTATGCCTCA TCTTCTTATT GGTTCTTCTG GATTATCAAG GTATGTTGCC CGTTTGTCCT     480
CTAATTCCAG GATCAACAAC AACCAGTACG GGACCATGCA AAACCTGCAC GACTCCTGCT     540
CAAGGCAACT CTAAGTTTCC CTCATGTTGC TGTACAAAAC CTACGGATGG AAATTGCACC     600
TGTATTCCCA TCCCATCGTC CTGGGCTTTC GCAAATACC TATGGGAGTG GCCTCAGTC      660
CGTTTCTCTT GGCTCAGTTT ACTAGTGCCA TTTGTTCAGT GGTTCGTAGG GCTTTCCCCC     720
ACTGTTTGGC TTTCAGCTAT ATGGATGATG TGGTATTGGG GGCCAAGTCT GTACAGCATC     780
GTGAGTCCCT TTATACCGCT GTTACCAATT TTCTTTTGTC TCTGGGTATA CATTTAAACC     840
CTAACAAAAC AAAAAGATGG GGTTATTCCC TAAACTTCAT GGGCTACATA ATTGGAAGTT     900
GGGGAACTTT GCCACAGGAT CATATTGTAC AAAAGATCAA ACACTGTTTT AGAAAACTTC     960
CTGTTAACAG GCCTATTGAT TGGAAAGTAT GTCAAAGAAT TGTGGGTCTT TTGGGCTTTG    1020
CTGCTCCATT TACACAATGT GGATATCCTG CCTTAATGCC TTTGTATGCA TGTATACAAG    1080
CTAAACAGGC TTTCACTTTC TCGCCAACTT ACAAGGCCTT TCTAAGTAAA CAGTACATGA    1140
ACCTTTACCC CGTTGCTCGG CAACGGCCTG GTCTGTGCCA AGTGTTTGCT GACGCAACCC    1200
CCACTGGCTG GGGCTTAGCC ATAGGCCATC AGCGCATGCG TGGAACCTTT GTGGCTCCTC    1260
TGCCGATCCA TACTGCGGAA CTCCTAGCCG CTTGTTTTGC TCGCAGCCGG TCTGGAGCAA    1320
AGCTCATCGG AACTGACAAT TCTGTCGTCC TCTCGCGGAA ATATACATCA TTTCCATGGC    1380
TGCTAGGCTG TACTGCCAAC TGGATCCTTC GCGGGACGTC CTTTGTTTAC GTCCCGTCGG    1440
CGCTGAATCC CGCGGACGAC CCCTCTCGGG GCCGCTTGGG ACTCTCTCGT CCCCTTCTCC    1500
GTCTGCCGTT CCAGCCGACC ACGGGGCGCA CCTCTCTTTA CGCGGTCTCC CCGTCTGTGC    1560
CTTCTCATCT GCCGGTCCGT GTGCACTTCG CTTCACCTCT GCACGTTGCA TGGCGACCAC    1620
CGTGAACGCC CATCAGATCC TGCCCAAGGT CTTACATAAG AGGACTCTTG GACTCCCAGC    1680
AATGTCAACG ACCGACCTTG AGGCCTACTT CAAAGACTGT GTGTTAAGG ACTGGGAGGA     1740
GTTGGGGGAG GAGATTAGGT TAATGATCTT TGTATTAGGA GGCTGTAGGC ATAAATTGGT    1800
```

```
CTGCGCACCA GCACCATGCA ACTTTTTCAC CTCTGCCTAA TCATCTCTTG TACATGTCCC    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCC    1980

GTACGAGATC TCCTAGACAC CGCCTCAGCT CTGTATCGAG AAGCCTTAGA GTCTCCTGAG    2040

CATTGCTCAC CTCACCATAC TGCACTCAGG CAAGCCATTC TCTGCTGGGG GGAATTGATG    2100

ACTCTAGCTA CCTGGGTGGG TAATAATTTG CAAGATCCAG CATCCAGAGA TCTAGTAGTC    2160

AATTATGTTA ATACTAACAT GGGTTTAAAG ATCAGGCAAC TATTGTGGTT TCATATATCT    2220

TGCCTTACTT TTGGAAGAGA GACTGTACTT GAATATTTGG TCTCTTTCGG AGTGTGGATT    2280

CGCACTCCTC CAGCCTATAG ACCACCAAAT GCCCCTATCT TATCAACACT TCCGGAAACT    2340

ACTGTTGTTA GACGACGGGA CCGAGGCAGG TCCCCTAGAA GAAGAACTCC CTCGCCTCGC    2400

AGACGCAGAT CTCAATCGCC GCGTCGCAGA AGATCTCAAT CTCGGGAATC TCAATGTTAG    2460

TATTCCTTGG ACTCATAAGG TCGGAAACTT TACGGGGCTT TATTCCTCTA CAGTACCTAT    2520

CTTTAATCCT GAATGGCAAA CTCCTTCCTT TCCTAAGATT CATTTACAAG AGGACATTAT    2580

TAATAGGTGT CAACAATTTG TGGGCCCTCT CACTGTAAAT GAAAAGAGAA GATTGAAATT    2640

AATTATGCCT GCTAGATTCT ATCCTACCCA CACTAAATAT TTGCCCTTAG ACAAAGGAAT    2700

TAAACCTTAT TATCCAGATC AGGTAGTTAA TCATTACTTC CAAACCAGAC ATTATTTACA    2760

TACTCTTTGG AAGGCTGGTA TTCTATATAA GAGGGAAACC ACACGTAGCG CATCATTTTG    2820

CGGGTCACCA TATTCTTGGG AACAAGAGCT ACAGCATTCG CAAAGGCATG GGACGAATC    2880

TTTCTGTTCC CAACCCTCTG GGATTCCTTC CCGATCATCA GTTGGACCCT GCATTCGGAG    2940

CCAACTCAAC AAATCCAGAT TGGGACTTCA ACCCCATCAA GGACCACTGG CCAGCAGCCA    3000

ACCAGGTAGG AGTGGGAGCA TTCGGGCCAG GGCTCACCCC TCCACACGGC GGTATTTTGG    3060

GGTGGAGCCC TCAGGCTCAG GGCATATTGA CCACAGTGTC AACAATTCCT CCTCCTGCCT    3120

CCACCAATCG GCAGTCAGGA AGGCAGCCTA CTCCCATCTC TCCACCTCTA AGAGACAGTC    3180

ATCCTCAGGC CATGCAGTGG                                              3200

(2) INFORMATION FOR SEQ ID NO: 281:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 281:

AATTCCACTG CCTTCCACCA AGCTCTGCAA GACCCCAGAG TCAGGGGTCT GTATTTTCCT      60

GCTGGTGGCT CCAGTTCAGG AACAGTAAAC CCTGCTCCGA ATATTGCCTC TCACATCTCG     120

TCAATCTCCG CGAGGACCGG GGACCCTGTG ACGAACATGG AGAACATCAC ATCAGGATTC     180

CTAGGACCCC TGCCCGTGTT ACAGGCGGGG TTTTTCTTGT TGACAAGAAT CCTCACAATA     240

CCGCAGAGTC TAGACTCGTG GTGGACTTCT CTCAATTTTC TAGGGGGATC ACCCGTGTGT     300

CTTGGCCAAA ATTCGCGATC CCCAACCTCC AATCACTCAC CAACCTCCTG TCCTCCAATT     360

TGTCCTGGTT ATCGCTGGAT GTGTCTGCGG CGTTTTATCA TATTCCTCTT CATCCTGCTG     420
```

```
CTATGCCTCA TCTTCTTATT GGTTCTTCTG GATTATCAAG GTATGTTGCC CGTTTGTCCT    480

CTAATTCTAG GATCAACAAC AACCAGTACG GGACCATGCA AAACCTGCAC GACTCCTGCT    540

CAAGGCAACT CTATGTTTCC CTCATGTTGC TGTACAAAAC CTACGGATGG AAATTGCACC    600

TGTATTCCCA TCCCATCGTC TTGGGCTTTC GCAAAATACC TATGGGAGTG GGCCTCAGTC    660

CGTTTCTCTT GGCTCAGTTT ACTAGTGCCA TTTGTTCAGT GGTTCGTAGG GCTTTCCCCC    720

ACTGTTTGGC TTTCAGCTAT ATGGATGATG TGGTATTGGG GGCCAAGTCT GTACAGCATC    780

GTGAGTTCCT TTATACCGCT GTTACCAATT TTCTTTTGTC TCTGGGTATA CATTTAAACC    840

CTAACAAAAC AAAAAGATGG GGTTATTCCC TAAACTTCAT GGGTTATGTA ATTGGAAGTT    900

GGGGAACATT GCCACAGGAT CATATTGTAC AAAAAATCAA ACACTGTTTT AGAAAACTTC    960

CTGTTAACAG GCCTATTGAT TGGAAAGTAT GTCAAAGAAT TGTGGGTCTT TTGGGCTTTG    1020

CTGCTCCTTT TACACAATGT GGATATCCTG CCTTAATGCC CTTGTATGCA TGTATACAAG    1080

CTAAACAGGC TTTCACTTTC TCGCCAACTT ACAAGGCCTT TCTAAGTAAA CAGTACATGA    1140

ACCTTTACCC CGTTGCTCGG CAACGGCCTG GTCTGTGCCA AGTATTTGCT GATGCAACCC    1200

CCACTGGCTG GGGCTTGGCC ATAGGCCATC AGCGCATGCG CGGAACCTTT GTGGCTCCTC    1260

TGCCGATCCA TACTGCGGAA CTCCTAGCCG CTTGTTTTGC TCGCAGCCGG TCTGGAGCGA    1320

AACTCATCGG AACTGACAAT TCTGTCGTCC TCTCGCGGAA ATATACCTCG TTTCCATGGC    1380

TACTAGGCTG TGCTGCCAAC TGGATCCTTC GCGGGACGTC CTTTGTTTAC GTCCCGTCGG    1440

CGCTGAATCC CGCGGACGAC CCCTCTCGGG GCCGCTTGGG ACTCTCTCGT CCCCTTCTCC    1500

GTCTGCCGTT CCAGCCGACC ACGGGGCGCA CCTCTCTTTA CGCGGTCTCC CCGTCTGTGC    1560

CTTCTCATCT GCCGGTCCGT GTGCACTTCG CTTCACCTCT GCACGTTGCA TGGAGACCAC    1620

CGTGAACGCC CATCAGATCC TGCCCAAGGT CTTACATAAG AGGACTCTTG GACTCCCAGC    1680

AATGTCAACG ACCGACCTTG AGGCCTACTT CAAAGACTGT GTGTTTAAGG ACTGGGAGGA    1740

GCTGGGGGAG GAGATTAGGT TAAAGGTCTT TGTATTAGGA GGCTGTAGGC ATAAATTGGT    1800

CTGCGCACCA GCACCATGCA ACTTTTTCAC CTCTGCCTAA TCATCTCTTG TACATGTCCC    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCC    1980

GTCAGAGATC TCCTAGACAC CGCCTCGGCT CTGTATCGGG AAGCCTTAGA GTCTCCTGAG    2040

CATTGCTCAC CTCACCATAC CGCACTCAGG CAAGCCATTC TCTGCTGGGG GGAATTGATG    2100

ACTCTAGCTA CCTGGGTGGG TAATAATTTG GAAGATCCAG CATCCAGGGA TCTAGTAGTC    2160

AATTATGTTA ATACTAACAT GGGATTAAAG ATCAGGCAAC TCTTGTGGTT TCATATCTCT    2220

TGCCTTACTT TTGGAAGAGA AACTGTACTT GAATATTTGG TCTCTTTCGG AGTGTGGATT    2280

CGCACTCCTC CAGCCTATAG ACCACCAAAT GCCCCTATCT TATCAACACT TCCGGAAACT    2340

ACTGTTGTTA GACGACGGGA CCGAGGCAGG TCCCCTAGAA GAAGAACTCC CTCGCCTCGC    2400

AGACGCAGAT CTCAATCGCC GCGTCGCAGA AGATCTCAAT CTCGGGAATC TCAATGTTAG    2460

TATTCCTTGG ACTCATAAGG TGGGAAACTT CACTGGGCTT TATTCCTCTA CAGCACCTAT    2520

CTTTAATCCT GAATGGCAAA CTCCTTCCTT TCCTAAAATT CATTTACAAG AGGACATTAT    2580

TAATAGGTGT CAACAATTTG TGGGCCCTCT CACTGTAAAT GAAAAGAGAA GATTGAAATT    2640

AATTATGCCT GCTAGATTCT ATCCTACCCA CACTAAATAT TTGCCCTTAG ACAAAGGAAT    2700

TAAACCTTAT TATCCAGATC AGGTAGTTAA TCATTACTTC CAAACCAGAC ATTATTTACA    2760
```

| | |
|---|---|
| TACTCTTTGG AAGGCGGGTA TTCTATATAA GAGAGAAACC ACACGTAGCG CATCATTTTG | 2820 |
| CGGGTCACCA TATTCTTGGG AACAAGAGCT ACAGCATGGG AGGTTGGTCA TCAAAACCTC | 2880 |
| GCAAAGGCAT GGGGACGAAT CTTTCTGTTC CCAACCCTCT GGGATTCTTT CCCGATCATC | 2940 |
| AGTTGGACCC TGTATTCGGA GCCAACTCAA ACAATCCAGA TTGGGACTTC AACCCCATCA | 3000 |
| AGGACCACTG GCCAGCAGCC AACCAGGTAG GAGTGGGAGC ATTCGGGCCA GGGTTCACCC | 3060 |
| CTCCACACGG CGGTGTTTTG GGGTGGAGCC CTCAGGCTCA GGGCATGTTG ACCCCAGTGT | 3120 |
| CAACAATTCC TCCTCCTGCC TCCGCCAATC GGCAGTCAGG AAGGCAGCCT ACTCCCATCT | 3180 |
| CTCCACCTCT AAGAGACAGT CATCCTCAGG CCATGCAGTG G | 3221 |

(2) INFORMATION FOR SEQ ID NO: 282:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 282:

| | |
|---|---|
| AATTCCACTG CCTTCCACCA AGCTCTGCAG GATCCCAGAG TCAGGGGTCT GTATCTTCCT | 60 |
| GCTGGTGGCT CCAGTTCAGG AACAGTAAAC CCTGCTCCGA ATATTGCCTC TCACATCTCG | 120 |
| TCAATCTCCG CGAGGACTGG GGACCCTGTG ACGAACATGG AGAACATCAC ATCAGGATTC | 180 |
| CTAGGACCCC TGCTCGTGTT ACAGGCGGGG TTTTCCTTGT TGACAAGAAT CCTCACAATA | 240 |
| CCGCAGAGTC TAGACTCGTG GTGGACTTCT CTCAATTTTC TAGGGGGGTC ACCCGTGTGC | 300 |
| CTTGGCCAAA ATTCGCAGTC CCCAACCTCC AATCACTCAC CAACCTCCTG TCCTCCAATT | 360 |
| TGTCCTGGTT ATCGCTGGAT GTGTCTGCGG CGTTTTATCA TATTCCTCTT CATCCTGCTG | 420 |
| CTATGCCTCA TCTTCTTATT GGTTCTTCTG GATTATCAAG GTATGTTGCC CGTTTGTCCT | 480 |
| ATAATTCCAG GATCAACAAC AACCAGTACG GGACCATGCA AAACCTGCAC GACTCCTGCT | 540 |
| CAAGGCAACT CTTTGTTTCC CTCATGTTGC TGTACAAAAC CTACGGATGG AAATTGCACC | 600 |
| TGTATTCCCA TCCCATCGTC CTGGGCTTTC GCAAATACC TATGGGAGCG GCCTCAGTC | 660 |
| CGTTTCTCTT GGCTCAGTTT ACTAGTGCCA TTTGTTCAGT GGTTCGTAGG GCTTTCCCCC | 720 |
| ACTGTTTGGC TTTTAGCTAT ATGGATGATG TGGTATTGGG GGCCAAGTCT GTACAGCATC | 780 |
| GTGAGGCCCT TTATACCGCT GTTACCAATT TTCTTTTGTC TCTGGGTATA CATTTAAACC | 840 |
| CTAACAAAAC AAAAAGATGG GGTTATTCCC TAAACTTCAT GGGTTACAGA ATTGGAAGTT | 900 |
| GGGGAACATT GCCACAGGAT CACATTGTAC AAAAGATCAA ACACTGTTTT AGAAAACTTC | 960 |
| CTGTTAACAG GCCTATTGAT TGGAAGGTAT GTCAAAGAAT TGTGGGTCTT TTGGGCTTTG | 1020 |
| CTGCTCCTTT TACACAATGT GGATATCCTG CCTTAATGCC TTTGTATGCA TGTATACAAG | 1080 |
| CTAAACAGGC TTTCTCTTTC TCGCCAACTT ACAAGGCCTT TCTAAGTAAA CAGTACCTGA | 1140 |
| ACCTTTACCC CGTTGCTCGG CAACGGCCTG GTCTGTGCCA AGTGTTTGCT GACGCAACCC | 1200 |
| CCACTGGCTG GGGCTTAGCC ATAGGCCATC AGCGCATGCG TGGAACCTTT GTGGCTCCTC | 1260 |
| TGCCGATCCA TACTGCGGAA CTCCTAGCCG CTTGTTTTGC TCGCAGCCGG TCTGGAGCAA | 1320 |
| AGCTCATCGG AACTGACAAT TCTGTCGTCC TCTCGCGGAA ATATACATCG TTTCCATGGC | 1380 |

| | |
|---|---:|
| TGCTAGGCTG TGCTGCCAAC TGGATCCTTC GCGGGACGTC CTTTGTTTAC GTCCCGTCGG | 1440 |
| CGCTGAATCC CGCGGACGAC CCCTCTCGGG GCCGCTTGGG ACTCTATCGT CCCCTTCTCC | 1500 |
| GTCTGCCGTT CCAGCCGACC ACGGGGCGCA CCTCTCTTTA CGCGGTCTCC CCGTCTGTGC | 1560 |
| CTTCTCATCT GCCGGTCCGT GTGCACTTCG CTTCACCTCT GCACGTTGCA TGGAGACCAC | 1620 |
| CGTGAACGCC CATCAGAGCC TGCCCAAGGT CTTACATAAG AGAACTCTTG GACTCCCAGC | 1680 |
| AATGTCAACG ACCGACCTTG AGGCCTACTT CAAAGACTGT GTGTTTAAGG ACTGGGAGGA | 1740 |
| GCTGGGGGAG GAGATTAGGT TAATGATCTT TGTATTAGGA GGCTGTAGGC ATAAATTGGT | 1800 |
| CTGCGCACCA GCACCATGCA ACTTTTTCAC CTCTGCCTAA TCATCTCTTG TTCATGTCTC | 1860 |
| ACTGTTCAAG CCTCCAAGCT GTGCCTTGGG TGGCTTTGAG GCATGGACAT TGACCCTTAT | 1920 |
| AAAGAATTTG GAGCTAGTGT GGAGTTACTC TCGTTTTTGC CTCATGACTT CTTTCCTTCC | 1980 |
| GTCAGAGATC TCCTAGACAC CGCCTCAGCT CTGTATCGAG AAGCCTTAGA GTCTCCTGAG | 2040 |
| CATTGCTCAC CTCACCATAC TGCACTCAGG CAAGCCGTTC TCTGCTGGGG GGAATTAATG | 2100 |
| ACTCTAGCTA CCTGGGTGGG TAATAATTTG CAAGATCCAG CATCCAGGGA TCAAGTAGTC | 2160 |
| AATTATGTTA ATACTAACAT GGGTTTAAAG ATCAGGCAAC TATTGTGGTT TCATATATCT | 2220 |
| TGTCTTATGT TTGGAAGAGA CACTGTACTT GAATATTTGG TCTCTTTCGG AGTGTGGATT | 2280 |
| CGCACTCCTC CAGCCTATAG ACCACCAAAT GCCCCTATCT TATCAACACT TCCGGAAACT | 2340 |
| ACTGTTGTTA GATGTCGGGA CCGACGCAGG TCCCCTAGAA GAAGAACTCC CTCGCCTCGC | 2400 |
| AGACGCAGAT CTCAATCGCC GCGTCGCAGA AGATCTCAAT CTCGGGAATC TCAATGTTAG | 2460 |
| TATTCCTTGG ACTCATAAGG TGGGAAACTT TACTGGGCTT TATTCCTCTA CAGTACCTAT | 2520 |
| CTTTAATCCT GAATGGCAAA CTCCTTCCTT TCCTAAGATT CATTTACAAG AGGACATTAT | 2580 |
| TAATAGGTGT CAACAATTTG TGGGCCCTCT TACTGTAAAT GAAAAGAGAA GATTGAAATT | 2640 |
| AATTATGCCT GCTAGATTCT ATCCTACCCA CACAAAATAT TTGCCCTTAG ACAAAGGAAT | 2700 |
| TAAACCTTAT TATCCAGATC AGGTAGTTAA TCATTACTTC CAAACCAGAC ACTATTTACA | 2760 |
| TACTCTTTGG AAGGCTGGTA TTCTATATAA GAGGGAACCC ACACGTAGCG CATCATTTTC | 2820 |
| CCGGTCACCA TATTCTTGGG AACAAGAGCT ACAGCATGGG AGGTGGGACA TCAAAACCTC | 2880 |
| GCAAAGGCAT GGGGACGAAT CTTTCTGTTC CCAACCCTCT GGGATTCTTT CCCGATCATC | 2940 |
| AGTTGGACCC TGCATTCGGA GCCAACTCAA ACAATCCAGA TTGGGACTTC AACCCCATCA | 3000 |
| AGGACCACTG GCCAGCAGCC AACCAGGTGG GAGTGGGAGC ATTCGGGCCA GGGCTCACCC | 3060 |
| CTCCACACGG CGGTATTTTG GGGTGGAGCC CTCAGGCTCA AGGCATATTG ACCACAGTGT | 3120 |
| CAACAATTCC TCCTCCTGCC TCCACCAATC GGCAGTCAGG AAGGCAGCCT ACTCCCATCT | 3180 |
| CTCCACCTCT GAGAGAAAGT CATCCTCAGG CCATGCAGTG G | 3221 |

(2) INFORMATION FOR SEQ ID NO: 283:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 283:

```
AATTCCACAG CTTTCCACCA AGCTCTGCAA GATCCCAGAG TCAGGGGCCT GTATTTTCCT    60

GCTGGTGGCT CCAGTTCAGG AACACTCAAC CCTGTTCCAA CTATTGCCTC TCACATCTCG   120

TCAATCTCCT CGAGGATTGG GGACCCTGCA CCGAACATGG AGAACATCAC ATCAGGATTC   180

CTAGGACCCC TGCTCGTGTT ACAGGCGGGG TTTTTCTTGT TGACAAGAAT CCTCACAATA   240

CCGCAGAGTC TAGACTCGTG GTGGACTTCT CTCAATTTTC TAGGGGAGC ACCCGTGTGT    300

CTTGGCCAAA ATTCGCAGTC CCCAACCTCC AATCACTCAC CAACCTCCTG TCCTCCAATT   360

TGTCCTGGTT ATCGCTGGAT GTGTCTGCGG CGTTTTATCA TATTCCTCTT CATCCTGCTG   420

CTATGCCTCA TCTTCTTATT GGTTCTTCTG GATTATCAAG GTATGTTGCC CGTTTGTCCT   480

CTAATTCCAG GATCAACAAC AACCAGCACG GGACCCTGCA AAACCTGCAC GACTCCTGCT   540

CAAGGCAACT CTATGTTTCC CTCATGTTGC TGTACAAAAC CTACGGATGG AAATTGCACC   600

TGTATTCCCA TCCCATCATC TTGGGCTTTC GCAAAATACC TATGGGAGTG GCCTCAGTC    660

CGTTTCTCTT GGCTCAGTTT ACTAGTGCCA TTTGTTCAGT GGTTCGTAGG GCTTTCCCCC   720

ACTGTTTGGC TTTCAGCTAT ATGGATGATG TGGTACTGGG GGCCAAGTCT GTACAACATC   780

TTGAGTCCCT TTATACCGCT GTTACCAATT TTCTTTTGTC TTTGGGTATA CATTTAAACC   840

CTAACAAAAC AAAGAGATGG GGTTATTCCC TGAATTTCAT GGGTTATGTA ATTGGAAGTT   900

GGGGTACATT GCCACAGGAT CATATTGTAC AAAAAATCAA ACACTGTTTT AGAAAACTTC   960

CTGTTAATCG ACCTATTGAT TGGAAAGTAT GTCAGAGACT TGTAGGTCTT TTAGGCTTTG  1020

CCGCTCCATT TACACAATGT GGTTACCCTG CATTAATGCC TTTGTATGCA TGTATACAAG  1080

CGAAACAGGC TTTTACTTTC TCGCCAACTT ACAAGGCCTT TCTAAGTAAA CAGTATATGA  1140

ACCTTTACCC CGTTGCCCGG CAACGGCCTG GTCTGTGCCA AGTGTTTGCT GACGCAACCC  1200

CCACTGGCTG GGGCTTGGCC ATCGGCCATC AGCGCATGCG TGAAACCTTT GTGGCTCCTC  1260

TGCCGATCCA TACTGCAGAA CTCCTAGCCG CTTGTTTTGC TCGCAGCCGG TCTGGAGCAA  1320

AACTCATCGG GACTGACAAT TCTGTCGTCC TTTCTCAGAA ATATACATCC TTTCCATAGC  1380

TGCTAGGTTG TACTGCCAAC TAGATTCTTC GCGGGACGTC CTTTGTCTAC GTCCCGTCGG  1440

CGCTGAATCC CGCGGACGAC CCCTCGCGAG GCCGCTTGGG ACTGTATCGT CCCCTTCTCC  1500

GTCTGCCGTA CCGTCCGACC ACGGGGCGCA CCTCTCTTTA CGCGGTCTCC CCGTCTGTGC  1560

CTTCTCATCT GCCGGTCCGT GTGCACTTCG CTTCACCTCT GCACGTTGCA TGGAGACCAC  1620

CGTGAACGCC CATCAGGTCC TGCCCAAGGT CTTACATAAG AGGACTCTTG GACTCTCAGC  1680

AATGTCAACG ACCGACCTTG AGGCCTACTT CAAAGACTGT GTGTTTAAAG ACTGGGAGGA  1740

GTTGGGGGAG GAGATTAGGT TAAAGGTCTT TGTATTAGGA GGCTGTAGGC ATAAATTGGT  1800

CTGCGCACCA TTATCATGCA ACTTTTTCAC CTCTGCCTAA TCATCTCTTG TACATGTCCC  1860

ACTTTTCAAG CCTCCAAGCT GTGCCTTGGA TGGCTTTGGG GCATGGACAT TGACCCTTAT  1920

AAAGAATTTG AGCTACTGTG GAGTTACTCT CATTTTTGCC TTCTGACTTC TTTCCTTCCG  1980

TCCGGGATCT ACTAGAATAC AGCCTCAGCT CTATATCGGG AAGCCTTAGA GTCTCCTGAG  2040

CATTGCTCAC CTCACCATAC AGCACTCAGG CAAGCCATTC TCTGCTGGGG GAAATTAATG  2100

ACTCTAGCTA CCTGGGTGGG TAATAATTTG GAAGATCCAG CATCCAGGGA TCTAGTAGTC  2160

AATTATGTTA ATACTAACAT GGGCCTAAAG ATCAGGCAAT TATTGTGGTT TCATATTTCT  2220

TGCCTTACTT TTGGAAGAGA AACTGTCCTT GAGTATTTGG TCTCTTTCGG AGTGTGGATT  2280

CGCACTCCTC CAGCCTATAG ACCACCAAAT GCCCCTATCT TATCAACACT TCCGGAAACT  2340

ACTGTTGTTA GACGACGAGA CCGAGGCAGG TCCCCTAGAA GAAGAACTCC CTCGCCTCGC  2400
```

```
AGACGCAGAT CTCAATCGCC GCGTCGCAGA AGATCTCAAT CTCGGGAATC TCAATGTTAG     2460

TATTCCTTGG ACTCATAAGG TGGGAAATTT TACTGGGCTT TATTCTTCTA CTGTCCCTAT     2520

CTTTAATCCT GAATGGCAAA CACCTTCTTT TCCTAAAATT CATTTACATG AAGACATTGC     2580

TAATAGGTGT CAGCAATTTG TAGGCCCTCT CACTGTAAAT GAAAAAGAA GACTGAAATT      2640

AATTATGCCT GCTAGGTTTT ATCCTAACAG CACAAAATAT TTGCCCTTAG ACAAAGGGAT    2700

TAAAACTTAT TATCCTGATC ATGTAGTTAA TCATTACTTT CAAACCCGAC ATTATTTACA    2760

TACTCTTTGG AAGGCTGGGA TTCTATATAA GAGGGAAACT ACACGTAGCG CCTCATTTTG    2820

CGGGTCACCA TATTCTTGGG AACAAGAGCT ACATCATGGG AGGTTGGTCA TCAAAACCTC    2880

GCAAAGGCAT GGGGACGAAC CTTTCTGTTC CCAACCCTCT GGGATTCTTT CCCGATCATC    2940

AGTTGGACCC TGCATTCGGA GCCAATTCAA ACAATCCAGA TTGGGACTTC AACCCCATCA    3000

AGGACCACTG GCCACAAGCC AACCAGGTAG GAGTGGGAGC ATTTGGGCCA GGGTTCACTC    3060

CCCCACACGG AGGTGTTTTG GGGTGGAGCC CTCAGGCTCA GGGCATATTG GCCACCGTGC    3120

CAGCGATGCC TCCTCCTGCC TCCACCAATC GGCAGTCAGG AAGGCAGCCT ACTCCCATCT    3180

CTCCACCTCT AAGAGACAGT CATCCTCAGG CCATGCAGTG G                        3221

(2) INFORMATION FOR SEQ ID NO: 284:

(i) SEQUENCE CHARACTERISTICS:
         (A) LENGTH: 3215 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 284:

AACTCCACCA CGTTCCACCA AACTCTTCAA GATCCCAGAG TCAGGGCTCT GTACTTTCCT      60

GCTGGTGGCT CCAGTTCAGG AACAGTAAAC CCTGTTCAGA ACACTGCCTC TTCCATATCG     120

TCAATCTTAT CGACGACTGG GGACCCTGTG CCGAACATGG AGAACATCGC ATCAGGACTC     180

CTAGGACCCC TGCTCGTGTT ACAGGCGGGG TTTTTCTCGT TGACAAAAAT CCTCACAATA    240

CCTCTGAGTC TAGACTCGTG GTGGACTTCT CTCAATTTTC TAGGGGAAAC ACCCGTGTGT    300

CTTGGCCAAA ATTCGCAGTC CCAAATCTCC AGTCACTCAC CAACTTGTTG TCCTCCGATT    360

TGTCCTGGTT ATCGCTGGAT GTGTCTGCGG CGTTTTATCA TCTTCCTCTG CATCCTGCTG    420

CTATGCCTCA TCTTCTTGTT GGTTCTTCTG GACTATCAAG GTATGTTGCC CGTTTGTCCT    480

CTAATTCCAG GATCATCAAC CACCAGCACA GGACCATGCA AAACCTGCAC GACTCCTGCT    540

CAAGGAACCT CTATGTTTCC CTCATGTTGC TGTACAAAAC CTACGACGG AAACTGCACC     600

TGTATTCCCA TCCCATCATC TTGGGCTTTC GCAAATACC TATGGGAGTG GCCTCAGTC      660

CGTTTCTCTT GGCTCAGTTT ACTAGTGCCA TTTGTTCAGT GGTTCGTAGG CTTTCCCCC     720

ACTGTCTGGC TTTCAGTTAT ATGGATGATG TGGTTTTGGG GGCCAAGTCT GTACAACATC    780

TTGAGTCCCT TTATGCCGCT GTTACCAATT TTCTTTTGTC TTTGGGTATA CATTTAAACC    840

CTCAGAAAAC AAAAAGATGG GGCTACTCCC TTAACTTCAT GGGGTATGTA ATTGGAAGTT    900

GGGGGACCTT ACCCCAAGAA CATATTGTGT TGAAAATCAA ACAATGTTTT AGGAAACTTC    960

CTGTAAACAG GCCTATTGAT TGGAAAGTAT GTCAACGAAT TGTGGGTCTT TTGGGATTTG   1020
```

```
CTGCTCCTTT CACACAATGT GGATATCCTG CTTTAATGCC TTTATATGCA TGTATACAAG   1080

CTAAACAGGC TTTTACTTTT TCGCCAACGT ATAAGGCCTT TCTAAACAAA CAATATCTGA   1140

ACCTTTACCC CGTTGCTCGG CAACGGCCAG GTCTGTGCCA AGTGTTTGCT GACGCAACCC   1200

CCACTGGCTG GGGCTTGGCC ATAGGCCATC AGCGCATGCG TGGGACCTTT GTGTCTCCTC   1260

TGCCGATCCA TACTGTGGAA CTCCTAGCAG CTTGTTTTGC TCGCAGCAGG TCTGGAGCAA   1320

AACTTATCGG GACTGACAAT TCTGTCGTCC TTTCCCGCAA ATATACATCG TTTCCATGGC   1380

TGCTAGGCTG TGCTGCCAAC TGGATCCTGC GCGGGACGTC CTTTGTCTAC GTCCCGTCGG   1440

CGCTGAATCC CGCGGACGAC CCCTCCCGGG GCCGCTGGG GCTCTACCGC CCGCTTCTCC   1500

GCCTGCCGTA CCGTCCGACC ACGGGGCGCA CCTCTCTTTA CGCGGACTCC CCGTCTGTGC   1560

CTTCTCATCT GCCGGACCGT GTGCACTTCG CTTCACCTCT GCACGTCGCA TGGAGACCAC   1620

CGTGAACGCC CATCGGAACC TGCCCAAGGT CTTGCATAAG AGGACTCTTG GACTTTCAGC   1680

AATGTCAACG ACCGACCTTG AGGCACACTT CAAAGACTGT GTGTTTACTG AGTGGGAGGA   1740

GTTGGGGGAG GAGATCAGGT TAAAGGTCTT TGTACTAGGA GGCTGTAGGC ATAAATTGGT   1800

CTGTTCACCA GCACCATGCA ACTTTTTCAC CTCTGCCTAA TCATCTCATG TTCATGTCCT   1860

ACTGTTCAAG CCTCCAAGCT GTGCCTTGGG TGGCTTTGGG GCATGGACAT TGACCCGTAT   1920

AAAGAATTTG GAGCTTCTGT GGAGTTACTC TCTTTTTTGC CTTCTGACTT CTTTCCTTCT   1980

ATTCGAGATC TTCTCGACAC CGCCTCTGCT CTGTATCGGG AGGCCTTAGA GTCTCCGGAA   2040

CATTGTTCAC CTCACCATAC GGCACTCAGG CAAGCTATTC TGTGTTGGGG TGAGTTGATG   2100

AATCTAGCCA CCTGGGTGGG AAGTAATTTG GAAGACCCAG CCTCCCGGGA ATTAGTAGTC   2160

AGTTATGTCA ATGTTAATAT GGGCCTAAAA ATCAGACAAC TATTGTGGTT TCACATTTCC   2220

TGTCTTACGT TTGGAAGAGA AACTGTTCTT GAATATTTGG TGTCTTTTGG AGTGTGGATT   2280

CGCACACCTC CAGCATATAG ACCACCAAAT GCCCTATCT TATCAACACT TCCGAAAACT   2340

ACTGTTGTTA GACGACGAGG CAGGTCCCCT AGAAGAAGAA CTCCCTCGCC TCGCAGACGA   2400

AGGTCTCAAT CGCCGCGTCG CAGAAGATCT CAATCTCGGG AATCTCAATG TTAGTATTCC   2460

TTGGACTCAT AAGGTGGGAA ACTTTACGGG GCTTTATTCT TCTACGGTAC CTAGCTTTAA   2520

TCCTCAATGG CAAACTCCTT CATTTCCTGA CATTCATTTG CAGGAGGACA TCATTAATAA   2580

GTGTAAACAA TTTGTGGGAC CCCTTACAGT GAATGAAAAA AGGAGACTAA AATTGATTAT   2640

GCCTGCTAGG TTCTATCCCA ATGTTACTAA ATATTTGCCC TTAGATAAAG GAATTAAACC   2700

TTATTATCCA GAGCATGTAG TTAATCATTA CTTCCAGACG AGACATTATT TACATACTCT   2760

TTGGAAGGCG GGTATCTTAT ATAAAAGAGA GACAACACGT AGCGCCTCAT TTTGCGGGTC   2820

ACCATATTCT TGGGAACAAG AGCTACAGCA TGGGAGGTTG GTCCTCCAAA CCTCGACAAG   2880

GCATGGGGAC AAATCTTTCC GTCCCCAATC CTCTGGGATT CTTTCCCGAT CACCAGTTGG   2940

ACCCTGCATT CAAAGCCAAC TCCGACAATC CCGATTGGGA CCTCAACCCA CACAAGGACA   3000

ACTGGCCGGA CTCCAACAAG GTGGGAGTGG GAGCATTCGG GCCGGGATTC ACTCCACCCC   3060

ATGGGGGACT GTTGGGGTGG AGCCCTCAAG CTCAGGGCAT ACTCACAACT GTGCCAACAG   3120

CTCCTCCTCC TGCCTCCACC AATCGGCAGT TAGGAAGGAA GCCTACTCCC CTGTCTCCAC   3180

CTCTAAGAGA CACTCATCCT CAGGCAATGC AGTGG                              3215

(2) INFORMATION FOR SEQ ID NO: 285:

(i) SEQUENCE CHARACTERISTICS:
```

(A) LENGTH: 3215 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 285:

```
AACTCCACCA CGTTCCACCA AACTCTTCAA GATCCCAGAG TCAGGGCTCT GTACTTTCCT      60
GCTGGTGGCT CCAGTTCAGG AACAGTAAAC CCTGTTCAGA ACACTGTCTC TTCCATATCG     120
TCAATCTTAT CGAAGACTGG GGACCCTGTG CCGAACATGG AGAACATCGC ATCAGGACTC     180
CTAGGACCCC TGCTCGTGTT ACAGGCGGGG TTTTTCTTGT TGACAAAAAT CCTCACAATA     240
CCACAGAGTC TAGACTCGTG GTGGACTTCT CTCAATTTTC TAGGGGAAC ACCCGTGTGT      300
CTTGGCCAAA ATTCGCAGTC CCAAATCTCC AGTCACTCAC CAACTTGTTG TCCTCCGATT     360
TGTCCTGGTT ATCGCTGGAT GTGTCTGCGG CGTTTTATCA TCTTCCTCTG CATCCTGCTG     420
CTATGCCTCA TCTTCTTGTT GGTTCTTCTG GACTATCAAG GTATGTTGCC CGTTTGTCCT     480
CTAATTCCAG GATCATCAAC CACCAGCACC GGACCATGCA AAACCTGCAC GACTCCTGCT     540
CAAGGAACCT CTATGTTTCC CTCATGTTGC TGTACAAAAC CTACGACGG  AAACTGCACC     600
TGTATTCCCA TCCCATCATC TTGGGCTTTC GCAAATACC  TATGGGAGTG GCCTCAGTC      660
CGTTTCTCTT GGCTCAGTTT ACTAGTGCCA TTTGTTCAGT GGTTCGTAGG GCTTTCCCCC     720
ACTGTCTGGC TTTCAGTTAT ATGGATGATG TGGTTTTGGG GGCCAAGTCT GTACAACATC     780
TTGAGTCCCT TTATGCCGCT GTTACCAATT TTCTTTTGTC TTTGGGTATA CATTTAAACC     840
CTCAGAAAAC AAAAAGATGG GGCTACTCCC TCAACTTCAT GGGGTATGTA ATTGGAAGTT     900
GGGGCACCTT ACCCCAAGAA CATATTGTGT TGAAACTCAA ACAATGCTTT AGAAAACTTC     960
CTGTAAACAG ACCTATTGAT TGGAAGGTGT GTCAACGAAT TGTGGGTCTT TTGGGATTTG    1020
CTGCTCCTTT CACACAATGT GGTTATCCTG CTTTAATGCC TTTATATGCA TGTATACAAG    1080
CTAAACAGGC TTTTACTTTT TCGCCAACGT ATAAGGCCTT TCTAACCAAA CAATATCTGA    1140
ACCTTTACCC CGTTGCTCGG CAACGGCCAG GTCTGTGCCA AGTGTTTGCT GACGCAACCC    1200
CCACTGGCTG GGGCTTGGCC ATAGGCCATC AGCGCATGCG TGGAACCTTT GTGTCTCCTC    1260
TGCCGATCCA TACTGCGGAA CTCCTAGCCG CTTGTTTTGC TCGCAGCAGG TCTGGAGCAA    1320
AACTTATCGG GACTGACAAT TCTGTTGTCC TTTCCCGCAA ATATACATCG TTTCCATGGC    1380
TGCTAGGCTG TGCTGCCAAC TGGATCCTGC GCGGGACGTC CTTTGTCTAC GTTCCGTCGG    1440
CGCTGAATCC CGCGGACGAC CCCTCCCGGG GCCGCTTGGG GCTCTACCGC CCGCTTCTCC    1500
GTCTGCCGTA CCGACCGACC ACGGGGCGCA CCTCTCTTTA CGCGGACTCC CCGTCTGTGC    1560
CTTCTCGTCT GCCGGACCGT GTGCACTTCG CTTCACCTCT GCACGTCGCA TGGAGACCAC    1620
CGTGAACGCC CATCGGAACC TGCCCAAGGT CTTGCATAAG AGGACTCTTG GACTTTCAGC    1680
AATGTCACCG ACCGACCTTG AGGCATACTT CAAAGACTGT GTGTTTACTG AGTGGGAGGA    1740
GTTGGGGGAG GAGATCAGGT TAAAGGTCTT TGTACTAGGA GGCTGTAGGC ATAAATTGGT    1800
CTGTTCACCA GCACCATGCA ACTTTTTCAC CTCTGCCTAA TCATCTCATG TTCATGTCCT    1860
ACTGTTCAAG CCTCCAAGCT GTGCCTTGGG TGGCTTGGG  GCATGGACAT TGACCCGTAT    1920
AAAGAATTTG GAGCTTCTGT GGAGTTACTC TCTTTTTTGC CTTCTGACTT CTTTCCTTCT    1980
```

```
ATTCGAGATC TTCTCGACAC CGCCTCTGCT CTGTATCGGG AGGCCTTAGA GTCTCCGGAA    2040

CATTGTTCAC CTCACCATAC GGCACTCAGG CAAGCTATTT TGTGTTGGGG TGAGTTGATG    2100

AATCTAGCCA CCTGGGTGGG AAGTAATTTG GAAGACCCAG CATCCCGGGA ATTAGTAGTC    2160

AGTTATGTCA ATGTTAATAT GGGCCTAAAA ATCAGACAAC TATTGTGGTT TCACATTTCC    2220

TGTCTTACTT TTGGAAGAGA AACTGTTCTT GAATATTTGG TGTCTTTTGG AGTGTGGATT    2280

CGCACACCTC CTGCATATAG ACCACCAAAT GCCCCTATCT TATCAACACT TCCGAAACT     2340

ACTGTTGTTA GACGACGAGG CAGGTCCCCT AGAAGAAGAA CTCCCTCACC TCGCAGACGA    2400

AGGTCTCAAT CGCCCGGTCG CAGAAGATCT CAATCTCGGG AATCTCAATG TTAGTATCCC    2460

TTGGACTCAT AAGGTGGGAA ACTTTACGGG GCTTTATTCT TCTACGGTAC CTAGCTTTAA    2520

TCCTAAATGG CAAACTCCTT CCTTTCCTGA CATTCATTTG CAGGAGGATA TCATTAATAG    2580

GTGTGAACAA TTTGTGGGAC CCCTCACAGT GAATGAAAAC AGGAGACTAA AATTGATTAT    2640

GCCTGCTAGG TTCTATCCCA ATGTTACTAA ATATTTGCCC TTAGATAAAG GAATCAAACC    2700

TTATTATCCA GAGCATGTAG TTAATCATTA CTTCCAGACG AGACATTATT TACATACTCT    2760

TTGGAAGGCG GGTATCTTAT ATAAAAGAGA GACAACACGT AGCGCCTCAT TTTGCGGGTC    2820

ACCATATTCT TGGGAACAAG ATCTACAGCA TGGGAGGTTG GTCCTCCAAA CCTCGACAAG    2880

GCATGGGGAC AAATCTTTCC GTCCCCAATC CTCTGGGATT CTTTCCCGAT CACCAGTTGG    2940

ACCCTGCATT CAAAGCCAAC TCCGACAATC CCGATTGGGA CCTCAACCCA CACAAGGACA    3000

ACTGGCCGGA CTCCAACAAG GTGGGAGTGG GAGCATTCGG GCCGGGATTC ACTCCACCCC    3060

ATGGGGGACT GTTGGGGTGG AGCCCTCAAG CTCAGGGCAT ACTCACAACT GTGCCAACAG    3120

CTCCTCCTCC TGCCTCCACC AATCGGCAGT TAGGAAGGAA GCCTACTCCC CTGTCTCCAC    3180

CTCTAAGAGA CACTCATCCT CAGGCCATGC AGTGG                              3215

(2) INFORMATION FOR SEQ ID NO: 286:

(i) SEQUENCE CHARACTERISTICS:
         (A) LENGTH: 3215 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 286:

AACTCCACCA CTTTCCACCA AACTCTTCAA GATCCCAGAG TCAGGGCTCT GTACTTTCCT      60

GCTGGTGGCT CCAGTTCAGG AACAGTAAGC CCTGCTCAGA ATACTGTCTC AGCCATATCG    120

TCAATCTTAT CGAAGACTGG GGACCCTGTG CCGAACATGG AGAACATCGC ATCAGGACTC    180

CTAGGACCCC TGCTCGTGTT ACAGGCGGGG TTTTTCTTGT TGACAAAAAT CCTCACAATA    240

CCACAGAGTC TAGACTCGTG GTGGACTTCT CTCAATTTTC TAGGGGGAAC ACCCGTGTGT    300

CTTGGCCAAA ATTCGCAGTC CCAAATCTCC AGTCACTCAC CAACCTGTTG TCCTCCAATT    360

TGTCCTGGTT ATCGCTGGAT GTGTCTGCGG CGTTTTATCA TCTTCCTCTG CATCCTGCTG    420

CTATGCCTCA TCTTCTTGTT GGTTCTTCTG GACTATCAAG GTATGTTGCC CGTTTGTCCT    480

CTAATTCCAG GATCATCAAC CACCAGCACG GGACCATGCA AGACCTGCAC AACTCCTGCT    540

CAAGGAACCT CTATGTTTCC CTCATGTTGC TGTACAAAAC CTATGGATGG AAACTGCACC    600
```

```
TGTATTCCCA TCCCATCATC TTGGGCTTTC GCAAAATACC TATGGGAGTG GGCCTCAGTC    660

CGTTTCTCTT GGCTCAGTTT ACTAGTGCCA TTTGTTCAGT GGTTCGTAGG GCTTTCCCCC    720

ACTGTCTGGC TTTCAGTTAT ATGGATGATG TGGTATTGGG GGCCAAGTCT GTACAACATC    780

TTGAGTCCCT TTATGCCGCT GTTACCAATT TTCTTTTGTC TTTGGGTATA CATTTAAACC    840

CTAACAAAAC AAAAAGATGG GGATATTCCC TTAACTTCAT GGGATATGTA ATTGGGAGTT    900

GGGGCACATG GCCACAGGAT CATATTGTAC AAAACTTCAA ACTATGTTTT AGAAAACTTC    960

CTGTAAACAG GCCTATTGAT TGGAAAGTTT GTCAACGAAT TGTGGGTCTT TTGGGGTTTG   1020

CTGCCCCTTT TACGCAATGT GGATATCCTG CTTTAATGCC TTTATATGCA TGTATACAAG   1080

CAAAACAGGC TTTTACTTTC TCGCCAACTT ACAAGGCCTT TCTCAGTAAA CAGTATATGA   1140

CCCTTTACCC CGTTGCTCGG CAACGGCCTG GTCTGTGCCA AGTGTTTGCT GACGCAACCC   1200

CCACTGGTTG GGGCTTGGCC ATAGGCCATC AGCGCATGCG TGGAACCTTT GTGTCTCCTC   1260

TGCCGATCCA TACTGCGGAA CTCCTAGCCG CTTGTTTTGC TCGCAGCAGG TCTGGAGCAA   1320

ACCTCATCGG GACCGACAAT TCTGTCGTAC TCTCCCGCAA GTATACATCG TTTCCATGGC   1380

TGCTAGGCTG TGCTGCCAAC TGGATCCTGC GCGGGACGTC CTTTGTTTAC GTCCCGTCGG   1440

CGCTGAATCC CGCGGACGAC CCCTCCCGGG GCCGCTTGGG GCTCTACCGC CCGCTTCTCC   1500

GTCTGCCGTA CCGTCCGACC ACGGGGCGCA CCTCTCTTTA CGCGGACTCC CCGTCTGTGC   1560

CTTCTCATCT GCCGGACCGT GTGCACTTCG CTTCACCTCT GCACGTCGCA TGGAGACCAC   1620

CGTGAACGCC CACCGGAACC TGCCCAAGGT CTTGCATAAG AGGACTCTTG GACTTTCAGC   1680

AATGTCAACG ACCGACCTTG AGGCATACTT CAAAGACTGT GTGTTTAATG AGTGGGAGGA   1740

GCTGGGGGAG GAGATTAGGT TAAAGGTCTT TGTACTCGGA GGCTGTAGGC ATAAATTGGT   1800

CTGTTCACCA GCACCATGCA ACTTTTTCAC CTCTGCCTAG TCATCTCTTG TTCATGTCCT   1860

ACTGTTCAAG CCTCCAAGCT GTGCCTTGGG TGGCTTTGGG GCATGGACAT TGACCCCTAT   1920

AAAGAATTTG GAGCTACTGT GGAGTTACTC TCTTTTTTGC CTTCTGACTT CTTTCCGTCG   1980

GTGCGGGACC TCCTAGATAC CGTCTCTGCT CTGTATCGGG AAGCCTTAAA ATCTCCTGAG   2040

CATTGCTCAC CTCACCACAC AGCACTCAGG CAAGCTATTC TGTGCTGGGG GGAATTAATG   2100

ACTCTAGCTA CCTGGGTGGG TAATAATTTG GAAGATCCAG CATCCCGGGA TCTAGTAGTC   2160

AATTATGTTA ACACTAACAT GGGCCTAAAG ATCAGGCAAC TATGGTGGTT TCACATTTCC   2220

TGTCTTACTT TTGGAAGAGA AACTGTTCTG GAATATTTGG TATCTTTTGG AGTGTGGATT   2280

CGCACTCCTC CTGCCTACAG ACCACCAAAT GCCCCTATCT TATCAACACT TCCGGAAACT   2340

ACTGTTGTTA GACGACGAGG CAGGTCCCCT AGAAGAAGAA CTCCCTCGCC TCGCAGACGA   2400

AGGTCTCAAT CACCGCGTCG CAGAAGATCT CAATCTCGGG AATCCAATG TTAGTATCCC    2460

TTGGACTCAT AAGGTGGGAA ACTTTACGGG GCTTTATTCT TCTACAGTAC CTGTCTTTAA   2520

TCCTGAATGG CAAACTCCTT CTTTTCCAGA CATTCATTTA CAGGAGGACA TTGTTGATAG   2580

ATGTAAGCAA TTTGTGGGAC CCCTTACAGT AAATGAAAAC AGGAGACTAA AATTAATAAT   2640

GCCTGCTAGA TTTTATCCCA ATGTTACCAA ATATTTGCCC TTAGATAAAG GTATCAAACC   2700

TTATTATCCA GAGCATGTAG TTAATCATTA CTTCCAGACT AGACATTATT TGCATACTCT   2760

TTGGAAGGCG GGTATCTTAT ATAAAAGAGA GTCAACACAT AGCGCCTCAT TTTGCGGGTC   2820

ACCTTATTCT TGGGAACAAG ATCTACAGCA TGGGAGGTTG GTCTTCCAAA CCTCGAAAAG   2880

GCATGGGGAC AAATCTTTCT GTCCCCAATC CCCTGGGATT CTTCCCCGAT CATCAGTTGG   2940

ACCCTGCATT CAAAGCCAAC TCAGAAAATC CAGATTGGGA CCTCAACCCA CACAAGGACA   3000
```

```
ACTGGCCGGA CGCCCACAAG GTGGGAGTGG GAGCATTCGG GCCAGGATTC ACCCCTCCCC    3060

ATGGGGGACT GTTGGGGTGG AGCCCTCAGG CTCAGGGCAT ACTCACATCT GTGCCAGCAG    3120

CTCCTCCTCC TGCCTCCACC AATCGGCAGT CAGGACGGCA GCCTACTCCC CTATCTCCAC    3180

CTCTAAGGGA CACTCATCCT CAGGCCATGC AGTGG                               3215

(2) INFORMATION FOR SEQ ID NO: 287:

(i) SEQUENCE CHARACTERISTICS:
         (A) LENGTH: 3215 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 287:

AACTCCACCA CTTTCCACCA AACTCTTCAA GATCCCGGAG TCAGGGCCCT GTACTTTCCT      60

GCTGGTGGCT CCAGTTCAGG AACAGTGAGC CCTGCTCAGA ATACTGTCTC TGCCATATCG     120

TCAATCTTAT CGAAGACTGG GGACCCTGTA CCGAACATGG AGAACATCGC ATCAGGACTC     180

CTAGGACCCC TGCTCGTGTT ACAGGCGGGG TTTTTCTTGT TGACAAAAAT CCTCACAATA     240

CCACAGAGTC TAGACTCGTG GTGGACTTCT CTCAATTTTC TAGGGGAAC  ACCCGTGTGT     300

CTTGGCCAAA ATTCGCAGTC CCAAATCTCC AGTCACTCAC CAACCTGTTG TCCTCCAATT     360

TGTCCTGGTT ATCGCTGGAT GTGTCTGCGG CGTTTTATCA TCTTCCTCTG CATCCTGCTG     420

CTATGCCTCA TCTTCTTGTT GGTTCTTCTG GACTATCAAG GTATGTTGCC CGTTTGTCCT     480

CTAATTCCAG GATCATCAAC AACCAGCACC GGACCATGCA AAACCTGCAC AACTCCTGCT     540

CAAGGAACCT CTATGTTTCC CTCATGTTGC TGTACAAAAC CTACGGATGG AAACTGCACC     600

TGTATTCCCA TCCCATCATC TTGGGCTTTC GCAAAATACC TATGGGAGTG GCCTCAGTC     660

CGTTTCTCTT GGCTCAGTTT ACTAGTGCCA TTTGTTCAGT GGTTCGTAGG GCTTTCCCCC     720

ACTGTCTGGC TTTCAGTTAT ATGGATGATA TGGTTTTGGG GGCCAAGTCT GTACAACATC     780

TTGAGTCCCT TTATGCCGCT GTTACCAATT TTCTTTTGTC TTTGGGTATA CATTTAAACC     840

CTCACAAAAC AAAAAGATGG GGATATTCCC TTAACTTCAT GGGATATGTA ATTGGGAGCT     900

GGGGCACATT GCCACAGGAA CATATTGTAC AAAAAATCAA AATGTGGTTT AGGAAACTTC     960

CTGTAAACAG GCCTATTGAT TGGAAAGTAT GTCAACGAAT TGTGGGTCTT TTGGGGTTTG    1020

CCGCCCCTTT CACGCAATGT GGATATCCTG CTTTAATGCC TTTATATGCA TGTATACAAG    1080

CAAAACAGGC TTTTACTTTC TCGCCAACTT ACAAGGCCTT TCTAACTAAA CAGTATCTGA    1140

ACCTTTACCC CGTTGCTCGG CAACGGCCAG GTCTGTGCCA AGTGTTTGCT GACGCAACCC    1200

CCACTGGTTG GGGCTTGGCC ATAGGCCATC AGCGCATGCG TGGAACCTTT GTGTCTCCTC    1260

TGCCGATCCA TACTGCGGAA CTCCTAGCCG CTTGTTTTGC TCGCAGCCGG TCTGGGGCAA    1320

AACTCATCGG GACTGACAAT TCTGTCGTGC TCTCCCGCAA GTATACATCA TTTCCATGGC    1380

TGCTAGGCTG TGCTGCCAAC TGGATCCTGC GCGGGACGTC CTTTGTTTAC GTCCCGTCGG    1440

CGCTGAATCC CGCGGACGAC CCTTCCCGGG GCCGCTTGGG GCTCTACCGC CCGCTTCTCC    1500

GCCTGTTGTA CCGACCGACC ACGGGGCGCA CCTCTCTTTA CGCGGACTCC CCGTCTGTGC    1560

CTTCTCATCT GCCGGACCGT GTGCACTTCG CTTCACCTCT GCACGTCGCA TGGAGACCAC    1620
```

```
CGTGAACGCC CACGGGAACC TGCCCAAGGT CTTGCATAAG AGGACTCTTG GACTTTCAGC      1680

AATGTCAACG ACCGACCTTG AGGCATACTT CAAAGACTGT GTGTTTAATG AGTGGGAGGA      1740

GTTGGGGGAG GAGGTTAGGT TAAAGGTCTT TGTACTAGGA GGCTGTAGGC ATAAATTGGT      1800

GTGTTCACCA GCACCATGCA ACTTTTTCAC CTCTGCCTAA TCATCTCATG TTCATGTCCT      1860

ACTGTTCAAG CCTCCAAGCT GTGCCTTGGG TGGCTTTGGG GCATGGACAT TGACCCGTAT      1920

AAAGAATTTG GAGCTTCTGT GGAGTTACTC TCTTTTTTGC CTTCTGACTT CTTTCCGTCG      1980

GTGCGAGATC TCCTCGACAC CGCCTCTGCT TTGTATCGGG AGGCCTTAGA GTCTCCGGAA      2040

CATTGTTCAC CTCACCATAC GGCACTCAGG CAAGCTATTC TGTGTTGGGG TGAGTTAATG      2100

AATCTAGCCA CCTGGGTGGG AAGTAATTTG GAAGATCCGG CATCCAGGGA ATTAGTAGTC      2160

AGCTATGTCA ACGTTAATAT GGGCCTAAAA ATCAGACAAC TATTGTGGTT TCACATTTCC      2220

TGTCTTACTT TTGGGAGAGA AACTGTTCTT GAATATTTGG TGTCTTTTGG AGTGTGGATT      2280

CGCACTCCTC CTGCATATAG ACCACCAAAT GCCCCTATCT TATCAACACT TCCGAAACT       2340

ACTGTTGTTA GACGAAGAGG CAGGTCCCCT AGAAGAAGAA CTCCCTCGCC TCGCAGACGA      2400

AGGTCTCAAT CGCCGCGTCG CAGAAGATCT CAATCTCGGG AATCTCAATG TTAGTATTCC      2460

TTGGACACAT AAGGTGGGAA ACTTTACGGG GCTTTATTCT TCTACGGTAC CTTGCTTTAA      2520

TCCTAAATGG CAAACTCCTT CTTTTCCTGA CATTCATTTG CAGGAGGACA TTGTTGATAG      2580

ATGTAAGCAA TTTGTGGGGC CCCTTACAGT AAATGAAAAC AGGAGACTAA AATTAATTAT      2640

GCCCGCTAGG TTTTATCCCA ATGTTACTAA ATATTTGCCC TTAGATAAAG GGATCAAACC      2700

GTATTATCCA GAGTATGTAG TTAATCATTA CTTCCAGACG CGACATTATT TACACACTCT      2760

TTGGAAGGCG GGGATCTTAT ATAAAAGAGA GTCCACACGT AGCGCCTCAT TTTGCGGGTC      2820

ACCATATTCT TGGGAACAAG ATCTACAGCA TGGGAGGTTG GTCTTCCAAA CCTCGAAAAG      2880

GCATGGGGAC AAATCTTTCT GTCCCCAATC CTCTGGGATT CTTCCCCGAT CATCAGTTGG      2940

ACCCTGCATT CAAAGCCAAC TCAGAAAATC CAGATTGGGA CCTCAACCCG AACAAGGACA      3000

ACTGGCCGGA CGCCAACAAG GTGGGAGTGG GAGCATTCGG GCCAGGGTTC ACCCCTCCCC      3060

ATGGGGGACT GTTGGGGTGG AGCCCTCAGG CTCAGGGCCT ACTCACAACT GTGCCAGCAG      3120

CTCCTCCTCC TGCCTCCACC AATCGGCAGT CAGGAAGGCA GCCTACTCCC TTATCCCCAC      3180

CTCTAAGGGA CACTCATCCT CAGGCCATGC AGTGG                                3215

(2) INFORMATION FOR SEQ ID NO: 288:

(i) SEQUENCE CHARACTERISTICS:
        (A) LENGTH: 3213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 288:

AACTCCACCA CATTTCACCA AGTCCTGCTA GATCCCAGAG TGAGGGGCCT ATATTTTCCT       60

CCTGGTGGCT CCAGTTCCGG AACAGTAAAC CCTGTTGCGA CTACTGCCTC ACCCATATCG      120

TCAATCTCCT CGAGGACTGG GGACCCTGCA CCGAACATGG AGAGCACAAC ATCAGGATTC      180

CTAGGACCCC TGCTCGTGTT ACAGGCGGGG TTTTTCTTGT TGACAAGAAT CCTCACAATA      240
```

```
CCACAGAGTC TAGACTCGTG GTGGACTTCT CTCAATTTTC TAGGGGGAGC ACCCACGTGT    300
CCTGGCCAAA ATTCGCAGTC CCCAACCTCC AATCACTCAC CAACCTCTTG TCCTCCAATT    360
TGTCCTGGCT ATCGCTGGAT GTGTCTGCGG CGTTTTATCA TATTCCTCTT CATCCTGCTG    420
CTATGCCTCA TCTTCTTGTT GGTTCTTCTG GACTACCAAG GTATGTTGCC CGTTTGTCCT    480
CTACTTCCAG GAACATCAAC CACCAGCACG GGACCATGCA AGACCTGCAC GATTCCTGCT    540
CAAGGAACCT CTATGTTTCC CTCTTGTTGC TGTACAAAAC CTTCGGACGG AAACTGCACT    600
TGTATTCCCA TCCCATCATC CTGGGCTTTC GCAAGATTCC TATGGGAGGG GGCCTCAGTC    660
CGTTTCTCCT GGCTCAGTTT ACTAGTGCCA TTTGTTCAGT GGTTCGTAGG GCTTTCCCCC    720
ACTGTTTGGC TTTCAGTTAT ATGGATGATG TGGTATTGGG GGCCAAGTCT GTACAACATC    780
TTGAGTCCCT TTTTACCTCT ATTACCAATT TTCTTTTGTC TTTGGGTATA CATTTGAACC    840
CTAATAAAAC CAAACGTTGG GGCTACTCCC TTAACTTCAT GGGATATGTA ATTGGCAGTT    900
GGGGTACTTT ACCGCAAGAA CATATTGTAC TAAAAATCAA GCAATGTTTT CGGAAACTGC    960
CTGTAAATAG ACCTATTGAC TGGAAAGTAT GTCAAAGAAT TGTGGGTCTT TTGGGCTTTG   1020
CTGCCCCTTT TACACAATGT GGCTATCCTG CCTTAATGCC TTTATATGCA TGTATACAAT   1080
CTAAGCAGGC TTTCACTTTC TCGCCAACTT ACAAGGCCTT TCTGTGTAAA CAATATCTGC   1140
ACCTTTACCC CGTTGCCCGG CGAACGGCTC TCTGCCAAGT ATTTGCTGAC GCAACCCCCA   1200
CTGGATGGGG CTTGGCCATA GGCCATCGGC GCATGCGTGG AACCTTTGTG GCTCCTCTGC   1260
CGATCCATAC TGCGGAACTC CTAGCAGCTT GTTTTGCTCG CAGCCGGTCT GGAGCGAAAC   1320
TCATCGGGAC TGACAACTCG GTTGTTCTCT CTCGGAAATA CACCTCATTC CCATGGCTGC   1380
TCGGGTGTGC TGCCAACTGG ATCCTGCGCG GGACGTACTT TGTTTACGTC CCGTCGGCGC   1440
TGAATCCCGC GGACGACCCG TCTCGCGGCC GTTTGGGCCT CATCCGTCCC CTTCTTCATC   1500
TGCGGTTCCG GCCGACCACG GGGCGCACCT CTCTTTACGC GGTCTCCCCG TCTGTGCCTT   1560
CTCATCTGCC GGACCGTGTG CACTTCGCTT CACCTCTGCA CGTCGCATGG AGACCACCGT   1620
GAACGCCGAT CAGGTCTTGC CCAAGGTCTT ACATAAGAGG ACTCTTGGAC TCTCAGCAAT   1680
GTCAACGTCC GACCTTGAGG CATACTTCAA AGACTGCTTG TTTAAAGACT GGGAGGACTT   1740
GGGGGAGGAG ATTAGGTTAA TGATCTTTGT ACTAGGAGGC TGTAGGCATA AATTGGTCTG   1800
TTCACCAGCA CCATGCAACT TTTTTCACCT CTGCCTAATC ATCTCATGTT CATGTCCTAC   1860
TGTTCACGCC TCCAAGCTGT GCCTTGGGTG GCTTTGGGGC ATGGACATTG ACCCGTATAA   1920
AGAATTTGGA GCTTCTGTGG AGTTACTCTC TTTTTTGCCT TCTGATTTCT TTCCTTCCAT   1980
TCGAGATCTC CTCGACACCG CCTCTGCTCT GTATAGGGAG GCCTTAGAGT CTCCGGAACA   2040
TTGTTCACCT CATCATACAG CACTCAGGCA AGCTATTCTG TGTTGGGGTG AGTTGATGAA   2100
TCTGGCCACC TGGGTGGGAA GTAATTTGGA AGACCCAGCA TCCAGGGAAC TAGTAGTCAG   2160
CTATGTCAAT GTTAATATGG GCCTAAAAAT CAGACAACTA TTGTGGTTTC ACATTTCCTG   2220
CCTTACTTTT GGAAGAGAAA CTGTTTTGGA GTATTTGGTA TCTTTTGGAG TGTGGATTCG   2280
CACTCCTCCC GCTTACAGAC CACCAAATGC CCCTATCTTA TCAACACTTC CGGAAACTAC   2340
TGTTGTTAGA CGACGAGGCA GGTCCCCTAG AAGAAGAACT CCCTCGCCTC GCAGACGAAG   2400
ATCTGAATCG CCGCGTCGCA GAAGATCTCA ATCTCGGGAA TCTCAATGTT AGTATCCCTT   2460
GGACTCATAA GGTGGGAAAC TTTACTGGGC TTTATTCTTC TACTGTACCT GTCTTTAATC   2520
CTGAGTGGCA AACTCCCTCC TTTCCTCACA TTCATTTACA GGAGGACATT ATTAATAGAT   2580
```

```
GTCAACAATA TGTGGGCCCT CTTACAGTTA ATGAAAAAAG GAGATTAAAA TTAATTATGC    2640

CTGCTAGGTT TTATCCTAAA CTTACCAAAT ATTTGCCCTT GGATAAAGGC ATTAAACCTT    2700

ATTATCCTGA ACATGCAGTT AATCATTACT TCAAAACTAG GCATTATTTA CATACTCTGT    2760

GGAAGGCGGG CATTCTATAT AAGAGAGAAA CTACACGCAG CGCCTCATTT TGTGGGTCAC    2820

CATATTCTTG GGAACAAGAG CTACAGCATG GGAGGTTGGT CTTCCAAACC TCGACAAGGC    2880

ATGGGGACGA ATCTTTCTGT TCCCAATCCT CTGGGATTCT TTCCCGATCA CCAGTTGGAC    2940

CCTGCGTTCG GAGCCAACTC AAACAATCCA GATTGGGACT TCAACCCCAA CAAGGATCGT    3000

TGGCCAGAGG CAAATCAGGT AGGAGCGGGA GCATTCGGGC CAGGGTACCC CCCACCACAC    3060

GGCGGTCTTT TGGGGTGGAG CCCTCAGGCT CAGGGCATAT TGACAACCGT GCCAGCAGCA    3120

CCTCCTCCTG CCTCCACCAA TCGGCAGTCA GGAAGACAGC CTACTCCCAT CTCTCCACCT    3180

CTAAGAGACA GTCATCCTCA GGCCATGCAG TGG                                3213

(2) INFORMATION FOR SEQ ID NO: 289:

(i) SEQUENCE CHARACTERISTICS:
        (A) LENGTH: 3213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 289:

AACTCCACCA CATTTCACCA AGTCCTGCTA GATCCCAGAG TGAGGGGCCT ATATTTTCCT      60

CCTGGTGGCT CCAGTTCCGG AACAGTAAAC CCTGTTCCGA CTACTGCCTC ACCCATATCG     120

TCAATCTCCT CGAGGACTGG GGACCCTGCA CCGAACATGG AGAGCACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGGAGC ACCCACGTGT     300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC CACCAGCACG GGACCATGCA AGACCTGCAC GATTCCTGCT     540

CAAGGAACCT CTATGTTTCC CTCTTGTTGC TGTACAAAAC CTTCGGACGG AAACTGCACT     600

TGTATTCCCA TCCCATCATC CTGGGCTTTC GCAAGATTCC TATGGGAGGG GGCCTCAGTC     660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTGAACC     840

CTAATAAAAC CAAACGTTGG GGCTACTCCC TTAACTTCAT GGGATATGTA ATTGGCAGTT     900

GGGGTACTTT ACCGCAAGAA CATATTGTAC TAAAAATCAA GCAATGTTTT CGGAAACTGC     960

CTGTAAATAG ACCTATTGAC TGGAAAGTAT GTCAAGGAAT TGTGGGTCTT TTGGGCTTTG    1020

CTGCCCCTTT TACACAATGT GGCTATCCTG CCTTAATGCC TTTATATGCA TGTATACAAT    1080

CTAAGCAGGC TTTCACTTTC TCGCCAACTT ACAAGGCCTT TCTGTGTAAA CAATATCTGC    1140

ACCTTTACCC CGTTGCCCGG CGAACGGCTC TCTGCCAAGT ATTTGCTGAC GCAACCCCCA    1200
```

| | |
|---|---|
| CTGGATGGGG CTTGGCCATA GGCCATCGGC GCATGCGTGG AACCTTTGTG GCTCCTCTGC | 1260 |
| CGATCCATAC TGCGGAACTC CTAGCAGCTT GTTTTGCTCG CAGCCGGTCT GGAGCGAAAC | 1320 |
| TCATCGGGAC TGACAACTCG GTTGTTCTCT CTCGGAAATA CACCTCATTC CCATGGCTGC | 1380 |
| TCGGGTGTGC TGCCAACTGG ATCCTGCGCG GGACGTACTT TGTTTACGTC CCGTCGGCGC | 1440 |
| TGAATCCCGC GGACGACCCG TCTCGCGGCC GTTTGGGCCT CATCCGTCCC CTTCTTCATC | 1500 |
| TGCGGTTCCG GCCGACCACG GGGCGCACCT CTCTTTACGC GGTCTCCCCG TCTGTGCCTT | 1560 |
| CTCATCTGCC GGACCGTGTG CACTTCGCTT CACCTCTGCA CGTCGCATGG AGACCACCGT | 1620 |
| GAACGCCGAT CAGGTCTTGC CCAAGGTCTT ACATAAGAGG ACTCTTGGAC TCTCAGCAAT | 1680 |
| GTCAACGTCC GACCTTGAGG CATACTTCAA AGACTGCTTG TTTAAAGACT GGGAGGACTT | 1740 |
| GGGGGAGGAG ATTAGGTTAA TGATCTTTGT ACTAGGAGGC TGTAGGCATA AATTGGTCTG | 1800 |
| TTCACCAGCA CCATGCAACT TTTTTCACCT CTGCCTAATC ATCTCATGTT CATGTCCTAC | 1860 |
| TGTTCACGCC TCCAAGCTGT GCCTTGGGTG GCTTTGGGGC ATGGACATTG ACCCGTATAA | 1920 |
| AGAATTTGGA GCTTCTGTGG AGTTACTCTC TTTTTTGCCT TCTGATTTCT TTCCTTCCAT | 1980 |
| TCGAGATCTC CTCGACACCG CCTCTGCTCT GTATAGGGAG GCCTTAGAGT CTCCGGAACA | 2040 |
| TTGTTCACCT CATCATACAG CACTCAGGCA AGCTATTCTG TGTTGGGGTG AGTTGATGAA | 2100 |
| TCTGGCCACC TGGGTGGGAA GTAATTTGGA AGACCCAGCA TCCAGGGAAC TAGTAGTCAG | 2160 |
| CTATGTCAAT GTTAATATGG GCCTAAAAAT CAGACAACTA TTGTGGTTTC ACATTTCCTG | 2220 |
| CCTTACTTTT GGAAGAGAAA CTGTTTTGGA GTATTTGGTA TCTTTTGGAG TGTGGATTCG | 2280 |
| CACTCCTCCC GCTTACAGAC CACCAAATGC CCCTATCTTA TCAACACTTC GGAAACTAC | 2340 |
| TGTTGTTAGA CGACGAGGCA GGTCCCCTAG AAGAAGAACT CCCTCGCCTC GCAGACGAAG | 2400 |
| ATCTGAATCG CCGCGTCGCA GAAGATCTCA ATCTCGGGAA TCTCAATGTT AGTATCCCTT | 2460 |
| GGACTCATAA GGTGGGAAAC TTTACTGGGC TTTATTCTTC TACTGTACCT GTCTTTAATC | 2520 |
| CTGAGTGGCA AACTCCCTCC TTTCCTCACA TTCATTTACA GGAGGACATT ATTAATAGAT | 2580 |
| GTCAACAATA TGTGGGCCCT CTTACAGTTA ATGAAAAAAG GAGATTAAAA TTAATTATGC | 2640 |
| CTGCTAGGTT TTATCCTAAA CTTACCAAAT ATTTGCCCTT GGATAAAGGC ATTAAACCTT | 2700 |
| ATTATCCTGA ACATGCAGTT AATCATTACT TCAAAACTAG GCATTATTTA CATACTCTGT | 2760 |
| GGAAGGCGGG CATTCTATAT AAGAGAGAAA CTACACGCAG CGCCTCATTT TGTGGGTCAC | 2820 |
| CATATTCTTG GGAACAAGAG CTACAGCATG GGAGGTTGGT CTTCCAAACC TCGACAAGGC | 2880 |
| ATGGGGACGA ATCTTTCTGT TCCCAATCCT CTGGGATTCT TTCCCGATCA CCAGTTGGAC | 2940 |
| CCTGCGTTCG GAGCCAACTC AAACAATCCA GATTGGGACT TCAACCCCAA CAAGGATCGT | 3000 |
| TGGCCAGAGG CAAATCAGGT AGGAGCGGGA GCATTCGGGC CAGGGTACCC CCACCACAC | 3060 |
| GGCGGTCTTT TGGGGTGGAG CCCTCAGGCT CAGGGCATAT TGACAACCGT GCCAGCAGCA | 3120 |
| CCTCCTCCTG CCTCCACCAA TCGGCAGTCA GGAAGACAGC CTACTCCCAT CTCTCCACCT | 3180 |
| CTAAGAGACA GTCATCCTCA GGCCATGCAG TGG | 3213 |

(2) INFORMATION FOR SEQ ID NO: 290:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 290:

```
AACTCCACAA CATTCCACCA AGCTCTGCTA GATCCCAGAG TGAGGGGCCT ATATTTTCCT    60
GCTGGTGGCT CCAGTTCCGG AACAGTAAAC CCTGTTCCGA CTACTGTCTC ACCCATATCG   120
TCAATCTTCT CGAGGACTGG GGACCCTGCA CCGAACATGG AGAGCACAAC ATCAGGATTC   180
CTAGGACCCC TGCTCGTGTT ACAGGCGGGG TTTTTCTTGT TGACAAGAAT CCTCACAATA   240
CCACAGAGTC TAGACTCGTG GTGGACTTCT CTCAATTTTC TAGGGGGAGC ACCCACGTGT   300
CCTGGCCAAA ATTCGCAGTC CCCAACCTCC AATCACTCAC CAACCTCTTG TCCTCCAATT   360
TGTCCTGGTT ATCGCTGGAT GTGTCTGCGG CGTTTTATCA TATTCCTCTT CATCCTGCTG   420
CTATGCCTCA TCTTCTTGTT GGTTCTTCTG GACTACCAAG GTATGTTGCC CGTTTGTCCT   480
CTACTTCCAG GAACATCAAC TACCAGCACG GGACCATGCA AGACCTGCAC GATTCCTGCT   540
CAAGGAACCT CTATGTTTCC CTCTTGTTGC TGTACAAAAC CTTCGGACGG AAACTGCACT   600
TGTATTCCCA TCCCATCATC CTGGGCTTTC GCAAGATTCC TATGGGAGTG GGCCTCAGTC   660
CGTTTCTCCT GGCTCAGTTT ACTAGTGCCA TTTGTTCAGT GGTTCGCAGG GCTTTCCCCC   720
ACTGTTTGGC TTTCAGTTAT ATGGATGATG TGGTATTGGG GGCCAAGTCT GTACAACATC   780
TTGAGTCCCT TTTTACCTCT ATTACCAATT TTCTTTTGTC TTTGGGTATA CATTTGAACC   840
CTAATAAAAC CAAACGTTGG GGCTACTCCC TTAACTTCAT GGGATATGTA ATTGGAAGTT   900
GGGGTACTTT ACCACAGGAA CATATTGTAT TAAAACTCAA GCAATGTTTT CGAAAACTGC   960
CTGTAAATAG ACCTATTGAT TGGAAAGTAT GTCAAAGAAT TGTGGGTCTT TTGGGCTTTG  1020
CTGCCCCTTT TACACAATGT GGCTATCCTG CCTTGATGCC TTTGTATGCA TGTATACAAT  1080
CTAAGCAGGC TTTCACTTTC TCGCCAACTT ATAAGGCCTT TCTGTGTCAA CAATACCTGC  1140
ACCTTTACCC CGTTGCCCGG CAACGGTCAG GTCTCTGCCA AGTGTTTGCT GACGCAACCC  1200
CCACTGGATG GGGCTTGGCC ATAGGCCATC GGCGCATGCG TGGAACCTTT GTGGTTCCTC  1260
TGCCGATCCA TACTGCGGAA CTCCTAGCAG CTTGTTTTGC TCGCGACCGG TCTGGAGCAA  1320
AACTTATCGG GACTGACAAC TCGGTTGTCC TCTCTCGGAA ATACACCTCC TTCCCATGGC  1380
TGCTCGGGTG TGCTGCCAAC TGGATCCTGC GCGGGACGTC CTTTGTCTAC GTCCCGTCGG  1440
CGCTGAATCC CGCGGACGAC CCGTCTCGGG GCCGTTTGGG CCTCTACCGT CCCTTGCTTT  1500
CTCTGCCGTT CCAGCCGACC ACGGGGCGCA CCTCTCTTTA CGCGGTCTCC CCGTCTGTGC  1560
CTTCTCATCT GCCGGACCGT GTGCACTTCG CTTCACCTCT GCACGTCGCA TGGAGACCAC  1620
CGTGAACGGC CACCAGGTCT TGCCCAAGCT CTTACATAAG AGGACTCTTG GACTCTCAGC  1680
AATGTCAACA ACCGACCTTG AGGCATACTT CAAAGACTGT TTGTTTAAAG ACTGGGAGGA  1740
GTTGGGGGAG GAGATTAGGT TAAAGGTCTT TGTACTAGGA GGCTGTAGGC ATAAATTGGT  1800
CTGTTCACCA GCACCATGCA ACTTTTTCAC CTCTGCCTAA TCATCTCATG TTCATGTCCT  1860
ACTGTTCAAG CCTCCAAGCT GTGCCTTGGG TGGCTTTGGG GCATGGACAT TGACCCGTAT  1920
AAAGAATTTG GAGCTTCTGT GGAGTTACTC TCTTTTTTGC CTTCTGACTT CTTTCCTTCT  1980
ATTCGAGATC TCCTCGACAC CGCCTCTGCT CTGTATCGGG AGGCCTTAGA GTCTCCGGAA  2040
CATTGTTCAC CTCACCATAC AGCACTCAGG CAAGCTATTC TGTGTTGGGG TGAGTTGATG  2100
AATTTGGCCA CCTGGGTGGG AAGTAATTTG GAAGACCCAG CATCCAGGGA ATTAGTAGTC  2160
AGCTATGTCA ATGTTAATAT GGGCCTAAAA ATCAGACAAC TATTGTGGTT TCATATTTCC  2220
```

```
TGTCTTACTT TTTGGAAGAGA AACTGTTCTT GAGTATTTGG TGTCTTTTGG AGTGTGGATT      2280

CGCACTCCTC CCGCTTACAG ACCACCAAAT GCCCCTATCT TATCAACACT TCCGAAACT       2340

ACTGTTGTTA GACGACGAGG CAGGTCCCCT AGAAGAAGAA CTCCCTCGCC TCGCAGACGA      2400

AGGTCTCAAT CGCCGCGTCG CAGAAGATCT CAATCTCGGG AATCTCAATG TTAGTATCCC      2460

TTGGACTCAT AAGGTGGGAA ACTTTACTGG GCTTTATTCT TCTACTGTAC CTGTCCTTAA      2520

TCCTGAGTCC CAAACTCCCT CCTTTCCTAA CATTCATTTA CAGGAGGACA TTATTAATAG     2580

ATGTCAACAA TATGTGGGCC CTCTTACAGT TAATGAAAAA AGGAGATTAA AATTAATTAT     2640

GCCTGCTAGG TTCTATCCTA ACCTTACCAA ATATTTGCCC TTGGATAAAG GCATTAAACC     2700

TTATTATCCT GAACATGCAG TTAATCATTA CTTCAAAACT AGGCATTATT TACATACTCT     2760

GTGGAAGGCT GGCATTCTAT ATAAAAGAGA AACTACACGC AGCGCTTCAT TTTGTGGGTC     2820

ACCATATTCT TGGGAACAAG AGCTACGGCA TGGGAGGTTG GTCTTCCAAA CCTCGACAAG     2880

GCATGGGGAC GAATCTTTCT GTTCCCAATC CTCTGGGATT CTTTCCCGAT CACCAGTTGG     2940

ACCCTGCGTT CGGAGCCAAC TCAAACAATC CAGATTGGGA CTTCAACCCC AACAAGGATC     3000

ACTGGCCAGA GGCAATCAAG GTAGGAGCGG GAGACTTCGG GCCAGGGTTC ACCCCACCAC     3060

ACGGCGGTCT TTTGGGGTGG AGCCCTCAGG CTCAGGGCAT ATTGACAACA GTGCCAGCAG     3120

CGCCTCCTCC TGTTTCCACC AATCGGCAGT CAGGAAGACA GCCTACTCCC ATCTCTCCAC     3180

CTCTAAGAGA CAGTCATCCT CAGGCCATGC AGTGG                                3215

(2) INFORMATION FOR SEQ ID NO: 291:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 291:

AACTCCACAA CATTCCACCA AGCTCTGCTA GATCCCAGAG TGAGGGGCCT ATATTTTCCT        60

GCTGGTGGCT CCAGTTCCGG AACAGTAAAC CCTGTTCCGA CTACTGCCTC ACCCATATCG       120

TCAATCTTCT CGAGGACTGG GGACCCTGCA CCGAACATGG AGAGCACAAC ATCAGGATTC       180

CTAGGACCCC TGCTCGTGTT ACAGGCGGGG TTTTTCTTGT TGACAAGAAT CCTCACAATA       240

CCACAGAGTC TAGACTCGTG GTGGACTTCT CTCAATTTTC TAGGGGGAGC ACCCACGTGT       300

CCTGGCCAAA ATTCGCAGTC CCCAACCTCC AATCACTCAC CAACCTCTTG TCCTCCAATT       360

TGTCCTGGCT ATCGCTGGAT GTGTCTGCGG CGTTTTATCA TATTCCTCTT CATCCTGCTG       420

CTATGCCTCA TCTTCTTGTT GGTTCTTCTG GACTACCAAG GTATGTTGCC CGTTTGTCCT       480

CTACTTCCAG GAACATCAAC TACCAGCACG GGACCATGCA AGACCTGCAC GATTCCTGCT       540

CAAGGAACCT CTATGTTTCC CTCTTGTTGG TGTACAAAAC CTTCGGACGG AAACTGCACT       600

TGTATTCCCA TCCCATCATC CTGGGCTTTC GCAAGATTCC TATGGGAGTG GCCTCAGTC       660

CGTTTCTCCT GGCTCAGTTT ACTAGTGCCA TTTGTTCAGT GGTTCGCAGG GCTTTCCCCC      720

ACTGTTTGGC TTTCAGTTAT ATGGATGATG TGGTATTGGG GGCCAAGTCT GTACAACATC      780

TTGAGTCCCT TTTTACCTCT ATTACCAATT TTCTTTTGTC TTTGGGTATA CATTTGAACC      840
```

```
CTAATAAAAC CAAACGTTGG GGCTACTCCC TTAACTTCAT GGGATATGTA ATTGGAAGTT      900

GGGGTACTTT ACCACAGGAA CATATTGTAT TAAAACTCAA GCAATGTTTT CGGAAACTGC      960

CTGTAAATAG ACCTATTGAT TGGAAAGTAT GTCAAAGAAT TGTGGGTCTT TTGGGCTTTG     1020

CTGCCCCTTT TACACAATGT GGCTATCCTG CCTTGATGCC TTTATATGCA TGTATACAAT     1080

CTAAGCAGGC TTTCACTTTC TCGCCAACTT ATAAGGCCTT TCTGTGTCAA CAATACCTGC     1140

ACCTTTACCC CGTTGCCCGG CAACGGTCAG GTCTCTGCCA AGTGTTTGGT GACGCAACCC     1200

CCACTGGATG GGGCTTGGCC ATAGGCCATC GGCGCATGCG TGGAACCTTT GTGGCTCCTC     1260

TGCCGATCCA TACTGCGGAA CTCCTAGCAG CTTGTTTTGC TCGCAGCCGG TCTGGAGCAA     1320

AACTTATCGG GACTGACAAC TCTGTTGTCC TCTCTCGGAA ATACACCTCC TTCCCATGGC     1380

TGCTCGGGTG TGCTGCCAAC TGGATCCTGC GCGGGACGTC CTTTGTCTAC GTCCCGTCGG     1440

CGCTGAATCC CGCGGACGAC CCGTCTCGGG GCCGTTTGGG CCTCTACCGT CCCCTTCTTC     1500

ATCTGCCGTT CCAGCCGACC ACGGGGCGCA CCTCTCTTTA CGCGGTCTCC CCGTCTGTGC     1560

CTTCTCATCT GCCGGTCCGT GTGCACTTCG CTTCACCTCT GCACGTCGCA TGGAGACCAC     1620

CGTGAACGCC CACCAGGTCT TGCCTAAGCT CTTACATAAG AGGACTCTTG GACTCTCAGC     1680

AATGTCAACG ACCGACCTTG AGGCATACTT CAAAGACTGT TGTTTAAAG ACTGGGAGGA      1740

GTTGGGGGAG GAGATTAGGT TAAAGGTCTT TGTACTAGGA GGCTGTAGGC ATAAATTGGT     1800

CTGTTCACCA GCACCATGCA ACTTTTTCAC CTCTGCCTAA TCATCTCATG TTCATGTCCT     1860

ACTGTTCAAG CCTCCAAGCT GTGCCTTGGG TGGCTTTGGG GCATGGACAT TGACCCGTAT     1920

AAAGAATTTG GAGCTTCTGT GGAGTTACTC TCTTTTTTGC CTTCTGACTT CTTTCCTTCT     1980

ATTCGAGATC TCCTCGACAC CGCCTCTGCT CTGTATCGGG AGGCCTTAGA GTCTCCGGAA     2040

CATTGTTCAC CTCACCATAC AGCACTCAGG CAAGCTATCC TGTGTTGGGG TGAGTTGATG     2100

AATTTGGCCA CCTGGGTGGG AAGTAATTTG GAAGACCCAG CATCCAGGGA ATTAGTAGTC     2160

AGCTATGTCA ATGTTAATAT GGGCCTAAAA ATCAGACAAC TATTGTGGTT TCACATTTCC     2220

TGTCTTACTT TTGGAAGAGA AACTGTTCTT GAGTATTTGG TGTCTTTTGG AGTGTGGATT     2280

CGCACTCCTC CCGCTTACAG ACCACCAAAT GCCCCTATCT TATCAACACT TCCGGAAACT     2340

ACTGTTGTTA GACGACGAGG CAGGTCCCCT AGAAGAAGAA CTCCCTCGCC TCGCAGACGA     2400

AGGTCTCAAT CGCCGCGTCG CAGAAGATCT CAATCTCGGG AATCTCAATG TTAGTATCCC     2460

TTGGACTCAT AAGGTGGGAA ACTTACTGG GCTTTATTCT TCTACTGTAC CTGTCTTTAA      2520

TCCTGAGTGC CAAACTCCCT CCTTTCCTAA CATTCATTTA CAAGAGGATA TTATTAATAG     2580

ATGTCAACAA TATGTGGGCC CTCTTACAGT TAATGAAAAA AGGAGATTAA AATTAATTAT     2640

GCCTGCTAGG TTCTATCCTA ACCTTACCAA ATATTTGCCC TTGGATAAAG GCATTAAACC     2700

TTATTATCCT GAACATGCAG TTAATCATTA CTTCAAAACT AGGCATTATT TACATACGCT     2760

GTGGAAGGCT GGCATTCTAT ATAAAAGAGA AACTACACGC AGCGCTTCAT TTTGTGGGTC     2820

ACCATATTCT TGGGAACAAG AGCTACAGCA TGGGAGGTTG GTCTTCCAAA CCTCGACAAG     2880

GCATGGGGAC GAATCTTTCT GTTCCCAATC CTCTGGGATT CTTTCCCGAT CACCAGTTGG     2940

ACCCTGCGTT CGGAGCCAAC TCAAACAATC CAGATTGGGA CTTCAACCCC AACAAGGATC     3000

ACTGGCCAGA CGGAATCAAG GTAGGAGCGG GAGACTTCGG GCCAGGGTTC ACCCCACCAC     3060

ACGGCGGTCT TTTGGGGTGG AGCCCTCAGG CTCAGGGCAT CTTGACAACA GTGCCAGCAG     3120

CTCCTCCTCC TGCCTCCACC AATCGGCAGT CAGGAAGACA GCCTACTCCC ATCTCTCCAC     3180
```

```
CTCTAAGAGA CAGTCATCCT CAGGCCATGC AGTGG                            3215
```

(2) INFORMATION FOR SEQ ID NO: 292:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 292:

```
AACTCCACAA CATTCCACCA AGCTCTGCTA GATCCCAGAG TGAGGGGCCT ATATTTTCCT    60
GCTGGTGGCT CCAGTTCCGG AACAGTAAAC CCTGTTCCGA CTACTGCCTC ACCCATATCG   120
TCAATCTTCT CGAGGACTGG GGACCCTGCA CCGAACATGG AGAGCACAAC ATCAGGATTC   180
CTAGGACCCC TGCTCGTGTT ACAGGCGGGG TTTTTCTTGT TGACAAGAAT CCTCACAATA   240
CCACAGAGTC TAGACTCGTG GTGGACTTCT CTCAATTTTC TAGGGGGAGC ACCCACGTGT   300
CCTGGCCAAA ATTCGCAGTC CCCAACCTCC AATCACTCAC CAACCTCTTG TCCTCCAACT   360
TGTCCTGGCT ATCGCTGGAT GTGTCTGCGG CGTTTTATCA TATTCCTCTT CATCCTGCTG   420
CTATGCCTCA TCTTCTTGTT GGTTCTTCTG GACTACCAAG GTATGTTGCC CGTTTGTCCT   480
CTACTTCCAG GAACATCAAC TACCAGCACG GGACCATGCA GAACCTGCAC GATTCCTGCT   540
CAAGGAACCT CTATGTTTCC CTCTTGTTGC TGTACAAAAC CTTCGGACGG AAACTGCACT   600
TGTATTCCCA TCCCATCATC CTGGGCTTTC GCAAGATTCC TATGGGAGTG GGCCTCAGTC   660
CGTTTCTCCT GGCTCAGTTT ACTAGTGCCA TTTGTTCAGT GGTTCGTAGG CTTTCCCCC   720
ACTGTTTGGC TTTCAGCTAT ATGGATGATG TGGTATTGGG GGCCAAGTCT GTACAACATC   780
TTGAGTCCCT TTTTACCTCT ATTACCAATT TTCTTTTGTC TTTGGGTATA CATTTGAACC   840
CTAATAAAAC CAAACGTTGG GGCTACTCCC TTAACTTCAT GGGATATGTA ATTGGAAGTT   900
GGGGTACTTT ACCGCAGGAA CATATTGTAC AAAAACTCAA GCAATGTTTT CGAAAATTGC   960
CTGTAAATAG ACCTATTGAT TGGAAAGTAT GTCAAAGAAT TGTGGGTCTT TTGGGCTTTG  1020
CTGCCCCTTT TACACAATGT GGCTATCCTG CCTTGATGCC TTTATATGCA TGTATACAAT  1080
CTAAGCAGGC TTTCACTTTC TCGCCAACTT ACAAGGCCTT TCTGTGTAAA CAATATCTAA  1140
ACCTTTACCC CGTTGCCCGG CAACGGTCAG GTCTCTGCCA AGTGTTTGCT GACGCAACCC  1200
CCACGGGTTG GGGCTTGGCC ATAGGCCATC GGCGCATGCG TGGAACCTTT GTGGCTCCTC  1260
TGCCGATCCA TACTGCGGAA CTCCTAGCAG CTTGTTTTGC TCGCAGCCGG TCTGGAGCGA  1320
AACTTATCGG AACCGACAAC TCAGTTGTCC TCTCTCGGAA ATACACCTCC TTTCCATGGC  1380
TGCTAGGCTG TGCTGCCAAC TGGATCCTGC GCGGGACGTC CTTTGTCTAC GTCCCGTCGG  1440
CGCTGAATCC CGCGGACGAC CCGTCTCGGG GCCGTTTGGG CCTCTACCGT CCCCTTCTTC  1500
ATCTGCCGTT CCGGCCGACC ACGGGGCGCA CCTCTCTTTA CGCGGTCTCC CCGTCTGTGC  1560
CTTCTCATCT GCCGGACCGT GTGCACTTCG CTTCACCTCT GCACGTAGCA TGGAGACCAC  1620
CGTGAACGCC CACCAGGTCT TGCCCAAGGT CTTACACAAG AGGACTCTTG GACTCTCAGC  1680
AATGTCAACG ACCGACCTTG AGGCATACTT CAAAGACTGT TTGTTTAAAG ACTGGGAGGA  1740
GTTGGGGGAG GAGATTAGGT TAAAGGTCTT TGTACTAGGA GGCTGTAGGC ATAAATTGGT  1800
```

```
CTGTTCACCA GCACCATGCA ACTTTTTCCC CTCTGCCTAA TCATCTCATG TTCATGTCCT    1860

ACTGTTCAAG CCTCCAAGCT GTGCCTTGGG TGGCTTTGGG GCATGGACAT TGACCCGTAT    1920

AAAGAATTTG GAGCTTCTGT GGAGTTACTC TCTTTTTTGC CTTCTGACTT CTTTCCTTCT    1980

ATTCGAGATC TCCTCGACAC CGCCTCTGCT CTGTATCGGG AGGCCTTAGA GTCTCCGGAA    2040

CATTGTTCAC CTCACCATAC AGCACTCAGG CAAGCTATTC TGTGTTGGGG TGAGTTGATG    2100

AATCTGGCCA CCTGGGTGGG AAGTAATTTG GAAGACCCAG CATCCAGGGA ATTAGTAGTC    2160

AGCTATGTCA ATGTTAATAT GGGCCTAAAA ATTAGACAAC TATTGTGGTT TCACATTTCC    2220

TGCCTTACTT TTGGAAGAGA AACTGTCCTT GAGTATTTGG TGTCTTTTGG AGTGTGGATT    2280

CGCACTCCTC CCGCTTACAG ACCACCAAAT GCCCCTATCT TATCAACACT TCCGGAAACT    2340

ACTGTTGTTA GACGACGAGG CAGGTCCCCT AGAAGAAGAA CTCCCTCGCC TCGCAGACGA    2400

AGGTCTCAAT CGCCGCGTCG CAGAAGATCT CAATCTCGGG AATCTCAATG TTAGTATCCC    2460

TTGGACTCAT AAGGTGGGAA ACTTTACTGG GCTTTATTCT TCTACTGTAC CTGTCTTTAA    2520

TCCTGATTGG AAAACTCCCT CCTTTCCTCA CATTCATTTA CAGGAGGACA TTATTAATAG    2580

ATGTCAACAA TATGTGGGCC CTCTGACAGT TAATGAAAAA AGGAGATTAA AATTAATTAT    2640

GCCTGCTAGG TTCTATCCTA ACCTTACCAA ATATTTGCCC TTGGACAAAG GCATTAAACC    2700

GTATTATCCT GAATATGCAG TTAATCATTA CTTCAAAACT AGGCATTATT TACATACTCT    2760

GTGGAAGGCT GGCATTCTAT ATAAGAGAGA AACTACACGC AGCGCCTCAT TTTGTGGGTC    2820

ACCATATTCT TGGGAACAAG AGCTACAGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCGTT CGGAGCCAAC TCAAACAATC CAGATTGGGA CTTCAACCCC AACAAGGATC    3000

ACTGGCCAGA GGCAAATCAG GTAGGAGCGG GAGCATTTGG TCCAGGGTTC ACCCCACCAC    3060

ACGGAGGCCT TTTGGGGTGG AGCCCTCAGG CTCAGGGCAT ATTGACAACA CTGCCAGCAG    3120

CACCTCCTCC TGCCTCCACC AATCGGCAGT CAGGAAGACA GCCTACTCCC ATCTCTCCAC    3180

CTCTAAGAGA CAGTCATCCT CAGGCCATGC AGTGG                               3215
```

(2) INFORMATION FOR SEQ ID NO: 293:

(i) SEQUENCE CHARACTERISTICS:
        (A) LENGTH: 3188 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 293:

```
AATTCCACAA CATTCCACCA AGCTCTGCTA GATCCCAGAG TGAGGGGCCT ATATTTTCCT      60

GCTGGTGGCT CCAGTTCCGG AACAGTAAAC CCTGTTCCGA CTACTGCCTC ACCCATATCG     120

TCAATCTTCT CGAGGACTGG GGACCCTGCA CCGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGAGC ACCCACGTGT      300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420
```

```
CTATGCCTCA TCTTCTTGTT GGTTCTTCTG GACTACCAAG GTATGTTGCC CGTTTGTCCT    480
CTACTTCCAG GAACATCAAC CACCAGCACG GGGCCATGCA AGACCTGCAC GATTCCTGCT    540
CAAGGAACCT CTATGTTTCC CTCTTGTTGC TGTACAAAAC CTTCGGACGG AAACTGCACT    600
TGTATTCCCA TCCCATCATC CTGGGCTTTC GCAAGATTCC TATGGGAGTG GGCCTCAGTC    660
CGTTTCTCCT GGCTCAGTTT ACTAGTGCCA TTTGTTCAGT GGTTCGTAGG GCTTTCCCCC    720
ACTGTTTGGC TTTCAGTTAT ATGGATGATG TGGTATTGGG GGCCAAGTCT GTACAACATC    780
TTGAGTCCCT TTTTACCTCT ATTACCAATT TTCTTTTGTC TTTGGGTATA CATTTAAACC    840
CTAATAAAAC CAAACGTTGG GGCTACTCCC TTAACTTCAT GGGATATGTA ATTGGAAGTT    900
GGGGTACTTT ACCGCAGGAA CATATTGTAC TAAAACTCAA GCAATGTTTT CGAAAATTGC    960
CTGTAAATAG CCCTATTGAT TGGAAAGTAT GTCAAAGAAT TGTGGGTCTT TTGGGCTTTG   1020
CTGCCCCTTT TACACAATGC GGCTATCCTG CCTTGATGCC TTTATATGCA TGTATACAAT   1080
CTAAGCAGGC TTTCACTTTC TCGCCAACTT ATAAGGCCTT TCTGTGTAAA CAATATCTGA   1140
ACCTTTACCC CGTTGCCCGG CAACGGTCAG GTCTCTGCCA AGTGTTTGCT GACGCAACCC   1200
CCACTGGATG GGGCTTGGCC ATAGGCCATC GGCGCATGCG TGGAACCTTT GTGGCTCCTC   1260
TGCCGATCCA TACTGCGGAA CTCCTAGCAG CTTGTTTTGC TCGCAGCCGG TCTGGAGCGA   1320
AACTTATCGG AACCGACAAC TCTGTTGTCC TCTCTCGGAA ATACACCTCC TTTCCATGGC   1380
TGCTAGGGTG TGCTGCCAAC TGGATCCTGC GCGGACGTC  CTTTGTCTAC GTCCCGTCGG   1440
CGCTGAATCC CGCGGACGAC CCGTCTCGGG GCCGTTTGGG GCTCTACCGT CCCCTTCTTC   1500
TTCTGCCGTT CCGGCCGACC ACGGGGCGCA CCTCTCTTTA CGCGGTCTCC CCGTCTGTGC   1560
CTTCTCATCT GCCGGACCGT GTGCACTTCG CTTCACCTCT GCACGTCGCA TGGAGACCAC   1620
CGTGAACGCC CACCAGGTCT TGCCCAAGGT CTTACATAAG AGGACTCTTG GACTCTCAGC   1680
CATGTCAACG ACCGACCTTG AGGCATACTT CAAAGACTGT GTGTTTAAAG ACTGGGAGGA   1740
GTTGGGGGAG GAGATTAGGT TAAAGGTCTT TGTACTAGGA GGCTGTAGGC ATAACTTTTT   1800
CACCTCTGCC TAATCATCTC ATGTTCATGT CCTACTGTTC AAGCCTCCAA GCTGTGCCTT   1860
GGGTGGCTTT GGGGCATGGA CATTGACCCG TATAAAGAAT TTGGAGCATC TGTGGAGTTA   1920
CTCTCTTTTT TGCCTTCTGA CTTCTTTCCG TCTATTCGAG ATCTCCTTGA CACCGCCTCT   1980
GCTCTGTATC GGGAGGCCTT AGAGTCTCCG GAACATTGTT CACCTCACCA TACAGCACTC   2040
AGGCAAGCTA TTCTGTGTTG GGGTGAGTTA ATGAATCTGG CCACCTGGGT GGGAAGTAAT   2100
TTGGAAGACC CAGCATCCAG GGAATTAGTA GTCAGCTATG TCAATGTTAA TATGGGCCTA   2160
AAAATCAGAC AACTATTGTG GTTTCACATT TCCTGCCTTA CTTTTGGAAG AGAAACTGTT   2220
TTGGAGTATT TGGTATCTTT TGGAGTGTGG ATTCGCACTC CTCCCGCTTA CAGACCACCA   2280
AATGCCCCTA TCTTATCAAC ACTTCCGGAA ACTACTGTTG TTAGACGACG AGGCAGGTCC   2340
CCTAGAAGAA GAACTCCCTC GCCTCGCAGA CGAAGGTCTC AATCGCCGCG TCGCAGAAGA   2400
TCTCAATCTC GGGAATCTCA ATGTTAGTAT CCCTTGGACT CATAAGGTGG GAAACTTTAC   2460
TGGGCTTTAT TCTTCTACTG TACCTGTCTT TAATCCCGAG TGGCAAACTC CTCCTTTCC    2520
TCACATTCAT TTACAGGAGG ACATTATTAA TAGATGTCAA CAATATGTGG GCCCTCTTAC   2580
GGTTAATGAA AAAAGGAGAT TAAAATTAAT TATGCCTGCT AGGTTCTATC CTAACCTTAC   2640
TAAATATTTG CCCTTAGACA AAGGCATTAA ACCGTATTAT CCTGAACATG CAGTTAATCA   2700
TTACTTCAAA ACTAGGCATT ATTTACATAC TCTGTGGAAG GCTGGCATTC TATATAAGAG   2760
AGAAACTACA CGCAGCGCCT CATTTTGTGG GTCACCATAT TCTTGGGAAC AAGAGCTACA   2820
```

```
GCATGGGAGG TTGGTCTTCC AAACCTCGAC AAGGCATGGG GACGAATCTT TCTGTTCCCA    2880

ATCCTCTGGG ATTCTTTCCC GATCACCAGT TGGACCCTGC GTTCGGAGCC AACTCAAACA    2940

ATCCAGATTG GGACTTCAAC CCCAACAAGG ATCAATGGCC AGAGGCAAAT CAGGTAGGAG    3000

CGGGAGCATT CGGGCCAGGG TTCACCCCAC CACACGGCGG TCTTTTGGGG TGGAGCCCTC    3060

AGGCTCAGGG CATATTGACA ACAGTGCCAG CAGCACCTCC TCCTGCCTCC ACCAATCGGC    3120

AGTCAGGAAG ACAGCCTACT CCCATCTCTC CACCTCTAAG AGACAGTCAT CCTCAGGCCA    3180

TGCAGTGG                                                            3188

(2) INFORMATION FOR SEQ ID NO: 294:

(i) SEQUENCE CHARACTERISTICS:
        (A) LENGTH: 3214 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 294:

AACTCCACAA CATTCCACCA AGCTCTGCTA GACCCCAGAG TGAGGGGCCT ATACTTTCCT      60

GCTGGTGGCT CCAGTTCCGG AACAGTAAAC CCTGTTCCGA CTACTGCCTC ACCCATATCG     120

TCAATCTCCT CGAGGACTGG GGACCCTGCA CCGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGGAGC ACCCACGTGT     300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCTTGTTGC TGTACAAAAC CTTCGGACGG AAACTGCACT     600

TGTATTCCCA TCCCATCATC CTGGGCTTTC GCAAGATTCC TATGGGAGGG GGCCTCAGTC     660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTAAACC     840

CTAATAAAAC CAAACGTTGG GGCTACTCCC TTAACTTCAT GGGATATGTA ATTGGATGTT     900

GGGGTACTTT ACCGCAAGAA CATATTGTAC TAAAAATCAA GCAATGTTTT CGAAAACTGC     960

CTGTAAATAG ACCTATTGAT TGGAAAGTAT GTCAGAGACT TGTGGGTCTT TTGGGCTTTG    1020

CTGCCCCTTT TACACAATGT GGCTATCCTG CCTTAATGCC TTTATATGCA TGTATACAAT    1080

CTAAGCAGGC TTTCACTTTC TCGCCAACTT ACAAGGCCTT TCTGTGTAAA CAATATCTGA    1140

ACCTTTACCC CGTTGCCCGG CAACGGTCAG GTCTCTGCCA AGTGTTTGCT GACGCAACCC    1200

CCACTGGATG GGGCTTGGCT ATCGGCCATA GCCGCATGCG CGGACCTTTG TGGCTCCTCT    1260

GCCGATCCAT ACTGCGGAAC TCCTAGCAGC TTGTTTTGCT CGCAGGCGGT CTGGAGCGAA    1320

ACTTATCGGC ACCGACAACT CTGTTGTCCT CTCTCGGAAA TACACCTCCT TTCCATGGCT    1380

GCTAGGGTGT GCTGCCAACT GGATCCTGCG CGGGACGTCC TTTGTCTACG TCCCGTCGGC    1440
```

```
GCTGAATCCC GCGGACGACC CGTCTCGGGG CCGTTTGGGA CTCTACCGTC CCCTTCTTCA    1500

TCTGCCGTTC CGGCCGACCA CGGGGCGCAC CTCTCTTTAC GCGGTCTTTT TGTCTGTGCC    1560

TTCTCATCTG CCGGTCCGTG TGCACTTCGC TTCACCTCTG CACGTCGCAT GGAGACCACC    1620

GTGAACGCCC ACCAGGTCTT GCCCAAGGTC TTACATAAGA GGACTCTTGG ACTCTCAGCG    1680

ATGTCAACGA CCGACCTTGA GGCATACTTC AAAGACTGTT TGTTTAAGGA CTGGGAGGAG    1740

TTGGGGGAGG AGATTAGGTT AAAGGTCTTT GTACTAGGAG GCTGTAGGCA TAAATTGGTC    1800

TGTTCACCAG CACCATGCAA CTTTTTCACC TCTGCCTAAT CATCTCATGT TCATGTCCTA    1860

CTGTTCAAGC CTCCAAGCTG TGCCTTGGGT GGCTTTGGGG CATGGACATT GACCCGTATA    1920

AAGAATTTGG AGCTTCTGTG GAGTTACTCT CTTTTTTGCC TTCTGACTTC TTTCCTTCTA    1980

TTCGAGATCT CCTCGACACC GCCTCAGCTC TATATCGGGA GGCCTTAGAG TCTCCGGAAC    2040

ATTGTTCTCC TCATCATACA GCACTCAGGC AAGCTATTCT GTGTTGGGGT GAGTTGATGA    2100

ATCTGGCCAC CTGGGTGGGA AGTAATTTGG AAGACCCAGC ATCCAGGGAA TTAGTAGTCA    2160

GCTATGTCAA TGTTAATATG GGCCTAAAAA TCAGACAACT ACTGTGGTTT CACATTTCCT    2220

GTCTTACTTT TGGAAGAGAA ACTGTTCTTG AGTATTTGGT GTCTTTTGGA GTGTGGATTC    2280

GCACTCCTCC TGCTTACAGA CCACCAAATG CCCCTATCTT ATCAACACTT CCGGAAACTA    2340

CTGTTGTTAG ACGACGAGGC AGGTCCCCTA GAAGAAGAAC TCCCTCGCCT CGCAGACGAA    2400

GGTCTCAATC GCCGCGTCGC AGAAGATCTC AATCTCGGGA ATCTCAATGT TAGTATCCCT    2460

TGGACTCATA AGGTGGGAAA CTTTACTGGG CTTTATTCTT CTACTGTACC TGTCTTTAAT    2520

CCTGAGTGGC AAACTCCCTC CTTTCCTCAC ATTCATTTAC AGGAGGACAT TATTAATAGA    2580

TGTCAACAAT ATGTGGGCCC TCTTACAGTT AATGAAAAAA GGAGATTAAA ATTAATTATG    2640

CCTGCTAGGT TCTATCCTAA CCTTACCAAA TATTTGCCAT GGACAAAGG CATTAAACCA    2700

TATTATCCTG AACATGCAGT TAATCATTAC TTCAAAACTA GGCATTATTT ACATACTCTG    2760

TGGAAGGCGG GCATTCTATA TAAGAGAGAA ACTACACGCA GTGCCTCATT CTGTGGGTCA    2820

CCATATTCTT GGGAACAAGA GCTACAGCAT GGGAGGTTGG TCTTCCAAAC CTCGACAAGG    2880

CATGGGACG AATCTTTCTG TTCCCAATCC TCTGGGATTC TTTCCCGATC ACCAGTTGGA    2940

CCCTGCGTTC GGAGCCAACT CACACAATCC CGATTGGGAC TTCAACCCCA ACAAGGATCA    3000

TTGGCCAGAG GCAAATCAGG TAGGAGCGGG AGCATTCGGG CCAGGGTTCA CCCCACCACA    3060

CGGCGGTCTT TTGGGGTGGA GCCCGCAGGC TCAGGGCGTA TTGACAACCG TGCCAGTAGC    3120

ACCTCCTCCT GCCTCCACCA ATCGGCAGTC AGGAAGACAG CCTACTCCCA TCTCTCCACC    3180

TCTAAGAGAC AGTCATCCTC AGGCCATGCA GTGG                                3214
```

(2) INFORMATION FOR SEQ ID NO: 295:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 295:

```
AACTCCACAA CATTCCACCA AGCTCTGCTA GACCCCAGAG TGAGGGGCCT ATACTTTCCT      60
```

```
GCTGGTGGCT CCAGTTCCGG AACAGTAAAC CCTGTTCCGA CTACTGCCTC ACCCATATCG    120

TCAATCTTCT CGAGGACTGG GGACCCTGCA CCGAACATGG AGAACACAAC ATCAGGATTC    180

CTAGGACCCC TGCTCGTGTT ACAGGCGGGG TTTTTCTTGT TGACAAGAAT CCTCACAATA    240

CCACAGAGTC TACACTCGTG GTGGACTTCT CTCAATTTTC TAGGGCAGC ACCCACGTGT     300

CTTGGCCAAA ATTCGCAGTC CCCAACCTCC AATCACTCAC CAACCTCTTG TCCTCCAATT    360

TGTCCTGGTT ATCGTTGGAT GTGTCTGCGG CGTTTTATCA TATTCCTCTT CATCCTGCTG    420

CTATGCCTCA TCTTCTTGTT GGTTCTTCTG GACTACCAAG GTATGTTGTC TGTTTGTCCT    480

CTACTTCCAA GAACATCAAC TACCAGCACG GGACCATGCA AGACCTGCAC GATTCCTGCT    540

CAAGGAACCT CTATGTTTCC CTCTTCTTGC TGTACAAAAC CTTCGGACGG AAACTGCACT    600

TGTATTCCCA TCCCATCATC TTGGGCTTTC GCAAGATTCC TATGGGAGTG GGCCTCAGTC    660

CGTTTCTCCT GGCTCAGTTT ACTAGTGCCA TTTGTTCAGT GGTTCGTAGG GCTTTCCCCC    720

ACTGTTTGGC TTTCAGTTAT ATGGATGATG TGGTATTGGG GGCCAAGTCT GTACAACATC    780

TTGAGTCCCT TTTTACCTCT ATTACCAATT TTCTTTTGTC TTTGGGTATA CATTTGAACC    840

CCAATAAAAC CAAACGTTGG GGCTATTCCC TTAATTTCAT GGGATATGTA ATTGGATGTT    900

GGGGTACTTT ACCGCAAGAA CATATTGTAC TAAAAATCAA GCAATGTTTT CGAAAACTGC    960

CTGTAAATAG ACCTATTGAT TGGAAAGTAT GTCAGAGAAT TGTGGGTCTT TTGGGCTTTG   1020

CTGCCCCTTT TACACAATGT GGCTATCCTG CCTTGATGCC TTTATATGCA TGTATACAAT   1080

CTAAGCAAGC TTTCACTTTC TCGCCAACTT ACAAGGCCTT TCTGTGTAAA CAATATCTGA   1140

ACCTTTACCC CGTTGCCCGG CAACGGTCAG GTCTCTGCCA AGTGTTTGCT GACGCAACCC   1200

CCACTGGATG GGGCTTGGCT ATTGGCCATC GCCGCATGCG TGGAACCTTT GTGGCTCCTC   1260

TGCCGATCCA TACTGCGGAA CTCCTGGCAG CCTGTTTTGC TCGCAGCCGG TCTGGAGCAA   1320

AACTTATCGG AACCGACAAC TCTGTTGTCC TCTCTCGGAA ATACACCTCC TTTCCATGGC   1380

TGCTCGGGTG TGCTGCCAAC TGGATCCTGC GCGGGACGTC CTTTGTCTAC GTCCCGTCGG   1440

CGCTGAATCC CGCGGACGAC CCGTCTCGGG GCCGTTTGGG CCTCTATCGT CCCCTTCTTC   1500

ATCTACCGTT CCGGCCGACC ACGGGGCGCA CCTCTCTTTA CGCGGTCTCC CCGTCTGTGC   1560

CTTCTCATCT GCCGGACCGT GTGCACTTCC CTTCACCTCT GCACGTCGCA TGGAGACCAC   1620

CGTGAACGCC CACCAGGTCT TGCCCAAGGT CTTACATAAG AGCACTCTTG GACTCTCAGC   1680

AATGTCAACG ACCGACCTTG AGGCATACTT CAAAGACTGT TGTTTAAGG ACTGGGAGGA    1740

GTTGGGGGAG GAGATTAGGT TAAAGGTCTT TGTACTGGGA GGCTGTAGGC ATAAATTGGT   1800

CTGTTCACCA GCACCATGCA ACTTTTTCAC CTCTGCCTAA TCATCTCATG TTCATGTCCT   1860

ACTGTTCAAG CCTCCAAGCT GTGCCTTGGG TGGCTTTGGG GCATGGACAT TGACCCGTAT   1920

AAAGAATTTG GAGCTTCTGT GGAGTTACTC TCTTTTTTGC CTTCTGACTT CTTTCCTTCT   1980

ATTCGAGATC TCCTCGACAC CGCCTCAGCT CTGTATCGGG AGGCCTTAGA GTCTCCGGAA   2040

CATTGCTCAC CTCACCATAC CGCACTCAGG CAAGCTATTC TGTGTTGGCG TGAGTTGATG   2100

AATCTGGCCA CCTGGGTGGG AAGTAATTTG GAAGACCCAG CATCCAGGGA ATTAGTAGTC   2160

AGCTATGTCA ATGTTAATAT CGGCCTAAAA ATCAGACAAC TACTGTGGTT TCACATTTCC   2220

TGTCTTACTT TTGGAAGAGA AACTGTTCTT GAGTATTTGG TGTCTTTTGG AGTGTGGATT   2280

CGCACTCCTC CTGCTTACAG ACCACCAAAT GCCCCTATCT TATCAACACT TCCGAAAACT   2340

ACTGTTGTTA GACGACGAGG CAGGTCCCCT AGAAGAAGAA CTCCCTCGCC TCGCAGACGA   2400
```

| | |
|---|---|
| AGGTCTCAAT CGCCGCGTCG CAGAAGATCT CAATCTCGGG AATCTCAATG TTAGTATCCC | 2460 |
| TTGGACTCAT AAGGTGGGAA ACTTTACTGG GCTTTATTCT TCTACTGTAC CTATCTTTAA | 2520 |
| TCCTGAGTGG CAAACTCCCT CCTTTCCTCA CATTCATTTA CAGGAGGACA TTATTAATAG | 2580 |
| ATGTCAACAA TATGTGGGCC CTCTTACAGT TAATGAAAAA AGGAGATTAA AGTTAATTAT | 2640 |
| GCCTGCTAGG TTCTATCCTA ACCTTACCAA ATATCTGCCC TTGGACAAAG GCATTAAACC | 2700 |
| ATATTATCCT GAACATGCAG TTAATCATTA CTTCAAAACT AGGCATTATT TACATACTCT | 2760 |
| GTGGAAGGCG GGCATTCTAT ATAAGAGAGA AACTACGCGC AGCGCCTCAT TTTGTGGGTC | 2820 |
| ACCATATTCT TGGGAACAAG AGCTACAGCA TGGGAGGTTG GTCTTCCAAA CCTCGACAAG | 2880 |
| GCATGGGGAC GAATCTTTCT GTTCCCAATC CTCTGGGATT CTTTCCCGAT CACCAGTTGG | 2940 |
| ACCCTGCGTT CGGAGCCAAC TCAAACAATC CAGATTGGGA CTTCAACCCC AACAAGGATC | 3000 |
| ACTGGCCAGA GGCAAATCAG GTAGGAGCGG GAGCATTCGG GCCAGGGTTC ACCCCACCAC | 3060 |
| ACGGCGGTCT TTTGGGGTGG AGCCCTCAGG CTCAGGGCAT ATTGACAACA GTGCCAGTAG | 3120 |
| CACCTCCTCC TGCCTCCACC AATCGGCAGT CAGGAAGACA GCCTACTCCC ATCTCTCCAC | 3180 |
| CTCTAAGAGA CAGTCATCCT CAGGCCATGC AGTGG | 3215 |

(2) INFORMATION FOR SEQ ID NO: 296:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 296:

| | |
|---|---|
| AACTCCACAA CATTCCACCA AGCTGTGCTA GATCCCAGAG TGAGGGGCCT ATATCTTCCT | 60 |
| GCTGGTGGCT CCAGTTCCGG AACAGTGAAC CCTGTTCCGA CTACTGCCTC ACCCATATCG | 120 |
| TCAATCTTCT CGAGGACTGG GGACCCTGCA CCGAACATGG AGAACACAAC ATCAGGATTC | 180 |
| CTAGGACCCC TGCTCGTGTT ACAGGCGGGG TTTTTCTTGT TGACAAGAAT CCTCACAATA | 240 |
| CCACAGAGTC TAGACTCGTG GTGGACTTCT CTCAATTTTC TAGGGGGAGC ACCCACGTGT | 300 |
| CCTGGCCCAA ATTCGCAGTC CCCAACCTCC AATCACTCAC CAACCTCTTG TCCTCCAATT | 360 |
| TGTCCTGGCT ATCGCTGGAT GTGTCTGCGG CGTTTTATCA TATTCCTCTT CATCCTGCTG | 420 |
| CTATGCCTCA TCTTCTTGTT GGTTCTTCTG GACTACCAAG GTATGTTGCC CGTTTGTCCT | 480 |
| CTACTTCCAG GAACATCAAC TACCAGCACG GGACCATGCA AGACCTGCAC GATTCCTGCT | 540 |
| CAAGGAACCT CTATGTTTCC CTCCTGTTGC TGTACAAAAC CTTCGGACGG AAACTGCACT | 600 |
| TGTATTCCCA TCCCATCATC CTGGGCTTTC GCAAGATTCC TATGGGAGTG GCCTCAGTC | 660 |
| CGTTTCTCCT GGCTCAGTTT ACTAGTGCCA TTTGTTCAGT GGTTCGTAGG GCTTTCCCCC | 720 |
| ACTGTTTGGC TTTCAGTTAT ATGGATGATG TGGTATTGGG GGCCAAGTCT GTACAACATC | 780 |
| TTGAGTCCCT TTTTACCTCT ATTACCAATT TTCTTTTGTC TTTGGGTATA CATTTGAACC | 840 |
| CTCATAAAAC CAAACGTTGG GGCTACTCCC TTAACTTCAT GGGATATGTA ATTGGAAGTT | 900 |
| GGGGTACTTT ACCACAGGAA CATATTGTAC TAAAAATCAA GCAATGTTTT CGGAAGCTGC | 960 |
| CTGTAAATAG ACCTATTGAT TGGAAAGTAT GTCAAAGGAT TGTGGGTCTT TTGGGCTTTG | 1020 |

| | |
|---|---|
| CTGCCCCTTT TACACAATGT GGCTATCCTG CCTTGATGCC TTTATATGCA TGTATACAAT | 1080 |
| CTAAGCAGGC TTTCACTTTC TCGCCAACTT ACAAGGCCTT TCTGTGTAAA CAATATCTGC | 1140 |
| ACCTTTACCC CGTTGCCCGG CAACGGTCAG GTCTCTGCCA AGTGTTTGCT GACGCAACCC | 1200 |
| CCACTGGATG GGGCTTGGCC ATTGGCCAAT CGGGCATGCG TGGAACCTTT GTGGCTCCTC | 1260 |
| TGCCGATCCA TACTGCGGAA CTCCTAGCAG CTTGTTTTGC TCGCAGCCGG TCTGGAGCGA | 1320 |
| AACTTATCGG GACTGACAAC TCTGTTGTCC TCTCTCGGAA ATACACCTCC TTCCCATGGC | 1380 |
| TGCTCGGGTG TGCTGCCAAC TGGATCCTGC GCGGGACGTC CTTTGTCTAC GTCCCGTCGG | 1440 |
| CGCTGAATCC CGCGGACGAC CCGTCTCGGG GCCGTTTGGG CCTCTACCGT CCCCTTCTTC | 1500 |
| ATCTGCCGTT CCGGCCGACC ACGGGGCGCG CCTCTCTTTA CGCGGTCTCC CCGTCTGTGC | 1560 |
| CTTCTCATCT GCCGGTCCGT GTGCACTTCG CTTCACCTCT GCACGTCGCA TGGAGACCAC | 1620 |
| CGTGAACGCC CACCAGGTCT TGCCCAAGGT CTTACATAAG AGGACTCTTG GACTCTCAGC | 1680 |
| GATGTCAACG ACCGACCTTG AGGCATATTT CAAAGACTGT TTGTTTAAAG ACTGGGAGGA | 1740 |
| GTTGGGGGAG GAGATTAGGT TAATGGTCTT TGTACTAGGA GGCTGTAGGC ATAAATTGGT | 1800 |
| CTGTTCACCA GCACCATGCA ACTTTTTCAC CTCTGCCTAA TCATCTCCTG TTCATGTCCT | 1860 |
| ACTGTTCAAG CCTCCAAGCT GTGCCTTGGG TGGCTTAGGG GCATGGACAT TGACACGTAT | 1920 |
| AAAGAATTTG GAGCTTCTGT GGAGTTACTC TCTTTTTTGC CTTCTGACTT CTTTCCTTCT | 1980 |
| ATTCGAGATC TCCTCGACAC CGCCTTTGCT CTGCATCGGG AGGCCTTAGA GTCTCCGGAA | 2040 |
| CATTGTTCAC CTCACCATAC AGCACTCAGG CAAGCTATTG TGTGTTGGGG TGAGTTGATG | 2100 |
| AATCTGGCCA CCTGGGTGGG AAGTAATTTG GAAGACCCAG CATCCAGGGA ATTGGTAGTC | 2160 |
| AGCTATGTCA ATGTTAATAT GGGCCTAAAA ATCAGACAAC TATTGTGGTT TCACATTTCC | 2220 |
| TGTCTTACTT TTGGAAGAGA AACGGTTCTT GAGTATTTGG TATCTGTTGG AGTGTGGATT | 2280 |
| CGCACTCCTC AAGCCTACAG ACCACCAAAT GCCCCTATCT TATCAACACT TCCGGAAACT | 2340 |
| ACTGTTGTTA GACGACGAGG CAGGTCCCCT AGAAGAAGAA CTCCCTCGCC TCGCAGACGA | 2400 |
| AGGTCTAAAT CGCCGCGTCG CAGAAGATCT CAATCTCGGG AATCTCAATG TTAGTATCCC | 2460 |
| TTGGACTCAT AAGGTGGGAA ACTTTACTGG TCTCTATTCT TCTACTGTAC CTGTCTTTAA | 2520 |
| TCCTGAGTGG CAAACTCCCT CCTTTCCTAA TATTCATTTA CAGGAGGATA TTATTAATAG | 2580 |
| ATGTCAACAA TATGTAGGCC CTCTTACAGT TAATGAAAAA AGGAGATTAA AATTAATTAT | 2640 |
| GCCTGCTAGG TTCTATCCTA ACCTTACCAA ATATTTGCCC TTGGATAAAG GTATTAAACC | 2700 |
| TTATTATCCT GAACATGCAG TTAATCATTA TTTCAAAACT AGGCATTATT TACATACTCT | 2760 |
| GTGGAAGGCT GGCATTCTAT ATAAGAGAGA AACTACACGT AGTGCCTCAT TTTGTGGGTC | 2820 |
| ACCATATTCT TGGGAACAAG AGCTACAGCA TGGGAGGTTG GTCTTCCAAA CCTCGACAAG | 2880 |
| GCATGGGAC GAATCTTTCT GTTCCCAATC CTCTGGGATT CTTTCCCGAT CACCAGTTGG | 2940 |
| ACCCTGCATT CGGAGCCAAC TCAAACAATC CAGATTGGGA CTTCAACCCC AACAAGGATC | 3000 |
| ATTGGCCAGA GGCAAATCAG GTAGGAGCGG GAGCATTTGG GCCAGGGTTC ACTCCACCAC | 3060 |
| ACGGCGGTCT TTTGGGGTGG AGCCCTCAGG CTCAGGGCAT ATTGACAACA GTGCCAGCAG | 3120 |
| CGCCTCCTCC TGCCTCTACC AATCGGCAGT CAGGAAGACA GCCTACTCCC ATCTCTCCAC | 3180 |
| CTCTAAGAGA CAGTCATCCT CAGGCCATGC AGTGG | 3215 |

(2) INFORMATION FOR SEQ ID NO: 297:

(i) SEQUENCE CHARACTERISTICS:
        (A) LENGTH: 3215 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 297:

```
AACTCCACAA CATTCCACCA AGCTGTGCTA GATCCCAGAG TGAGGGGCCT ATATCTTCCT      60
GCTGGTGGCT CCAGTTCCGG AACAGTGAAC CCTGTTCCGA CTACTGCCTC ACCCATATCG     120
TCAATCTTCT CGAGGACTGG GGACCCTGCA CCGAACATGG AGAACACAAC ATCAGGATTC     180
CTAGGACCCC TGCTCGTGTT ACAGGCGGGG TTTTTCTTGT TGACAAGAAT CCTCACAATA     240
CCACAGAGTC TAGACTCGTG GTGGACTTCT CTCAATTTTC TAGGGGGAGC ACCCACGTGT     300
CCTGGCCCAA ATTCGCAGTC CCCAACCTCC AATCACTCAC CAACCTCTTG TCCTCCAATT     360
TGTCCTGGCT ATCGCTGGAT GTGTCTGCGG CGTTTTATCA TATTCCTCTT CATCCTGCTG     420
CTATGCCTCA TCTTCTTGTT GGTTCTTCTG GACTACCAAG GTATGTTGCC CGTTTGTCCT     480
CTACTTCCAG GAACATCAAC TACCAGCACG GGACCATGCA AGACCTGCAC GATTCCTGCT     540
CAAGGAACCT CTATGTTTCC CTCCTGTTGC TGTACAAAAC CTTCGGACGG AAACTGCACT     600
TGTATTCCCA TCCCATCATC CTGGGCTTTC GCAAGATTCC TATGGGAGTG GCCTCAGTC      660
CGTTTCTCCT GGCTCAGTTT ACTAGTGCCA TTTGTTCAGT GGTTCGTAGG GCTTTCCCCC     720
ACTGTTTGGC TTTCAGTTAT ATGGATGATG TGGTATTGGG GGCCAAGTCT GTACAACATC     780
TTGAGTCCCT TTTTACCTCT ATTACCAATT TTCTTTTGTC TTTGGGTATA CATTTGAACC     840
CTCATAAAAC CAAACGTTGG GGCTACTCCC TTAACTTCAT GGGATATGTA ATTGGAAGTT     900
GGGGTACTTT ACCACAGGAA CATATTGTAC TAAAAATCAA GCAATGTTTT CGGAAGCTGC     960
CTGTAAATAG ACCTATTGAT TGGAAAGTAT GTCAAAGGAT TGTGGGTCTT TTGGGCTTTG    1020
CTGCCCCTTT TACACAATGT GGCTATCCTG CCTTGATGCC TTTATATGCA TGTATACAAT    1080
CTAAGCAGGC TTTCACTTTC TCGCCAACTT ACAAGGCCTT TCTGTGTAAA CAATATCTGC    1140
ACCTTTACCC CGTTGCCCGG CAACGGTCAG GTCTCTGCCA AGTGTTTGCT GACGCAACCC    1200
CCACTGGATG GGGCTTGGCC ATTGGCCAAT CGGGCATGCG TGGAACCTTT GTGGCTCCTC    1260
TGCCGATCCA TACTGCGGAA CTCCTAGCAG CTTGTTTTGC TCGCAGCCGG TCTGGAGCGA    1320
AACTTATCGG GACTGACAAC TCTGTTGTCC TCTCTCGGAA ATACACCTCC TTCCCATGGC    1380
TGCTCGGGTG TGCTGCCAAC TGGATCCTGC GCGGGACGTC CTTTGTCTAC GTCCCGTCGG    1440
CGCTGAATCC CGCGGACGAC CCGTCTCGGG GCCGTTGGG CCTCTACCGT CCCCTTCTTC    1500
ATCTGCCGTT CCGGCCGACC ACGGGGCGCG CCTCTCTTTA CGCGGTCTCC CCGTCTGTGC    1560
CTTCTCATCT GCCGGTCCGT GTGCACTTCG CTTCACCTCT GCACGTCGCA TGGAGACCAC    1620
CGTGAACGCC CACCAGGTCT TGCCCAAGGT CTTACATAAG AGGACTCTTG GACTCTCAGC    1680
GATGTCAACG ACCGACCTTG AGGCATATTT CAAAGACTGT TTGTTTAAAG ACTGGGAGGA    1740
GTTGGGGGAG GAGATTAGGT TAATGGTCTT TGTACTAGGA GGCTGTAGGC ATAAATTGGT    1800
CTGTTCACCA GCACCATGCA ACTTTTTCAC CTCTGCCTAA TCATCTCCTG TTCATGTCCT    1860
ACTGTTCAAG CCTCCAAGCT GTGCCTTGGG TGGCTTAGGG GCATGGACAT TGACACGTAT    1920
AAAGAATTTG GAGCTTCTGT GGAGTTACTC TCTTTTTTGC CTTCTGACTT CTTTCCTTCT    1980
ATTCGAGATC TCCTCGACAC CGCCTTTGCT CTGCATCGGG AGGCCTTAGA GTCTCCGGAA    2040
```

```
CATTGTTCAC CTCACCATAC AGCACTCAGG CAAGCTATTG TGTGTTGGGG TGAGTTGATG    2100

AATCTGGCCA CCTGGGTGGG AAGTAATTTG GAAGACCCAG CATCCAGGGA ATTGGTAGTC    2160

AGCTATGTCA ATGTTAATAT GGGCCTAAAA ATCAGACAAC TATTGTGGTT TCACATTTCC    2220

TGTCTTACTT TTGGAAGAGA AACGGTTCTT GAGTATTTGG TATCTGTTGG AGTGTGGATT    2280

CGCACTCCTC AAGCCTACAG ACCACCAAAT GCCCCTATCT TATCAACACT TCCGGAAACT    2340

ACTGTTGTTA GACGACGAGG CAGGTCCCCT AGAAGAAGAA CTCCCTCGCC TCGCAGACGA    2400

AGGTCTAAAT CGCCGCGTCG CAGAAGATCT CAATCTCGGG AATCTCAATG TTAGTATCCC    2460

TTGGACTCAT AAGGTGGGAA ACTTTACTGG TCTCTATTCT TCTACTGTAC CTGTCTTTAA    2520

TCCTGAGTGG CAAACTCCCT CCTTTCCTAA TATTCATTTA CAGGAGGATA TTATTAATAG    2580

ATGTCAACAA TATGTAGGCC CTCTTACAGT TAATGAAAAA AGGAGATTAA AATTAATTAT    2640

GCCTGCTAGG TTCTATCCTA ACCTTACCAA ATATTTGCCC TTGGATAAAG GTATTAAACC    2700

TTATTATCCT GAACATGCAG TTAATCATTA TTTCAAAACT AGGCATTATT TACATACTCT    2760

GTGGAAGGCT GGCATTCTAT ATAAGAGAGA AACTACACGT AGTGCCTCAT TTTGTGGGTC    2820

ACCATATTCT TGGGAACAAG AGCTACAGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCATT CGGAGCCAAC TCAAACAATC CAGATTGGGA CTTCAACCCC AACAAGGATC    3000

ATTGGCCAGA GGCAAATCAG GTAGGAGCGG GAGCATTTGG GCCAGGGTTC ACTCCACCAC    3060

ACGGCGGTCT TTTGGGGTGG AGCCCTCAGG CTCAGGGCAT ATTGACAACA GTGCCAGCAG    3120

CGCCTCCTCC TGCCTCTACC AATCGGCAGT CAGGAAGACA GCCTACTCCC ATCTCTCCAC    3180

CTCTAAGAGA CAGTCATCCT CAGGCCATGC AGTGG                              3215

(2) INFORMATION FOR SEQ ID NO: 298:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 298:

AACTCCACCA CATTCCACCA AGCTCTGCTA GATCCCAGAG TGAGGGGCCT ATATTTTCCT      60

GCTGGTGGCT CCAGTTCCGG AACAGTAAAC CCTGTTCCGA CTACTGCCTC ACCCATATCG    120

TCAATCTTCT CGAGGACTGG GGACCCTGCG CCGAACATGG AGAACACAAC ATCAGGATTC    180

CTAGGACCCC TGCTCGTGTT ACAGGCGGGG TTTTTCTTGT TGACAAGAAT CCTCACAATA    240

CCACAGAGTC TAGACTCGTG GACTTCTCTC AATTTTCTAG GGGAGCACC CACGTGTCCT    300

GGCCAAAATT CGCAGTCCCC AACCTCCAAT CACTCACCAA CCTCTTGTCC TCCAATTTGT    360

CCTGGCTATC GCTGGATGTG TCTGCGGCGT TTTATCATAT TCCTCTTCAT CCTGCTGCTA    420

TGCCTCATCT TCTTGTTGGC TCTTCTGGAC TACCAAGGTA TGTTGCCCGT TGTCCTCTA    480

CTTCCAGGAA CATCAACTAC CAGCACGGGA CCATGCAAGA CCTGCACGAT TCCTGCTCAA    540

GGAACCTCTA TGTTTCCCTC TTGTTGCTGT ACAAAACCTT CGGACGGAAA TTGCACTTGT    600

ATTCCCATCC CGTCATCTTG GGCTTTCGCA AGATTCCTAT GGGAGTGGGC CTCAGTCCGT    660
```

```
TTCTCCTGGC TCAGTTTACT AGTGCCATTT GTTCAGTGGT TCGCAGGGCT TTCCCCCACT    720

GTTTGGCTTT CAGTTATATG GATGATGTGG TATTGGGGGC CAAGTCTGTA CAACATCTTG    780

AGTCCCTTTA TACCTCTATT ACCAATTTTC TTGTGTCTTT GGGTATACAT TTGAACCCTA    840

ATAAAACCAA ACGTTGGGGC TACTCCCTTA ACTTCATGGG ATATGTAATT GGAAGTTGGG    900

GTACGTTACC ACAGGAACAT ATTGTACAAA AAATCAAGCA ATGTTTTCGG AAACTGCCTG    960

TAAATAGACC TATTGATTGG AAAGTATGTC AAGAATTGT GGGTCTTTTG GGCTTTGCTG     1020

CCCCTTTTAC ACAATGTGGT TATCCTGCCT TGATGCCTTT ATATGCATGT ATACAAGCTA    1080

AGCAGGCTTT TACTTTCTCG TCAACTTACA AGGCCTTTCT GTGTAAACAA TATCTGCACC    1140

TTTACCCCGT TGCCCGGCAA CGGTCAGGTC TCTGCCAAGT GTTTGCTGAC GCAACCCCCA    1200

CTGGATGGGG CTTGGCCATA GGCCATCGGC GCATGCGTGG AACCTTTGTG GCTCCTCTGC    1260

CGATCCATAC TGCGGAACTC CTAGCAGCTT GTTTTGCTCG CAGCCGGTCT GGAGCGAAAC    1320

TTATCGGGAC TGACAACTCT GTTGTCCTCT CTCGGAAATA CACCTCCTTC CCATGGCTGC    1380

TCGGATGTGC TGCCAACTGG ATCCTGCGCG GGACGTCCTT TGTCTACGTC CCGTCGGCGC    1440

TGAATCCCGC GGACGACCCG TCTCGGGGTC GTTTGGGCCT CTACCGTCCC CTTCTTCATC    1500

TGCCGTTCCG GCCGACCACG GGGCGCACCT CTCTTTACGC GGTCTCCCCG TCTGTGCCTT    1560

CTCATCTGCC GGACCGTGTG CACTTCGCTT CACCTCTGCA CGTCGCATGG AGACCACCGT    1620

GAACGCCCAT CAGGTGTTGC CCAAGGTCTT ATATAAGAGG ACTCTTGGAC TTTCAGCAAT    1680

GTCAACGACC GACCTTGAGG CATACTTCAA AGACTGTTTG TTTAAGGACT GGGAGGAGTT    1740

GGGGGAGGAA CTTAGGTTAA TGATCTTTGT ACTAGGAGGC TGTAGGCATA AATTGGTCTG    1800

TTCACCAGCA CCATGCAACT TTTTCACCTC TGCCTAATCA TCTCTTGTTC ATGTCCTACT    1860

GTTCAAGCCT CCAAGCTGTG CCTTGGGTGG CTTTAGGACA TGGACATTGA CCCATATAAA    1920

GAATTTGGAG CTTCTGTGGA GTTACTCTCT TTTTTGCCTT CTGACTTCTT TCCTTCTATT    1980

CGAGATCTCC TCGACACCGC CTCTGCTCTG TATCGGGAGG CCCTAGAGTC TCCGGAGCAT    2040

TGTACACCTC ACCATACAGC ACTCAGGCAA GCTATTCTGT GTTGGGGTGA GTTGATGAAC    2100

CTGGCCACCT GGGTGGGAAG TAATTTGGAA GATCCAACAT CCAGGGAAGC AGTAGTCAGC    2160

TATGTCAATG TTAATATGGG CCTAAAACTC AGACAACTAT TGTGGTTTCA CATTTCCTGT    2220

CTTACTTTTG GAAGAGATAC TGTTCTTGAG TATTTGGTGT CTTTTGGAGT GTGGATTCGC    2280

ACTCCTACCG CTTACAGACC ACCAAATGCC CCTATCTTAT CAACACTTCC GGAAACTACT    2340

GTTGTTAGAC GACGAGGCAG GTCCCCTAGA AGAAGAACTC CCTCGCCTCG CAGACGAAGG    2400

TCTCAATCGC CGCGTCGCAG AAGATCTCAA TCTCGGGAAC CTCAATGTTA ATGTCCCTTG    2460

GACTCATAAG GTGGGAAACT TTACAGGACT TTACTCTTCT ACTGTACCTG TCTTTAATCC    2520

TGAGTGGCAA ACTCCCTCCT TTCCTAACAT TCATTTACAG GAGGACATTA TTGATAGATG    2580

TCAACAATAT GTGGGCCCTC TTACAGTTAA TGAAAAAAGG AGATTAAAAT TAATTATGCC    2640

TGCTAGGTTT TATCCAAACC TTACCAAATA TTTGCCCTTG GATAAAGGCA TTAAACCTTA    2700

TTATCCTGAA CATGCAGTTA ATCATTACTT TCAAACTAGG CATTATTTAC ATACTCTGTG    2760

GAAGGCTGGC ATTCTATATA AGAGAGAAAC TACCCGCAGC GCTTCATTTT GTGGGTCACC    2820

ATATTCTTGG GAACAAGAGC TACAGCATGG GAGGTTGGTC TTCCAAACCT CGACAAGGCA    2880

TGGGGACGAA TCTTTCTGTT CCCAATCCTC TGGGATTCTT TCCCGATCAC CAGTTGGACC    2940

CTGCGTTCGG AGCCAACTCA AACAATCCAG ATTGGGACTT CAACCCCAAC AAGGATCATT    3000
```

```
GGCCAGAGGC CAATCAGGTA GGAGTGGGAG CATTCGGGCC AGGGTTCACC CCACCACACG      3060

GCGGTCTTTT GGGGTGGAGC CCTCAGGCTC AGGGCATATT GACAACAGTG CCAGCAGCGC      3120

CTCCTCCTGC CTCTACCAAT CGGCAGTCAG GAAGACAGCC AACTCCCATC TCTCCACCTC      3180

TAAGAGACAG TCATCCTCAG GCCATGCAGT GG                                    3212

(2) INFORMATION FOR SEQ ID NO: 299:

(i) SEQUENCE CHARACTERISTICS:
         (A) LENGTH: 3215 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 299:

AACTCCACAA CATTCCAACA AGCTCTGCAG GATCCCAGAG TCAGGGTCCT TTATTTTCCT        60

GCTGGTGGCT CCAGTTCCGG AACAGTAAAC CCTGTTCCGA CTACTGCCTC TCTCATTTCG       120

TCAATCTTCT CGAGGATTGG GGACCCTGTA ACGAACATGG AGAACACAAC ATCAGGATTC       180

CTAGGACCCC TGCTCGTGTT ACAGGCGGGG TTTTTCTTGT TGACAAAAAT CCTCACAATA       240

CCACAGAGTC TAGACTCGTG GTGGACTTCT CTCAATTTTC TAGGGGGAGC ACCCGTGTGT       300

CCTGGCCAAA ATTCGCAGTC CCCAACCTCC AATCACTCAC CAACCTCTTG TCCTCCAATT       360

TGTCCTGGCT ATCGCTGGAT GTGTCTGCGG CGTTTTATCA TCTTCCTCTT CATCCTGCTG       420

CTATGCCTCA TCTTCTTGTT GGTTCTTCTG GACTACCAAG GTATGTTGCC CGTTTGTCCT       480

CTACTTCCAG GAACATCAAC TACCAGCACG GGACCATGCA AGACCTGCAC GATTCCTGCT       540

CAAGGAACCT CTATGTTTCC CTCATGTTGC TGTACAAAAC CTTCGGACGG AAACTGCACT       600

TGTATTCCCA TCCCATCATC CTGGGCTTTC GTAAGATTCC TATGGGAGTG GCCTCAGTC        660

CGTTTCTCCT GGCTCAGTTT ACTAGCGCCA TTTGTTCAGT GGTTCGTAGG GCTTCCCCC       720

ACTGTTTGGC TTTCAGTTAT ATGGATGATG TGGTATTGGG GGCCAAGTCT GTACAACATC       780

TTGAGTCCCT TTATACCTCT ATTACCAATT TTCTTTTGTC TTTGGGTATA CATTTAAACC       840

CTAATAAAAC CAAAAGATGG GGCTATTCCC TTAACTTCAT GGGCTATGTA ATTGGAAGTT       900

GGGGTACCTT ACCACAAGAA CATATTGTAC TAAAAATCAC ACAATGTTTT CGAAAACTTC       960

CTGTTAATAG GCCTATTGAT TGGAAAGTGT GTCAAAGAAT TGTGGGTCTT TTGGGCTTTG      1020

CTGCCCCTTT TACACAATGT GGGTATCCTG CCTTAATGCC CTTGTATGCC TGTATTCAAG      1080

CTAAGCAGGC TTTCACTTTC TCGCCAACTT ATAAGGCCTT TCTGTGTAAA CAATATCTGA      1140

ACCTTTACCC CGTTGCCCGG CAACGGTCTG GTCTTTGCCA AGTGTTTGCT GACGCAACCC      1200

CCACTGGCTG GGGCTTGGCC ATGGGCCATC AGCGCATGCG TGGAACCTTT GTGGCTCCTC      1260

TGCCGATCCA TACTGCGGAA CTCCTAGCGG CTTGTTTTGC TCGCAGCCGG TCTGGAGCAA      1320

ACATTATCGG AACCGACAAC TCTGTCGTCC TCTCTCGGAA ATACACATCC TTTCCATGGC      1380

TGCTCGGGTG TGCTGCCAAC TGGATCCTAC GCGGGACGTC CTTTGTTTAC GTCCCGTCGG      1440

CGCTGAATCC CGCGGACGAC CCGTCTCGCG GCCGTTTGGG GCTCTACCGT CCCCTTCTTT      1500

GTCTGCGGTT CCGGCCAACC ACGGGGCGCA CCTCTCTTTA CGCGGTCTCC CCGTCTGTGC      1560

CTTCTCATCT GCCGGACCGT GTGCACTTCG CTTCACCTCT GCACGTCGCA TGGAAACCAC      1620
```

| | |
|---|---|
| CGTGAACGCC CACATGGTCT TGCCCAAGGT CTTGCATAAG AGAACTCTTG GACTCTCAGC | 1680 |
| AATGTCAACG ACCGACCTTG AGGCATATTT CAAAGACTGT GTGTTCAAAG ACTGGGAGGA | 1740 |
| GTTGGGGGAG GAGGTTAGAT TAAAGGTCTT TGTACTAGGA GGCTGTAGGC ATAAATTGGT | 1800 |
| CTGCGCACCA GCACCATGCA ACTTTTTCAC CTCTGCCTAA TCATCTCATG TTCATGTCCT | 1860 |
| ACTGTTCAAG CCTCCAAGCT GTGCCTTGGG TGGCTTTGGG GCATGGACAT TGACCCTTAT | 1920 |
| AAAGAATTTG GAGCTTCTGT GGAGTTACTC TCTTTTTTGC CTTCTGATTT CTTTCCATCT | 1980 |
| ATTCGAGACC TCCTCGACAC CGCCTCAGCT CTGTATCGGG AGGCCTTAGA GTCTCCGGAG | 2040 |
| CATTGTTCAC CTCACCATAC AGCACTCAGG CAAGCTGTTC TGTGTTGGGG TGAGTTAATG | 2100 |
| AATCTGGCTA CCTGGGTGGG AAGTAATTTG GAAGACCCAG CATCAAGAGA ATTGGTAGTC | 2160 |
| AGTTATGTCA ATGTTAATAT GGGCCTAAAA ATCAGGCAAC TGTTGTGGTT TCATATTTCC | 2220 |
| TGTCTTACTT TTGGAAGAGA AACTGTTCTT GAGTACTTGG TGTCCTTTGG AGTGTGGATT | 2280 |
| CGCACTCCTC CCGCTTACAG ACCACCAAAT GCCCCTATCT TATCAACACT TCCGAAACT | 2340 |
| ACTGTTGTTA GACGAAGAGG CAGGTCCCCT AGAAGAAGAA CTCCCTCGCC TCGCAGACGA | 2400 |
| AGGTCTCAAT CGCCGCGTCG CAGAAGATCT CAATCTCGGG AATCCCAATG TTAGTATCCC | 2460 |
| TTGGACTCAT AAGGTGGGAA ACTTTACTGG GCTTTATTCT TCTACTGTAC CTGTCTTTAA | 2520 |
| TCCTGAATGG CAAACTCCCT CTTTTCCTGA CATTCATTTG CAGGAGGACA TTATTAATAG | 2580 |
| ATGTCAACAA TATGTGGGCC CTCTTACAGT TAATGAAAAA AGAAGATTAA AATTAATTAT | 2640 |
| GCCTGCTAGG TTTTATCCTA ACCTTACTAA ATATTTGCCC TTAGACAAAG GCATTAAACC | 2700 |
| TTATTATCCA GAACAGACAG TTAATCATTA CTTCAAAACT AGGCATTATT TGCATACTCT | 2760 |
| GTGGAAGGCT GGTAGTCTAT ATAAGAGAGA AACTACACGC AGCGCCTCAT TTTGTGGGTC | 2820 |
| ACCATATTCT TGGGAACAAG AGCTACAGCA TGGGAGGTTG GTCTTCAAAA CCTCGGAAAG | 2880 |
| GCATGGGGAC GAATCTTTCG GTACCCAATC CTCTGGGATT CTTTCCCGAT CACCAGTTGG | 2940 |
| ACCCTGCGTT CGGAGCCAAC TCAAACAATC CCGATTGGGA CTTCAACCCC AACAAGGATC | 3000 |
| ACTGGCCAGA GGCAAATCAG GTAGGAGCGG GAGCATTCGG GCCAGGGTTC ACCCCACCAC | 3060 |
| ACGGAGGTCT TTTGGGGTGG AGCCCTCAGG CCCAGGGCAT ATTGACAACA GTGCCAGCAG | 3120 |
| CTCCTCCTTC TGCCTCCACC AATCGGCAGT CAGGAAGACA GCCTACGCCC ATCTCTCCAC | 3180 |
| CTCTAAGAGA CAGTCATCCT CAGGCCATGC AGTGG | 3215 |

(2) INFORMATION FOR SEQ ID NO: 300:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 300:

| | |
|---|---|
| AACTCCACAA CATTCCAACA AGCTCTGCTA GATCCCAGAG TGAGGGGCCT ATATTTTCCT | 60 |
| GCTGGTGGCT CCAGTTCCGG AACAGTAAAC CCTGTTCCGA CTACTGCCTC TCTCATTTCG | 120 |
| TCAATCTTCT CGAGGACTGG GGACCCTGTA ACGAACATGG AGAACACAAC ATCAGGATTC | 180 |
| CTAGGACCCC TGCTCGTGTT ACAGGCGGGG TTTTTCTTGT TGACAAGAAT CCTCACAATA | 240 |

```
CCACAGAGTC TAGACTCGGG GTGGACTTCT CTCAATTTTC TAGGGGAAGC ACCAAGGTGT    300
CCTGGCCAAA ATTCGCAGTC CCCAACCTCC AATCACTCAC CAACCTCTTG TCCTCCAATT    360
TGTCCTGGCT ATCGCTGGAT GTGTCTGCGG CGTTTTATCA TCTTCCTCTT CATCCTGCTG    420
CTATGCCTCA TCTTCTTGTT GGTTCTTCTG GACTACCAAG GTATGTTGCC CGTTTGTCCT    480
CTACTTCCAG GAACATCAAC TACCAGCACG GGACCATGCA AGACCTGCAC GATTCCTGCT    540
CAAGGAACCT CTATGTTTCC CTCATGTTGC TGTACAAAAC CTTCGGACGG AAACTGCACT    600
TGTATTCCCA TCCCATCATC CTGGGCTTTC GTAAGATTCC TATGGGAGTG GGCCTCAGTC    660
CGTTTCTCCT GGCTCAGTTT ACTAGCGCCA TTTGTTCAGT GGTTCGTAGG GCTTTCCCCC    720
ACTGTTTGGC TTTCAGTTAT ATGGATGATG TGGTATTGGG GGCCAAGTCT GTACAACATC    780
TTGAGTCCCT TTATACCTCT ATTACCAATT TTCTTTTGTC TTTGGGTATA CATTTGAACC    840
CTAATAAGAC CAAAAGATGG GGCTATTCCC TTAACTTCAT GGGCTATGTA ATTGGAAGTT    900
GGGGTACCTT ACCACAAGAA CATATTGTAC TAAAAATCAA ACAATGTTTT CGAAAACTTC    960
CTGTAAATAG GCCTATTGAT TGGAAGGTCT GCCAAAGAAT TGTGGGTCTT TTGGGATTTG   1020
CTGCCCCTTT TACACAATGT GGATATCCTG CCTTAATGCC TTTGTATGCA TGTATTCAAG   1080
CTAAGCAAGC TTTCACTTTT TCGTCAACTT ACAAAGCCTT TCTGTGTAAA CAATATCTGA   1140
ACCTTTACCC CGTTGCCCGG CAACGGTCTG GTCTCTGCCA AGTGTTTGCT GACGCAACCC   1200
CCACTGGCTG GGGCTTGGCC ATTGGCAATC AGCGCATGCG TGGAACCTTT GTGGCTCCTC   1260
TGCCGATCCA TACTGCGGAA CTCCTAGCAG CTTGTTTTGC TCGCAGCCGG TCTGGAGCAA   1320
AACTTATCGG AACTGACAAC TCTGTCGTCC TCTCTCGCAA ATACACATCC TTTCCATGGC   1380
TGCTCGGCTG TGCTGCCAAC TGGATCCTAC GAGGGACGTC CTTTGTTTAC GTCCCGTCGG   1440
CGCTGAATCC CGCGGACGAC CCGTCTCGGG GCCGTTTGGG GATCTACCGT CCCCTTCTTC   1500
GTCTGCGGTT CCGGCCAACC ACGGGGCGCA CCTCTCTTTA CGCGGTCTCC CCGTCTGTGC   1560
CTTCTCATCT GCCGGACCGT GTGCACTTCG CTTCACCTCT GCACGTCGCA TGGAGACCAC   1620
CGTGAACGCC CACATGGTAT TGCCCAAGGT CTTGCATAAG AGGACTCTTG GACTCTCAGC   1680
GATGTCAACG ACCGACCTTG AGGCATACTT CAAAGACTGT GTATTAAAG ACTGGGAGGA   1740
GTTGGGGGAG GAGATTAGAT TAAAGGTCTT TGTACTAGGA GGCTGTAGGC ATAAATTGGT   1800
CTGCGCACCA GCACCATGCA ACTTTTTCAC CTCTGCCTAA TCATCTCATG TTCATGTCCT   1860
ACTGTTCAAG CCTCCAAGCT GTGCCTTGGG TGGCTTTGGG GCATGGACAT TGACCCTTAT   1920
AAAGAATTTG GAGCTTCTGT GGAGTTACTC TCTTTTTTGC CTTCTGATTT CTTTCCATCT   1980
ATTCGAGACC TCCTCGACAC CGCCTCAGCT CTGTATCGGG AGGCCTTAGA GTCTCCGGAA   2040
CATTGTTCAC CTCACCATAC AGCACTCAGG CAAGCTGTTC TGTGTTGGGG TGAGTTAATG   2100
AATCTGGCTA CCTGGGTGGG AAGTAATTTG GAAGACCCAG CATCCAGGGA ATTAGTGGTC   2160
AGTTATGTCA ACATTAATAT GGGCCTAAAA ATCAGACAAC TATTGTGGTT TCACATTTCC   2220
TGTCTTACTT TTGGAAGAGA AACTGTTCTT GAGTATTTGG TGTCTTTTGG AGTGTGGATT   2280
CGCACTCCTC CCGCTTACAG ACCACCAAAT GCCCCTATCT TATCAACACT TCCGGAAACT   2340
ACTGTTGTTA GACGTCGAGG CAGGTCCCCT AGAAGAAGAA CTCCCTCGCC TCGCAGACGA   2400
AGGTCTCAAT CACCGCGTCG CAGAAGATCT CAATCTCGGG AATCCCAATG TTAGTATCCC   2460
TTGGACTCAT AAGGTGGGAA ACTTACTGG GCTTTATTCT TCTACTGTAC CTGTCTTTAA   2520
TCCTGAATGG CAAACTCCCT CTTTTCCTGA CATTCATTTG CAGGAGGACA TTATTAATAG   2580
ATGTCAACAA TATGTGGGCC CTCTTACAGT TAATGAAAAA AGAAGATTAA AATTAATTAT   2640
```

```
GCCTGCTAGG TTTTATCCTA ACCTTACCAA ATATTTGCCC TTAGATAAAG GCATTAAACC    2700

TTATTATCCT GAACATGCAG TTAATCATTA CTTCAAAACA AGGCATTATT TACATACTCT    2760

GTGGAAGGCT GGCATCTTAT ATAAAAGAGA AACTACACGC AGTGCCTCAT TTTGTGGGTC    2820

ACCATATTCT TGGGAACAAG AGCTACAGCA TGGGAGGTTG GTCTTCCAAA CCTCGGAAAG    2880

GCATGGGGAC GAATCTTTCT GTTCCCAATC CTCTGGGATT CTTTCCCGAT CACCAGTTGG    2940

ACCCTGCATT CGGAGCCAAC TCAAACAATC CAGATTGGGA CTTCAACCCC AACAAGGATC    3000

AATGGCCAGA GGCAAATCAG GTAGGAGCGG GAGCATTCGG GCCAGGGTTC ACCCCACCAC    3060

ACGGAGGTCT TTTGGGGTGG AGCCCTCAGG CACAAGGCAT ATTGACAACA CTGCCAGCAG    3120

CTCCTCCTCC TGCCTCCACC AATCGGCAGT CAGGAAGACA GCCTACGCCC ATCTCTCCAC    3180

CTCTAAGAGA CAGTCATCCT CAGGCCATGC AGTGG                              3215

(2) INFORMATION FOR SEQ ID NO: 301:

(i) SEQUENCE CHARACTERISTICS:
          (A) LENGTH: 3161 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 301:

AATTCCACAA CCTTCCACCA AACTCTACAA GATCCCCCTG CTGGTGGCTC CAGTTCAGGA      60

ACAGTAAACC CTGTTCCGAC TACTGTCTCT CACATATCGT CAATCTTCAC GAGGATTGGG     120

GACCCTGCAC TGAACATGGA GAACATCACA TCAGGATTCC TAGGACCCCT GCTCGTGTTA     180

CAGGCGGGGT TTTTCTTGTT GACAAGAATC CTCACAATAC CGCAGAGTCT AGACTCGTGG     240

TGGACTTCTC TCAATTTTCT AGGGGGAACT ACCGTGTGTC TTGGCCAAAA TTCGCAGTCC     300

CCAACCTCCA ATCACTCACC AACCTCCTGT CCTCCAACTT GTCCTGGTTA TCGCTGGATG     360

TGTCTGCGGC GTTTTATCAT CTTCCTCTTC ATCCTGCTGC TATGCCTCAT CTTCTTGTTG     420

GTTCTTCTGG ACTATCAAGG TATGTTGCCC GTTTGTCCTC TAATTCCAGG ATCTTCAACC     480

ACCAGCACGG GACCATGCAG GACCTGCACG ACTCCTGCTC AAGGCAACTC TATGTATCCC     540

TCCTGTTGCT GTACCAAACC TTCGGACGGA AATTGCACCT GTATTCCCAT CCCATCATCT     600

TGGGCTTTCG GAAAATTCCT ATGGGAGTGG GCCTCAGCCC GTTTCTCCTG GCTCAGTTTA     660

CTAGTGCCAT TTGTTCAGTG GTTCGTAGGG CTTTCCCCCA CTGTTGGCT TTCAGTTATA      720

TGGATGATGT GGTATTGGGG GCCAAGTCTG TACAGCATCT TGAGTCCCTT TTTACCGCTG     780

TTACCAATTT TCTTTTGTCT TTGGGCATAC ATTTAAACCC TAACAAAACA AAAGATGGG      840

GTTACTCTTT ACACTTCATG GGCTATGTCA TTGGATGTTA TGGGTCATTG CCACAAGATC     900

ACATCAGACA GAAAATCAAA GAATGTTTTA GAAAACTTCC TGTTAACAGG CCTATTGATT     960

GGAAAGGCTG TCAACGAATT GTGGGTTTAT TGGGTTTTGC TGCCCCTTTT ACACAATGTG    1020

GTTATCCTGC GTTGATGCCT TTGTATGCAT GTATTCAATC TAAGCAGGCT TTCACTTTCT    1080

CGCCAACTTA CAAGGCCTTT CTGTGTAAAC AATACCTGAA CCTTTACCCC GTTGCCCGGC    1140

AACGGCCAGG TCTGTGCCAA GTGTTTGCTG ACGCAACCCC CACTGGCTGG GCTTGGTCA     1200

TGGGCCATCA GCGCATGCGT GGAACCTTTC GGGCTCCTCT GCCGATCCAT ACTGCGGAAC    1260
```

```
TCCTAGCCGC TTGTTTTGCT CGCAGCAGGT CTGGAGCAAA CATTCTCGGG ACGGATAACT    1320

TTGTTGTCCT ATCCCGCAAA TATACATCGT TTCCATGGCT GCTAGGCTGT GCTGCCAACT    1380

GGATCCTGAG CGGGACGTCC TTCGTTTACG TCCCGTCGGC GCTGAATCCA GCGGACGACC    1440

CTTCTCGGGG CCGCTTGGGA CTCTCTCGTC CCCTTCTCCG TCTGCCGTTT CGTCCGACCA    1500

CGGGGCGCAC CTCTCTTTAC GCGGACTCCC CGTCTGTGCC TTCTCATCTG CCGGACCGTG    1560

TGCACTTCGC TTCACCTCTG CACGTCGCAT GGAGACCACC GTGAACGCCC ACCAATTCTT    1620

GCCCAAGGTC TTACATAAGA GGACTCTTGG ACTCTCAGCA ATGTCAACGA CCGACCTTGA    1680

GGCATACTTC AAAGACTGTT TGTTTAAAGA GTGGGAGGAG TTGGGGGAGG AGATTAGATT    1740

AAAGTTGTTT GTATTAGGAG CTGTAGGCA TAAATTGGTC TGCGCACCAG CACCATGCAA     1800

CTTTTTCACC TCTGCCTAAT CATCTCTTGT TCATGTCCTA CTGTTCAAGC CTCCAAGCTG    1860

TGCCTTGGGT GGCTTAGGA CATGGACATT GATCCTTATA AGAATTTGG AGCTTCTATG      1920

GAGTTGCTCT CGTTTTTGCC TTCTGACTTC TATCCTTCAG TACGAGATCT TCTAGATACC    1980

GCCTCAGCTC TATATCGGGA AGCCTTAGAG TCTCCTGAGC ATTGTACACC TCATCATACT    2040

GCACTCAGGC AAGCAATTCT TTGCTGGGGG GAATTAATGA CTCTAGCCAC CTGGGTGGGT    2100

GGTAATTTGC AAGATCCAAC ATCCAGGGAC CTAGTAGTCA GTTATGTTAA CACTAATATG    2160

GGCCTAAAGT TCAGGCAACT ATTGTGGTTT CACGTTTCTT GTCTCACTTT TGGAAGAGAA    2220

ACAGTCGTAG AGTATTTGGT GTCTTTTGGA GTGTGGATTC GCACTCCTCA AGCTTATAGA    2280

CCACCAAATG CCCCTATCTT ATCAACACTT CCGGAGACTT GTGTTGTTAG ACGACGAGGC    2340

AGGTCCCCTA GAAGAAGAAC TCCCTCGCCT CGCAGACGAA GGTCTCAATC GCCGCGTCGC    2400

AGAAGATCTC AATCTCGGGA ATCTCAATGT TAGTATTCCT TGGACTCATA AGGTGGGAAA    2460

CTTTACGGGG CTTTATTCTT CTACTGTTCC TGTCTTTAAC CCTCATTGGA AACACCCTC     2520

TTTTCCTAAT ATACATTTAC ACCAAGACAT TATCAAAAAA TGTGAACAAT TTGTAGGCCC    2580

ACTCACAGTC AATGAGAAAA GAAGACTGCA ATTGATTATG CCTGTCAGGT TTTATCCAAT    2640

GGTTACCAAA TATTTGCCAT TGGATAAGGG TATTAAACCG TATTATCCAG AACATCTAGT    2700

TAATCATTAC TTCCAAACCA GACATTATTT ACACACTCTA TGGAAGGCGG GTGTATTATA    2760

TAAGAGAGAA ACAACACATA GCGCCTCATT TTGTGGATCA CCATATTCTT GGGAACAAGA    2820

GATACAGCAT GGGGCAGAAT CTTTCCACCA GCAATCCTCT GGGATTCTTT CCCGACCACC    2880

AGTTGGATCC AGCCTTCAGA GCAAACACCG CAAATCCAGA TTGGGACTTC AATCCCAACA    2940

AGGACACCTG GCCAGACGCC AACAAGGTAG GAGCTGGAGC ATTCGGGCTG GGACTCACCC    3000

CACCGCACGG AGGCCTTTTG GGGTGGAGCC CTCAGGCTCA GGGCATACTA CAGACCGTGC    3060

CAGCAAATCC GCCTCCTGCC TCTACCAATC GCCAGACAGG AAGGCAGCCT ACCCCTCTGT    3120

CTCCACCTTT GAGAGACACT CATCCTCAGG CCATGCAGTG G                       3161
```

(2) INFORMATION FOR SEQ ID NO: 302:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 302:

```
AACTCCACAA CCTTCCACCA AACTCTGCAA GATCCCAGAG TGAGAGGCCT GTATTTCCCT      60
GCTGGTGGCT CCAGTTCAGG AACAGTAAAC CCTGTTCCGA CTACTGCCTC TCACTTATCG     120
TCAATCTTCT CGAGGATTGG GGACCCTGCG CTGAACATGG AGAACATCAC ATCAGGATTC     180
CTAGGACCCC TTCTCGTGTT ACAGGCGGGG TTTTTCTTGT TGACAAGAAT CCTCACAATA     240
CCGCAGAGTC TAGACTCGTG GTGGACTTCT CTCAATTTTC TAGGGGGAAC TACCGTGTGT     300
CTTGGCCAAA ATTCGCAGTC CCCAACCTCC AATCACTCAC CAACCTCCTG TCCTCCAACT     360
TGTCCTGGTT ATCGCTGGAT GTGTCTGCGG CGTTTTATCA TCTTCCTCTT CATCCTGCTG     420
CTATGCCTCA TCTTCTTGTT GGTTCTTCTG GACTATCAAG GTATGTTGCC CGTTTGTCCT     480
CTAATTCCAG GATCCTCAAC CACCAGCACG GGACCATGCC GAACCTGCAC GACTCCTGCT     540
CAAGGAACCT CTATGTATCC CTCCTGTTGC TGTACCAAAC CTTCGGACGG AAATTGCACC     600
TGTATTCCCA TCCCATCATC CTGGGCTTTC GGAAAATTCC TATGGGAGTG GGCCTCAGCC     660
CGTTTCTCCT GGCTCAGTTT ACTAGTGCCA TTTGTTCAGT GGTTCGTAGG GCTTTCCCCC     720
ACTGTTTGGC TTTCAGTTAT ATGGATGATG TGGTATTGGG GGCCAAGTCT GTACAGCATC     780
TTGAGTCCCT TTTTACCGCT GTTACCAATT TTCTTTTGTC TTTGGGTATA CATTTAAACC     840
CTAACAAAAC AAAGAGATGG GGTTACTCTC TAAATTTTAT GGGCTATGTC ATTGGATGTT     900
ATGGGTCCTT GCCACAAGAA CACATCATAC AAAAAATCAA AGAATGTTTT AGAAAACTTC     960
CTGTTAACAG GCCTATTGAT TGGAAAGTAT GTCAACGAAT TGTGGGTCTT TTGGGTTTTG    1020
CTGCCCCTTT TACTCAATGT GGTTATCCTG CTTTAATGCC CTTGTATGCA TGTATTCAAT    1080
CTAAGCAGGC TTTCACTTTC TCGCCAACTT ACAAGGCCTT TCTGTGTAAA CAATACCTGA    1140
ACCTTTACCC CGTTGCCGGG CAACGGCCAG GTCTATGCCA AGTGTTTGCT GACGCAACCC    1200
CCACTGGCTG GGGCTTGGCT ATGGGCCATC AGCGCATGCG TGGAACCTTT TCGGCTCCTC    1260
TGCCGATCCA TACTGCGGAA CTCCTAGCCG CTTGTTTTGC TCGCAGCAGG TCTGGAGCAA    1320
ACATTATCGG GACTGATAAC TCTGTTGTCC TCTCCCGCAA ATATACATCG TTTCCATGGC    1380
TGCTAGGCTG TGCTGCCAAC TGGATCCTGC GCGGGACGTC CTTTGTTTAC GTCCCGTCGG    1440
CGCTGAATCC CGCGGACGAC CCGTCTCGGG GTCGCTTGGG ACTCTCTCGT CCCCTTCTCC    1500
GTCTGCCGTT CCGACCGACC ACGGGGCGCA CCTCTCTTTA CGCGGACTCC CCGTCTGTGC    1560
CTTCTCATCT GCCTGACCTT GTGCACTTCG CTTCACCTCT GCACGTCGCA TGGAGACCAC    1620
CGTGAACGCC CACCAAATAT TGCCCAAGGT CTTACATAAG AGGACTCTTG GACTCTCTGC    1680
AATGTCAACG ACCGACCTTG AGGCATACTT CAAAGACTGT TGTTTAAAG ACTGGGAGGA     1740
GTTGGGGGAG GAGATTAGAT TAAAGGTCTT TGTACTAGGA GGCTGTAGGC ATAAATTGGT    1800
CTGCGCACCA GCACCATGCA ACTTTTTCAC CTCTGCCTAA TCATCTCTTG TTCATGTCCT    1860
ACTGTTCAAG CCTCCAAGCT GTGCCTTGGG TGGCTTTGGG GCATGGACAT TGACCCTTAT    1920
AAAGAATTTG GAGCTACCGT GGAGTTACTC TCGTTTTTGC CTTCTGACTT CTTTCCTTCA    1980
GTACGAGATC TTCTAGATAC CGCCTCAGCT CTGTATCGGG ATGCCTTAGA GTCTCCTGAG    2040
CATTGTTCAC CTCACCATAC TGCACTCAGG CAAGCAATTC TTTGCTGGGG GGAACTAATG    2100
ACTCTAGCTA CCTGGGTGGG TGTTAATTTG GAAGATCCAG CATCTAGGGA CCTAGTAGTC    2160
AGTTATGTCA ACACTAATAT GGGCCTAAAG TTCAGACAAC TCTTGTGGTT TCACATTTCT    2220
TGTCTCATTT TTGGAAGAGA AACAGTTATA GAGTATTTGG TGTCTTCGG AGTGTGGATT     2280
```

| | | |
|---|---|---|
| CGCACTCCTC CAGCTTATAG ACCACCAAAT GCCCCTATCC TATCAACACT TCCGGAGACT | 2340 |
| ACTGTTGTTA GACGACGAGG CAGGTCCCCT AGAAGAAGAA CTCCCTCGCC TCGCAGACGA | 2400 |
| AGGTCTCAAT CGCCGCGTCG CAGAAGATCT CAATCTCGGG AATCTCAATG TTAGTATTCC | 2460 |
| TTGGACTCAT AAGGTGGGGA ATTTTACTGG GCTTTATTCT TCTACTGTAC CTGTCTTTAA | 2520 |
| TCCTCATTGG AAAACACCAT CTTTTCCTAA TATACATTTA CACCAAGACA TTATCAAAAA | 2580 |
| ATGTGAACAG TTTGTAGGCC CACTCACAGT TAATGAGAAA AGAAGATTGC AATTGATCAT | 2640 |
| GCCTGCTAGG TTTTATCCAA AGGTTACCAA ATATTTACCA TTGGATAAGG GTATTAAACC | 2700 |
| TTATTATCCA GAACATCTAG TTAATCATTA CTTCCAAACT AGACACTATT TACACACTCT | 2760 |
| ATGGAAGGCG GGTATATTAT ATAAGAGAGA AACAACACAT AGCGCCTCAT TTTGTGGGTC | 2820 |
| ACCATATTCT TGGGAACAAG ATCTACAGCA TGGGGCAGAA TCTTTCCACC AGCAATCCTC | 2880 |
| TGGGATTCTT TCCCGACCAC CAGTTGGATC CAGCCTTCAG AGCAAACACC GCAAATCCAG | 2940 |
| ATTGGGACTT CAATCCCAAC AAGGACACCT GGCCAGACGC CAACAAGGTA GGAGCTGGAG | 3000 |
| CATTCGGGCT GGGTTTCACC CCACCGCACG GAGGCCTTTT GGGGTGGAGC CCTCAGGCTC | 3060 |
| AGGGCATACT ACAAACTTTG CCAGCAAATC CGCCTCCTGC CTCCACCAAT CGCCAGTCAG | 3120 |
| GAAGGCAGCC TACCCCTCTG TCTCCACCTT TGAGAAACAC TCATCCTCAG GCCATGCAGT | 3180 |
| GG | 3182 |

(2) INFORMATION FOR SEQ ID NO: 303:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 303:

| | | |
|---|---|---|
| AACTCCACAA CTTTCCACCA AACTCTGCAA GATCCCAGAG TGAGAGGCCT ATATTTCCCT | 60 |
| GCTGGTGGCT CCAGTTCAGG AACAGTAAAC CCTGTTCCGA CTACTGCCTC TCCCTTATCG | 120 |
| TCAATCTTCT CGAGGATTGG GGACCCTGTG ACGAATATGG AGAACATCAC ATCAGGATTC | 180 |
| CTAGGACCCC TGCTCGTGTT ACAGGCGGGG TTTTTCTTGT TGACAAGAAT CCTCACAATA | 240 |
| CCGCAGAGTC TAGACTCGTG GTGGACTTCT CTCAATTTTC GAGGGGGAAC TACCGTGTGT | 300 |
| CTTGGCCAAA ATTCGCAGTC CCCAACCTCC AATCACTCAC CAACCTCCTG TCCTCCAACT | 360 |
| TGTCCTGGTT ATCGCTGGAT GTGTCTGCGG GGTTTTATCA TCTTCCTCTT CATCCTGCTG | 420 |
| CTATGCCTCA TCTTCTTGTT GGTTCTTCTG GAGTATCAAG GTATGTTGCA CGTTTGTCCT | 480 |
| CTAATTCCAG GAACAACAAC AACCAGTACG GGACCATGCA AAACCTGCAC GACTCCTGCT | 540 |
| CAAGGCAACT CTATGTTTCC CTCATGTTGC TGTACCAAAA CTTCGGATGG AAATTGCACC | 600 |
| TGTATTCCCA TCCCATCGTC TTGGGCTTTC GCAAAATACC TATGGGAGTG GCCTCAGTC | 660 |
| CGTTTCTCTT GGCTCAGTTT ACTAGTGCCA TTTGTTCAGT GGTTCGTAGG GCTTTCCCCC | 720 |
| ACTGTTTGGC TTTCAGCTAT ATGGATGATG TGGTATTGGG GGCCAAGTCT GTACAGCATC | 780 |
| TTGAGTCCCT TTTTACCGCT GTTACCAATT TTCTTTTGTC TTTGGGTATA CATTTAAACC | 840 |
| CTAACAAAAC AAAGAGATGG GGTTACTCTT TACATTTCAT GGGCTATGTC ATTGGATGTT | 900 |

| | |
|---|---|
| ATGGGTCCTT GCCACAAGAA CACATCATAC AAAAAATCAA GAATGTTTT AGAAAAGTTC | 960 |
| CTGTTAACAG GCCTATTGAT TGGAAAGTAT GTCAACGAAT TGTGGGTCTT TTAGGTTTTG | 1020 |
| CTGCCCCTTT CACACAATGT GGTTATCCTG CTTTAATGCC CTTGTATGCT TGTATTCAAT | 1080 |
| TTAAGCAGGC TTTCACTTTC TCGCCAACTT ACAAGGCCTT TCTGTGTAAA CAATACCTGA | 1140 |
| ACCTTTACCC CGTTGCCCGG CAACGGCCAG GTCTATGCCA AGTGTTTGCT GACGCAACCC | 1200 |
| CCACTGGCTG GGGCTTGGGT ATGGGCCATC AGCGCATGCG TGGAACCTTT TCGGCTCCTC | 1260 |
| TGCCGATCCA TACTGCGGAA CTCCTAGCCG CCTGTTTTGC TCGCAGCAGG TCTGGAGCAA | 1320 |
| ACATTCTCGG GACGGATAAC TCTGTTGTTC TCTCCCGCAA ATATACATCG TTTCCATGGC | 1380 |
| TGCTAGGCTG TGCTGCCAAC TGGATCCTGC GCGGGACGTC CTTTGTTTAC GTCCCGTCGG | 1440 |
| CGCTGAATCC CGCGGACGAC CCTTCTCGGG GCCGCTTGGG ACTCTCTCGT CCCCTTCTCT | 1500 |
| GTCTGCCGTT TCGACCGACC ACGGGGCGCA CCTCTCTTTA CGCGGACTCC CCGTCTGTGC | 1560 |
| CTTCTCATCT GCCGGACCGT GTGCACTTCG CTTCACCTCT GCACGTCGCA TGGAGACCAC | 1620 |
| CGTGAACGCC CATCAGATCC TGCCCAAGGT CTTACATAAG AGGACTCTTG GACTCCCAGC | 1680 |
| AATGTCAACG ACCGACCTTG AGGCCTACTT CAAAGACTGT GTGTTTAAGG ACTGGGAGGA | 1740 |
| GCTGGGGGAG GAGATTAGGT TAAAGGTCTT TGTATTAGGA GGCTGTAGGC ATAAATTGGT | 1800 |
| CTGCGCACCA GCACCATGCA ACTTTTTCAC CTCTGCCTAA TCATCTCTTG TACATGTCCC | 1860 |
| ACTGTTCAAG CCTCCAAGCT GTGCCTTGGG TGGCTTGGG GCATGGACAT TGACCCTTAT | 1920 |
| AAAGAATTTG GAGCTACTGT GGAGTTACTC TCGTTTTTGC CTTCTGACTT CTTTCCTTCC | 1980 |
| GTACGAGATC TCCTAGACAC CGCCTCAGCT CTGTATCGGG AAGCCTTAGA GTCTCCTGAG | 2040 |
| CATTGTTCAC CTCACCATAC TGCACTCAGG CAAGCAATTC TTTGCTGGGG GAACTAATG | 2100 |
| ACTCTAGCTA CCTGGGTGGG TGTTAATTTG GAAGATCCAG CATCTAGAGA CCTAGTAGTC | 2160 |
| AGTTATGTCA ACACTAATAT GGGCTTAAAG TTCAGGCAAC TCTTGTGGTT TCACATTTCT | 2220 |
| TGTCTCACTT TTGGAAGAGA AACAGTTATA GAGTATTTGG TGGCTTTCGG AGTGTGGATT | 2280 |
| CGCACTCCTC CAGCTTATAG ACCACCAAAT GCCCCTATCC TATCAACACT TCCGGAGACT | 2340 |
| ACTGTTGTTA GACGACGAGG CAGGTCCCCT AGAAGAAGAA CTCCCTCGCC TCGCAGACGA | 2400 |
| AGGTCTCAAT CGCCGCGTCG CAGAAGATCT CAATCTCGGG AATCTCAATG TTAGTATTCC | 2460 |
| TTGGACTCAT AAGGTGGGAA ACTTTACGGG GTTTTATTCT TCTACTGTTC CTGTCTTTAA | 2520 |
| CCCTCATTGG GAAACCCCCT CTTTTCCTAA TATACATTTA CACCAAGACA TTATCAAAAA | 2580 |
| ATGTGAACAG TTTGTAGGCC CACTCACAGT TAATGAGAAA AGAAGATTGC AATTGATTAT | 2640 |
| GCCTGCTAGG TTTTATCCAA AGGTTACCAA ATATTTACCA TTGGATAAGG GTATTAAACC | 2700 |
| TTATTATCCA GAACATCTAG TTAATCATTA CTTCCAAACT AGACACTATT TACACACTCT | 2760 |
| ATGGAAGGCG GGTATATTAT ATAAGAGAGA AACAACACAT AGCGCCTCAT TTTGTGGGTC | 2820 |
| ACCATATTCT TGGGAACAAG ATCTACAGCA TGGGGCAGAA TCTATCCACC AGCAATCCTC | 2880 |
| TGGGATTCTT TCCCGACCAC CAGTTGGATC CAGCCTCCAG AGCAAACACC GCAAATCCAG | 2940 |
| ATTGGGACTT CAATCCCAAC AAGGACACCT GGCCAGACGC CAACAAGGAT GGAGCTGGAG | 3000 |
| CATTCGGGCT GGGACTCACC CCACCGCACG GAGGCCTTTT GGGGTGGAGC CCTCAGGCTC | 3060 |
| AGGGCATACT ACACACCGTG CCAGCAAATC CGCCTCCTGC CTCTACCAAT CGCCAGACAG | 3120 |
| GAAGGCAACC TACCCCTCTG TCTCCACCTT TGAGAGACAC TCATCCTCAG GCCGTGCAGT | 3180 |
| GG | 3182 |

(2) INFORMATION FOR SEQ ID NO: 304:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 304:

```
AACTCCACAA CCTTCCACCA AACTCTGCAA GATCCCAGAG TGAGAGGCCT GTATTTCCCT      60
GCTGGTGGCT CCAGTTCAGG AACAGTAAAC CCTGTTCTGA CTACTGCCTC TCCCTTATCG     120
TCAATCTCCG CGAGGACTGG GGACCCTGCA CTGAACATGG AGAACATCAC ATCAGGATTC     180
CTAGGACCCC TGCTCGTGTT ACAGGCGGGG TTTTTCTTGT TGACAAGAAT CCTCACAATA     240
CCGCAGAGTC TAGACTCGTG GTGGACTTCT CTCAATTTTC TAGGGGGAAC TACCGTGTGT     300
CTTGGCCAAA ATTCGCAGTC CCCAACCTCC AATCACTCAC CAACCTCTTG TCCTCCAACT     360
TGTCCTGGTT ATCGCTGGAT GTGTCTGCGG CGTTTTATCA TCTTCCTCTT CATCCTGCTG     420
CTATGCCTCA TCTTCTTGTT GGTTCTTCTG GACTATCAAG GTATGTTGCC CGTTTGTCCT     480
CTAATTCCAG GATCTTCAAC AACCAGCACG GGACCATGCA GAACCTGCAC GACTCCTGCT     540
CAAGGAACCT CTATGTATCC CTCCTGTTGC TGTACCAAAC CTTCGGACGG AAATTGCACC     600
TGTATTCCCA TCCCATCATC TTGGGCTTTC GGAAAATTCC TATGGGAGTG GGCCTCAGCC     660
CGTTTCTCCT GGCTCAGTTT ACTAGTGCCA TTTGTTCAGT GGTTCGTAGG GCTTTCCCCC     720
ACTGTTTGGC TTTCAGTTAT ATGGATGATG TGGTATTGGG GGCCAAGTCT GTACAGCATC     780
TTGAGTCCCT TTTTACCGCT GTTACCAATT TTCTTTTGTC TCTGGGTATA CATTTAAACC     840
CTAACAAAAC AAAAAGATGG GGTTATTCCC TAAACTTCAT GGGTTACATA ATTGGAAGTT     900
GGGGAACGTT GCCACAAGAT CATATTGTAC AAAAGATCAA AGAATGTTTT AGAAAACTTC     960
CTGTTAACAG GCCTATTGAT TGGAAAGTAT GGCAACGAAT TGTGGGTCTT TTGGGCTTTG    1020
CTGCTCCATT TACACAATGT GGATATCCTG CCTTAATGCC TTTGTATGCC TGTATACAAG    1080
CTAAACAGGC TTTCACTTTC TCGCCAACTT ACAAGGCCTT TCTAAGTAAA CAGTACATGA    1140
ACCTTTACCC CGTTGCTCGG CAACGGCCTG GTCTGTGCCA AGTGTTTGCT GACGCAACCC    1200
CCACTGGCTG GGGCTTGGCA ATAGGCAATC AGCGCATGCG TGGAACCATT GTGGCTCCTC    1260
TGCCGATCCA TACTGCGGAA CTCCTAGCCG CTTGTTTTGC TCGCAGCCGG TCTGGGCAA     1320
AGCTCATCGG AACTGACAAT TCTGTTGTCC TCTCGCGGAA ATATACATCG TTTCCATGGC    1380
TGCTAGGTTG TACTGCCAAC TGGATCCTTC GCGGGACGTC CTTTGTTTAC GTCCCGTCGG    1440
CGCTGAATCC CGCGGACGAC CCTTCTCGGG GCCGCTTGGG ACTCTCTCGT CCCCTTCTCC    1500
GTCTGCCGTT CCAGCCGACC ACGGGGCGCA CCTCTCTTTA CGCGGTCTCC CCGTCTGTGC    1560
CTTCTCATCT GCCGGTCCGT GTGCACTTCG CTTCACCTCT GCACATTGCA TGGAGACCAC    1620
CGTGAACGCC CATCAGATTA TGCCCAAGGT TTTACATAAG AGGACTCTTG GACTCCCAGC    1680
AATGTCAACG ACCGACCTTG AGGCCTACTT CAAAGACTGT GTGTTTAAGG ACTGGGAGGA    1740
GCTGGGGGAG GAGATTAGGT TAAAGGTCTT TGTATTAGGA GGCTGTAGGC ATAAATTGGT    1800
CTGCGCACCA GCACCATGCA ACTTTTTCAC CTCTGCCTAA TCATCTCTTG TTCATGTCCT    1860
ACTGTTCAAG CCTCCAAGCT GTGCCTTGGG TGGCTTTAGG GCATGGACAT TGACCCTTAT    1920
```

```
AAACAATTTG GAGCTACTGT GGAGTTACTC CCGTATTTGC CTTCTGACTT CTTTCTCTAC    1980

GTACGAGATC TCCTAGATAC CGCCTCAGCT CTGTATCGGG AAGCCTTAGA GTCTCCTGAG    2040

CATTGTTCAC CTCACCATAC TGCACTCAGG CAAGCAATTC TTTGCTGGGG GGAACTAATG    2100

ACTCTAGCTA CCTGGGTGGG TGTTAATTTG GAAGATCCAG CATCTAGAGA CTTAGTAGTC    2160

AGTTATGTCA ACACTAATAT GGGCCTAAAG TTCAGGCAAC TCTTGTGGTT TCACATTTCT    2220

TGTCTCACTT TTGGAAGAGA AACAGTTATA GAGTATTTGG TGTCTTTCGG AGTGTGGATT    2280

CGCACTCCTC CAGCTTATAG ACCACCAAAT GCCCCTATCC TATCAACACT TCCGGAGACT    2340

ACTGTTGTTA CACGACGAGG CAGGTCCCCT AGAAGAAGAA CTCCCTCGCC TGCCAGACCA    2400

AGGTCTCAAT CGCCGCGTCG CAGAAGATCT CAATCTCGGG AATCTCAATG TTAGTATTCC    2460

TTGGACTCAT AAGGTGGGGA ACTTTACGGG GCTTTATTCT TCTACTGTTC CTGTCTTTAA    2520

TCCTCATTGG AAAACACCTT CTTTTCCTAA TATACATTTA CACCAAGACA TTATCAAAAA    2580

ATGTGAACAA TTTGTAGGCC CACTCACAGT CAATGAGAAA AGAAGACTGC AATTGATTAT    2640

GCCTGCTAGG TTTTATCCAA ATGTCACCAA ATATTTGCCA TTGGATAAGG GTATTAAACC    2700

TTATTATCCA GAGCATCTAG TTAATCATTA CTTCCAAACC AGACATTATT TACACACTCT    2760

ATGGAAGGCG GTATATTAT ATAAGAGAGA AACAACACAT AGCGCCTCAT TTTGTGGGTC     2820

ACCATATTCT TGGGAACAAG AGCTACAGCA TGGGGCAGAA TCTTTCCACC AGCAATCCTC    2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGTTTCACC CCACCGCACG GAGGTCTTTT GGGGTGGAGC CCTCAGGCTC    3060

AGGGCATACT ACATACCGTG CCAGCAAATC CGCCTCCTGC CTCTACCAAT CGCCAGTCAG    3120

GAAGGCAGCC TACCCCTCTG TCTCCACCTT TGAGAAACAC TCATCCTCAG GCCATGCAGT    3180

GG                                                                  3182

(2) INFORMATION FOR SEQ ID NO: 305:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 305:

AACTCCACAA CCTTCCACCA AACTCTGCAA GATCCAAGAG TGAGAGGCCT GTATTTCCCT      60

GCTGGTGGCT CCAGTTCAGG AACAGTAAAC CCTGTTCTGA CTACTGCCTC TCCCTTATCG    120

TCAATCTCCG CGAGGACTGG GGACCCTGTG ACGATCATGG AGAACATCAC ATCAGGATTC    180

CTAGGACCCC TGCTCGTGTT AGAGGCGGGG TTTTTCTTGT TGACAAGAAT CCTCACAATA    240

CCGCAGAGTC TAGACTCGTG GTGGACTTCT CTCAATTTTC TAGGGGGAAC TACCGTGTGT    300

CTTGGCCAAA ATTCGCAGTC CCCAACCTCC CATCACTCAC CAACCTCCTG TCCTCCAATT    360

TGTCCTGGTT ATCGCTGGAT GTGTCTGCGG CGTTTTATCA TATTCCTCTT CATCCTGCTG    420

CTATGCCTCA TCTTCTTGTT GGTTCTTCTG GACTATCAAG GTATGTTGCC CGTTTGTCCT    480

CTAATTCCAG GTACTTCAAC AACCAGCACG GGACCATGCA GAACCTGCAC GACTCCTGCT    540
```

```
CAAGGAACCT CTATGTATCC CTCCTGTTGC TGTACCAAAC CTTCGGACGG AAATTGCACC      600

TGTATTCCCA TCCCATCATC TTGGGCTTTC GGAAAATTCC TATGGCAGTG GGCCTCAGCC      660

CGTTTCTCCT GGCTCAGTTT ACTAGTGCCA TTTGTTCAGT GGTTCGTAGG GCTTTCCCCC      720

ACTGTTTGGG TTTCAGCTAT ATGGATGATG TGGTATTGGG GGCCAAGTCT GTACAGCATC      780

GTGAGTCCCT TTATACCGCT GTTACCAATT TTCTTTTGTC TCTGGGTATA CATTTAAACC      840

CTAACAAAAC AAAAGATGG GGTTATTCCC TAAACTTCAT GGGTTACATA ATTGGAAGTT       900

GGGGAACGTT GCCACAGGAT CATATTGTAC AAAAGATCAA ACACTGTTTT AGAAAACTTC      960

CTGTTAACAG GCCTATTGAT TGGAAAGTAT GGCAACGAAT TGTGGGTCTT TTGGGTTTTG     1020

CTGCTCCATT TACACAATGT GGTTATCCTG CCTTAATGCC TTTGTATGCC TGTATACAAG     1080

CTAAACAGGC TTTCACTTTC TCGCCAACTT ACAAGGCCTT TCTAAGTAAA CAGTACATGA     1140

ACCTTTACCC CGTTGCTCGG CAACGGCCTG GTCTGTGCCA AGTGTTTGCT GACGCAACCC     1200

CCACTGGCTG GGGCTTGGCA TAGGGCCATC AGCGCATGCG TGGAACCTTT GAGGCTCCTC     1260

TGCCGATCCA TACTGCGGAA CTCCTAGCCG CTTGTTTTGC TCGCAGCAGG TCTGGAGCAA     1320

ACATTATCGG GACTGATAAC TCTGTTGTCC TATCGCGGAA ATATACATCG TTTCCATGGC     1380

TGCTAGGTTG TACTGCCAAC TGGATCCTTC GCGGGACGTC CTTTGTTTAC GTCCCGTCGG     1440

CGCTGAATCC CGCGGACGAC CCCTCTCGGG GCCGCTTGGG ACTCTCTCGT CCCCTTCTCC     1500

GTCTGCCGTT CCAGCCGACC ACGGGGCGCA CCTCTCTTTA CGCGGTCTCA CCGTCTGTGC     1560

CTTCTCATCT GCCGGTCCGT GTGCACTTCG CTTCACCTCT GCACGTCGCA TGGAGACCAC     1620

CGTGAACGCC CATCAAAGTC TGCCCAAGGT CTTACATAAG AGGACTCTTG GACTCCCAGC     1680

AATGTCAACG ACCGACCTTG AGGCCTACTT CAAAGACTGT GTGTTTAAGG ACTGGGAGGA     1740

GCTGGGGGAG GAGATTAGGT TAAAGGTCTT TGTATTAGGA GGCTGTAGGC ATAAATTGGT     1800

CTGCGCACCA GCACCATGCA ACTTTTTCAC CTCTGCCTAA TCATCTCTTG TTCATGTCCC     1860

ACTGTTCAAG CCTCCAAGCT GTGCCTTGGG TGGCTTTGGG GCATGGACAT TGACCCTTAT     1920

AAAGAATTTG GAGCTACTGT GGAGTTACTC TCGTTTTTGC CTTCTGACTT CTTTCCTTCC     1980

GTAAGAGATC TCCTAGACAC CGCCTCAGCT CTGTATCGAG AAGCCTTAGA GTCTCCTGAG     2040

CATTGCTCAC CTCACCATAC TGCACTCAGG CAAGCCATTC TCTGCTGGGG GAACTGATG      2100

ACTCTAGCAT CCTGGGTGGG TGATAATTTG GAAGATCCAG CGTCTAGGGA CCTAGTAGTC     2160

AGTTATGTTA ACACTAATAT GGGCCTAAAG ATCAGGCAAC TATTGTGGTT TCATATATCT     2220

TGCCTTACTT TTGGAAGAGA GACTGTACTT GAATATTTGG TCTCTTTCGG AGTGTGGATT     2280

CGCACTCCTC CAGCCTATAG ACCACCAAAT GCCCCTATCT TATCAACACT TCCGGAAACT     2340

ACTGTTGTTA GACGACGGGA CAGGTCCCCT AGAAGAAGAA CTCCCTCGCC TCGCAGACGA     2400

AGGTCTCAAT CGCCGCGTCG CAGAAGATCT CAATCTCGGG AATCTCAATG TTAGTATTCC     2460

TTGGACTCAT AAGGTGGGGA ACTTTACTGG GCTTTATTCT TCTACTGTAC CTGTCTTTAA     2520

TCCTCATTGG AAAACACCAT CTTTTCCTAA TATACATTTA CACCAAGACA TTATCAAAAA     2580

ATGTGAACAG TTTGTAGGCC CACTCACAGT TAATGAGAAA AGAAGATTGC AATTGATTAT     2640

GCCTGCTAGG TTTTATCCAA AGGTTACCAA ATATTTACCA TTGGATAAGG GTATTAAACC     2700

TTATTATCCA GAACATCTAG TTAATCATTA CTTCCAAACT AGACACTATT TACACACTCT     2760

ATGGAAGGCG GGTATATTAT ATAAGAGAGA ACAACACAT AGCGCCTCAT TTTGTGGGTC      2820

ACCATATTCT TGGGAACAAG ATCTACAGCA TGGGGCAGAA TCTATCCACC AGCAATCCTC     2880
```

```
TGGGATTCTT TCCCGACCAC CAGTTGGATC CAGCCTTCAG AGCAAACACC GCAAATCCAG        2940

ATTGGGACTT CAATCCCAAC AAGGACACCT GGCCAGACGC CAACAAGGTA GGAGCTGGAG        3000

CATTCGGGCT GGGTTTCACC CCACCGCACG GAGGCCTTTT GGGGTGGAGC CCTCAGGCTC        3060

AGGGCATACT ACAAACTTTG CCAGCAAATC CGCCTCCTGC CTCCACCAAT CGCCAGTCAG        3120

GAAGGCAGCC TACCCCTCTG TCTCCACCTT TGAGAAACAC TCATCCTCAG GCCATGCAGT        3180

GG                                                                      3182

(2) INFORMATION FOR SEQ ID NO: 306:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 306:

AACTCCACAA CCTTCCACCA AACTCTGCAA GATCCCAGAG TGAGAGGCCT GTATCTCCCT          60

GCTGGTGGCT CCAGTTCAGG AACAGTAAAC CCTGTTCCGA CTACTGTCTC TCCCATATCG         120

TCAATCTTCT CGAGGATTGG GGACCCTGCG CTGAACATGG AGAACATCAC ATCAGGATTC         180

CTAGGACCCC TGCTCGTGTT ACAGGCGGGG TTTTTCTTGT TGACAAAAAT CCTCACAATA         240

CCGAAGAGTC TAGACTCGTG GTGGACTTCT CTCAATTTTC TAGGGGGAAC CACCGTGTGT         300

CTTGGCCAAA ATTCGCAGTC CCCAACCTCC AATCACTCAC CAACCTCCTG TCCTCCAACT         360

TGTCCTGGTT ATCGCTGGAT GTGTCTGCGG CGTTTTATCA TCTTCCTCTT CATCCTGCTG         420

CTATGCCTCA TCTTCTTGTT GGTTCTTCTG GACTATCAAG GTATGTTGCC CGTTTGTCCT         480

CTGATTCCAG GATCTTCAAC CACCAGCACG GGACCATGCA GAACCTGCAC GACTCCTGCT         540

CAAGGAACCT CTATGTATCC CTCCTGTTGC TGTACCAAAC CTTCGGACGG AAATTGCACC         600

TGTATTCCCA TCCCATCATC CTGGGCTTTC GGAAAATTCC TATGGGAGTG GGCCTCAGCC         660

CGTTTCTCCT GGCTCAGTTT ACTAGTGCCA TTTGTTCAGT GGTTCGTAGG CTTTCCCCC          720

ACTGTTTGGC TTTTAGTTAT ATGGATGATG TGGTATTGGG GGCCAAAACT GTTCACCATC         780

TTGAGTCCCT TTTTACCGCT GTTACCAATT TTCTTTTGTC TTTGGGTATA CATCTAAACC         840

CTAACAAAAC AAAAAGATGG GGTTACTCTT TACATTTTAT GGGCTATGTC ATTGGATGTT         900

ATGGGTCTTT GCCACAAGAT CACATCATAC AGAAAATCAA AGAATGTTTT AGAAAACTTC         960

CTGTTAACAG GCCTATTGAT TGGAAAGTCT GTCAACGTAT TGTGGGTCTT TTGGGATTTG        1020

CTGCTCCTTT TACACAATGT GGTTATCCTG CTTTAATGCC CTTGTATGCA TGTATTCAAT        1080

CTAAGCAGGC TTTCACTTTC TCGCCAACTT ACAAGGCCTT TCTGTGTAAA CAATACCTGA        1140

ACCTTTACCC CGTTGCCCGG CAACGCCCAG GTCTGTGCCA AGTGTTTGCT GACGCAACCC        1200

CCACTGGCTG GGGCTTGGTC ATGGGCCATC AGCGCATGCG TGGAACCTTT CAGGCTCCTC        1260

TGCCGATCCA TACTGCGGAA CTCCTAGCCG CTTGTTTTGC TCGCAGCCGG TCTGGAGCAA        1320

ACATTCTCGG GACGGATAAC TCTGTTGTTC TCTCCCGCAA ATATACGTCG TTTCCATGGC        1380

TGCTAGGCTG TGCTGCCAAC TGGATCCTGC GCGGGACGTC CTTTGTTTAC GTCCCGTCGG        1440

CGCTGAATCC CGCGGACGAC CCTTCTCGGG GCCGCTTGGG ACTCTCTCGT CCCCTTCTCC        1500
```

```
GTCTGCCGTT TCGACCGACC ACGGGGCGCA CCTCTCTTTA CGCGGACTCC CCGTCTGTGC    1560

CTTCTCATCT GCCGGACCGT GTGCACTTCG CTTCACCTCT GCACGTCGCA TGGAGACCAC    1620

CGTGAACGCC CACCAATTCT TGCCCAAGGT CTTACATAAG AGGACTCTTG GACTCTCTGT    1680

AATGTCAACG ACCGACCTTG AGGCATACTT CAAAGACTGT TTGTTTAAGG ACTGGGAGGA    1740

GTCGGGGGAG GAGATTAGAT TAATGATCTT TGTACTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTAGG ACATGGACAT TGATCCTTAT    1920

AAAGAATTTG GAGCTACTGT GGAGTTACTC TCGTTTCTGC CTTCTGACTT CTTTCCTTCA    1980

GTACGAGATC TTCTAGATAC CGCCTCAGCT CTATATCGGG AAGCCTTAGA ATCTCCTGAG    2040

CATTGTTCAC CTCACCATAC TGCACTCAGG CAAGCAATTC TCTGCTGGGG GGATCTAATA    2100

ACTCTATCCA CCTGGGTGGG TGGTAATTTG GAAGATCCAA CATCTAGGGA CCTAGTAGTC    2160

AGTTATGTTA ACACTAATAT GGGCCTAAAG TTCAGGCAAC TATTGTGGTT TCACATTTCT    2220

TGTCTCACTT TTGGAAGAGA AACGGTCATA GAGTATTTGG TGTCTTTTGG AGTGTGGATT    2280

CGCACTCCTC CAGCTTATAG ACCACCAAAT GCCCCTATCT TATCAACACT TCCGGAGACT    2340

ACTGTTGTTA GACGACGAGG CAGGTCCCCT AGAAGAAGAA CTCCCTCGCC TCGCAGACGA    2400

AGGTCTCAAT CGCCACGTCG CAGAAGAACT CAATCTCGGG AATCTCAATG TTAGTATTCC    2460

CTGGACTCAT AAGGTGGGAA ACTTTACGGG GCTTTATTCT TCTACTGTTC CTGTCTTTAA    2520

CCCTCATTGG AAAACACCCT CTTTTCCTAA TATACATTTA CACCAAGACA TTATCAAAAA    2580

ATGTGAACAA TTTGTAGGCC CACTCACAGT CAATGAGAAA AGAAGACTGC AATTGATTAT    2640

GCCTGCTAGG TTTTATCCAA AGGTTACCAA ATATTTGCCA TTGGATAAGG GTATTAAACC    2700

TTATTATCCA GAACATCTAG TTAATCATTA CTTCCAAACC AGACATTATT TACACACTCT    2760

ATGGAAGGCG GGTGTATTAT ATAAGAGAGA AACTACACAT AGCGCCTCAT TTTGTGGGTC    2820

ACCATATTCC TGGGAACAAG AGCTACAGCA TGGGGCAGAA TCTTTCCACC AGCAATCCTC    2880

TGGGATTCTT TCCCGACCAC CAGTTGGATC CAGCCTTCAG AGCAAACACT GCAAATCCAG    2940

ATTGGGACTT CAATCCCAAC AAGGACTCCT GGCCAGACGC CAACAAGGTA GGAGCTGGAG    3000

CATTCGGGCT GGGATTCACC CCACCGCACG GAGGCCTTTT GGGGTGGAGC CCTCAGGCTC    3060

AGGGCATACT ACAAACCTTG CCAGCAAATC CGCCTCCTGC CTCCACCAAT CGCCAGTCAG    3120

GAAGGCAACC TACCCCTCTG TCTCCACCTT TGAGAAACAC TCATCCTCAG GCCATGCAGT    3180

GG                                                                  3182
```

(2) INFORMATION FOR SEQ ID NO: 307:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 307:

```
AACTCCACAA CCTTCCACCA AACTCTGCAA GATCCCAGAG TGAGAGGCCT GTATTTCCCT      60

GCTGGTGGCT CCAGTTCAGG AACAGTAAAC CCTGTTCCGA CTACTGTCTC TCCCATATCG     120
```

-continued

| | |
|---|---|
| TCAATCTTCT CGAGGATTGG GGACCCTGCG CTGAACATGG AGAACATCAC ATCAGGATTC | 180 |
| CTAGGACCCC TGCTCGTGTT ACAGGCGGGG TTTTTCTTGT TGACAAGAAT CCTCACAATA | 240 |
| CCGCAGAGTC TAGACTCGTG GTGGACTTCT CTCAATTTTC TAGGGGGAAC TACCGTGTGT | 300 |
| CTTGGCCAAA ATTCGCAGTC CCCAACCTCC AATCACTCAC CAACCTCCTG TCCTCCAACT | 360 |
| TGTCCTGGTT ATCGCTGGAT GTGTCTGCGG CGTTTTATCA TCTTCCTCTT CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCTTCAAC TACCAGCACG GGACCATGCA GAACCTGCAC GACTCCTGCT | 540 |
| CAAGGAACCT CTATGTATCC CTCCTGTTGC TGTACCAAAC CTTCGGACGG AAATTGCACC | 600 |
| TGTATTCCCA TCCCATCATC CTGGGCTTTC GGAAAATTCC TATGGGAGTG GGCCTCAGCC | 660 |
| CGTTTCTCCT GGCTCAGTTT ACTAGTGCCA TTTGTTCAGT GGTTCGTAGG GCTTTCCCCC | 720 |
| ACTGTTTGGC TTTCAGTTAT ATGGATGATG TGGTATTGGG GGCCAAGTCT GTACAGCATC | 780 |
| TTGAGTCCCT TTTTACCGCT GTTACCAATT TTCTTCTGTC TTTGGGTATA CATTTAAACC | 840 |
| CTAACAAAAC AAAAAGATGG GGTTACTCTT TACATTTCAT GGGCTATGTC ATTGGATGTT | 900 |
| ATGGGTCATT GCCACAAGAT CACATCATAC AGAAAATCAA AGAATGCTTT AGAAAACTTC | 960 |
| CTGTTAACAG GCCTATTGAT TGGAAAGTCT GTCAACGTAT TGTGGGTCTT TTGGGTTTTG | 1020 |
| CTGCCCCTTT TACACAATGT GGTTATCCTG CTTTAATGCC TTTGTATGCA TGTATTCAGT | 1080 |
| CGAAGCAGGC TTTTACTTTC TCGCCAACTT ACAAGGCCTT TCTGTGTAAA CAATACCTGA | 1140 |
| ACCTTTACCC CGTTGCCCGG CAACGGCCAG GTCTGTGCCA AGTGTTTGCT GACGCAACCC | 1200 |
| CCACTGGCTG GGGCTTGGTC ATGGGCCATC AGCGCATGCG TGGAACCTTT CTGGCTCGTC | 1260 |
| TGCCGATCCA TACTGCGGAA CTCCTAGCCG CTTGTTTTGC TCGCAGCAGG TCTGGAGCAA | 1320 |
| ACATTCTCGG GACGGATAAC TCTGTTGTTC TCTCCCGCAA ATATACATCG TATCCATGGC | 1380 |
| TGCTAGGCTG TGCTGCCAAC TGGATCCTGC GCGGGACGTC CTTTGTTTAC GTCCCGTCGG | 1440 |
| CGCTGAATCC CGCGGACGAC CCTTCTCGGG GTCGCTTGGG ACTCTCTCGT CCCCTTCTCC | 1500 |
| GTCTGCCGTT TCGACCGACC ACGGGGCGCA CCTCTCTTTA CGCGGACTCC CCGTCTGTGC | 1560 |
| CTTCTCATCT GCCGGACCGT GTGCACTTCG CTTCACCTCT GCACGTCGCA TGGAGACCAC | 1620 |
| CGTGAAAGCC CAACCATTCT TGCCCAAGGT CTTACATAAG AGGACTCTTG GACTCTCTGT | 1680 |
| AATGTCAACG ACCGACCTTG AGGCATACTT CAAAGACTGT TTGTTTAAAG ACTGGGAGGA | 1740 |
| GTTGGGGGAG GAGATTAGAT TAAAGGTCTT TGTATTAGGA GGCTGTAGGC ATAAATTGGT | 1800 |
| CTGCGCACCA GCACCATGCA ACTTTTTCAC CTCTGCCTAA TCATCTCTTG TTCATGTCCT | 1860 |
| ACTGTTCAAG CCTCCAAGCT GTGCCTTGGG TGGCTTTGGG GCATGGACAT TGATCCTTAT | 1920 |
| AAAGAATTTG GAGCTACTGT GGAGTTACTC TCGTTTTTGC CTTCTGACTT CTTTCCTTCA | 1980 |
| GTACGAGATC TTCTAGATAA CGCCTCAGCT CTGTATCGGG AAGCCTTAGA GTCTCCTGAG | 2040 |
| CATTGTTCAC CTCACCATAC TGCACTCAGG CAAGCAATAC TGTGCTGGGG GAACTAATG | 2100 |
| ACTCTAGCTA CCTGGGTGGG TGGTAATTTG GAAGATCCAA TATCCAGGGA CCTAGTAGTC | 2160 |
| AGTTATGTCA ACACTAATAT GGGCCTAAAA TTCAGGCAAC TATTGTGGTT TCACATTTCT | 2220 |
| TGTCTCACTT TTGGAAGAGA AACAGTTATA GAGTATTTGG TGTCTTTTGG AGTGTGGATT | 2280 |
| CGCACTCCTC CAGCTTATAG ACCACCAAAT GCCCCTATCT TATCAACACT TCCGGAGACT | 2340 |
| ACTGTTGTTA GACGACGAGG CAGGTCCCCT AGAAGAAGAA CTCCCTCGCC TCGCAGACGA | 2400 |
| AGGTCTCAAT CGCCGCGTCG CAGAAGATCT CAATCTCGGG AATCTCAATG TTAGTATTCC | 2460 |
| TTGGACTCAT AAGGTGGGAA ACTTTACGGG GCTTTATTCT TCTACTGTAC CTGTCTTTAA | 2520 |

```
CCCTCATTGG AAAACACCCT CTTTTCCTAA TATACATTTA CACCAAGACA TTATCAAAAA    2580

ATGTGAACAA TTTGTAGGCC CACTCACAGT CAATGAGAAA AGAAGACTGC AATTGATTAT    2640

GCCAGCTAGG TTTTATCCAA ATGTTACCAA ATATTTGCCA TTGGATAAGG GTATTAAACC    2700

TTATTATCCA GAATATTTAG TTAATCATTA CTTCCAAACT AGACATTATT TACACACTCT    2760

ATGGAAGGCG GGTATATTAT ACAAGAGAGA AACTACACAT AGCGCCTCAT TTTGTGGGTC    2820

ACCATATTCT TGGGAACAAG AGCTACAGCA TGGGGCAGAA TCTTTCCACC AGCAATCCTC    2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGATTCACC CCACCACACG GAGGCCTTTT GGGGTGGAGC CCTCAGGCTC    3060

AGGGCATACT AGAAACGTTG CCAGCAAATC CGCCTCCTGC CTCTACCAAT CGCCAGTCAG    3120

GAAGGCAGCC TACCCCGCTG TCTCCACCTT TGAGAAACAC TCATCCTCAG GCCATGCAGT    3180

GG                                                                   3182

(2) INFORMATION FOR SEQ ID NO: 308:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 308:

AACTCCACAA CTTTCCACCA AACTCTGCAA GATCCCAGGG TGAGAGGCCT GTATTTCCCT      60

GCTGGTGGCT CCAGTTCAGG AACAGTAAAC CCTGTTCCGA CTACTGCCTC TCCCATATCG     120

TCAATCTTCT CGAGGATTGG GGACCCTGCA CTGAACATGG AGAACATCAC ATCAGGATTC     180

CTAGGACCCC TGCTCGTGTT ACAGGCGGGG TTTTTCTTGT TGACAAGAAT CCTCACAATA     240

CCGCAGAGTC TAGACTCGTG GTGGACTTCT CTCAATTTTC TAGGGGGAAC CACCGTGTGT     300

CTTGGCCAAA ATTCGCAGTC CCCAACCTCC AATCACTCAC CAACCTCCTG TCCTCCAACT     360

TGTCCTGGTT ATCGCTGGAT GTGTCTGCGG CGTTTTATCA TCTTCCTCTT CATCCTGCTT     420

CTATGCCTCA TCTTCTTGTT GGTTCTACTG GACTATCAAG GTATGTTGCC CGTGTGTCCT     480

CTAATTCCAG GATCTTCAAC CACCAGCGCG GGACCATGCA GAACCTGCAC GACTACTGCT     540

CAAGGAACCT CTATGTATCC CTCCTGTTGC TGTACCAAAC CTTCGGACGG AAATTGCACC     600

TGTATTCCCA TCCCATCATC CTGGGCTTTC GGAAAATTCC TATGGGAGTG GGCCTCAGCC     660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAGCATC     780

TTGAGTCCCT TTTTACCGCT GTTACCAATT TTCTTTTGTC TTTGGGTATA CATTTAAACC     840

CTAACAAAAC TAAGAGATGG GGTTACTCTT TACATTTCAT GGGCTATGTC ATTGGAAGTT     900

ATGGGTCATT GCCACAAGAT CACATCATAC AGAAAATCAA AGAATGTTTT AGAAAACTTC     960

CTATTAACAG GCCTATTGAT TGGAAAGTCT GTCAACGTAT TGTGGGTCTT TTGGGTTTTG    1020

CTGCCCCTTT TACACAATGT GGTTATCCTG CTTTAATGCC CTTGTATGCC TGTATTCAAT    1080

CTAAACAGGC TTTCACTTTC TCGCCAACTT ACAAGGCCTT TCTGTGTAAA CAATACCTGA    1140
```

```
ACCTTTACCC CGTTGCTAGG CAACGGCCAG GTCTGTGCCA AGTGTTTGCT GACGCAACCC    1200

CCACTGGCTG GGGCTTGGTC ATGGGCCATC AGCGCATGCG TGGAACCTTT CTGGCTCCTC    1260

TGCCGATCCA TACTGCGGAA CTCCTAGCCG CTTGTTTTGC TCGCAGCAGG TCTGGAGCAA    1320

ACATTCTCGG GACGGATAAC TCTGTTGTTC TCTCCCGCAA ATATACATCG TTTCCATGGC    1380

TGCTAGGCTG TGCTGCCAAC TGGATCCTGC GCGGGACGTC CTTTGTTTAC GTCCCGTCGG    1440

CGCTGAATCC CGCGGACGAC CCTTCTCGGG GCCGCTTGGG GATCTTTCGT CCCCTTCTCC    1500

GTCTGCCGTT CCGTCCGACC ACGGGGCGCA CCTCTCTTTA CGCGGACTCC CCGTCTGTGC    1560

CTTCTCATCT GCCGGTCCGT GTGCACTTCG CTTCACCTCT GCACGTCGCA TGGAGACCAC    1620

CGTGAACGCC CACCACTTCT TGCCCAAGGT CTTACATAAG AGGACTCTTG GACTCTCAGC    1680

AATGTCAACG ACCGACCTTG AGGCATACTT CAAAGACTGT TTGTTTAAGG ACTGGGAGGA    1740

GTTGGGGGAG GAGATTAGAT TAAAGGTCTT TGTACTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCATTTTTGC CTTCTGACTT TTTTCCTTCG    1980

GTACGAGATC TTCTAGATAC CGCCTCAGCT CTGTATCGGG ATGCCTTAGA GTCTCCTGAG    2040

CATTGTTCAC CTCACCATAC TGCACTCAGG CAAGCAATTC TTTGCTGGGG GAACTAATG     2100

ACTCTAGCTA CCTGGGTGGG TGTTAATTTG GAAGATCCAG CATCTAGGGA CCTAGTAGTC    2160

AGTTATGTCA ACACTAATAT GGGCCTAAAG TTCAGGCAAC TATTGTGGTT TCACATTTCT    2220

TGTCTCACTT TTGGAAGAGA AACAGTCATA GAGTATTTGG TGTCTTTCGG AGTGTGGATT    2280

CGCACTCCTC CAGCTTATAG ACCACCAAAT GCCCCTATCT TATCAACACT TCCGAAAACT    2340

ACTGTTGTTA GACGACGAGG CAGGTCCCCT AGAAGAAGAA CTCCCTCGCC TCGCAGACGA    2400

AGATCTCAAT CGCCGCGTCG CAGAAGATCT CAATCTCGGG AATCTCAATG TTAGTATTCC    2460

TTGGACTCAT AAAGTGGGTA ACTTTACGGG GCTTTATTCC TCTACTGTAC CTGTCTTTAA    2520

CCCTCATTGG AAAACACCCT CTTTTCCTAA TATACATCTA CACCAAGACA TTATCAAAAA    2580

ATGTGAACAA TTTGTAGGCC CACTCACAGT AAATGAGAAA CGAAGACTGC AATTAATTAT    2640

GCCTGCTAGG TTTTATCCAA ATGTTACTAA ATATTTGCCA TTAGATAAGG GTATTAAACC    2700

TTATTATCCG GAACATTTAG TTAATCATTA CTTCCAAACC AGACATTATT TACACACTCT    2760

ATGGAAGGCG GGTATATTAT ATAAGAGGGA AACAACACGT AGCGCCTCAT TTTGTGGGTC    2820

ACCATATTCT TGGGAACAAG AGCTACAGCA TGGGGCAGAA TCTTTCCACC AGCAATCCTC    2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGATTCACC CCACCGCACG GAGGCCTTTT GGGGTGGAGC CCTCAGGCTC    3060

AGGGCATAAT ACAAACCTTG CCAGCAAATC CGCCTCCTGC ATCTACCAAT CGCCAGTCAG    3120

GAAGGCAGCC TACCCCGCTG TCTCCACCTT TGAGAAACAC TCATCCTCAG GCCATGCAGT    3180

GG                                                                  3182

(2) INFORMATION FOR SEQ ID NO: 309:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 309:

| | | | | | |
|---|---|---|---|---|---|
| AACTCCACAA | CATTTCATCA | AGCTCTGCAG | GATCCCAGAG | TAAGAGGCCT | GTATTTTCCT | 60 |
| GCTGGTGGCT | CCAGTTCCGG | AACAGTGAAC | CCTGTTCCGA | CTACTGCCTC | ACTCATCTCG | 120 |
| TCAATCTTCT | CGAGGATTGG | GGACCCTGCA | CCGAACATGG | AAAGCATCAC | ATCAGGATTC | 180 |
| CTAGGACCCC | TGCTCGTGTT | ACAGGCGGGG | TTTTTCTTGT | TGACAAAAAT | CCTCACAATA | 240 |
| CCGCAGAGTC | TAGACTCGTG | GTGGACTTCT | CTCAATTTTC | TAGGGGAGC | TCCCGTGTGT | 300 |
| CTTGGCCAAA | ATTCGCAGTC | CCCAACCTCC | AATCACTCAC | CAACCTCTTG | TCCTCCAATT | 360 |
| TGTCCTGGCT | ATCGCTGGAT | GTGTCTGCGG | CGTTTTATCA | TCTTCCTCTT | CATCCTGCTG | 420 |
| CTATGCCTCA | TCTTCTTGTT | GGTTCTTCTG | GACTATCAAG | GTATGTTGCC | CGTTTGTCCT | 480 |
| CTAATTCCAG | GATCATCAAC | CACCAGCACG | GGACCCTGCC | GAACCTGCAT | GACTCTTGCT | 540 |
| CAAGGAACCT | CTATGTTTCC | CTCATGTTGC | TGTTCAAAAC | CTTCGGACGG | AAATTGCACT | 600 |
| TGTATTCCCA | TCCCATCATC | ATGGGCTTTC | GGAAAATTCC | TATGGGAGTG | GCCTCAGCC | 660 |
| CGTTTCTCCT | GGCTCAGTTT | ACTAGTGCCA | TTTGTTCAGT | GGTTCGCCGG | GCTTTCCCCC | 720 |
| ACTGTCTGGC | TTTCAGTTAT | ATGGATGATG | TGGTATTGGG | GGCCAAGTCT | GTACGACATC | 780 |
| TTGAGTCCCT | TTATACCTCT | GTTACCAATT | TTCTTTTGTC | TTTGGGTATA | CATTTAAATC | 840 |
| CCAACAAAAC | AAAAAGATGG | GGATATTCCC | TAAATTTCAT | GGGTTATGTA | ATTGGAAGTT | 900 |
| GGGGGTCATT | ACCACAGGAA | CACATCATAC | AAAAAATCAA | ACACTGTTTT | GGAAAACTCC | 960 |
| CTGTTAACCG | GCCTATTGAT | TGGAAAGTAT | GTCAAGGAAT | TGTGGGTCTT | TTGGGCTTTG | 1020 |
| CTGCCCCTTT | TACACAATGT | GGGTATCCTG | CTTTAATGCC | TCTGTATACG | TGTATTCAAT | 1080 |
| CTAAGCAGGC | TTTCACTTTC | TCGCCAACTT | ACAAGGCCTT | TCTGTGTAAA | CAATACCTGA | 1140 |
| ACCTTTACCC | CGTTGCCCGG | CAACGGCCAG | GTCTGTGCCA | AGTGTTTGCT | GATGCAACCC | 1200 |
| CCACTGGCTG | GGGCTTGGCC | ATAGGCATTC | AGCGCATGCG | CGGAACCTTT | GTGGCTCCTC | 1260 |
| TGCCGATCCA | TACTGCGGAA | CTCCTAGCCG | CTTGTTTTGC | TCGCAGCAGG | TCTGGAGCAA | 1320 |
| AACTTATCGG | GACCGATAAT | TCTGTCGTTC | TCTCCCGGAA | ATATACATCC | TTTCCATGGC | 1380 |
| TGCTAGGCTG | TGCTGCCAAC | TGGATCCTGC | GAGGGACGTC | CTTTGTCTAC | GTCCCGTCAG | 1440 |
| CGCTGAATCC | TGCGGACGAC | CCGTCTCGGG | GTCGCTTGGG | GATCTTTCGT | CCCCTTCTCC | 1500 |
| GTCTGCGGTT | CCGGCCGACC | ACGGGGCGCA | CCTCTCTTTA | CGCGGTCTCC | CCGTCTGTGC | 1560 |
| CTTCTCATCT | GCCGGACCGT | GTGCACTTCG | CTTCACCTCT | GCACGTCGCA | TGGAGACCAC | 1620 |
| CGTGAACGCC | CACCAAATCT | TGCCCAAGGT | CTTACATAAG | AGGACTCTTG | GACTCTCTGC | 1680 |
| AATGTCAACG | ACCGACCTTG | AGGCATACTT | CAAAGACTGT | TGTTTAAAG | ACTGGGAGGA | 1740 |
| GTTGGGGGAG | GAGATTAGAT | TAAAGGTCTT | TGTACTAGGA | GGCTGTAGGC | ATAAATTGGT | 1800 |
| CTGCGCACCA | GCACCATGCA | ACTTTTTCAC | CTCTGCCTAA | TCATCTCTTG | TTCATGTCCT | 1860 |
| ACTGTTCAAG | CCTCCAAGCT | GTGCCTTGGG | TGGCTTTGGG | GCATGGACAT | TGACCCTTAT | 1920 |
| AAAGAATTTG | GAGCTACTGT | GGAGTTACTC | TCGTTTTTGC | CTTCTGACTT | CTTTCCTTCA | 1980 |
| GTAAGAGATC | TTCTAGATAC | CGCCTCAGCT | CTGTATCGGG | ATGCCTTAGA | ATCTCCTGAA | 2040 |
| CATTGTTCAC | CGCACCACAC | TGCACTCAGG | CAAGCCATTC | TTTGCTGGGG | GGAACTAATG | 2100 |

```
ACTCTAGCTA CCTGGGTGGG TGTAAATTTG GAAGATCCAG CATCCAGGGA CCTAGTAGTC      2160

AGTTATGTCA ATACTAATAT GGGCCTAAAG TTCAGGCAAT TATTGTGGTT TCACATTTCT      2220

TGTCTCACTT TTGGAAGAGA AACCGTCATA GAGTATTTGG TGTCTTTTGG AGTGTGGATT      2280

CGCACTCCTC CAGCTTATAG ACCACCAAAT GCCCCTATCT TATCAACACT TCCGGAGAAT      2340

ACTGTTGTTA GACGAAGAGG CAGGTCCCCT AGAAGAAGAA CTCCCTCGCC TCGCAGACGA      2400

AGATCTCAAT CGCCGCGTCG CAGAAGATCT CAATCTCCAG CTTCCCAATG TTAGTATTCC      2460

TTGGACTCAT AAGGTGGGAA ATTTTACGGG GCTCTACTCT TCTACTATTC CTGTCTTTAA      2520

TCCTAACTGG AAAACTCCAT CTTTTCCTGA TATTCATTTG CACCAGGACA TTATTAACAA      2580

ATGTGAACAA TTTGTAGGTC CTCTAACAGT AAATGAAAAA CGAAGATTAA ACTTAGTCAT      2640

GCCTGCTAGA TTTTTTCCCA TCTCTACAAA ATATTTGCCC CTAGAAAAG GTATAAAACC       2700

TTATTATCCA GATAATGTAG TTAATCATTA CTTCCAAACC AGACACTATT TACATACCCT      2760

ATGGAAGGCT GGGCATCTAT ATAAAAGAGA AACTACACGT AGCGCCTCAT TTTGTGGGTC      2820

ACCATATTCT TGGGAACAAG AGCTACATCA TGGGGCTTTC TTGGACGGTC CCTCTCGAAT      2880

GGGGGAAGAA TATTTCCACC ACCAATCCTC TGGGATTTTT TCCCGACCAC CAGTTGGATC      2940

CAGCATTCAG AGCAAACACC AGAAATCCAG ATTGGGACCA CAATCCCAAC AAAGACCACT      3000

GGACGGAAGC CAACAAGGTA GGAGTGGGAG CCTTCGGGCC GGGGTTCACT CCCCCACACG      3060

GAGGCCTTTT GGGGTGGAGC CCTCAGGCTC AAGGCATGCT AAAAACATTG CCAGCAGACC      3120

CGCCTCCTGC CTCCACCAAT CGGCAGTCAG GAAGGCAGCC TACCCCAATC ACTCCACCTT      3180

TGAGAGACAC TCATCCTCAG GCCATGCAGT GG                                    3212

(2) INFORMATION FOR SEQ ID NO: 310:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 310:

AATTCCACAA CATTCCACCA AGCTCTGCAG GATCCCAGAG TAAGAGGCCT GTATTTTCCT        60

GCTGGTGGCT CCAGTTCCGG AACAGTGAAC CCTGTTCCGA CTACTGCCTC ACTCATCTCG       120

TCAATCTTCT CGAGGATTGG GGACCCTGCA CCGAACATGG AAAGCATCAC ATCAGGATTC       180

CTAGGACCCC TGCTCGTGTT ACAGGCGGGG TTTTTCTTGT TGACAAAAAT CCTCACAATA       240

CCGCAGAGTC TAGACTCGTG GTGGACTTCT CTCAATTTTC TAGGGGAGC TCCCGTGTGT        300

CTTGGCCAAA ATTCGCAGTC CCCAACCTCC AGTCACTCAC CAACCTCTTG TCCTCCAATT       360

TGTCCTGGCT ATCGCTGGAT GTGTCTGCGG CGTTTTATCA TCTTCCTCTT CATCCTGCTG       420

CTATGCCTCA TCTTCTTGTT GGTTCTTCTG GACTATCAAG GTATGTTGCC CGTTGTCCT        480

CTAATTCCAG GATCATCAAC CACCAGTACG GGACCCTGCC GAACCTGCAC GACTCTTGCT       540

CAAGGAACCT CTATGTTTCC CTCATGTTGC TGTTCAAAAC CTTCGGACGG AAATTGCACT       600

TGTATTCCCA TCCCATCATC ATGGGCTTTC GGAAAATTCC TATGGGAGTG GCCTCAGCC       660

CGTTTCTCCT GGCTCAGTTT ACTAGTGCCA TTTGTTCAGT GGTTCGCCGG GCTTTCCCCC      720
```

```
ACTGTCTGGC TTTCAGTTAT ATGGATGATG TGGTATTGGG GGCCAAGTCT GTACAACATC    780

TTGAGTCCCT TTATACCGCT GTTACCAATT TTCTTTTGTC TTTGGGTATA CATTTAAATC    840

CCAACAAAAC AAAAAGATGG GGCTATTCCC TTAATTTCAT GGGTTATGTA ATTGGAAGTT    900

GGGGCTCATT ACCACAGGAA CACATCATAC AAAAAATCAA AGACTGTTTT AGAAAACTCC    960

CTGTTAACCG GCCTATTGAT TGGAAAGTAT GTCAAAGAAT GTGGGTCTT TTGGGCTTTG    1020

CTGCCCCCTT TACACAATGT GGATATCCTG CTTTAATGCC TCTGTATGCA TGTACTCAAT   1080

CTAAGCAGGC TTTCACTTTC TCGCCAACTT ACAAGGCCTT TCTGTGTAAA CAATACCTGA   1140

ACCTTTACCC CGTTGCCCGG CAACGGCCAG GTCTGTGCCA AGTGTTTGCT GATGCAACCC   1200

CCACTGGCTG GGGCTTGGCC ATAGGCATTC AGCGCATGCG CGGAACCTTT GTGGCTCCTC   1260

TGCCGATCCA TACTGCGGAA CTCCTAGCCG CTTGTTTTGC TCGCAGCAGG TCTGGAGCAA   1320

AACTTATCGG GACCGATAAT TCTGTCGTTC TCTCCCGGAA GTATACATCC TTTCCATGGC   1380

TGCTAGGCTG TGCTGCCAAC TGGATCCTGC GAGGGACGTC CTTTGTCTAC GTCCCGTCAG   1440

CGCTGAATCC TGCGGACGAC CCGTCTCGGG GTCGCTTGGG GATCTATCGT CCCCTTCTCC   1500

GTCTGCCGTT CCAGCCGACC ACGGGGCGCA CCTCTCTTTA CGCGGTCTCC CCGTCTGTTC   1560

CTTCTCATCT GCCGGACCGT GTGCACTTCG CTTCACCTCT GCACGTCGCA TGGAGACCAC   1620

CGTGAACGCC CACCAAATAT TGCCCAAGGT CTTACATAAG AGGACTCTTG GACTCTCTGC   1680

AATGTCAACG ACCGACCTTG AGGCATACTT CAAAGACTGT TTGTTTAAAG ACTGGGAGGA   1740

GTCGGGGGAG GAGATTAGAT TAAAGGTCTT TGTACTAGGA GGCTGTAGGC ATAAATTGGT   1800

CTGCGCACCA GCACCATGCA ACTTTTTCAC CTCTGCCTAA TCATCTCTTG TTCATGTCCT   1860

ACTGTTCAAG CCTCCAAGCT GTGCCTTGGG TGGCTTTGGG GCATGGACAT TGACCCTTAT   1920

AAAGAATTTG GAGCTACTGT GGAGTTACTC TCGTTTTTGC CTTCTGACTT CTTTCCTTCA   1980

GTAAGAGATC TTCTAGATAC CGCCTCAGCT CTGTATCGGG ATGCCTTAGA GTCTCCTGAG   2040

CATTGTTCAC CTCACCACAC TGCACTCAGG CAAGCCATTC TTTGCTGGGG AGAACTAATG   2100

ACTCTAGCTA CCTGGGTGGG TGTAAATTTG GAAGATCCAG CATCCAGGGA CCTAGTAGTC   2160

AGTTATGTCA ATACTAATAT GGGCCTAAAG TTCAGGCAAT TATTGTGGTT TCACATTTCT   2220

TGTCTCACTT TTGGAAGAGA AACCGTCATA GAGTATTTGG TGTCTTTTGG AGTGTGGATT   2280

CGCACTCCTC CAGCTTATAG ACCACCAAAT GCCCCTATCT TATCAACACT TCCGGAGAAT   2340

ACTGTTGTTA GACGAAGAGG CAGGTCCCCT AGAAGAAGAA CTCCCTCGCC TCGCAGACGA   2400

AGATCTCAAT CGCCGCGTCG CAGAAGATCT CAATCTCCAG CTTCCCAATG TTAGTATTCC   2460

TTGGACTCAT AAGGTGGGAA ATTTTACGGG GCTTTACTCT TCTACTATAC CTGTCTTTAA   2520

TCCTAACTGG AAAACTCCAT CTTTTCCTGA TATTCATTTG CACCAGGACA TTATTAACAA   2580

ATGTGAACAA TTTGTAGGTC CTCTAACTGT AAATGAAAAA CGAAGATTAA ACTTAGTCAT   2640

GCCTGCTAGA TTTTTTCCCA TCTCTACGAA ATATTTGCCC CTAGAGAAAG GTATAAAACC   2700

TTATTATCCA GATAATGTAG TTAATCATTA CTTCCAAACC AGACACTATT TACATACCCT   2760

ATGGAAGGCG GGCATCTTAT ATAAAAGAGA AACTACACGT AGCGCCTCAT TTTGTGGGTC   2820

ACCTTATTCT TGGGAACAAG AGCTACATCA TGGGGCTTTC TTGGACGGTC CCTCTCGAAT   2880

GGGGGAAGAA TATTTCCACC ACCAATCCTC TGGGATTTTT TCCCGACCAC CAGTTGGATC   2940

CAGCATTCAG AGCAAACACC AGAAATCCAG ATTGGGACCA CAATCCCAAC AAAGACCACT   3000

GGACAGAAGC CAACAAGGTA GGAGTGGGAG CATTCGGGCC TGGGTTCACT CCCCCACACG   3060

GAGGCCTTTT GGGGTGGAGC CCTCAGGCTC AAGGCATGCT AAAAACATTG CCAGCAGATC   3120
```

| | |
|---|---|
| CGCCTCCTGC CTCCACCAAT CGGCAGTCAG GAAGGCAGCC TACCCCAATC ACTCCACCTT | 3180 |
| TGAGAGACAC TCATCCTCAG GCCATGCAGT GG | 3212 |

(2) INFORMATION FOR SEQ ID NO: 311:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 311:

| | |
|---|---|
| AACTCAACTC ACTTCCACCA AGCTCTGTTG GATCCCAGGG TAAGGGCACT GTATTTTCCT | 60 |
| GCTGGTGGCT CCAGTTCAGG AACACAGAAC CCTGCTCCGA CTATTGCCTC TCTCACATCA | 120 |
| TCAATCTCCT CGAAGACTGG GGGCCCTGCT ATGAACATGG AGAACATCAC ATCAGGACTC | 180 |
| CTAGGACCCC TGCGCGTGTT ACAGGCGGTG TGTTTCTTGT TGACAAAAAT CCTCACAATA | 240 |
| CCACAGAGTC TAGACTCGTG GTGGACTTCT CTCAATTTTC TAGGGGGACT ACCCAGGTGT | 300 |
| CCTGGCCAAA ATTCGCAGTC CCCAACCTCC AATCACTTAC CAACCTCCTG TCCTCCAACT | 360 |
| TGTCCTGGCT ATCGTTGGAT GTGTCTGCGG CGTTTTATCA TCTTCCTCTT CATCCTGCTG | 420 |
| CTATGCCTCA TCTTCTTGTT GGTTCTTCTG GACTACCAAG GTATGTTGCC CGTTTGTCCT | 480 |
| CTACTTCCAG GATCCACGAC CACCAGCACG GGACCATGCA AAACCTGCAC AGCTCTTGCT | 540 |
| CAAGGAACCT CTATGTTTCC CTCCTGTTGC TGTTCCAAAC CCTCGGACGG AAACTGCACC | 600 |
| TGTATTCCCA TCCCATCATC TTGGGCTTTA GGAAAATACC TATGGGAGTG GCCTCAGCC | 660 |
| CGTTTCTCCT GGCTCAGTTT ACTAGTGCAA TTTGTTCAGT GGTGCGTAGG CTTTCCCCC | 720 |
| ACTGTCTGGC TTTTAGTTAT ATGGATGATC TGGTATTGGG GGCCAAATCT GTGCAGCATC | 780 |
| TTGAGTCCCT TTATACCGCT GTTACCAATT TTCTGTTATC TGTGGGTATC CATTTAAATA | 840 |
| CTGCTAAAAC AAAAAGATGG GGTTACAACC TACATTTCAT GGGTTATGTT ATTGGTAGTT | 900 |
| GGGGAACGTT ACCCCAAGAT CATATTGTAC ACAAAATCAA AGATTGTTTT CGAAAAGTTC | 960 |
| CTGTAAATCG CCCAATTGAT TGGAAAGTTT GTCAAAGTAT TGTGGGTCTT TTGGGCTTTG | 1020 |
| CGGCCCCTTT TACCCAATGT GGTTATCCTG CTCTCATGCC TTTGTATGCC TGTATTACTG | 1080 |
| CTAAACAGGC TTTTGTCTTC TCGCCAACTT ACAAGGCCTT TCTGTGTAAA CAATACATGA | 1140 |
| ACCTTTACCC CGTTGCTCGG CAACGGCCAG GCCTGTGCCA AGTGTTTGCT GACGCAACCC | 1200 |
| CCACTGGCTG GGGCTTGGCC ATAGGCCATC AGCGCATGCG TGGAACCTTT GTGGCTCCTC | 1260 |
| TGCCGATCCA TACTGCGGAA CTCCTTGCAG CTTGCTTCGC TCGCAGCCGG TCTGAGCAA | 1320 |
| TCCTCATCGG CACAGACAAT TCTGTCGTCC TCTCTCGGAA GTATACATCC TTTCCATGGC | 1380 |
| TGCTCGGTTG TGCTGCCAAC TGGATCCTGC GCGGGACGTC CTTTGTTTAC GTCCCGTCGG | 1440 |
| CGCTGAATCC AGCGGACGAA CCCTCCCGGG GTCGCTTGGG GCTGTACCGC CCCCTTCTTC | 1500 |
| GTCTGCCGTT CCAGCCGACA ACGGGTCGCA CCTCTCTTTA CGCGGACTCC CCGTCTGTTC | 1560 |
| CTTCTCATCT GCCGGACCGT GTGCACTTCG CTTCACCTCT GCACGTCGCA TGGAGACCAC | 1620 |
| CGTGAACGCC CCCTGGAGTT TGCCAACAGT CTTACATAAG AGGACTCTTG GACTTTCAGG | 1680 |
| ACGGTCAATG ACCTGGATCG AAGACTACAT CAAAGACTGT GTATTTAAGG ACTGGGAGGA | 1740 |

```
GCTGGGGGAG GAGATCAGGT TAAAGGTCTT TGTACTAGGA GGCTGTAGGC ATAAATTGGT      1800

CTGTTCACCA GCACCATGCA ACTTTTTCAC CTCTGCCTAA TCATCTCTTG TTCATGTCCC      1860

ACTGTTCAAG CCTCCAAGCT GTGCCTTGGG TGGCTTTGGG GCATGGACAT TGACCCTTAT      1920

AAAGAATTTG GAGCTTCTGT GGAATTGTTC TCTTTTTTGG CTTCTGACTT CTTTCCGTCT      1980

GTTCGGGACC TCCTCGACAC CGCCTCAGCC CTGTACCGGG ATGCCTTAGA GTCACCGGAA      2040

CATTGCACCC CCAATCATAC CGCTCTCAGG CAAGCTATTT TGTGCTGGGG TGAGTTAATG      2100

ACTTTGGCTT CCTGGGTGGG TAATAATTTG GAAGACCCTG CAGCTAGGGA TTTAGTAGTT      2160

AATTATGTCA ACACTAATAT GGGCTTAAAG ATTAGACAAC TATTGTGGTT TCACATCTCC      2220

TGTCTTACTT TTGGAAGAGA AACAGTTCTT GAGTATTTGG TGTCCTTTGG AGTGTGGATT      2280

CGCACTCCAC CTGCTTATAG ACCACCAAAT GCCCCTATCC TATCCACACT TCCGGAAACT      2340

ACTGTTGTTA GACGACGAGG CAGGTCCCCT AGAAGAAGAA CTCCCTCGCC TCGCCGACGA      2400

AGGTCTCAAT CGCCGCGTCG CAGAAGATCT CAATCTCCAG CTTCCCAATG TTAGTATTCC      2460

TTGGACTCAT AAGGTGGGAA ATTTTACGGG GCTCTACTCT TCTACTGTAC CTGCTTTCAA      2520

TCCTAACTGG TTAACTCCTT CTTTTCCTGA TATTCATTTA CATCAGGATA TGATATCTAA      2580

ATGTGAACAA TTTGTAGGCC CGCTCACTAA AAATGAATTG AGAAGATTAA AATTGGTCAT      2640

GCCAGCTAGA TTTTATCCTA AGCATACCAA ATATTTCCTA TTGGAGAAAG GGATTAAACC      2700

CTATTATCCA GATCAGGCAG TTAATCATTA TTTTCAAACC AGACATTATT TGCATACTTT      2760

ATGGAAGGCG GGAATTCTAT ATAAGAGAGA ACCACACGT AGCGCCTCAT TTTGTGGGTC       2820

ACAATATTCC TGGGAACAAG AGCTACAGCA TGGGAGCACC TCTCTCAACG ACAAGAAGGG      2880

GCATGGGACA GAATCTTTCT GTGCCCAATC CACTGGGCTT CTTGCCAGAC CATCAGCTGG      2940

ATCCGCTATT CAGAGCAAAT TCCAGCAGTC CCGACTGGGA CTTCAACACA AACAAGGACA      3000

GTTGGCCAAT GGCAAACAAG GTAGGAGTGG GAGGCTACGG TCCAGGGTTC ACACCCCCAC      3060

ACGGTGGCCT GCTGGGGTGG AGCCCTCAGG CACAGGGTGT TTTAACAACC TTGCCAGCAG      3120

ATCCGCCTCC TGCTTCCACC AATCGGCTGT CCGGGAGGAA GCCAACCCAA GTCTCTCCAC      3180

CTCTAAGAGA CACACATCCT CAGGCCATGC AGTGG                                3215

(2) INFORMATION FOR SEQ ID NO: 312:

(i) SEQUENCE CHARACTERISTICS:
         (A) LENGTH: 3215 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 312:

AACTCAACTC ACTTCCACCA GGCTCTGTTG GATCCGAGGG TAAGGGCACT GTATTTTCCT        60

GCTGGTGGCT CCAGTTCAGG CACGCAGAAC CCTGCTCCGA CTATTGCCTC TCTCACATCA       120

TCAATCTCCT CGAAGACTGG GGGCCCTGCT ATGAACATGG ACAACATCAC ATCAGGACTC       180

CTAGGACCCC TGCTCGTGTT ACAGGCGGTG TGTTTCTTGT TGACAAAAAT CCTCACAATA       240

CCACAGAGTC TAGACTCGTG GTGGACTTCT CTCAATTTTC TAGGGGGACT ACCCGGGTGT       300

CCTGGCCAAA ATTCGCAGTC CCCAACCTCC AATCACTTAC CAACCTCCTG TCCTCCAACT       360
```

```
TGTCCTGGCT ATCGTTGGAT GTGTCTGCGG CGTTTTATCA TCTTCCTCTT CATCCTGCTG      420

CTATGCCTCA TCTTCTTGTT GGTTCTTCTG GACTATCAAG GTATGTTGCC CGTTTGTCCT      480

CTAATTCCAG GATCTACGAC CACCAGCACG GGACCATGCA AAACCTGCAC AACTCTTGCT      540

CAAGGAACCT CTATGTTTCC CTCCTGTTGC TGTTCCAAAC CCTCGGACGG AAACTGCACC      600

TGTATTCCCA TCCCATCATC TTGGGCTTTA GGAAAATACC TATGGGAGTG GCCTCAGCC       660

CGTTTCTCCT GGCTCAGTTT ACTAGTGCAA TTTGTTCAGT GGTGCGTAGG GCTTTCCCCC      720

ACTGTCTGGC TTTTAGTTAT ATGGATGATC TGGTATTGGG AGCCAAATCT GTGCAGCATC      780

TTGAGTCCCT TTATACCGCT GTTACCAATT TTCTGTTATC TGTGGGTATC CATTTGAATA      840

CCTCTAAAAC AAAAGATGG GGTTACAATT TACATTTCAT GGGTTATGTC ATTGGCAGTT       900

GGGGAGCATT ACCCCAAGAT CATATTGTAC ACAAAATCAA AGAATGTTTT CGAAAAGTTC      960

CTGTAAATCG TCCAATTGAC TGGAAAGTTT GTCAACGTAT TGTGGGACTT TTGGGCTTTG     1020

CTGCTCCTTT TACCCAATGT GGTTATCCTG CTCTCATGCC TCTGTATAAC TGTATCACTG     1080

CGAAACAGGC TTTTGTCTTT TCGCCAACTT ACAAGGCCTT TCTCTGTAAA CAGTACATGA     1140

ACCTTTACCC CGTTGCTCGG CAACGGCCAG GCCTGTGCCA AGTGTTTGCT GACGCAACCC     1200

CCACTGGTTG GGGCTTGGCC ATTGGCCATC AGCGCATGCG TGGAACCTTT GTGGCTCCTC     1260

TGCCGATCCA TACTGCGGAA CTCCTTGCAG CTTGCTTCGC TCGCAGCCGG TCTGGAGCAA     1320

TCCTCATCGG CACAGACAAT TCTGTCGTCC TCTCCCGGAA GTATACATCC TTTCCATGGC     1380

TGCTCGGATG TGCTGCCAAC TGGATCCTGC GCGGGACGTC CTTTGTTTAC GTCCCGTCGG     1440

CGCTGAATCC AGCGGACGAA CCCTCCCGGG GCCGCTTGGG GCTCTACCGC CCTCTTCTGC     1500

GTCTGCCGTT CCAGCCGACC ACGGGTCGCA CCTCTCTTTA CGCGGACTCC CCGTCTGTTC     1560

CTTCTCATCT GCCGGTCCGT GTGCACTTCG CTTCACCTCT GCACGTCGCA TGGAGACCAC     1620

CGTGAACGCC CCCTGGAGTT TGCCAACAGT CTTACATAAG AGGACTATTG GACTTTCAGG     1680

ACGGTCAATG ACCTGGATCG AAGAATACAT CAAAGACTGT GTATTTAAAG ACTGGGAGGA     1740

GCTGGGGGAG GAGATCAGGT TAAAGGTCTT TGTACTAGGA GGCTGTAGGC ATAAATTGGT     1800

CTGCGCACCA GCACCATGCA ACTTTTTCAC CTCTGCCTAA TCATCTCTTG TTTATGTCCC     1860

ACTGTTCAAG CCTCCAAGCT GTGCCTTGGG TGGCTTGGG GCATGGACAT TGACCCTTAT      1920

AAAGAATTTG GAGCTTCTGT GGAATTGTTC TCTTTTTTGC CTTCTGACTT CTTTCCGTCA     1980

ATCCGAGACC TTCTCGACAC CGCCTCAGCT CTGTATCGGG ATGCGTTAGA GTCACCGGAA     2040

CATTGCACCC CCAATCATAC CGCTCTCAGG CAAGCTATTT TGTGTTGGGG TGAATTAATG     2100

ACTTTGGCTT CCTGGGTGGG CAATAATTTG GAGGACCCTG CAGCCAGGGA TTTAGTAGTT     2160

AACTATGTTA ACACTAATAT GGGCTTAAAG ATTAGACAAC TATTGTGGTT TCACATTTCC     2220

TGCCTTACTT TTGGAAGAGA AACAGTTCTT GAGTATTTGG TGTCCTTTGG AGTGTGGATT     2280

CGCACTCCTC CAGCTTATAG ACCACCAAAT GCCCCTATCC TATCCACACT TCCGGAAACT     2340

ACTGTTGTTA GACGACGAGG CAGGTCCCCT AGAAGAAGAA CTCCCTCGCC TCGCAGACGA     2400

AGGTCTCAAT CGCCGCGTCG CAGAAGATCT CAATCTCCAG CTTCCCAATG TTAGTATTCC     2460

TTGGACTCAT AAGGTGGGAA ATTTTACGGG GCTCTACTCT TCTACTGTAC CTGCTTTCAA     2520

TCCTCACTGG TTAACTCCTT CTTTTCCTGA TATTCATTTG CATCAAGACC TGATATCTAA     2580

ATGTGAACAA TTTGTAGGCC CACTTACCAA AAATGAATTG AGAAGGTTGA AATTGATTAT     2640

GCCAGCCAGA TTCTTTCCTA AACTTACTAA ATATTTCCCT CTGGAGAAAG ACATTAAACC     2700
```

```
TTATTATCCA GAGCATGCAG TTAATCATTA TTTTCAAACC AGACATTATT TGCATACTTT    2760

ATGGAAGGCG GGAATTTTAT ATAAGAGAGA ATCCACACGT AGCGCCTCAT TTTGTGGGTC    2820

ACCATATTCT TGGGAACAAG AGCTACAGCA TGGGAGCACC TCTCTCAACG ACAAGAAGGG    2880

GCATGGGACA GAATCTCTCT GTGCCCAATC CACTGGGATT CTTTCCAGAC CATCAACTGG    2940

ATCCTCTTTT CAGAGCAAAT TCCAGCAGTC CCGATTGGGA CTTCAACAAA AACAAGGACA    3000

CTTGGCCAAT GGCAAACAAG GTAGGAGTGG GAGGTTACGG TCCAGGGTTC ACACCCCAC     3060

ACGGTGGCCT GTTGGGGTGG AGCCCTCAGG CACAAGGTGT TCTAACAACC TTGCCAGCAG    3120

ATCCGCCTCC TGCCTCCACC AATCGGCTGT CCGGGAGGAA GCCAACCCCA GTCTCTCCAC    3180

CTCTAAGAGA CACACATCCA CAGGCAATGC AGTGG                               3215
```

(2) INFORMATION FOR SEQ ID NO: 313:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 313:

```
AACTCAACCC AGTTCCACCA AGCTCTGTTG GATCCCAGGG TAAGGGCTCT GTACTTCCCT      60

GCTGGTGGCT CCAGTTCAGG GACACAGAAC CCTGCTCCGA CTATTGCCTC TCTCACATCA     120

TCAATCTTCT CGAAGACTGG GGGCCCTGCT ATGAACATGG ACAACATTAC ATCAGGACTC     180

CTAGGACCCC TGCTCGTGTT ACAGGCGGTG TGTTTCTTGT TGACAAAAAT CCTCACAATA     240

CCACAGAGTC TAGACTCGTG GTGGACTTCT CTCAATTTTC TAGGGGGACT ACCCGGGTGT     300

CCTGGCCAAA ATTCGCAGTC CCCAACCTCC AATCACTTAC CAACCTCCTG TCCTCCAACT     360

TGTCCTGGCT ATCGTTGGAT GTGTCTGCGG CGTTTTATCA TCTTCCTCTT CATCCTGCTG     420

CTATGCCTCA TCTTCTTGTT GGTTCTTCTG GACTATCAAG GTATGTTGCC CGTTTGTCCT     480

CTACTTCCAG GATCCACGAC CACCAGCACG GGACCCTGCA AAACCTGCAC AACTCTTGCA     540

CAAGGAACCT CTATGTTTCC CTCCTGTTGC TGTTCCAAAC CCTCGGACGG AAACTGCACT     600

TGTATTCCCA TCCCATCATC CTGGGCTTTA GGAAAATACC TATGGGAGTG GCCTCAGCC      660

CGTTTCTCCT GGCTCAGTTT ACTAGTGCAA TTTGTTCAGT GGTGCGTCGG GCTTTCCCCC     720

ACTGTTTGGC TTTTAGTTAT ATGGATGATC TGGTATTGGG GGCCAAATCT GTGCAGCATC     780

TTGAGTCCCT TTATACCGCT GTTACCAATT TTCTGTTATC TGTGGGTATC CATTTAAATA     840

CCTCTAAAAC AAAAAGATGG GGTTACTCCC TACATTTTAT GGGTTATGTC ATTGGTAGTT     900

GGGGATCATT ACCCCAAGAT CACATTGTAC ACAAAATCAA GGAATGCTTT CGAAAACTGC     960

CTGTAAATCG TCCAATTGAT TGGAAAGTTT GTCAACGCAT AGTGGGTCTT TTGGGCTTTG    1020

CTGCCCCTTT CACCCAATGC GGTTATCCTG CTCTCATGCC TCTGTATGCC TGTATTACTG    1080

CTAAACAGGC TTTTGTCTTC TCGCCAACCT ACAAGGCCTT TCTGTGTAAA CAATACATGA    1140

ACCTTTACCC GGTTGCTCGG CAACGGCCAG GCCTGTGCCA AGTGTTTGCT GACGCAACCC    1200

CCACTGGTTG GGGCTTGGCC ATTGCCATCA GCGCATGCG TGGAACCTTT GTGGCTCCTC     1260

TGCCGATCCA TACTGCGGAA CTCCTAGCAG CTTGTTTCGC TCGCAGCAGG TCTGGAGCGA    1320
```

```
CTCTCATCGG CACGGACAAT TCTGTTGTCC TCTCTAGGAA GTACACCTCC TTTCCATGGC  1380
TGCTCGGATG TGCTGCAAAC TGGATCCTGC GCGGGACGTC CTTTGTTTAC GTCCCATCGG  1440
CGCTGAATCC CGCGGACGAC CCCTCCCGGG GCCGCTTGGG GCTGTACCGC CCTCTTCTCC  1500
GTCTGCCGTT CCAGCCGACG ACGGGTCGCA CCTCTCTTTA CGCGGACTCC CCGTCTGTTC  1560
CTTCTCATCT GCCGGACCGT GTGCACTTCG CTTCACCTCT GCACGTCGCA TGGAGACCAC  1620
CGTGAACGCC CCTGGAGTT TGCCAACAGT CTTACATAAG CGGACTCTTG GACTTTCAGG  1680
ATGGTCAATG ACCTGGATCG AAGAATACAT CAAAGACTGT GTATTTAAGG ACTGGGAGGA  1740
GTTGGGGGAG GAGATTAGGT TAAAGGTCTT TGTATTAGGA GGCTGTAGGC ATAAATTGGT  1800
CTGTTCACCA GCACCATGCA ACTTTTTCAC CTCTGCCTAA TCATCTTTTG TTCATGTCCC  1860
ACTGTTCAAG CCTCCAAGCT GTGCCTTGGG TGGCTTTGGG GCATGGACAT TGACCCTTAT  1920
AAAGAATTTG GAGCTTCTGT GGAGTTACTC TCGTTTTTGC CTTCTGATTT CTTCCCATCG  1980
GTTCGGGACC TACTCGACAC CGCTTCAGCT CTTTACCGGG ATGCTTTAGA GTCACCTGAA  2040
CATTGCACTC CCAACCATAC TGCTCTCAGG CAAGCTATTT TGTGTTGGGG TGAGTTAATG  2100
ACTTTGGCTT CCTGGGTGGG CAATAATTTG GAGGACCCTG CAGCTAGGGA TTTAGTAGTT  2160
AACTATGTTA ACACTAACAT GGGCCTAAAA ATTAGACAAC TGTTGTGGTT TCACATTTCC  2220
TGCCTTACTT TTGGAAGAGA AACAGTTCTA GAGTATTTGG TGTCCTTTGG AGTGTGGATT  2280
CGCACTCCTC CTGCTTACAG ACCACCAAAT GCCCCTATCC TATCCACACT TCCGGAAACT  2340
ACTGTTGTTA GACGACGAGG CAGGTCCCCT AGAAGAAGAA CTCCCTCGCC TCGCAGACGA  2400
AGATCTCAAT CGCCGCGTCG CCGCAGATCT CAATCTCCAG CTTCCCAATG TTAGTATTCC  2460
TTGGACTCAT AAGGTGGGAA ACTTTACGGG GCTTTACTCT TCTACTGTGC CTGCTTTTAA  2520
TCCTAACTGG TCCACTCCTT CTTTTCCTGA TATTCATTTG CATCAAGACC TGATTTCTAA  2580
ATGTGAACAA TTTGTAGGCC CACTTACTAA AAATGAATTA CGAAGATTAA AATTGGTTAT  2640
GCCAGCTAGA TTTTATCCTA AGGTTACCAA ATATTTTCCC ATGGATAAAG GCATCAAACC  2700
CTATTATCCT GAGCATGCAG TTAATCATTA CTTTAAAACC AGACATTATT TGCATACTTT  2760
ATGGAAGGCG GGAATTTTAT ATAAGAGAGA ATCCACACGT AGCGCCTCAT TTTGTGGGTC  2820
ACCATATTCC TGGGAACAAG AGCTACAGCA TGGGAGCACC TCTCTCAACG ACACGAAGAG  2880
GCATGGGACA GAATCTCTCT GTGCCCAATC CTCTGGGATT CTTTCCAGAC CATCAGCTGG  2940
ATCCGCTATT CAGAGCAAAT TCCAGCAGTC CCGACTGGGA CTTCAACACA AACAAGGACA  3000
GTTGGCCAAT GGCAAACAAG GTAGGAGTGG GAGGCTACGG TCCAGGGTTC ACACCCCAC  3060
ACGGTGGCCT GCTGGGGTGG AGCCCTCAAG CACAAGGTGT GTTAACAACC TTGCCAGCAG  3120
ATCCGCCTCC TGCTTCCACC AATCGGCGGT CCGGAGAAA GCCAACCCCA GTCTCTCCAC  3180
CTCTAAGAGA CACACATCCA CAGGCAATGC AGTGG                            3215
```